United States Patent
Basinger et al.

(10) Patent No.: US 10,040,759 B2
(45) Date of Patent: Aug. 7, 2018

(54) SUBSTITUTED AZETIDINYL COMPOUNDS AS GLYT1 INHIBITORS

(71) Applicant: DART NEUROSCIENCE (CAYMAN) LTD., Grand Cayman (KY)

(72) Inventors: Jillian Basinger, San Diego, CA (US); Brett Bookser, San Diego, CA (US); Mi Chen, San Diego, CA (US); Andrew Hudson, San Diego, CA (US); James Na, La Jolla, CA (US); Joel Renick, San Diego, CA (US); Vincent Santora, San Diego, CA (US)

(73) Assignee: Dart NeuroScience (Cayman) Ltd., Grand Cayman (KY)

( * ) Notice: Subject to any disclaimer, the term of this patent is extended or adjusted under 35 U.S.C. 154(b) by 0 days.

(21) Appl. No.: 15/524,548

(22) PCT Filed: Nov. 3, 2015

(86) PCT No.: PCT/US2015/058741
§ 371 (c)(1),
(2) Date: May 4, 2017

(87) PCT Pub. No.: WO2016/073420
PCT Pub. Date: May 12, 2016

(65) Prior Publication Data
US 2017/0334846 A1  Nov. 23, 2017

Related U.S. Application Data

(60) Provisional application No. 62/075,752, filed on Nov. 5, 2014.

(51) Int. Cl.
| | |
|---|---|
| *C07D 205/04* | (2006.01) |
| *C07D 401/04* | (2006.01) |
| *C07D 401/10* | (2006.01) |
| *C07D 401/12* | (2006.01) |
| *C07D 405/10* | (2006.01) |
| *C07D 405/14* | (2006.01) |
| *A61K 31/397* | (2006.01) |
| *C07D 413/04* | (2006.01) |
| *A61P 25/00* | (2006.01) |

(52) U.S. Cl.
CPC ......... *C07D 205/04* (2013.01); *C07D 401/04* (2013.01); *C07D 401/12* (2013.01); *C07D 405/10* (2013.01); *C07D 405/14* (2013.01); *C07D 413/04* (2013.01)

(58) Field of Classification Search
CPC .. C07D 205/04; C07D 401/04; C07D 401/10; C07D 401/12; C07D 405/10; C07D 405/14; C07D 413/04; A61K 31/397
USPC .............. 548/950.952, 950, 952; 514/210.01
See application file for complete search history.

(56) References Cited

U.S. PATENT DOCUMENTS

| | | | |
|---|---|---|---|
| 4,938,949 A | 7/1990 | Borch et al. |
| 6,710,071 B2 | 3/2004 | Lowe, III |
| 7,189,850 B2 | 3/2007 | Ceccarelli et al. |
| 7,220,744 B2 | 5/2007 | Jolidon et al. |
| 7,319,099 B2 | 1/2008 | Jolidon et al. |
| 7,427,612 B2 | 9/2008 | Alberati-Giani et al. |
| 7,462,617 B2 | 12/2008 | Alberati-Giani et al. |

(Continued)

FOREIGN PATENT DOCUMENTS

| | | |
|---|---|---|
| EP | 2231601 | 9/2010 |
| WO | WO 2004/013144 A1 | 2/2004 |

(Continued)

OTHER PUBLICATIONS

Vandenberg et al. Trends in Pharmacological Sciences, Aug. 2014, vol. 35, No. 8, 423-430.*
Barrow et al., Birth Defects Res B Dev Reprod Toxicol, Jun. 2016;107(3):148-56.*
Patani et al., "Bioisosterism: A Rational Approach in Drug Design", Chem Rev. (1996) 96: 3147-3176.
International Search Report and Written Opinion dated Jan. 8, 2016 for Application No. PCT/US2015/058741, filed Nov. 3, 2015.

*Primary Examiner* — Venkataraman Balasubramanian
(74) *Attorney, Agent, or Firm* — Knobbe Martens Olson & Bear LLP

(57) ABSTRACT

The invention provides a chemical entity of Formula (I) wherein $R^1$, $R^2$, $R^3$, $R^4$, X, and Y have any of the values described herein, and compositions comprising such chemical entities; methods of making them; and their use in a wide range of methods, including metabolic and reaction kinetic studies; detection and imaging techniques; radioactive treatments; modulating and treating disorders mediated by GlyT1 activity; treating neurological disorders, CNS disorders, dementia, neurodegenerative diseases, and trauma-dependent losses of function; treating stroke, including cognitive and motor deficits during stroke rehabilitation; facilitating neuroprotection and neurorecovery; enhancing the efficiency of cognitive and motor training, including animal skill training; and treating other disorders, including pain and alcohol-dependence.

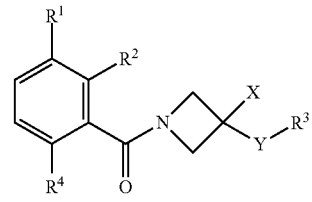

(I)

20 Claims, No Drawings

(56) References Cited

U.S. PATENT DOCUMENTS

| | | |
|---|---|---|
| 7,538,114 B2 | 5/2009 | Hitchcock et al. |
| 7,589,089 B2 | 9/2009 | Jolidon et al. |
| 7,626,056 B2 | 12/2009 | Blackaby et al. |
| 7,776,886 B2 | 8/2010 | Lindsley et al. |
| 7,868,015 B2 | 1/2011 | Tully et al. |
| 7,947,731 B2 | 5/2011 | Tully et al. |
| 7,951,836 B2 | 5/2011 | Jolidon et al. |
| 8,124,639 B2 | 2/2012 | McHardy et al. |
| 9,708,334 B2 | 7/2017 | Basinger et al. |
| 2006/0135508 A1 | 6/2006 | Villa et al. |
| 2008/0188525 A1 | 8/2008 | Hallam et al. |
| 2008/0275052 A1 | 11/2008 | Dhar et al. |
| 2009/0053140 A1 | 2/2009 | Scott et al. |
| 2011/0190292 A1 | 8/2011 | Dhar et al. |
| 2017/0044167 A1 | 2/2017 | Basinger et al. |

FOREIGN PATENT DOCUMENTS

| | | |
|---|---|---|
| WO | WO 2004/056784 | 7/2004 |
| WO | WO 2005/040166 A1 | 5/2005 |
| WO | WO 2005/046601 | 5/2005 |
| WO | WO 2006/072436 | 7/2006 |
| WO | WO 2006/077026 | 7/2006 |
| WO | WO 2006/094843 | 9/2006 |
| WO | WO 2007/147770 | 12/2007 |
| WO | WO 2010/010133 | 1/2010 |
| WO | WO 2010/100606 | 9/2010 |
| WO | WO 2013/037415 | 3/2013 |
| WO | WO 2013/037914 | 3/2013 |
| WO | WO 2015/164520 | 10/2015 |

\* cited by examiner

SUBSTITUTED AZETIDINYL COMPOUNDS AS GLYT1 INHIBITORS

CROSS REFERENCE TO RELATED APPLICATIONS

Any and all priority claims identified in the Application Data Sheet, or any correction thereto, are hereby incorporated by reference under 37 CFR 1.57. For example, this application is a U.S. National Phase of International Application No. PCT/US2015/058741, filed on Nov. 3, 2015 and published on May 12, 2016 as WO 2016/073420, which claims the benefit of U.S. Provisional Application 62/075,752, filed on Nov. 5, 2014, which is incorporated herein by reference in its entirety.

BACKGROUND

Field

The present disclosure relates to the fields of chemistry and medicine. More specifically, the present disclosure relates to compounds and compositions that can inhibit GlyT1 and are useful in various methods.

Description of the Related Technology

Glycine transporters, which form part of the sodium and chloride family of neurotransmitter transporters, play an important role in terminating of post-synaptic glycinergic actions and maintain low extracellular glycine concentration by reuptake of glycine into presynaptic nerve terminals and surrounding fine glial processes. Two distinct glycine transporter genes have been cloned from mammalian brain, GlyT1 and GlyT2, giving rise to two transporters with about 50% amino acid sequence homology. GlyT1 encodes four isoforms arising from alternative splicing and alternative promoter usage (1a, 1b, 1c and 1d). Only two of these isoforms have been found in rodent brain (GlyT1a and GlyT1b). GlyT2 also presents some degree of heterogeneity. Two GlyT2 isoforms (2a and 2b) have been identified in rodent brains.

GlyT1 is expressed in the CNS and in peripheral tissues, whereas GlyT2 appears to be specifically expressed in the CNS. GlyT1 has a predominantly glial distribution and is found not only in areas corresponding to strychnine sensitive glycine receptors but also outside these areas, where it has been postulated to be involved in modulating NMDA receptor function (Lopez-Corcurera et al., *Mol. Mem. Biol.*, 2001, 18, 13-20). Thus, one strategy to enhance NMDA receptor activity is to elevate the glycine concentration in the local microenvironment of synaptic NMDA receptors by inhibiting the GlyT1 transporter (Bergereon et al., *Proc. Natl. Acad. Sci. USA*, 1998, 95, 15730-15734; Chen et al., *J. Neurophysiol.*, 2003, 89 (2), 691-703).

Glycine transporter inhibition appears to be a viable strategy for treating neurological and neuropsychiatric disorders. Such disease states include psychoses; schizophrenia (Armer R. E. and Miller D. J., 2001, *Exp. Opin. Ther. Patents*, 11 (4), 563-572), psychotic mood disorders such as severe major depressive disorder, mood disorders associated with psychotic disorders such as acute mania or depression associated with bipolar disorders, and mood disorders associated with schizophrenia, (Pralong et al., *Prog. Neurobiol.*, 2002, 67, 173-202); autistic disorders (Carlsson M. L., *J. Neural Transm.*, 1998, 105(4-5), 525-535); cognitive disorders, such as dementias, including age related dementia and senile dementia of the Alzheimer type; and memory disorders in a mammal, including a human, attention deficit disorders and pain (Armer R. E. and Miller D. J., 2001). Thus, increasing activation of NMDA receptors via GlyT1 inhibition may provide a means for treating psychosis, schizophrenia, dementia and other diseases in which cognitive processes are impaired, such as attention deficit disorders or Alzheimer's disease.

However, there remains a need for effective GlyT1 inhibitors with improved pharmaceutical properties, such as potency, specificity, and side effect profiles for treating conditions associated with neurological processes. The present invention addresses these and other needs in the art by disclosing azetidinyl compounds as potent and well-tolerated GlyT1 inhibitors.

SUMMARY

Some embodiments provide a chemical entity of Formula (I):

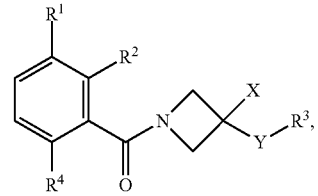

wherein $R^1$, $R^2$, $R^3$, $R^4$, X, and Y have any of the values described herein.

In one aspect the chemical entity is selected from the group consisting of, but not limited to, compounds of Formula (I) and all pharmaceutically acceptable forms thereof.

In certain embodiments, the compound of Formula (I) is a compound selected from those species described or exemplified in the detailed description herein.

Some embodiments provide pharmaceutical compositions for treating a disease, disorder, or medical condition mediated by GlyT1 activity, comprising an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of Formula (I).

In some embodiments, the pharmaceutical compositions may further comprise one or more pharmaceutically acceptable excipients.

Some embodiments provide a method of treating a subject suffering from or diagnosed with a disease, disorder, or condition mediated by GlyT1 activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

Chemical entities of compounds of Formula (I) are useful in wide range of methods, as described herein. Isotopically-labeled compounds and prodrugs can be used in metabolic and reaction kinetic studies, detection and imaging techniques and radioactive treatments. In some aaspects, the chemical entities can be used to inhibit GlyT1; to treat a disorder mediated by GlyT1; to enhance neuronal plasticity; to treat neurological disorders, including neurodegenerative disorders, cognitive disorders, and cognitive deficits associated with CNS disorders; to confer neuroprotection; and to treat peripheral disorders, as disclosed herein. In some aaspects, the chemical entities of the present disclosure are also useful as augmenting agents to enhance the efficiency of cognitive and motor training, including in stroke rehabilitation; to facilitate neurorecovery and neurorehabilitation; and to increase the efficiency of non-human animal training protocols. The invention is further directed to the general and specific embodiments defined, respectively, by the independent and dependent claims appended hereto, which are incorporated by reference herein.

Additional embodiments, features, and advantages of the disclosure will be apparent from the following detailed description and through practice of the exemplary embodiments.

DETAILED DESCRIPTION

The embodiments may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present embodiments, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present embodiments.

Terms and Definitions

The use of headings and subheadings provided in the sections of this specification is solely for convenience of reference and does not limit the various embodiments herein, which are to be construed by reference to the specification as a whole.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5-fold, or within 2-fold on either side of a value. Numerical quantities given herein are approximate unless stated otherwise, meaning that the term "about" or "approximately" can be inferred when not expressly stated. To provide a more concise description, some of the quantitative expressions given herein are not qualified with the term "about". It is understood that, whether the term "about" is used explicitly or not, every quantity given herein is meant to refer to the actual given value, and it is also meant to refer to the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or more.

Furthermore, although items, elements or components of the embodiments may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. Thus, the term "example" is used to provide exemplary instances of the item in discussion, not an exhaustive or limiting list thereof. Similarly, adjectives such as "conventional," "traditional," "normal," "criterion," "known," and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to," or other like phrases in some instances should not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Chemical Terms

The term "alkyl" refers to a fully saturated aliphatic hydrocarbon group. The alkyl moiety may be a straight- or branched-chain alkyl group having from 1 to 12 carbon atoms in the chain. Examples of alkyl groups include, but are not limited to, methyl (Me, which also may be structurally depicted by the symbol, "▬"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups may be optionally substituted with one or more substituents including, but not limited to, hydroxyl, alkoxy, thioalkoxy, amino, and aminoalkyl.

The term "alkenyl" refers to optionally substituted unsaturated aliphatic moieties having at least one carbon-carbon double bond and including E and Z isomers of said alkenyl moiety. Examples of alkenyl radicals include ethenyl, propenyl, butenyl, 1,4-butadienyl, cyclopentenyl, cyclohexenyl and the like.

The term "alkynyl" refers to optionally substituted unsaturated aliphatic moieties having at least one carbon-carbon triple bond and includes straight and branched chain alkynyl groups. Examples of alkynyl radicals include ethynyl, propynyl, butynyl and the like.

The term "haloalkyl" refers to a straight- or branched-chain alkyl group having from 1 to 12 carbon atoms in the chain, substituting one or more hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, —$CH_2CF_2CF_3$ and other groups that in light of the ordinary skill in the art and the teachings provided herein, would be considered equivalent to any one of the foregoing examples.

The term "alkoxy" includes a straight chain or branched alkyl group with an oxygen atom linking the alkyl group to the rest of the molecule. Alkoxy includes methoxy, ethoxy, propoxy, isopropoxy, butoxy, t-butoxy, pentoxy and so on. "Aminoalkyl," "thioalkyl," and "sulfonylalkyl" are analogous to alkoxy, replacing the terminal oxygen atom of alkoxy with, respectively, NH (or NR), S (sulfur), and $SO_2$.

The term "haloalkoxy" refer to alkoxy groups substituting one or more hydrogens with halogens. Examples of haloalkoxy groups include, but are not limited to, —$OCF_3$, —$OCH_2CF_3$, —$OCH_2CHF_2$, —$OCH_2CH_2Cl$, —$OCH_2CF_2CF_3$, —$OCH(CH_3)CHF_2$ and other groups that in light of the ordinary skill in the art and the teachings provided herein, would be considered equivalent to any one of the foregoing examples.

The term "cyano" refers to the group —CN.

The term "aryl" refers to a monocyclic, or fused, aromatic carbocycle (ring structure having ring atoms that are all carbon), having from 3 to 12 ring atoms per ring (carbon atoms in aryl groups are sp2 hybridized).

The term "phenyl" represents the following moiety:

The term "cycloalkyl" refers to a saturated or partially saturated carbocycle, such as monocyclic, fused polycyclic, bridged monocyclic, bridged polycyclic, spirocyclic, or spiro polycyclic carbocycle having from 3 to 12 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

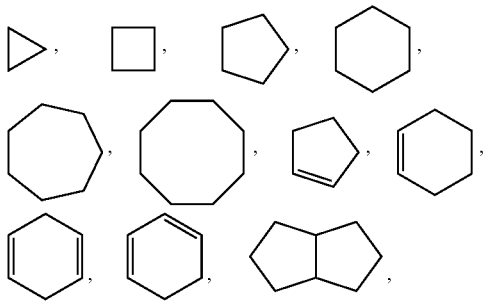

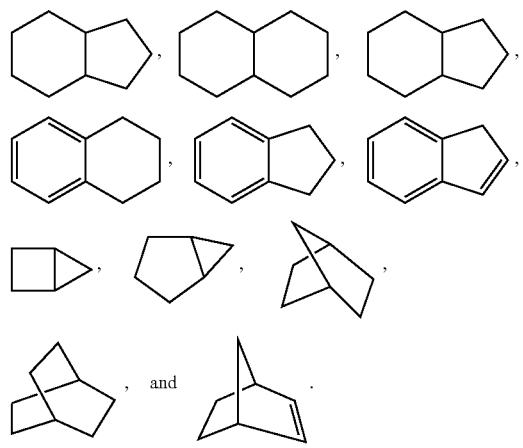

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

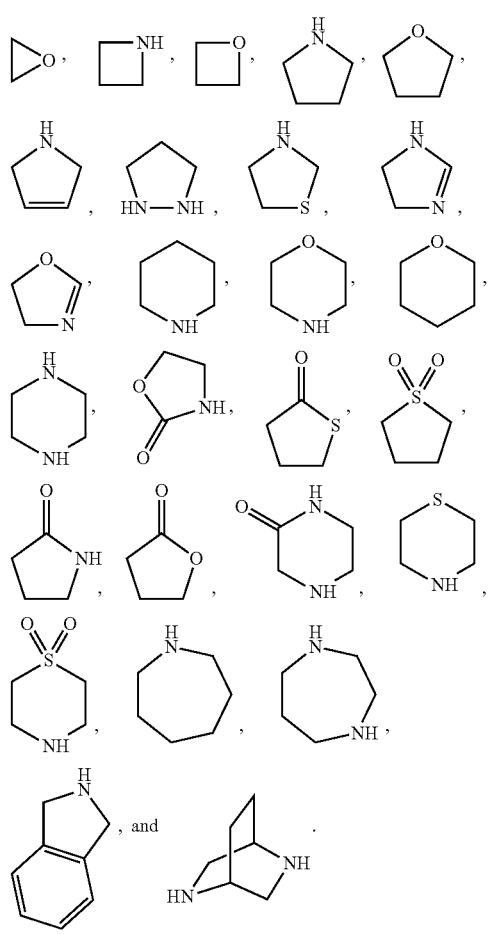

The term "oxane" represents the following moiety:

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

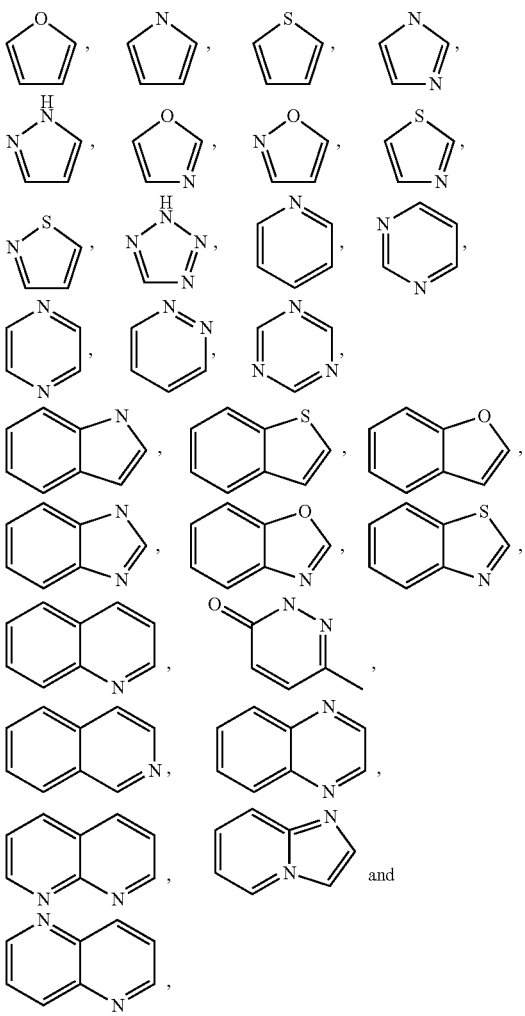

The term "pyridyl" represents the following moiety:

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur), or N (nitrogen).

By "optional" or "optionally" is meant that the subsequently described event or circumstance may or may not occur, and that the description includes instances where the event or circumstance occurs and instances or circumstances where it does not. For example, "optionally substituted alkyl" encompasses both "unsubstituted alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted" used herein means that any one or more hydrogens on the designated atom or group is replaced with a selection from the indicated group, provided that the designated atom's normal valence is not exceeded. When a substituent is oxo (i.e., =O) then 2 hydrogens on the atom are replaced.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

The symbols ▬ and ▬ are used as meaning the same spacial arrangement in chemical structures shown herein. Analogously, the symbols ''''' and ''''' are used as meaning the same spacial arrangement in chemical structures shown herein.

Chemical Entities

Generally

Chemical entities of the present embodiments include, but are not limited to compounds of Formula (I) and all pharmaceutically acceptable forms thereof. Pharmaceutically acceptable forms of the compounds recited herein include pharmaceutically acceptable chelates, solvates, conformers, crystalline forms/polymorphs, salts, prodrugs, pharmaceutically active metabolites, and mixtures thereof. In certain embodiments, the compounds described herein are in the form of pharmaceutically acceptable salts. Hence, the terms "chemical entity" and "chemical entities" also encompass pharmaceutically acceptable chelates, solvates, conformers, crystalline forms/polymorphs, salts, prodrugs, pharmaceutically active metabolites, and mixtures.

The term "pharmaceutically acceptable," as used in connection with compositions of the embodiments, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

Chelates

The term "chelate" refers to the chemical entity formed by the coordination of a compound to a metal ion at two (or more) points.

Solvates

Additionally, any formula given herein is intended to refer also to hydrates, solvates, and polymorphs of such compounds, and mixtures thereof, even if such forms are not listed explicitly. Some embodiments provide a solvate of a compound of Formula (I), and the use of such solvates in methods described herein. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the embodiments with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as MeOH, methyl t-butyl ether, EtOAc, mEtOAc, (S)-propylene glycol, (R)-propylene glycol, 1,4-butyne-diol, and the like. In some embodiments, hydrates include compounds formed by an incorporation of one or more water molecules.

Conformers and Crystalline Forms/Polymorphs

Some embodiments provide conformer and crystalline forms of a compound of Formula (I), and the use of these entities in methods of present disclosure. A conformer is a structure that is a conformational isomer.

Conformational isomerism is the phenomenon of molecules with the same structural formula but different conformations (conformers) of atoms about a rotating bond.

A polymorph is a composition having the same chemical formula, but a different solid state or crystal structure. In certain embodiments, compounds of Formula (I) are obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

As used herein, a "compound" refers to any one of: (a) the actually recited form of such compound; and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered.

In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in its chemically relevant form (or forms) that exists in the medium in which such reacting takes place, with (b) the chemically relevant form (or forms) of the compound R—COOH that exists in the medium in which such reacting takes place. In this regard, if such entity is for example in an aqueous environment, it is understood that the compound R—COOH is in the same such medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

In another example, a "zwitterionic" compound is encompassed herein by referring to a compound that may form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As is generally well known, a zwitterion or zwitterionic compound is a neutral compound that has formal unit charges of opposite sign. Sometimes these compounds are referred to by the term "inner salts".

Salts

Embodiments include pharmaceutically acceptable salts of the compounds represented by Formula (I), and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., Trends in Active Pharmaceutical Ingredient Salt Selection based on Analysis of the Orange Book Database, *J. Med. Chem.* 2007, 50, 6665-6672; Berge et al., Pharmaceutical Salts, *J. Pharm. Sci.* 1977, 66, 1-19; Stahl and Wermuth (eds), Pharmaceutical Salts; Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methane-sulfonates, propanesulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Prodrugs

Some embodiments provide prodrugs of the compounds of Formula (I), and the use of such pharmaceutically acceptable prodrugs in methods of the present disclosure, particularly therapeutic methods.

A "prodrug" is a drug precursor that is initially inactive or partially active and upon administration in vivo undergoes chemical conversion by metabolic processes into an active pharmacological agent. A "pharmaceutically acceptable prodrug" is a prodrug that is preferably non-toxic, biologically tolerable, and otherwise biologically suitable for administration to the subject. Prodrugs are often useful because, in some situations, they can be easier to administer than the parent drug. They can, for instance, be bioavailable by oral administration whereas the parent is not. The prodrug can also have improved solubility in pharmaceutical compositions over the parent drug.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alky)amines. Examples of esters include $C_{1-6}$alkyl, $C_{1-6}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130.

Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J. Med. Chem.* 1996, 39, 10-18. Free amines can also be derivatized as amides, sulfonamides or phosphonamides. All of these prodrug moieties may incorporate groups including ether, amine, and carboxylic acid functionalities.

Prodrugs may be determined using routine techniques known or available in the art (e.g., Bundgard (ed.), 1985, Design of prodrugs, Elsevier; Krogsgaard-Larsen et al., (eds.), 1991, Design and Application of Prodrugs, Harwood Academic Publishers).

Metabolites

Some embodiments provide pharmaceutically active metabolites of the compounds of Formula (I), which may also be used in the methods of the disclosure. A "pharmaceutically active metabolite" means a pharmacologically active product of metabolism in the body of a compound of Formula (I) or salt thereof.

Prodrugs and active metabolites of a compound may be determined using routine techniques known or available in the art. For example, isolated metabolites can be enzymatically and synthetically produced (e.g., Bertolini et al., *J. Med. Chem.* 1997, 40, 2011-2016; Shan et al., *J. Pharm. Sci.* 1997, 86, 765-767; Bagshawe, *Drug Dev. Res.* 1995, 34, 220-230; and Bodor, *Adv Drug Res.* 1984, 13, 224-231).

Isotopes

Isotopes may be present in the compounds described. Each chemical element present in a compound either specifically or generically described herein may include any isotope of said element. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present embodiments encompass any composition made by admixing a compound of Formula (I) and a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 21$^{st}$ Ed., Lippincott Williams & Wilkins (2005).

The term "carrier" refers to an adjuvant, vehicle, or excipients, with which the compound is administered. In preferred embodiments, the carrier is a solid carrier. Suitable pharmaceutical carriers include those described in Remington: The Science and Practice of Pharmacy, 21$^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refers to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

As used herein, "suitable for oral administration" refers to a sterile, pharmaceutical product produced under good manufacturing practices (GMP) that is prepared and presented in a manner such that the composition not likely to cause any untoward or deleterious effects when orally administered to a subject. Unless specified otherwise, all of the compositions disclosed herein are suitable for oral administration.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the embodiments, "an effective amount" of at least one compound according to the embodiments is administered to a subject (e.g., a mammal). An "effective amount" also means an amount or dose of a compound or composition effective to modulate activity of GlyT1 or an associated signaling pathway.

The "effective amount" will vary, depending on the compound, the disease, the type of treatment desired, and its severity, and age, weight, etc.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present embodiments are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing," or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training."

Reference will now be made to the embodiments of the present disclosure, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Chemical Entities

Some embodiments provide certain substituted azetidinyl derivatives, which are useful, for example, as inhibitors of GlyT1 enzymatic activity.

In certain embodiments, $R^1$ is —SO$_2$CH$_3$, —SO$_2$CH$_2$CH$_3$, or —CN.

In certain embodiments, $R^2$ is —Cl, or —OCH$_3$.

In some embodiments, X is —H, —F, or —OH.

In some embodiments, X is —H.

In some embodiments, Y is a bond, —CH$_2$—, —CF$_2$—, —O—, or —NH—.

In some embodiments, Y is a bond.

In some embodiments, X is —H and Y is a bond.

In some embodiments, $R^3$ is phenyl or pyridyl, unsubstituted or substituted with one to three members independently selected from the group consisting of halo, —C$_{1-6}$ alkyl, —C$_{2-6}$alkynyl, —C$_{1-6}$haloalkyl, —C$_{1-6}$alkoxy, —CN, —NO$_2$, -benzoxazole, -oxane optionally substituted with one or more —CH$_3$, and —C$_{3-6}$cycloalkyl optionally substituted with one or more —F.

In some embodiments, $R^3$ is phenyl or pyridyl, wherein each phenyl or pyridyl is unsubstituted or substituted with one, two or three members independently selected from the group consisting of: —Cl, —F, —CH$_3$, —CH$_2$CH$_3$, ethynyl, —CHF$_2$, —CF$_3$, —OCH$_3$, —OCH$_2$CH$_3$, —CN, —NO$_2$, oxan-4-yl, 2,2-dimethyloxan-4-yl, and 4,4-difluorocyclohexyl.

In some embodiments, $R^3$ is 1,3-benzoxazol-6-yl, 2-(trifluoromethyl)phenyl, 2,3,4-trifluorophenyl, 2,3,5-trifluorophenyl, 2,3-difluorophenyl, 2,4,5-trifluorophenyl, 2,5-difluorophenyl, 2-chloro-3-fluorophenyl, 2-chloro-4-(difluoromethyl)phenyl, 2-chloro-4-(trifluoromethyl)phenyl, 2-chloro-4,5-difluorophenyl, 2-chloro-4-cyano-3-ethoxyphenyl, 2-chloro-4-cyano-3-fluorophenyl, 2-chloro-4-cyano-3-methoxyphenyl, 2-chloro-4-cyanophenyl, 2-chloro-4-fluorophenyl, 2-cyano-4-fluorophenyl, 2-cyanophenyl, 2-fluoro-4-(trifluoromethyl)phenyl, 2-fluoro-5-methylphenyl, 2-fluorophenyl, 2-methoxy-4-(trifluoromethyl)phenyl, 2-methyl-4-(trifluoromethyl)phenyl, 3-(trifluoromethyl)phenyl, 3-(trifluoromethyl)phenyl, 3,4,5-trifluorophenyl, 3,4-difluorophenyl, 3,5-difluorophenyl, 3-chloro-2-fluorophenyl, 3-chloro-4-cyanophenyl, 3-fluoro-4-(oxan-4-yl)phenyl, 3-fluoro-4-(trifluoromethyl)phenyl, 3-methoxy-4-(trifluoromethyl)phenyl, 4-(2,2-dimethyloxan-4-yl)phenyl, 4-(4,4-difluorocyclohexyl)phenyl, 4-(difluoromethyl)-2-fluorophenyl, (difluoromethyl)-3-fluorophenyl, 4-(oxan-4-yl)phenyl, 4-(trifluoromethyl)phenyl, 4-chloro-2-cyanophenyl, 4-chlorophenyl, 4-cyano-2-methoxyphenyl, 4-cyano-3-fluorophenyl, 4-cyano-3-methoxyphenyl, 4-cyanophenyl, 4-fluorophenyl, 4-methoxyphenyl, 4-nitrophenyl, 5-chloro-2-fluorophenyl, or phenyl.

In some embodiments, $R^3$ is 5-difluoropyridin-2-yl, 3-chloro-5-(trifluoromethyl)pyridin-2-yl, 3-chloro-5-cyanopyridin-2-yl, 3-chloropyridin-2-yl, 3-ethyl-5-(trifluoromethyl)pyridin-2-yl, 3-ethynyl-5-(trifluoromethyl)pyridin-2-yl, 3-fluoro-5-(trifluoromethyl)pyridin-2-yl, 3-methoxy-5-(trifluoromethyl)pyridin-2-yl, 3-methyl-5-(trifluoromethyl)pyridin-2-yl, 5-(4,4-difluorocyclohexyl)pyridin-2-yl, 5-(difluoromethyl)pyridin-2-yl, 5-(oxan-4-yl)pyridin-2-yl, 5-(trifluoromethyl)pyridin-2-yl, 5-fluoropyridin-2-yl, 5-methylpyridin-3-yl, 6-(trifluoromethyl)pyridin-3-yl, pyridin-2-yl, pyridin-3-yl, pyridin-4-yl, or 1,3-benzoxazole.

In some embodiments, $R^4$ is —OC$_{1-6}$alkyl, —OC$_{1-6}$haloalkyl, —C$_{3-6}$cycloalkyl, or 4-fluorooxan-4-yl.

In some embodiments, $R^4$ is —OCH$_2$CH$_3$, —OCH(CH$_3$)$_2$, —OCH$_2$(CH$_3$)$_3$, —OCH$_2$ cyclopropyl, —OCH(CH$_3$)(CF$_3$), —OCH$_2$CF$_3$, 1-fluorocyclobutyl, 3,3-difluorocyclobutyl, cyclopentyl, 1-fluorocyclopentyl, cyclohexyl, 1,4,4-trifluorocyclohexyl, or 4-fluorooxan-4-yl.

In some embodiments, $R^4$ is [(2S)-1,1,1-trifluoropropan-2-yl]oxy, or [(2R)-1,1,1-trifluoropropan-2-yl]oxy.

In some embodiments, $R^1$ is —SO$_2$(C$_{1-6}$alkyl), $R^2$ is —OC$_{1-6}$alkyl, and $R^4$ is —OC$_{1-6}$alkyl or —OC$_{1-6}$haloalkyl.

In some embodiments, $R^1$ is —SO$_2$(C$_{1-6}$alkyl), $R^3$ is phenyl or pyridyl, wherein each phenyl or pyridyl is unsubstituted or substituted with one, two or three members independently selected from the group consisting of: halo, —C$_{1-6}$alkyl, —C$_{2-6}$alkynyl, —C$_{1-6}$haloalkyl, —C$_{1-6}$alkoxy, —CN, —NO$_2$, oxan-4-yl, 2,2-dimethyloxan-4-yl, and 4,4-difluorocyclohexyl; $R^4$ is —OCH$_2$CH$_3$, —OCH(CH$_3$)$_2$, —OCH$_2$C(CH$_3$)$_3$, —OCH$_2$ cyclopropyl, —OCH(CH$_3$)(CF$_3$), [(2S)-1,1,1-trifluoropropan-2-yl]oxy, [(2R)-1,1,1-trifluoropropan-2-yl]oxy, or —OCH$_2$CF$_3$.

In some embodiments $R^3$ is 2-chloro-4-(difluoromethyl)phenyl, 2-chloro-4-(trifluoromethyl)phenyl, 2-fluoro-4-(trifluoromethyl)phenyl, 4-(oxan-4-yl)phenyl, 4-cyanophenyl, 3-chloro-5-(trifluoromethyl)pyridin-2-yl, 3-fluoro-5-(trifluoromethyl)pyridin-2-yl, or 5-(trifluoromethyl)pyridin-2-yl and X is —H.

In some embodiments $R^3$ is 2,3-difluorophenyl, 2,4,5-trifluorophenyl, 2,4,6-trifluorophenyl, 2,4-difluorophenyl, 2,5-difluorophenyl, 2,6-difluorophenyl, 2,6-dimethylphenyl, 2-chlorophenyl, 2-methylphenyl, 3-chlorophenyl, 3-fluorophenyl, 3-methylphenyl, 4-fluoro-2-methylphenyl, 4-fluoro-3-methylphenyl, 4-methylphenyl, or 5-chloro-pyridin-2-yl.

In some embodiments, the chemical entity of Formula (I) has the structure of Formula (Ia):

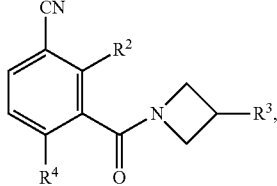

(Ia)

wherein the chemical entity is selected from the group consisting of compounds of Formula (Ia), pharmaceutically acceptable salts of compounds of Formula (Ia), pharmaceutically acceptable prodrugs of compounds of Formula (Ia), and pharmaceutically active metabolites of compounds of Formula (Ia).

In some embodiments, the chemical entity of Formula (I) has the structure of Formula (Ib):

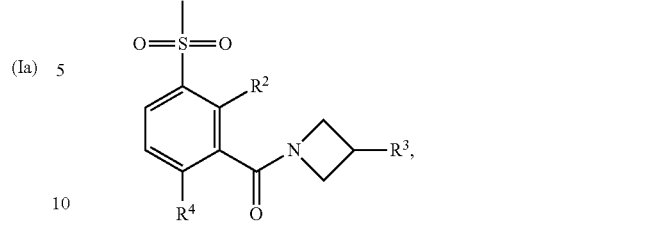

(Ib)

wherein the chemical entity is selected from the group consisting of compounds of Formula (Ib), pharmaceutically acceptable salts of compounds of Formula (Ib), pharmaceutically acceptable prodrugs of compounds of Formula (Ib), and pharmaceutically active metabolites of compounds of Formula (Ib).

In certain embodiments, a compound, or pharmaceutically acceptable salt thereof, of Formula (I) is selected from the group consisting of:

| Example | Compound Name |
|---|---|
| 1 | 4-(4-Fluorooxan-4-yl)-2-methoxy-3-[(3-{[5-(trifluoromethyl)pyridin-2-yl]amino}azetidin-1-yl)carbonyl]benzonitrile; |
| 2 | 2-Methoxy-3-[(3-{[5-(trifluoromethyl)pyridin-2-yl]amino}azetidin-1-yl)carbonyl]-4-{[(2S)-1,1,1-trifluoropropan-2-yl]oxy}benzonitrile; |
| 3 | 4-(1-Fluorocyclobutyl)-2-methoxy-3-({3-[4-(trifluoromethyl)phenyl]azetidin-1-yl}carbonyl)benzonitrile; |
| 4 | 3-[(3-{Difluoro[4-(trifluoromethyl)phenyl]methyl}azetidin-1-yl)carbonyl]-2-methoxy-4-{[(2S)-1,1,1-trifluoropropan-2-yl]oxy}benzonitrile; |
| 5 | 3-({3-[3-Fluoro-5-(trifluoromethyl)pyridin-2-yl]azetidin-1-yl}carbonyl)-2-methoxy-4-{[(2S)-1,1,1-trifluoropropan-2-yl]oxy}benzonitrile; |
| 6 | 2-Methoxy-3-({3-[4-(oxan-4-yl)phenyl]azetidin-1-yl}carbonyl)-4-[(1,1,1-trifluoropropan-2-yl)oxy]benzonitrile; |
| 7 | 3-({3-[3-Ethynyl-5-(trifluoromethyl)pyridin-2-yl]azetidin-1-yl}carbonyl)-2-methoxy-4-{[(2S)-1,1,1-trifluoropropan-2-yl]oxy}benzonitrile; |
| 8 | 3-({3-[3-Ethyl-5-(trifluoromethyl)pyridin-2-yl]azetidin-1-yl}carbonyl)-2-methoxy-4-{[(2S)-1,1,1-trifluoropropan-2-yl]oxy}benzonitrile; |
| 9 | 2-Methoxy-3-({3-[3-methoxy-5 -(trifluoromethyl)pyridin-2-yl]azetidin-1-yl}carbonyl)-4-{[(2S)-1,1,1-trifluoropropan-2-yl]oxy}benzonitrile; |
| 10 | 1-(3-Methanesulfonyl-2-methoxy-6-{[(2S)-1,1,1-trifluoropropan-2-yl]oxy}benzoyl)-3-[3-(trifluoromethyl)phenyl]azetidine; |
| 11 | 2-Methoxy-3-({3-[3-methyl-5-(trifluoromethyl)pyridin-2-yl]azetidin-1-yl}carbonyl)-4-{[(2S)-1,1,1-trifluoropropan-2-yl]oxy}benzonitrile; |
| 12 | 4-Cyclopentyl-2-methoxy-3-{3-[5-(trifluoromethyl)pyridin-2-yl]azetidine-1-carbonyl}benzonitrile; |
| 13 | 5-Chloro-6-{1-[(3-cyano-2-methoxy-6-{[(2S)-1,1,1-trifluoropropan-2-yl]oxy}phenyl)carbonyl]azetidin-3-yl}pyridine-3-carbonitrile; |
| 14 | 3-[(3-{[3-Fluoro-5-(trifluoromethyl)pyridin-2-yl]amino}azetidin-1-yl)carbonyl]-2-methoxy-4-{[(2S)-1,1,1-trifluoropropan-2-yl]oxy}benzonitrile; |
| 15 | 3-(3,4-Difluorophenyl)-1-({3-methanesulfonyl-2-methoxy-6-[(1,1,1-trifluoropropan-2-yl)oxy]phenyl}carbonyl)azetidine; |
| 16 | 3-(4-Fluorophenoxy)-1-({3-methanesulfonyl-2-methoxy-6-[(1,1,1-trifluoropropan-2-yl)oxy]phenyl}carbonyl)azetidine; |
| 17 | 3-({3-Fluoro-3-[4-(trifluoromethyl)phenyl]azetidin-1-yl}carbonyl)-4-(4-fluorooxan-4-yl)-2-methoxybenzonitrile; |
| 18 | 3-{[3-(3,4-Difluorophenyl)-3-fluoroazetidin-1-yl]carbonyl}-4-(4-fluorooxan-4-yl)-2-methoxybenzonitrile; |
| 19 | 3-{[3-(3,5-Difluorophenyl)azetidin-1-yl]carbonyl}-4-(4-fluorooxan-4-yl)-2-methoxybenzonitrile; |
| 20 | 3-{[3-(4-Chlorophenyl)azetidin-1-yl]carbonyl}-4-(4-fluorooxan-4-yl)-2-methoxybenzonitrile; |
| 21 | 3-{[3-(3,4-Difluorophenyl)azetidin-1-yl]carbonyl}-4-(4-fluorooxan-4-yl)-2-methoxybenzonitrile; |
| 22 | 4-(4-Fluorooxan-4-yl)-3-{[3-(4-fluorophenyl)azetidin-1-yl]carbonyl}-2-methoxybenzonitrile; |
| 23 | 4-(4-Fluorooxan-4-yl)-2-methoxy-3-({3-[3-(trifluoromethyl)phenyl]azetidin-1-yl}carbonyl)benzonitrile; |
| 24 | 4-(4-Fluorooxan-4-yl)-2-methoxy-3-({3-[4-(trifluoromethyl)phenoxy]azetidin-1-yl}carbonyl)benzonitrile; |
| 25 | 3-{[3-(3,4-Difluorophenoxy)azetidin-1-yl]carbonyl}-4-(4-fluorooxan-4-yl)-2-methoxybenzonitrile; |

-continued

| Example | Compound Name |
|---|---|
| 26 | 4-(4-Fluorooxan-4-yl)-3-{[3-(4-fluorophenoxy)azetidin-1-yl]carbonyl}-2-methoxybenzonitrile; |
| 27 | 4-(4-Fluorooxan-4-yl)-2-methoxy-3-({3-[6-(trifluoromethyl)pyridin-3-yl]azetidin-1-yl}carbonyl)benzonitrile; |
| 28 | 3-{[3-(4-Chlorophenoxy)azetidin-1-yl]carbonyl}-4-(4-fluorooxan-4-yl)-2-methoxybenzonitrile; |
| 29 | 3-{[3-(4-Chlorophenoxy)azetidin-1-yl]carbonyl}-2-methoxy-4-{[(2S)-1,1,1-trifluoropropan-2-yl]oxy}benzonitrile; |
| 30 | 2-Methoxy-3-({3-[4-(trifluoromethyl)phenoxy]azetidin-1-yl}carbonyl)-4-{[(2S)-1,1,1-trifluoropropan-2-yl]oxy}benzonitrile; |
| 31 | 2-Methoxy-3-({3-[6-(trifluoromethyl)pyridin-3-yl]azetidin-1-yl}carbonyl)-4-{[(2S)-1,1,1-trifluoropropan-2-yl]oxy}benzonitrile; |
| 32 | 3-{[3-(4-Chlorophenyl)azetidin-1-yl]carbonyl}-2-methoxy-4-{[(2S)-1,1,1-trifluoropropan-2-yl]oxy}benzonitrile; |
| 33 | 3-{[3-(4-Fluorophenoxy)azetidin-1-yl]carbonyl}-2-methoxy-4-{[(2S)-1,1,1-trifluoropropan-2-yl]oxy}benzonitrile; |
| 34 | 2-Methoxy-3-({3-[5-(trifluoromethyl)pyridin-2-yl]azetidin-1-yl}carbonyl)-4-{[(2S)-1,1,1-trifluoropropan-2-yl]oxy}benzonitrile; |
| 35 | 2-Methoxy-3-{[3-(pyridin-4-yloxy)azetidin-1-yl]carbonyl}-4-{[(2S)-1,1,1-trifluoropropan-2-yl]oxy}benzonitrile; |
| 36 | 2-Methoxy-3-({3-[5-(trifluoromethyl)pyridin-2-yl]azetidin-1-yl}carbonyl)-4-[(1,1,1-trifluoropropan-2-yl)oxy]benzonitrile; |
| 37 | 3-({3-[(4-Fluorophenyl)methyl]azetidin-1-yl}carbonyl)-2-methoxy-4-{[(2S)-1,1,1-trifluoropropan-2-yl]oxy}benzonitrile; |
| 38 | 3-{[3-(3-Chloropyridin-2-yl)azetidin-1-yl]carbonyl}-2-methoxy-4-{[(2S)-1,1,1-trifluoropropan-2-yl]oxy}benzonitrile; |
| 39 | 3-[(4-Fluorophenyl)methyl]-1-(3-methanesulfonyl-2-methoxy-6-{[(2R)-1,1,1-trifluoropropan-2-yl]oxy}benzoyl)azetidine; |
| 40 | 1-(3-Methanesulfonyl-2-methoxy-6-{[(2S)-1,1,1-trifluoropropan-2-yl]oxy}benzoyl)-3-[2-methyl-4-(trifluoromethyl)phenyl]azetidine; |
| 41 | 3-(2,5-Difluorophenyl)-1-(3-methanesulfonyl-2-methoxy-6-{[(2S)-1,1,1-trifluoropropan-2-yl]oxy}benzoyl)azetidine; |
| 42 | 3-(2-Fluoro-5-methylphenyl)-1-(3-methanesulfonyl-2-methoxy-6-{[(2S)-1,1,1-trifluoropropan-2-yl]oxy}benzoyl)azetidine; |
| 43 | 3-(4-Fluoro-3-methylphenoxy)-1-(3-methanesulfonyl-2-methoxy-6-{[(2S)-1,1,1-trifluoropropan-2-yl]oxy}benzoyl)azetidine; |
| 44 | 1-(3-Methanesulfonyl-2-methoxy-6-{[(2S)-1,1,1-trifluoropropan-2-yl]oxy}benzoyl)-3-[3-(trifluoromethyl)phenoxy]azetidine; |
| 45 | 3-(2,6-Dimethylphenoxy)-1-(3-methanesulfonyl-2-methoxy-6-{[(2S)-1,1,1-trifluoropropan-2-yl]oxy}benzoyl)azetidine; |
| 46 | 3-(2-Chlorophenoxy)-1-(3-methanesulfonyl-2-methoxy-6-{[(2S)-1,1,1-trifluoropropan-2-yl]oxy}benzoyl)azetidine; |
| 47 | 1-(3-Methanesulfonyl-2-methoxy-6-{[(2S)-1,1,1-trifluoropropan-2-yl]oxy}benzoyl)-3-(3-methylphenoxy)azetidine; |
| 48 | 1-(3-Methanesulfonyl-2-methoxy-6-{[(2S)-1,1,1-trifluoropropan-2-yl]oxy}benzoyl)-3-(2-methylphenoxy)azetidine; |
| 49 | 1-(3-Methanesulfonyl-2-methoxy-6-{[(2S)-1,1,1-trifluoropropan-2-yl]oxy}benzoyl)-3-phenylazetidine; |
| 50 | 2-Methoxy-3-(3-phenylazetidine-1-carbonyl)-4-{[(2S)-1,1,1-trifluoropropan-2-yl]oxy}benzonitrile; |
| 51 | 3-[3-(3,4-Difluorophenyl)azetidine-1-carbonyl]-2-methoxy-4-{[(2S)-1,1,1-trifluoropropan-2-yl]oxy}benzonitrile; |
| 52 | 3-[3-(4-Fluorophenyl)azetidine-1-carbonyl]-2-methoxy-4-{[(2S)-1,1,1-trifluoropropan-2-yl]oxy}benzonitrile; |
| 53 | 3-[3-(3,5-Difluorophenyl)azetidine-1-carbonyl]-2-methoxy-4-{[(2S)-1,1,1-trifluoropropan-2-yl]oxy}benzonitrile; |
| 54 | 2-Chloro-3-(3-phenylazetidine-1-carbonyl)-4-{[(2S)-1,1,1-trifluoropropan-2-yl]oxy}benzonitrile; |
| 55 | 2-Chloro-3-[3-(3,4-difluorophenyl)azetidine-1-carbonyl]-4-{[(2S)-1,1,1-trifluoropropan-2-yl]oxy}benzonitrile; |
| 56 | 2-Chloro-3-[3-(4-fluorophenyl)azetidine-1-carbonyl]-4-{[(2S)-1,1,1-trifluoropropan-2-yl]oxy}benzonitrile; |
| 57 | 2-Chloro-3-[3-(3,5-difluorophenyl)azetidine-1-carbonyl]-4-{[(2S)-1,1,1-trifluoropropan-2-yl]oxy}benzonitrile; |
| 58 | 3-(4-Fluoro-2-methylphenoxy)-1-(3-methanesulfonyl-2-methoxy-6-{[(2S)-1,1,1-trifluoropropan-2-yl]oxy}benzoyl)azetidine; |
| 59 | 1-(3-Methanesulfonyl-2-methoxy-6-{[(2S)-1,1,1-trifluoropropan-2-yl]oxy}benzoyl)-3-(2,4,6-trifluorophenoxy)azetidine; |
| 60 | 1-(3-Methanesulfonyl-2-methoxy-6-{[(2S)-1,1,1-trifluoropropan-2-yl]oxy}benzoyl)-3-(2,4,5-trifluorophenoxy)azetidine; |
| 61 | 2-{[1-(3-Methanesulfonyl-2-methoxy-6-{[(2S)-1,1,1-trifluoropropan-2-yl]oxy}benzoyl)azetidin-3-yl]oxy}-5-(trifluoromethyl)pyridine; |
| 62 | 4-{[1-(3-Methanesulfonyl-2-methoxy-6-{[(2S)-1,1,1-trifluoropropan-2-yl]oxy}benzoyl)azetidin-3-yl]oxy}pyridine; |
| 63 | 2-Chloro-3-({3-[4-(trifluoromethyl)phenyl]azetidin-1-yl}carbonyl)-4-[(1,1,1-trifluoropropan-2-yl)oxy]benzonitrile; |

-continued

| Example | Compound Name |
|---|---|
| 64 | 3-({3-Hydroxy-3-[4-(trifluoromethyl)phenyl]azetidin-1-yl}carbonyl)-2-methoxy-4-[(1,1,1-trifluoropropan-2-yl)oxy]benzonitrile; |
| 65 | 3-{[3-(5-Fluoropyridin-2-yl)azetidin-1-yl]carbonyl}-2-methoxy-4-[(1,1,1-trifluoropropan-2-yl)oxy]benzonitrile; |
| 66 | 2-Chloro-3-{[3-(5-fluoropyridin-2-yl)azetidin-1-yl]carbonyl}-4-[(1,1,1-trifluoropropan-2-yl)oxy]benzonitrile; |
| 67 | 3-{[3-(3,4-Difluorophenoxy)azetidin-1-yl]carbonyl}-2-methoxy-4-[(1,1,1-trifluoropropan-2-yl)oxy]benzonitrile; |
| 68 | 2-Chloro-3-{[3-(3,4-difluorophenoxy)azetidin-1-yl]carbonyl}-4-[(1,1,1-trifluoropropan-2-yl)oxy]benzonitrile; |
| 69 | 3-({3-Fluoro-3-[4-(trifluoromethyl)phenyl]azetidin-1-yl}carbonyl)-2-methoxy-4-{[(2S)-1,1,1-trifluoropropan-2-yl]oxy}benzonitrile; |
| 70 | 3-{[3-(3,4-Difluorophenyl)-3-fluoroazetidin-1-yl]carbonyl}-2-methoxy-4-{[(2S)-1,1,1-trifluoropropan-2-yl]oxy}benzonitrile; |
| 71 | 2-Chloro-3-{[3-(pyridin-3-yl)azetidin-1-yl]carbonyl}-4-[(1,1,1-trifluoropropan-2-yl)oxy]benzonitrile; |
| 72 | 2-Chloro-3-{[3-(pyridin-4-yl)azetidin-1-yl]carbonyl}-4-[(1,1,1-trifluoropropan-2-yl)oxy]benzonitrile; |
| 73 | 2-Chloro-3-{[3-(4-fluorophenoxy)azetidin-1-yl]carbonyl}-4-[(1,1,1-trifluoropropan-2-yl)oxy]benzonitrile; |
| 74 | 3-{[3-(4-Fluorophenoxy)azetidin-1-yl]carbonyl}-2-methoxy-4-[(1,1,1-trifluoropropan-2-yl)oxy]benzonitrile; |
| 75 | 2-Methoxy-3-{[3-(pyridin-4-yl)azetidin-1-yl]carbonyl}-4-[(1,1,1-trifluoropropan-2-yl)oxy]benzonitrile; |
| 76 | 2-Chloro-3-[(3-phenoxyazetidin-1-yl)carbonyl]-4-[(1,1,1-trifluoropropan-2-yl)oxy]benzonitrile; |
| 77 | 2-Chloro-3-{[3-(4-methylphenoxy)azetidin-1-yl]carbonyl}-4-[(1,1,1-trifluoropropan-2-yl)oxy]benzonitrile; |
| 78 | 2-Methoxy-3-{[3-(4-methylphenoxy)azetidin-1-yl]carbonyl}-4-[(1,1,1-trifluoropropan-2-yl)oxy]benzonitrile; |
| 79 | 2-Chloro-3-{[3-(4-cyanophenyl)azetidin-1-yl]carbonyl}-4-[(1,1,1-trifluoropropan-2-yl)oxy]benzonitrile; |
| 80 | 2-Chloro-3-{[3-(4-methoxyphenyl)azetidin-1-yl]carbonyl}-4-[(1,1,1-trifluoropropan-2-yl)oxy]benzonitrile; |
| 81 | 2-Chloro-3-{[3-(3,4-difluorophenyl)azetidin-1-yl]carbonyl}-4-[(1,1,1-trifluoropropan-2-yl)oxy]benzonitrile; |
| 82 | 2-Chloro-3-{[3-(3,5-difluorophenyl)azetidin-1-yl]carbonyl}-4-[(1,1,1-trifluoropropan-2-yl)oxy]benzonitrile; |
| 83 | 2-Chloro-3-{[3-(4-chlorophenyl)azetidin-1-yl]carbonyl}-4-[(1,1,1-trifluoropropan-2-yl)oxy]benzonitrile; |
| 84 | 2-Chloro-3-({3-[2-(trifluoromethyl)phenyl]azetidin-1-yl}carbonyl)-4-[(1,1,1-trifluoropropan-2-yl)oxy]benzonitrile; |
| 85 | 2-Chloro-3-({3-[3-(trifluoromethyl)phenyl]azetidin-1-yl}carbonyl)-4-[(1,1,1-trifluoropropan-2-yl)oxy]benzonitrile; |
| 86 | 2-Chloro-3-{[3-(4-fluorophenyl)azetidin-1-yl]carbonyl}-4-[(1,1,1-trifluoropropan-2-yl)oxy]benzonitrile; |
| 87 | 2-Chloro-3-{[3-(2-fluorophenyl)azetidin-1-yl]carbonyl}-4-[(1,1,1-trifluoropropan-2-yl)oxy]benzonitrile; |
| 88 | 2-Chloro-3-{[3-(pyridin-2-yl)azetidin-1-yl]carbonyl}-4-[(1,1,1-trifluoropropan-2-yl)oxy]benzonitrile; |
| 89 | 2-Chloro-3-{[3-(4-methoxyphenoxy)azetidin-1-yl]carbonyl}-4-[(1,1,1-trifluoropropan-2-yl)oxy]benzonitrile; |
| 90 | 2-Methoxy-3-({3-[2-(trifluoromethyl)phenyl]azetidin-1-yl}carbonyl)-4-[(1,1,1-trifluoropropan-2-yl)oxy]benzonitrile; |
| 91 | 3-{[3-(4-Fluorophenyl)azetidin-1-yl]carbonyl}-2-methoxy-4-[(1,1,1-trifluoropropan-2-yl)oxy]benzonitrile; |
| 92 | 3-{[3-(2-Fluorophenyl)azetidin-1-yl]carbonyl}-2-methoxy-4-[(1,1,1-trifluoropropan-2-yl)oxy]benzonitrile; |
| 93 | 2-Methoxy-3-{[3-(pyridin-2-yl)azetidin-1-yl]carbonyl}-4-[(1,1,1-trifluoropropan-2-yl)oxy]benzonitrile; |
| 94 | 2-Methoxy-3-{[3-(4-methoxyphenoxy)azetidin-1-yl]carbonyl}-4-[(1,1,1-trifluoropropan-2-yl)oxy]benzonitrile; |
| 95 | 3-{[3-(4-Cyanophenyl)azetidin-1-yl]carbonyl}-2-methoxy-4-[(1,1,1-trifluoropropan-2-yl)oxy]benzonitrile; |
| 96 | 2-Methoxy-3-{[3-(4-methoxyphenyl)azetidin-1-yl]carbonyl}-4-[(1,1,1-trifluoropropan-2-yl)oxy]benzonitrile; |
| 97 | 3-{[3-(4-Chlorophenyl)azetidin-1-yl]carbonyl}-2-methoxy-4-[(1,1,1-trifluoropropan-2-yl)oxy]benzonitrile; |
| 98 | 2-Methoxy-3-({3-[4-(trifluoromethyl)phenyl]azetidin-1-yl}carbonyl)-4-[(1,1,1-trifluoropropan-2-yl)oxy]benzonitrile; |
| 99 | 2-Methoxy-3-({3-[3-(trifluoromethyl)phenyl]azetidin-1-yl}carbonyl)-4-[(1,1,1-trifluoropropan-2-yl)oxy]benzonitrile; |
| 100 | 3-{[3-(3,5-Difluorophenyl)azetidin-1-yl]carbonyl}-2-methoxy-4-[(1,1,1-trifluoropropan-2-yl)oxy]benzonitrile; |
| 101 | 3-{[3-(3,4-Difluorophenyl)azetidin-1-yl]carbonyl}-2-methoxy-4-[(1,1,1-trifluoropropan-2-yl)oxy]benzonitrile; |

-continued

| Example | Compound Name |
|---|---|
| 102 | 2-Methoxy-3-{[3-(pyridin-3-yloxy)azetidin-1-yl]carbonyl}-4-[(1,1,1-trifluoropropan-2-yl)oxy]benzonitrile; |
| 103 | 2-Chloro-3-{[3-(pyridin-3-yloxy)azetidin-1-yl]carbonyl}-4-[(1,1,1-trifluoropropan-2-yl)oxy]benzonitrile; |
| 104 | 3-{[3-(4-Cyanophenyl)azetidin-1-yl]carbonyl}-4-(1-fluorocyclobutyl)-2-methoxybenzonitrile; |
| 105 | 2-Chloro-4-(2,2,2-trifluoroethoxy)-3-({3-[4-(trifluoromethyl)phenyl]azetidin-1-yl}carbonyl)benzonitrile; |
| 106 | 2-Chloro-3-{[3-(4-cyanophenyl)azetidin-1-yl]carbonyl}-4-(2,2,2-trifluoroethoxy)benzonitrile; |
| 107 | 2-Chloro-3-({3-[4-(trifluoromethyl)phenyl]azetidin-1-yl}carbonyl)-4-{[(2S)-1,1,1-trifluoropropan-2-yl]oxy}benzonitrile; |
| 108 | 3-{[3-(4-Cyanophenyl)azetidin-1-yl]carbonyl}-2-methoxy-4-{[(2S)-1,1,1-trifluoropropan-2-yl]oxy}benzonitrile; |
| 109 | 2-Chloro-3-{[3-(4-cyanophenyl)azetidin-1-yl]carbonyl}-4-{[(2S)-1,1,1-trifluoropropan-2-yl]oxy}benzonitrile; |
| 110 | 2-Chloro-3-{[3-(5-methylpyridin-3-yl)azetidin-1-yl]carbonyl}-4-[(1,1,1-trifluoropropan-2-yl)oxy]benzonitrile; |
| 111 | 2-Methoxy-3-{[3-(5-methylpyridin-3-yl)azetidin-1-yl]carbonyl}-4-[(1,1,1-trifluoropropan-2-yl)oxy]benzonitrile; |
| 112 | 2-Chloro-3-({3-[6-(trifluoromethyl)pyridin-3-yl]azetidin-1-yl}carbonyl)-4-[(1,1,1-trifluoropropan-2-yl)oxy]benzonitrile; |
| 113 | 2-Methoxy-3-({3-[6-(trifluoromethyl)pyridin-3-yl]azetidin-1-yl}carbonyl)-4-(1,1,1-trifluoropropan-2-yl)oxy]benzonitrile; |
| 114 | 3-({3-[3-Chloro-5-(trifluoromethyl)pyridin-2-yl]azetidin-1-yl}carbonyl)-2-methoxy-4-{[(2S)-1,1,1-trifluoropropan-2-yl]oxy}benzonitrile; |
| 115 | 3-({3-[5-(Difluoromethyl)pyridin-2-yl]azetidin-1-yl}carbonyl)-2-methoxy-4-[[(2S)-1,1,1-trifluoropropan-2-yl]oxy}benzonitrile; |
| 116 | 3-{[3-(4-Cyano-3-fluorophenyl)azetidin-1-yl]carbonyl}-2-methoxy-4-{[(2S)-1,1,1-trifluoropropan-2-yl]oxy}benzonitrile; |
| 117 | 3-({3-[3-Chloro-5-(trifluoromethyl)pyridin-2-yl]azetidin-1-yl}carbonyl)-4-(4-fluorooxan-4-yl)-2-methoxybenzonitrile; |
| 118 | 3-{[3-(2-Chloro-4-cyanophenyl)azetidin-1-yl]carbonyl}-2-methoxy-4-{[(2S)-1,1,1-trifluoropropan-2-yl]oxy}benzonitrile; |
| 119 | 3-({3-[3-Chloro-5-(trifluoromethyl)pyridin-2-yl]azetidin-1-yl}carbonyl)-2-methoxy-4-(2,2,2-trifluoroethoxy)benzonitrile; |
| 120 | 2-Chloro-3-({3-[5-(trifluoromethyl)pyridin-2-yl]azetidin-1-yl}carbonyl)-4-{[(2S)-1,1,1-trifluoropropan-2-yl]oxy}benzonitrile; |
| 121 | 3-{[3-(3,5-Difluoropyridin-2-yl)azetidin-1-yl]carbonyl}-2-methoxy-4-{[(2S)-1,1,1-trifluoropropan-2-yl]oxy}benzonitrile; |
| 122 | 3-{[3-(3-Chloro-4-cyanophenyl)azetidin-1-yl]carbonyl}-2-methoxy-4-{[(2S)-1,1,1-trifluoropropan-2-yl]oxy}benzonitrile; |
| 123 | 3-{[3-(2-Cyanophenyl)azetidin-1-yl]carbonyl}-2-methoxy-4-{[(2S)-1,1,1-trifluoropropan-2-yl]oxy}benzonitrile; |
| 124 | 3-Chloro-4-{1-[(3-cyano-2-methoxy-6-{[(2S)-1,1,1-trifluoropropan-2-yl]oxy}phenyl)carbonyl]azetidin-3-yl}-2-fluorobenzonitrile; |
| 125 | 2-Methoxy-4-(2,2,2-trifluoroethoxy)-3-({3-[5-(trifluoromethyl)pyridin-2-yl]azetidin-1-yl}carbonyl)benzonitrile; |
| 126 | 3-{[3-(4-Chloro-2-cyanophenyl)azetidin-1-yl]carbonyl}-2-methoxy-4-{[(2S)-1,1,1-trifluoropropan-2-yl]oxy}benzonitrile; |
| 127 | 3-{[3-(2-Cyano-4-fluorophenyl)azetidin-1-yl]carbonyl}-2-methoxy-4-{[(2S)-1,1,1-trifluoropropan-2-yl]oxy}benzonitrile; |
| 128 | 3-{[3-(4-Cyano-2-methoxyphenyl)azetidin-1-yl]carbonyl}-2-methoxy-4-{[(2S)-1,1,1-trifluoropropan-2-yl]oxy}benzonitrile; |
| 129 | 2-Methoxy-3-({3-[2-methoxy-4-(trifluoromethyl)phenyl]azetidin-1-yl}carbonyl)-4-{[(2S)-1,1,1-trifluoropropan-2-yl]oxy}benzonitrile; |
| 130 | 3-{[3-(1,3-Benzoxazol-6-yl)azetidin-1-yl]carbonyl}-2-methoxy-4-{[(2S)-1,1,1-trifluoropropan-2-yl]oxy}benzonitrile; |
| 131 | 2-Chloro-3-{[3-(2-chloro-4-cyanophenyl)azetidin-1-yl]carbonyl}-4-{[(2S)-1,1,1-trifluoropropan-2-yl]oxy}benzonitrile; |
| 132 | 3-{[3-(2-Chloro-4-cyanophenyl)azetidin-1-yl]carbonyl}-4-(4-fluorooxan-4-yl)-2-methoxybenzonitrile; |
| 133 | 3-{[3-(2-Chloro-4-cyanophenyl)azetidin-1-yl]carbonyl}-2-methoxy-4-(1,4,4-trifluorocyclohexyl)benzonitrile; |
| 134 | 3-{[3-(2-Chloro-4-cyanophenyl)azetidin-1-yl]carbonyl}-4-(1-fluorocyclobutyl)-2-methoxybenzonitrile; |
| 135 | 2-Methoxy-3-{3-[5-(trifluoromethyl)pyridin-2-yl]azetidine-1-carbonyl}-4-{[(2R)-1,1,1-trifluoropropan-2-yl]oxy}benzonitrile; |
| 136 | 3-{3-[3-Chloro-5-(trifluoromethyl)pyridin-2-yl]azetidine-1-carbonyl}-2-methoxy-4-{[(2R)-1,1,1-trifluoropropan-2-yl]oxy}benzonitrile; |
| 137 | 3-{3-[5-(Difluoromethyl)pyridin-2-yl]azetidine-1-carbonyl}-2-methoxy-4-{[(2R)-1,1,1-trifluoropropan-2-yl]oxy}benzonitrile; |
| 138 | 3-[2-Fluoro-4-(trifluoromethyl)phenyl]-1-(3-methanesulfonyl-2-methoxy-6-{[(2R)-1,1,1-trifluoropropan-2-yl]oxy}benzoyl)azetidine; |
| 139 | 3-[2-Fluoro-4-(trifluoromethyl)phenyl]-1-(3-methanesulfonyl-2-methoxy-6-{[(2S)-1,1,1-trifluoropropan-2-yl]oxy}benzoyl)azetidine; |

-continued

| Example | Compound Name |
|---|---|
| 140 | 3-[3-Fluoro-4-(trifluoromethyl)phenyl]-1-(3-methanesulfonyl-2-methoxy-6-{[(2R)-1,1,1-trifluoropropan-2-yl]oxy}benzoyl)azetidine; |
| 141 | 3-[3-Fluoro-4-(trifluoromethyl)phenyl]-1-(3-methanesulfonyl-2-methoxy-6-{[(2S)-1,1,1-trifluoropropan-2-yl]oxy}benzoyl)azetidine; |
| 142 | 3-[4-(Difluoromethyl)-3-fluorophenyl]-1-(3-methanesulfonyl-2-methoxy-6-{[(2S)-1,1,1-trifluoropropan-2-yl]oxy}benzoyl)azetidine; |
| 143 | 3-[4-(Difluoromethyl)-2-fluorophenyl]-1-(3-methanesulfonyl-2-methoxy-6-{[(2S)-1,1,1-trifluoropropan-2-yl]oxy}benzoyl)azetidine; |
| 144 | 1-(3-Methanesulfonyl-2-methoxy-6-{[(2S)-1,1,1-trifluoropropan-2-yl]oxy}benzoyl)-3-[3-methoxy-4-(trifluoromethyl)phenyl]azetidine; |
| 145 | 3-(2-Chloro-4-fluorophenyl)-1-(3-methanesulfonyl-2-methoxy-6-{[(2S)-1,1,1-trifluoropropan-2-yl]oxy}benzoyl)azetidine; |
| 146 | 3-[2-Chloro-4-(trifluoromethyl)phenyl]-1-(3-methanesulfonyl-2-methoxy-6-{[(2S)-1,1,1-trifluoropropan-2-yl]oxy}benzoyl)azetidine; |
| 147 | 3-[2-Chloro-4-(difluoromethyl)phenyl]-1-(3-methanesulfonyl-2-methoxy-6-{[(2S)-1,1,1-trifluoropropan-2-yl]oxy}benzoyl)azetidine; |
| 148 | 1-(3-Methanesulfonyl-2-methoxy-6-{[(2S)-1,1,1-trifluoropropan-2-yl]oxy}benzoyl)-3-(4-nitrophenyl)azetidine; |
| 149 | 1-(3-Methanesulfonyl-2-methoxy-6-{[(2R)-1,1,1-trifluoropropan-2-yl]oxy}benzoyl)-3-{[4-(trifluoromethyl)phenyl]methyl}azetidine; |
| 150 | 1-(3-Methanesulfonyl-2-methoxy-6-{[(2S)-1,1,1-trifluoropropan-2-yl]oxy}benzoyl)-3-(3,4,5-trifluorophenyl)azetidine; |
| 151 | 4-(3,3-Difluorocyclobutyl)-2-methoxy-3-{3-[5-(trifluoromethyl)pyridin-2-yl]azetidine-1-carbonyl}benzonitrile; |
| 152 | 3-{3-[3-Chloro-5-(trifluoromethyl)pyridin-2-yl]azetidine-1-carbonyl}-4-(3,3-difluorocyclobutyl)-2-methoxybenzonitrile; |
| 153 | 4-(3,3-Difluorocyclobutyl)-3-{3-[3-fluoro-5-(trifluoromethyl)pyridin-2-yl]azetidine-1-carbonyl}-2-methoxybenzonitrile; |
| 154 | 1-(3-Methanesulfonyl-2-methoxy-6-{[(2S)-1,1,1-trifluoropropan-2-yl]oxy}benzoyl)-3-(2,4,5-trifluorophenyl)azetidine; |
| 155 | 1-(3-Methanesulfonyl-2-methoxy-6-{[(2S)-1,1,1-trifluoropropan-2-yl]oxy}benzoyl)-3-(2,3,4-trifluorophenyl)azetidine; |
| 156 | 1-(3-Methanesulfonyl-2-methoxy-6-{[(2S)-1,1,1-trifluoropropan-2-yl]oxy}benzoyl)-3-(2,3,5-trifluorophenyl)azetidine; |
| 157 | 3-(2,3-Difluorophenyl)-1-(3-methanesulfonyl-2-methoxy-6-{[(2S)-1,1,1-trifluoropropan-2-yl]oxy}benzoyl)azetidine; |
| 158 | 2-Methoxy-3-{3-[4-(oxan-4-yl)phenyl]azetidine-1-carbonyl}-4-{[(2S)-1,1,1-trifluoropropan-2-yl]oxy}benzonitrile; |
| 159 | 2-Methoxy-3-{3-[5-(oxan-4-yl)pyridin-2-yl]azetidine-1-carbonyl}-4-{[(2S)-1,1,1-trifluoropropan-2-yl]oxy}benzonitrile; |
| 160 | 3-{3-[4-(2,2-Dimethyloxan-4-yl)phenyl]azetidine-1-carbonyl}-2-methoxy-4-{[(2S)-1,1,1-trifluoropropan-2-yl]oxy}benzonitrile; |
| 161 | 2-Methoxy-3-{3-[4-(oxan-4-yl)phenyl]azetidine-1-carbonyl}-4-{[(2R)-1,1,1-trifluoropropan-2-yl]oxy}benzonitrile; |
| 162 | 4-(1-Fluorocyclobutyl)-2-methoxy-3-{3-[5-(oxan-4-yl)pyridin-2-yl]azetidine-1-carbonyl}benzonitrile; |
| 163 | 3-{3-[3-Fluoro-4-(oxan-4-yl)phenyl]azetidine-1-carbonyl}-2-methoxy-4-{[(2S)-1,1,1-trifluoropropan-2-yl]oxy}benzonitrile; |
| 164 | 1-(3-Methanesulfonyl-2-methoxy-6-{ [(2R)-1,1,1-trifluoropropan-2-yl]oxy}benzoyl)-3-[4-(oxan-4-yl)phenyl]azetidine; |
| 165 | 4-Ethoxy-2-methoxy-3-{3-[5-(oxan-4-yl)pyridin-2-yl]azetidine-1-carbonyl}benzonitrile; |
| 166 | 2-Methoxy-3-{3-[5-(oxan-4-yl)pyridin-2-yl]azetidine-1 -carbonyl}-4-(propan-2-yloxy)benzonitrile; |
| 167 | 3-[4-(4,4-Difluorocyclohexyl)phenyl]-1-(3-methanesulfonyl-2-methoxy-6-{[(2R)-1,1,1-trifluoropropan-2-yl]oxy}benzoyl)azetidine; |
| 168 | 1-(3-Methanesulfonyl-2-methoxy-6-{[(2S)-1,1,1-trifluoropropan-2-yl]oxy}benzoyl)-3-[4-(oxan-4-yl)phenyl]azetidine; |
| 169 | 2-Chloro-3-{3-[5-(oxan-4-yl)pyridin-2-yl]azetidine-1-carbonyl}-4-{[(2S)-1,1,1-trifluoropropan-2-yl]oxy}benzonitrile; |
| 170 | 2-Chloro-3-{3-[5-(oxan-4-yl)pyridin-2-yl]azetidine-1-carbonyl}-4-{[(2R)-1,1,1-trifluoropropan-2-yl]oxy}benzonitrile; |
| 171 | 3-{3-[5-(4,4-Difluorocyclohexyl)pyridin-2-yl]azetidine-1-carbonyl}-2-methoxy-4-{[(2S)-1,1,1-trifluoropropan-2-yl]oxy}benzonitrile; |
| 172 | 3-{3-[5-(4,4-Difluorocyclohexyl)pyridin-2-yl]azetidine-1-carbonyl}-2-methoxy-4-{[(2R)-1,1,1-trifluoropropan-2-yl]oxy}benzonitrile; |
| 173 | 3-{[3-(4-Cyanophenyl)azetidin-1-yl]carbonyl}-4-(cyclopropylmethoxy)-2-methoxybenzonitrile; |
| 174 | 3-{[3-(4-Cyano-3-methoxyphenyl)azetidin-1-yl]carbonyl}-2-methoxy-4-{[(2S)-1,1,1-trifluoropropan-2-yl]oxy}benzonitrile; |
| 175 | 3-Chloro-4-{1-[(3-cyano-2-methoxy-6-{[(2S)-1,1,1-trifluoropropan-2-yl]oxy}phenyl)carbonyl]azetidin-3-yl}-2-methoxybenzonitrile; |
| 176 | 3-Chloro-4-[1-(3-cyano-2-methoxy-6-{[(2S)-1,1,1-trifluoropropan-2-yl]oxy}benzoyl)azetidin-3-yl]-2-ethoxybenzonitrile; |
| 177 | 3-[3-(4-Cyano-3-methoxyphenyl)azetidine-1-carbonyl]-2-methoxy-4-{[(2R)-1,1,1-trifluoropropan-2-yl]oxy}benzonitrile; |

-continued

| Example | Compound Name |
|---|---|
| 178 | 2-Methoxy-3-({3-[4-(trifluoromethyl)phenyl]azetidin-1-yl}carbonyl)-4-{[(2S)-1,1,1-trifluoropropan-2-yl]oxy}benzonitrile; |
| 179 | 1-({3-Methanesulfonyl-2-methoxy-6-[(1,1,1-trifluoropropan-2-yl)oxy]phenyl}carbonyl)-3-[4-(trifluoromethyl)phenyl]azetidine; |
| 180 | 3-(3,4-Difluorophenoxy)-1-({3-methanesulfonyl-2-methoxy-6-[(1,1,1-trifluoropropan-2-yl)oxy]phenyl}carbonyl)azetidine; |
| 181 | 2-Methoxy-3-[(3-{[4-(trifluoromethyl)phenyl]methyl}azetidin-1-yl)carbonyl]-4-{[(2S)-1,1,1-trifluoropropan-2-yl]oxy}benzonitrile; |
| 182 | 3-(3,5-Difluorophenyl)-1-({3-methanesulfonyl-2-methoxy-6-[(1,1,1-trifluoropropan-2-yl)oxy]phenyl}carbonyl)azetidine; |
| 183 | 1-(3-Methanesulfonyl-2-methoxy-6-{[(2R)-1,1,1-trifluoropropan-2-yl]oxy}benzoyl)-3-[4-(trifluoromethyl)phenyl]azetidine; |
| 184 | 2-[1-(3-Methanesulfonyl-2-methoxy-6-{[(2R)-1,1,1-trifluoropropan-2-yl]oxy}benzoyl)azetidin-3-yl]-5-(trifluoromethyl)pyridine; |
| 185 | 5-(Difluoromethyl)-2-[1-(3-methanesulfonyl-2-methoxy-6-{[(2R)-1,1,1-trifluoropropan-2-yl]oxy}benzoyl)azetidin-3-yl]pyridine; |
| 186 | 3-Chloro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine; |
| 187 | 1-(3-Methanesulfonyl-2-methoxy-6-{[(2S)-1,1,1-trifluoropropan-2-yl]oxy}benzoyl)-3-[4-(trifluoromethyl)phenyl]azetidine; |
| 188 | 3-(4-Fluorophenoxy)-1-(3-methanesulfonyl-2-methoxy-6-{[(2R)-1,1,1-trifluoropropan-2-yl]oxy}benzoyl)azetidine; |
| 189 | 3-Fluoro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine; |
| 190 | 3-Chloro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine; |
| 191 | 3-Ethynyl-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine; |
| 192 | 3-(4-Fluorophenoxy)-1-(3-methanesulfonyl-2-methoxy-6-{[(2S)-1,1,1-trifluoropropan-2-yl]oxy}benzoyl)azetidine; |
| 193 | 4-(1-Fluorocyclopentyl)-2-methoxy-3-{3-[5-(trifluoromethyl)pyridin-2-yl]azetidine-1-carbonyl}benzonitrile; |
| 194 | 1-(3-Methanesulfonyl-2-methoxy-6-{[(2S)-1,1,1-trifluoropropan-2-yl]oxy}benzoyl)-3-phenoxyazetidine; |
| 195 | 3-(3,4-Difluorophenoxy)-1-(3-methanesulfonyl-2-methoxy-6-{[(2S)-1,1,1-trifluoropropan-2-yl]oxy}benzoyl)azetidine; |
| 196 | 3-(3,5-Difluorophenyl)-1-(3-methanesulfonyl-2-methoxy-6-{[(2S)-1,1,1-trifluoropropan-2-yl]oxy}benzoyl)azetidine; |
| 197 | 4-(1-Fluorocyclopentyl)-2-methoxy-3-{3-[4-(trifluoromethyl)phenyl]azetidine-1-carbonyl}benzonitrile; |
| 198 | 3-(3,4-Difluorophenyl)-1-(3-methanesulfonyl-2-methoxy-6-{[(2S)-1,1,1-trifluoropropan-2-yl]oxy}benzoyl)azetidine; |
| 199 | 1-(3-Methanesulfonyl-2-methoxy-6-{[(2S)-1,1,1-trifluoropropan-2-yl]oxy}benzoyl)-3-[2-(trifluoromethyl)phenyl]azetidine; |
| 200 | 3-(3-Chlorophenoxy)-1-(3-methanesulfonyl-2-methoxy-6-{[(2S)-1,1,1-trifluoropropan-2-yl]oxy}benzoyl)azetidine; |
| 201 | 3-(4-Chlorophenoxy)-1-(3-methanesulfonyl-2-methoxy-6-{[(2S)-1,1,1-trifluoropropan-2-yl]oxy}benzoyl)azetidine; |
| 202 | 1-(3-Methanesulfonyl-2-methoxy-6-{[(2S)-1,1,1-trifluoropropan-2-yl]oxy}benzoyl)-3-[4-(trifluoromethyl)phenoxy]azetidine; |
| 203 | 3-(2,6-Difluorophenoxy)-1-(3-methanesulfonyl-2-methoxy-6-{[(2S)-1,1,1-trifluoropropan-2-yl]oxy}benzoyl)azetidine; |
| 204 | 3-(2,4-Difluorophenoxy)-1-(3-methanesulfonyl-2-methoxy-6-{[(2S)-1,1,1-trifluoropropan-2-yl]oxy}benzoyl)azetidine; |
| 205 | 3-(2,5-Difluorophenoxy)-1-(3-methanesulfonyl-2-methoxy-6-{[(2S)-1,1,1-trifluoropropan-2-yl]oxy}benzoyl)azetidine; |
| 206 | 3-(2,3-Difluorophenoxy)-1-(3-methanesulfonyl-2-methoxy-6-{[(2S)-1,1,1-trifluoropropan-2-yl]oxy}benzoyl)azetidine; |
| 207 | 3-(3-Fluorophenoxy)-1-(3-methanesulfonyl-2-methoxy-6-{[(2S)-1,1,1-trifluoropropan-2-yl]oxy}benzoyl)azetidine; |
| 208 | 4-(4-Fluorooxan-4-yl)-2-methoxy-3-({3-[4-(trifluoromethyl)phenyl]azetidin-1-yl}carbonyl)benzonitrile; |
| 209 | 3-{3-[3-Chloro-5-(trifluoromethyl)pyridin-2-yl]azetidine-1-carbonyl}-4-cyclopentyl-2-methoxybenzonitrile; |
| 210 | 4-Cyclopentyl-3-{3-[3-fluoro-5-(trifluoromethyl)pyridin-2-yl]azetidine-1-carbonyl}-2-methoxybenzonitrile; |
| 211 | 4-Cyclopentyl-2-methoxy-3-{3-[4-(trifluoromethyl)phenoxy]azetidine-1-carbonyl}benzonitrile; |
| 212 | 4-Cyclopentyl-2-methoxy-3-[3-(2,4,6-trifluorophenoxy)azetidine-1-carbonyl]benzonitrile; |
| 213 | 2-{1-[3-Methanesulfonyl-2-methoxy-6-(propan-2-yloxy)benzoyl]azetidin-3-yl}-5-(trifluoromethyl)pyridine; |
| 214 | 3-Chloro-2-{1-[3-methanesulfonyl-2-methoxy-6-(propan-2-yloxy)benzoyl]azetidin-3-yl}-5-(trifluoromethyl)pyridine; |
| 215 | 3-Fluoro-2-{1-[3-methanesulfonyl-2-methoxy-6-(propan-2-yloxy)benzoyl]azetidin-3-yl}-5-(trifluoromethyl)pyridine; |

-continued

| Example | Compound Name |
|---|---|
| 216 | 3-(3,4-Difluorophenyl)-1-[3-methanesulfonyl-2-methoxy-6-(propan-2-yloxy)benzoyl]azetidine; |
| 217 | 1-[3-Methanesulfonyl-2-methoxy-6-(propan-2-yloxy)benzoyl]-3-[4-(trifluoromethyl)phenyl]azetidine; |
| 218 | 1-[3-Methanesulfonyl-2-methoxy-6-(propan-2-yloxy)benzoyl]-3-[4-(trifluoromethyl)phenoxy]azetidine; |
| 219 | 3-(4-Chlorophenoxy)-1-[3-methanesulfonyl-2-methoxy-6-(propan-2-yloxy)benzoyl]azetidine; |
| 220 | 3-(2,4-Difluorophenoxy)-1-[3-methanesulfonyl-2-methoxy-6-(propan-2-yloxy)benzoyl]azetidine; |
| 221 | 1-[3-Methanesulfonyl-2-methoxy-6-(propan-2-yloxy)benzoyl]-3-(2,4,6-trifluorophenoxy)azetidine; |
| 222 | 3-(4-Chlorophenoxy)-1-[3-methanesulfonyl-2-methoxy-6-(2,2,2-trifluoroethoxy)benzoyl]azetidine; |
| 223 | 1-[3-Methanesulfonyl-2-methoxy-6-(2,2,2-trifluoroethoxy)benzoyl]-3-[4-(trifluoromethyl)phenoxy]azetidine; |
| 224 | 3-(4-Fluoro-2-methylphenoxy)-1-[3-methanesulfonyl-2-methoxy-6-(2,2,2-trifluoroethoxy)benzoyl]azetidine; |
| 225 | 1-[3-Methanesulfonyl-2-methoxy-6-(2,2,2-trifluoroethoxy)benzoyl]-3-(2,4,6-trifluorophenoxy)azetidine; |
| 226 | 1-[3-Methanesulfonyl-2-methoxy-6-(2,2,2-trifluoroethoxy)benzoyl]-3-(2,4,5-trifluorophenoxy)azetidine; |
| 227 | 3-(2,4-Difluorophenoxy)-1-[3-methanesulfonyl-2-methoxy-6-(2,2,2-trifluoroethoxy)benzoyl]azetidine; |
| 228 | 3-(3,4-Difluorophenyl)-1-[3-methanesulfonyl-2-methoxy-6-(2,2,2-trifluoroethoxy)benzoyl]azetidine; |
| 229 | 2-{1-[3-Methanesulfonyl-2-methoxy-6-(2,2,2-trifluoroethoxy)benzoyl]azetidin-3-yl}-5-(trifluoromethyl)pyridine; |
| 230 | 3-Chloro-2-{1-[3-methanesulfonyl-2-methoxy-6-(2,2,2-trifluoroethoxy)benzoyl]azetidin-3-yl}-5-(trifluoromethyl)pyridine; |
| 231 | 3-Fluoro-2-{1-[3-methanesulfonyl-2-methoxy-6-(2,2,2-trifluoroethoxy)benzoyl]azetidin-3-yl}-5-(trifluoromethyl)pyridine; |
| 232 | 5-Chloro-2-({1-[3-methanesulfonyl-2-methoxy-6-(2,2,2-trifluoroethoxy)benzoyl]azetidin-3-yl}oxy)pyridine; |
| 233 | 5-Chloro-2-{[1-(3-methanesulfonyl-2-methoxy-6-{[(2S)-1,1,1-trifluoropropan-2-yl]oxy}benzoyl)azetidin-3-yl]oxy}pyridine; |
| 234 | 3-Chloro-2-[1-(3-methanesulfonyl-2-methoxy-6-{[(2S)-1,1,1-trifluoropropan-2-yl]oxy}benzoyl)azetidin-3-yl]pyridine; |
| 235 | 1-[3-Methanesulfonyl-2-methoxy-6-(2,2,2-trifluoroethoxy)benzoyl]-3-[4-(trifluoromethyl)phenyl]azetidine; |
| 236 | 3-Chloro-4-[1-(3-methanesulfonyl-2-methoxy-6-{[(2S)-1,1,1-trifluoropropan-2-yl]oxy}benzoyl)azetidin-3-yl]benzonitrile; |
| 237 | 3-Chloro-4-{1-[3-methanesulfonyl-2-methoxy-6-(2,2,2-trifluoroethoxy)benzoyl]azetidin-3-yl}benzonitrile; |
| 238 | 1-[6-(2,2-Dimethylpropoxy)-3-methanesulfonyl-2-methoxybenzoyl]-3-[4-(trifluoromethyl)phenyl]azetidine; |
| 239 | 3-Chloro-2-{1-[6-(2,2-dimethylpropoxy)-3-methanesulfonyl-2-methoxybenzoyl]azetidin-3-yl}-5-(trifluoromethyl)pyridine; |
| 240 | 1-[6-(2,2-Dimethylpropoxy)-3-methanesulfonyl-2-methoxybenzoyl]-3-(2,4,6-trifluorophenoxy)azetidine; |
| 241 | 1-[6-(2,2-Dimethylpropoxy)-3-methanesulfonyl-2-methoxybenzoyl]-3-(2,4,5-trifluorophenoxy)azetidine; |
| 242 | 1-[3-(Ethanesulfonyl)-2-methoxy-6-(propan-2-yloxy)benzoyl]-3-[4-(trifluoromethyl)phenyl]azetidine; |
| 243 | 3-Chloro-2-{1-[3-(ethanesulfonyl)-2-methoxy-6-(propan-2-yloxy)benzoyl]azetidin-3-yl}-5-(trifluoromethyl)pyridine; |
| 244 | 1-[3-(Ethanesulfonyl)-2-methoxy-6-(propan-2-yloxy)benzoyl]-3-(2,4,6-trifluorophenoxy)azetidine; |
| 245 | 1-[3-(Ethanesulfonyl)-2-methoxy-6-(propan-2-yloxy)benzoyl]-3-(2,4,5-trifluorophenoxy)azetidine; |
| 246 | 6-[1-(3-Methanesulfonyl-2-methoxy-6-{[(2S)-1,1,1-trifluoropropan-2-yl]oxy}benzoyl)azetidin-3-yl]-1,3-benzoxazole; |
| 247 | 6-{1-[3-Methanesulfonyl-2-methoxy-6-(2,2,2-trifluoroethoxy)benzoyl]azetidin-3-yl}-1,3-benzoxazole; |
| 248 | 6-{1-[3-Methanesulfonyl-2-methoxy-6-(propan-2-yloxy)benzoyl]azetidin-3-yl}-1,3-benzoxazole; |
| 249 | 6-{1-[6-(2,2-Dimethylpropoxy)-3-methanesulfonyl-2-methoxybenzoyl]azetidin-3-yl}-1,3-benzoxazole; |
| 250 | 6-{1-[3-(Ethanesulfonyl)-2-methoxy-6-(propan-2-yloxy)benzoyl]azetidin-3-yl}-1,3-benzoxazole; |
| 251 | 3-(5-Chloro-2-fluorophenyl)-1-(3-methanesulfonyl-2-methoxy-6-{[(2S)-1,1,1-trifluoropropan-2-yl]oxy}benzoyl)azetidine; |
| 252 | 3-(3-Chloro-2-fluorophenyl)-1-(3-methanesulfonyl-2-methoxy-6-{[(2S)-1,1,1-trifluoropropan-2-yl]oxy}benzoyl)azetidine; |
| 253 | 3-(2-Chloro-3-fluorophenyl)-1-(3-methanesulfonyl-2-methoxy-6-{[(2S)-1,1,1-trifluoropropan-2-yl]oxy}benzoyl)azetidine; |

-continued

| Example | Compound Name |
|---------|---------------|
| 254 | 3-(2-Chloro-4,5-difluorophenyl)-1-(3-methanesulfonyl-2-methoxy-6-{[(2S)-1,1,1-trifluoropropan-2-yl]oxy}benzoyl)azetidine; |
| 255 | 3-Chloro-2-(1-{3-methanesulfonyl-2-methoxy-6-[(1,1,1-trifluoropropan-2-yl)oxy]benzoyl}azetidin-3-yl)-5-(trifluoromethyl)pyridine; and |
| 256 | 2-Methoxy-3-({3-[4-(trifluoromethyl)phenyl]azetidin-1-yl}carbonyl)-4-{[(2R)-1,1,1-trifluoropropan-2-yl]oxy}benzonitrile. |

Further embodiments are provided by pharmaceutically acceptable salts of compounds of Formula (I), pharmaceutically acceptable prodrugs of compounds of Formula (I), and pharmaceutically active metabolites of compounds of Formula (I).

Isotopically-Labeled Compounds

Compounds of Formula I may include any isotope where one or more atoms are replaced by an atom having an atomic mass or mass number different from the atomic mass or mass number usually found in nature. For example, the isotopes may be isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$.

Each chemical element as represented in a compound of Formula I (and derivatives of such compounds, such as pharmaceutically acceptable salts and prodrugs) may include any isotope of said element. Isotopically-labeled compounds of the present embodiments are useful in drug and substrate tissue distribution and target occupancy assays. For example, isotopically labeled compounds are particularly useful in SPECT (single photon emission computed tomography) and in PET (positron emission tomography), as discussed further herein.

Compositions

In some embodiments compounds of Formula (I) and pharmaceutically acceptable salts thereof are used, alone or in combination with one or more additional active ingredients, to formulate pharmaceutical compositions. Some embodiments provide a pharmaceutical composition comprising: (a) an effective amount of at least one active agent as disclosed and described herein; and (b) a pharmaceutically acceptable excipient.

Formulations and Administration

Numerous standard references are available that describe procedures for preparing various formulations suitable for administering the compounds according to the embodiments. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present embodiments is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present embodiments or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present embodiments or stabilized form of the compound (e.g., complex with a cyclodextrin derivative or other known complexation agent)) is dissolved in a suitable solvent in the presence of one or more of the excipients described above. The compound of the present embodiments is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Dosage Forms

The present compounds may be systemically administered, e.g., orally, in combination with a pharmaceutically acceptable vehicle such as an inert diluent or an assimilable edible carrier. Hence in some embodiments, chemical entities of the present embodiments are suitable for oral administration. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the compounds of Formula (I) can be determined by comparing their in vitro activity and in vivo activity in animal models. Methods for the extrapolation of effective dosages in mice, and other animals, to humans are known to the art. Useful dosages of the compounds of formula I can be determined by comparing their in vitro activity, and in vivo activity in animal models. Methods for the extrapolation of effective dosages in mice, and other animals, to humans are known to the art (e.g., U.S. Pat. No. 4,938,949).

Optimal dosages to be administered in the therapeutic methods of the present embodiments may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range from about 0.01 to about 100 mg/kg, more specifically from about 0.1 to about 100 mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in a unit dosage form; for example, containing about 1 to 1000 mg, particularly about 10 to 750 mg, and more particularly, about 50 to 500 mg of active ingredient per unit dosage form.

In some embodiments, the active ingredient can be administered to achieve peak plasma concentrations of the active compound of from about 0.5 to about 75 µM, preferably, about 1 to 50 µM, and more preferably, about 2 to about 30 µM. This may be achieved, for example, by the intravenous injection of a 0.05 to 5% solution of the active ingredient, optionally in saline, or orally administered as a bolus containing about 1 to 100 mg of the active ingredient. Desirable blood levels may be maintained by continuous infusion to provide about 0.01 to 5.0 mg/kg/hr or by intermittent infusions containing about 0.4 to 15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present disclosure.

Effective amounts or doses of the active agents of the present disclosure may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful composition is such that an effective dosage level will be obtained. An exemplary dose is in the range from about 0.001 to about 200 mg of active agent per kg of subject's body weight per day, preferably about 0.05 to 100 mg/kg/day, or about 1 to 35 mg/kg/day, or about 0.1 to 10 mg/kg/daily in single or divided dosage units (e.g., BID, TID, QID). For a 70-kg human, an illustrative range for a suitable dosage amount is from 1 to 200 mg/day, or about 5 to 50 mg/day.

Methods and Uses

Uses of Isotopically-Labeled Compounds

Some embodiments provide a method of using isotopically labeled compounds and prodrugs of the present disclosure in: (i) metabolic studies (preferably with $^{14}C$), reaction kinetic studies (with, for example $^2H$ or $^3H$); (ii) detection or imaging techniques [such as positron emission tomography (PET) or single-photon emission computed tomography (SPECT)] including drug or substrate tissue distribution assays; or (iii) in radioactive treatment of patients.

Isotopically labeled compounds and prodrugs of the embodiments thereof can generally be prepared by carrying out the procedures disclosed in the schemes or in the examples and preparations described below by substituting a readily available isotopically labeled reagent for a non-isotopically labeled reagent. An $^{18}F$ or $^{11}C$ labeled compound may be particularly preferred for PET, and an $I^{123}$ labeled compound may be particularly preferred for SPECT studies. Further substitution with heavier isotopes such as deuterium (i.e., $^2H$) may afford certain therapeutic advantages resulting from greater metabolic stability, for example increased in vivo half-life or reduced dosage requirements.

Therapeutic Methods

Generally

Chemical entities of the present embodiments are useful in methods (or in the manufacture of a medicament for use in such methods) of treating a disorder mediated by GlyT1 by administering to a subject in need thereof an effective amount of a chemical entity of the present embodiments. They are also useful in methods (or in the manufacture of a medicament for use in such methods) of enhancing cognitive or motor function by administering to a subject in need an effective amount of a chemical entity of the present embodiments.

Some embodiments provide a method of treating a subject suffering from or diagnosed with a disorder mediated by GlyT1 activity, comprising administering to a subject in need of such treatment an effective amount of at least one chemical entity of the present disclosure. In a further embodiment, the subject is diagnosed with a disorder mediated by GlyT1 activity.

In some embodiments, chemical entities as disclosed and described herein are also useful in enhancing neuronal plasticity—an essential property of the brain that can be augmented in healthy animals and impaired in numerous CNS disorders. Without being limited by mechanism, such chemical entities can enhance cyclic adenosine monophosphate (cAMP) response element binding protein (CREB) pathway function in cells, modulating transcription of multiple genes involved in synaptic plasticity. See, e.g., Tully et al., Nat. Rev. Drug Discov. 2003, 2, 267-277; Alberini, Physiol. Rev. 2009, 89, 121-145. Some embodiments provide a method of enhancing neuronal plasticity, comprising administering to a subject in need thereof an effective amount of a chemical entity of Formula I.

Chemical entities of the present embodiments are also useful as "agents" (also referred to as "augmenting agents") to augment the efficiency of training protocols, which facilitate functional reorganization in targeted "domains" (or "functions") in the brain. Training protocols can be directed to rehabilitating or enhancing a cognitive or motor function. The training protocol (cognitive or motor training) induces neuronal activity in specific brain regions and produces improved performance of a specific brain (cognitive or motor) function. Chemical entities of the present embodiments agents act as "augmenting agents," which shorten the time that methods of rehabilitating (or enhancing) a cognitive or motor function result in improved performance or a functional gain. Such augmented training therefore comprises a specific training protocol for a particular brain function, such as that underlying declarative memory, performance of a fine motor skill, a specific locomotor function, language acquisition, executive function, etc.; and a general administration of CREB pathway-enhancing drugs.

Neurological Disorders

Chemical entities of the present embodiments are useful in methods of treating a neurological disorder, comprising administering to a subject in need thereof an effective amount of a chemical entity of Formula (I). In a specific aspect, the methods are directed to a cognitive deficit ("cognitive impairment") or motor deficit ("motor impairment") associated with (or "due to") the neurological disorder.

A neurological disorder (or condition or disease) is any disorder of the body's nervous system. Neurological disorders can be categorized according to the primary location affected, the primary type of dysfunction involved, or the primary type of cause. The broadest division is between peripheral nervous system (PNS) disorders and central nervous system (CNS) disorders (such as mental and psychiatric disorders). Neurological disorders are well-known in the art, and they include, but are not limited to, the following mental and psychiatric disorders:

Neurodevelopmental (or "developmental" disorders), such as intellectual disability disorders (e.g., Rubinstein-Taybi syndrome, Down syndrome); communication disorders; autism-spectrum disorders; attention-deficit/hyperactivity disorders; specific learning, language, or reading (e.g., dyslexia) disorders; motor disorders; fetal alcohol spectrum disorders (FASD); and other neurodevelopmental disorders;

Schizophrenia spectrum and other psychotic disorders, such as schizophrenia, schizotypal (personality) disorder, delusional disorder, and schizophreniform disorder, and other schizophrenia spectrum and psychotic disorders;

Bipolar and related disorders, such as Bipolar I and II disorders, cyclothymic disorders, and other bipolar and related disorders;

Depressive disorders, such as major depressive disorder, persistent depressive disorder (dysthymia), and other depressive disorders;

Anxiety disorders, such as specific phobia, social anxiety disorder, panic disorder, generalized anxiety disorder (social phobia), posttraumatic stress disorder (PTSD), and other anxiety disorders;

Obsessive-compulsive and related disorders, such as obsessive-compulsive disorder, body dysmorphic disorder, and other obsessive-compulsive and related disorders;

Dissociative disorders, such as dissociative identity disorder, dissociative amnesia, and other dissociative disorders;

Disruptive, impulse-control, and conduct disorders, such as conduct disorders, antisocial personality disorders, and other disruptive, impulse-control, and conduct disorders;

Trauma- and stressor-related disorders, such as posttraumatic stress disorder, adjustment disorders, and other trauma- and stressor-related disorders;

Feeding and eating disorders, such as anorexia, bulimia, and binge-eating disorder;

Sleep-wake disorders, such as insomnia, narcolepsy, parasomnias, and other sleep-wake disorders;

Sexual disorders, such as arousal disorders, desire disorders, substance and medication-induced dysfunctions, and other sexual disorders;

Substance-related and addictive disorders, such as those involving alcohol, drugs, stimulants, opioids, tobacco, and non-substance-related disorders; and other substance-related and addictive disorders; and Personality disorders, such as paranoid personality disorders, antisocial and borderline personality disorders, avoidance personality disorders, and other personality disorders; and In particular embodiments, the disorder is schizophrenia, an attention deficit disorder, or an anxiety disorder.

In other embodiments, the neurological disorder is an acquired disorder, in which the primary clinical feature is impaired cognition. That is, it is a disorder in which the primary cognitive deficit has not been present since birth or very early life and therefore represents a decline from a previously attained level of functioning. Such disorders, which may be referred to herein as "cognitive disorders" or "neurocognitive disorders" include one or more of the following:

Delirium, such as substance-intoxication (or withdrawal) delirium, medication-induced delirium, and other forms of delirium;

Dementias and other cognitive impairments due to HIV infection or due to neurodegenerative diseases, such as Alzheimer's disease, Parkinson's disease, Huntington's disease, Lewy body disease, Pick's disease, a prion disease (e.g., Creutzfeldt-Jakob disease), Amyotrophic lateral sclerosis (ALS), multiple sclerosis, frontotemporal lobar degeneration, and corticobasal degeneration; dementia due to a vascular disease ("vascular disease"); and other dementias and neurodegenerative diseases;

Age-associated cognitive deficits, including age-associated memory impairment (AAMI), also referred to as age-related memory impairment (AMI) (See, e.g., Crook et al., *Devel. Neuropsychol.* 1986, 2, 261-276); and deficits affecting patients in early stages of cognitive decline, as in Mild Cognitive Impairment (MCI) (See, e.g., Arnáiz and Almkvist, *Acta Neurol. Scand. Suppl.* 2003, 179, 34-41), and;

Trauma-dependent losses of cognitive function, such as vascular diseases due to stroke (e.g., ischemic or hemorrhagic stroke) or ischemia; microvascular disease arising from diabetes or arthrosclerosis; traumatic brain injury (TBI), such as brain trauma, including subdural hematoma and brain tumor; head trauma (closed and penetrating); head injury; tumors, such as nervous system cancers, including cerebral tumors affecting the thalamic or temporal lobe; hypoxia, and viral infection (e.g., encephalitis); excitotoxicity; and seizures; and Cognitive impairments due to chemotherapy, such as post-chemotherapy cognitive impairments (PCCI); chemotherapy-induced cognitive dysfunction or impairments; chemo brain; or chemo fog.

Such acquired disorders are not necessarily limited to cognitive impairments. For example, trauma related disorders, such as stroke, traumatic brain injury, head trauma, and head injury, may also include impairments in other neurological functions, such as impairments in motor functions.

As used herein, the terms "Neurodevelopment disorders," "Schizophrenia spectrum and other psychotic disorders," "Bipolar and related disorders," "Depressive disorders," "Anxiety disorders," "Obsessive-compulsive and related disorders," "Dissociative disorders," "Disruptive, impulse-control, and conduct disorders," "Trauma- and stressor-related disorders," "Feeding and eating disorders," "Sleep-wake disorders," "Sexual disorders," "Substance-related and addictive disorders," Personality disorders," "Delirium," "Neurocognitive disorders," "Delirium," "Dementias," and "Trauma" includes treatment of those mental disorders as described in the Diagnostic and Statistical Manual of Mental Disorders (DSM-5; $5^{th}$ ed., 2013, American Psychiatric Association). The skilled artisan will recognize that there are alternative nomenclatures and classification systems for mental disorders, and that these systems evolve with medical and scientific progress. Thus the terms described in this paragraph are intended to include like disorders that are described in other diagnostic sources.

In other embodiments, the neurological disorder is a movement or motor disorder, a group that includes, but is not limited to: kinesias and akinetic-rigid syndromes, such as Parkinson's disease or corticobasal degeneration; Tourette's syndrome, epilepsy, muscular spasms, and disorders associated with muscular spasticity or weakness; dyskinesias, including tremors, such as rest tremor, postural tremor and intention tremor); chorea, such as that in Huntington's disease; myoclonus (including generalized myoclonus and focal myoclonus); tics (including simple tics, complex tics and symptomatic tics); dystonia; restless leg syndromes; Wilson's Disease; Hallerworden-Spatz disease; basal ganglia disorders; hyperkinetic, hypokinetic, and dyskinetic disorders; movement disorders induced by drugs; and other movement and motor disorders.

Augmented Training

In certain embodiments, chemical entities of the present invention provide augmenting agents to enhance the efficiency of training protocols, including cognitive training and motor training protocols. Such methods are known as "augmented training," and, more particularly, "augmented cognitive training" or "augmented motor training."

Training (or a "training protocol") generally requires many sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol. (See, e.g., U.S. Pat. No. 7,868,015; U.S. Pat. No. 7,947,731; US Pub. No. 2008-0188525). When administered in combination with training protocols (or "training"), augmenting agents enhance functional reorganization in targeted domains (or "functions") in the brain.

Cognitive domains (or functions) that can be targeted by training protocols include, but are not limited to, the following: attention (e.g., sustained attention, divided attention, selective attention, processing speed); executive function (e.g., planning, decision, and working memory); learning and memory (e.g., immediate memory; recent memory, including free recall, cued recall, and recognition memory; and long-term memory, which can be divided into explicit memory (declarative memory) memory, such as episodic, semantic, and autobiographical memory, and into implicit memory (procedural memory)); language (e.g., expressive language, including naming, word recall, fluency, grammar, and syntax; and receptive language); perceptual-motor functions (e.g., abilities encompassed under visual perception, visuo-constructional, perceptual-motor praxis, and gnosis); and social cognition (e.g., recognition of emotions, theory of mind). In specific embodiments, the cognitive function is learning and memory, and more particularly, long term memory.

Motor domains (or functions) that can be targeted by training protocols include, but are not limited to, those involved in gross body control, coordination, posture, and balance; bilateral coordination; upper and lower limb coordination; muscle strength and agility; locomotion and movement; motor planning and integration; manual coordination and dexterity; gross and fine motor skills; and eye-hand coordination.

Training Protocols

Training protocols (or "modules") are well known in the art and typically comprise a set of distinct exercises that can be process-specific or skill-based: See, e.g., Kim et al., *J. Phys. Ther. Sci.* 2014, 26, 1-6, Allen et al., *Parkinsons Dis.* 2012, 2012, 1-15; Jaeggi et al., *Proc. Natl. Acad. Sci. USA* 2011, 108, 10081-10086; Chein et al., *Psychon. Bull. Rev.* 2010, 17, 193-199; Klingberg, *Trends Cogn. Sci.* 2010, 14, 317-324; Owen et al., Nature 2010, 465, 775-778; Tsao et al., *J. Pain* 2010, 11, 1120-1128; Lustig et al., *Neuropsychol. Rev.* 2009, 19, 504-522; Park and Reuter-Lorenz, *Ann. Rev. Psych.* 2009, 60, 173-196; Oujamaa et al., *Ann. Phys. Rehabil. Med.* 2009, 52, 269-293; Frazzitta et al., *Movement Disorders* 2009, 8, 1139-1143; Jaeggi et al., *Proc. Natl. Acad. Sci. USA* 2008, 105, 6829-6833; Volpe et al., *Neurorehabil. Neural Repair* 2008, 22, 305-310; Fischer et al., *Top. Stroke Rehab.* 2007, 14, 1-12; Jonsdottir et al., *Neurorehabil. Neural Repair* 2007, 21, 191-194; Stewart et al., *J. Neurol. Sci.* 2006, 244, 89-95; Krakauer, *Curr. Opin. Neurol.* 2006, 19, 84-90; Belleville et al., *Dement. Geriatr. Cogn. Disord.* 2006, 22, 486-499; Klingberg et al., *J. Am. Acad. Child. Adolesc. Psychiatry* 2005, 44, 177-186; Dean et al., *Arch. Phys. Med. Rehabil.* 2000, 81, 409-417; Whitall et al., *Stroke* 2000, 31, 2390-2395; Hummelsheim and Eickhof, *Scand. J. Rehabil. Med.* 1999, 31, 250-256; Merzenich et al., *Science* 1996, 271, 77-81; Merzenich et al., *Cold Spring Harb. Symp. Quant. Biol.* 1996, 61, 1-8; Rider and Abdulahad, *Percept. Mot. Skills* 1991, 73, 219-224.

Process-specific training focuses on improving a particular domain such as attention, memory, language, executive function, or motor function. Here the goal of training is to obtain a general improvement that transfers from the trained activities to untrained activities based on the same cognitive or motor function or domain.

Skill-based training is aimed at improving performance of a particular activity or ability, such as learning a new language, performing a musical instrument, improving memory, or learning a fine motor skill. The different exercises within such a protocol will focus on core components within one or more domains underlying the skill. Modules for increasing memory, for example, may include tasks directed to specific domains involved in memory processing, e.g., the recognition and use of fact, and the acquisition and comprehension of explicit knowledge rules.

In some embodiments, the battery of exercises is administered as part of a single training session. In one aspect, the training protocol comprises multiple training sessions, each separated by a discrete interval. In another aspect, the number of training sessions sufficient to improve performance is reduced compared to that produced by training alone.

In a further aspect, the augmenting agent is a GlyT1 inhibitor, and more particularly, is a chemical entity of the present disclosure, and is administered in conjunction with training. By "in conjunction" is meant that the augmenting agent enhances CREB pathway function during training. In some embodiments, the deficit is a motor deficit. In other embodiments, the deficit is a cognitive deficit. In still other embodiments, the deficit may include both a cognitive and motor deficit. In other aspects, the compound is administered before and during each training session. In one aspect, the subject is a human. In some embodiments, the subject is a non-human, and more particularly, is a primate or a canine.

In one aspect, a compound or composition of the present disclosure can be used as an augmenting agent in conjunction with any psychotherapeutic approach intended to modulate cognitive function in the brain, thereby enhancing the efficacy of such therapy by reducing the number of sessions necessary to attain benefits.

Stroke

In some embodiments, chemical entities and compositions of the present disclosure are useful in treating stroke, and in more specific embodiments, treating motor or cognitive impairments during post-stroke rehabilitation. Stroke care is a temporal continuum that includes immediate (acute) treatments and subsequent rehabilitative therapy.

Acute treatments directly target the initial damage, such as that triggered by ischemic or hemorrhagic stroke; they usually involve using agents to dissolve clots and restore blood flow to reduce tissue damage and stabilize the patient. The efficacy of acute treatments is typically limited to a short time window extending only a few hours from stroke onset.

The focus of stroke treatment shifts to rehabilitation after the patient has been medically stabilized. Rehabilitation (also referred to as "stroke rehabilitation" or "post-stroke rehabilitation") is directed to cognitive and motor deficits that persist after the initial stroke injury, the goal being to restore and recover neurological function as much as possible to compensate for the permanent tissue loss (e.g., 1995 Clinical Guideline by the Department of Health and Human Services on Post-Stroke Rehabilitation).

Stroke rehabilitation is typically a comprehensive program coordinated by a team of medical professionals. A physical therapist on the team, for example, may focus on maintaining and restoring range of motion and strength in affected limbs, maximizing mobility in walking, improving manual dexterity, and rehabilitating other motor and sensorimotor functions. A mental health professional may be involved in the treatment of loss of cognitive skills. Rehabilitation services can occur in multiple environments, such as a rehabilitation hospital, long-term care facility, outpatient clinic, or at home.

Neurological functions impacted by stroke (and which can be targeted during rehabilitation) include impairments in cognitive and motor functions. Cognitive function impairments, for example, can manifest as deficits in understanding speech or writing (aphasia); knowing the right words but having trouble saying them clearly (dysarthria); as well as deficits in other cognitive functions, such as attention, reasoning, planning, execution, and learning and memory. Motor function impairments, for example, can manifest as weakness (hemiparesis) or paralysis (hemiplegia) on one side of the body that may affect the whole side or just the arm or leg; by problems with balance or coordination; deficits in gross motor skills such as gait and walking speed; deficits in fine motor skills or manual dexterity; and deficits in upper and lower extremity function.

Accordingly, the present disclosure provides the use of a GlyT1 inhibitor in the treatment of stroke, including post stroke rehabilitation. In certain embodiments, chemical entities are useful during stroke rehabilitation to treat stroke deficits (or "post-stroke deficits") resulting from impaired neurological functions. Some embodiments provide methods of treating a neurological deficit during post-stroke rehabilitation comprising: (a) administering to a subject in need thereof a GlyT1 inhibitor during recovery of the subject from stroke; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the GlyT1 inhibitor is a chemical entity of the present disclosure. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Traumatic Brain Injury

In some embodiments, chemical entities and compositions are useful in treating traumatic brain injury, and in more specific embodiments, treating motor or cognitive impairments during rehabilitation after the initial trauma. Like stroke care, TBI case is a temporal continuum that includes immediate (acute) treatments and subsequent rehabilitative therapy.

Some embodiments provide the use of a GlyT1 inhibitor in the treatment of TBI, including during TBI rehabilitation to treat TBI deficits (or "post-TBI deficits") resulting from impaired neurological functions. Some embodiments provide methods of treating a neurological deficit during post-TBI rehabilitation comprising: (a) administering to a subject in need thereof a GlyT1 inhibitor during recovery of the subject from TBI; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the GlyT1 inhibitor is a chemical entity of the present disclosure. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Schizophrenia

In particular embodiments, the chemical entities are useful in treating schizophrenia. Schizophrenia is a devastating neurological disorder, characterized by a combination of negative and positive symptoms. Negative symptoms can include flat affect (lack or decline in emotional response), alogia (lack or decline in speech), avolition (lack or decline in motivation), anhedonia (the inability to experience pleasure from activities usually found enjoyable), and asociality (lack of motivation to engage in social interaction, or a preference for solitary activities). Positive symptoms include paranoia, hallucinations, delusions, as well as impairments in cognitive functions, such as attention, memory, reasoning, and processing speed. See, e.g., Keefe, R S, and Harvey, P C, Cognitive Impairment in schizophrenia, 2012, Handb. Exp. Pharmacol. 213, 11-23.

Some embodiments provide a method of treating schizophrenia, comprising administering to a subject in need thereof an effective amount of a chemical entity of Formula (I). In particular embodiments, the treatment is directed to a positive symptom of schizophrenia. In other embodiments, treatment is directed to a negative symptom of schizophrenia, and more particularly, a cognitive deficit.

Some embodiments provide methods of treating pain or alcohol dependence, comprising administering to a subject in need thereof an effective amount of a chemical entity of Formula (I). See, e.g., Harvey and Yee, 2013, Nat. Rev. Drug. Discov. 12, 866-885.

Some embodiments provide methods of treating pain or alcohol dependence, comprising administering to a subject in need thereof an effective amount of a chemical entity of Formula (I). See e.g., Harvey and Yee, 2013, Nat. Rev. Drug. Discov. 12, 866-885.

Animal Skill Training

In some embodiments, chemical entities of the present disclosure are used to enhance the efficiency of training protocols directed to cognitive and motor skills in an animal.

Such augmented training reduces the time necessary to acquire or enhance a cognitive or motor skill in the non-human animal.

In particular embodiments, the animal is a non-human animal, and more particularly, is a service animal, a category that includes, but is not limited to, dogs, miniature horses, and capuchin monkeys. Service animals may be involved in public service or private service, and the training protocols will be appropriately matched to these objections. For example, training protocols directed to public service include public order maintenance, search and rescue, and contraband detection, and training protocols directed to private service include private security, handicap assistance, health care, psychiatric assistance, and pest control.

The training protocol may be directed to a single skill, such as the detection of a single drug in a service animal. In other embodiments, the training protocol may be directed to a complex set of skills, such as those underlying search and rescue training of a service animal; for a complex set of skills, training will therefore comprise more than one task.

Some embodiments provide a method of teaching a non-human animal one or more skills, comprising (a) administering to a non-human animal in need thereof a GlyT1 inhibitor; (b) providing training to the animal under conditions sufficient to improve performance of the one or more skills; and (c) repeating steps (a) and (b) one or more times, whereby the amount of training sufficient to improve the performance is reduced compared to that produced by training alone.

EXAMPLES

The present disclosure will be further illustrated by the following non-limiting Examples. These Examples are understood to be exemplary only, and they are not to be construed as limiting the scope of the one or more embodiments, and as defined by the appended claims.

PREPARATIVE EXAMPLES

Exemplary compounds will now be described by reference to the illustrative synthetic schemes for their general preparation below and the specific examples to follow.

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −78° C. and the reflux temperature of the solvent. Reactions may be heated employing conventional heating or microwave heating. Reactions may also be conducted in sealed pressure vessels above the normal reflux temperature of the solvent.

Abbreviations

The specification includes numerous abbreviations, whose meanings are listed in the following Table:

TABLE 1

| Abbreviation | Definition |
| --- | --- |
| ACN | Acetonitrile |
| AIBN | Azobisisobutyronitrile |
| BINAP | 2,2'-Bis(diphenylphosphino)-1,1'-binaphthyl |
| BOC | tert-butoxycarbonyl |
| CELITE ® | Diatomaceous earth |
| m-CPBA | meta-Chloroperoxybenzoic acid |
| DAST | Diethylaminosulfur trifluoride |
| DCC | Dicyclohexylcarbodiimide |
| DCM | Dichloromethane or methylene chloride |
| Deoxo-Fluor ® | Bis(2-methoxyethyl)aminosulfur trifluoride |
| DIPEA | N,N-Ethyl-diisopropylamine or N,N-Diisopropyl-ethyl amine |
| DMA | N,N-Dimethylacetamide |
| DMAP | 4-Dimethylamino pyridine |
| DMF | N,N-Dimethylformamide |
| DMSO | Dimethylsulfoxide |
| DPEphos | Bis[(2-diphenylphosphino)phenyl] ether |
| dppf | 1,1'-Bis(diphenylphosphino)ferrocene |
| EDCI | N-(3-Dimethylaminopropyl)-N'-ethylcarbodiimide hydrochloride |
| EtOAc, or EA | Ethyl acetate |
| EtOH | Ethanol |
| FCC | Flash column chromatography |
| IPA | Isopropyl alcohol |
| HATU | (1-[Bis(dimethylamino)methylene]-1H-1,2,3-triazolo[4,5-b]pyridinium 3-oxid hexafluorophosphate) |
| HOAc or AcOH | Acetic Acid |
| HOBt | 1-Hydroxybenzotriazole |
| HPLC | High-performance liquid chromatography |
| LAH | Lithium aluminum hydride |
| LiHMDS, LHMDS | Lithium bis(trimethylsilyl)amide |
| LDA | Lithium diisopropylamide |
| LCMS, LC/MS | Liquid chromatography-mass spectrometry |
| MeOH | Methanol |
| MPLC | Medium pressure liquid chromatography |
| MsCl | Methanesulfonyl chloride |
| Pd/C | Palladium on activated carbon |
| Pd$_2$(dba)$_3$ | Tris(dibenzylideneacetone)dipalladium (0) |
| PdCl$_2$(dppf)-Cl$_2$ adduct | [1'1'-Bis(diphenylphosphino)ferrocene]palladium(ll)dichloride DCM adduct |

TABLE 1-continued

| Abbreviation | Definition |
| --- | --- |
| Pd(PPh$_3$)$_4$ | Palladium-tetrakis(triphenylphosphine) |
| P(2-furyl)$_3$ | Tri-2-furylphosphine |
| PyBroP | Bromotripyrrolidinophosphonium hexafluorophosphate |
| rt | Room temperature |
| Selectfluor ® | 1-Chloromethyl-4-fluoro-1,4-diazoniabicyclo[2.2.2]octane |
| S-Phos | 2-Dicyclohexylphosphino-2',6'-dimethoxybiphenyl |
| TEA, Et$_3$N | Triethylamine |
| TFA | Trifluoroacetic acid |
| THF | Tetrahydrofuran |
| Xantphos ® | 4,5-Bis(diphenylphosphino)-9,9-dimethylxanthene |
| XtalFluor ® | Diethylaminodifluorosulfinium tetrafluoroborate |

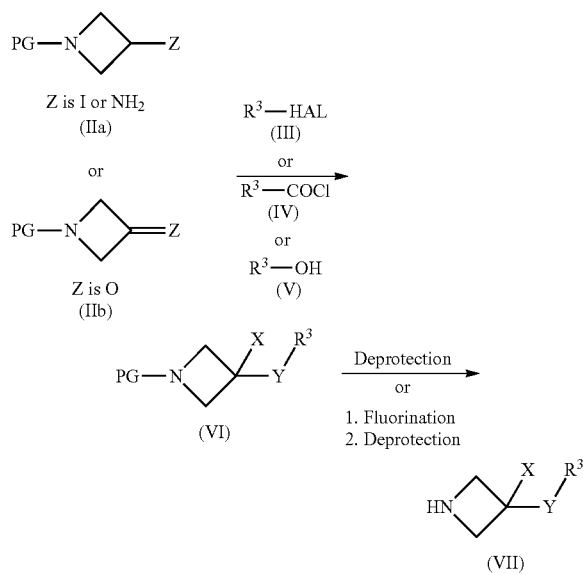

Referring to Scheme A, compounds of formula (VII) are prepared from compounds of formula (IIa or IIb). Compounds of formula (IIa or IIb) are suitably protected, shown by substitutent -PG. A preferred protecting group is the tert-butyl carbamate (BOC) group or benzhydryl (Bh) group. Coupling of aryl or heteroaryl halides of formula (III) with nitrogen heterocycles of formula (IIa), where Z is —I (iodine), employing Negishi cross-coupling chemistry provides compounds of formula (VI). For example, a compound of formula (IIa), where Z is —I (iodine), is reacted with activated Zn, a metal catalyst such as Pd$_2$(dba)$_3$, PdCl$_2$(Amphos)$_2$ and the like, a ligand such as P(2-furyl)$_3$, tri(t-butyl) phosphine, tricyclohexyl phosphine and the like, in a solvent such as THF, DMF, dioxane, and the like, at temperatures ranging from rt to 60° C., for a period of 12 to 24 h, provides compounds of formula (VI), where Y is a bond and X is hydrogen.

Coupling of acyl halides of formula R$^3$—COCl (IV) with nitrogen heterocycles of formula (IIa), where Z is —I (iodine), employing Negishi cross-coupling chemistry as previously described provides compounds of formula (VI), where Y is C=O, and X is hydrogen. Subsequent reaction of compounds of formula (VI), where Y is C=O, with a fluorinating agent such as Deoxo-Fluor®, employing conditions known to one skilled in the art, provides intermediates where Y is CF$_2$, and X is hydrogen.

Amine compounds of formula (IIa), where Z is a leaving group such as —I (iodine), mesylate, and the like, are alkylated with commercially available or synthetically accessible optionally unsubstituted or substituted aromatic alcohols (V), in a solvent such as DMF, DMA, THF, toluene, and the like, in the presence of a base such as NaHCO$_3$, Na$_2$CO$_3$, K$_2$CO$_3$, NaH, or Cs$_2$CO$_3$, to afford intermediates of formula (VI), where Y is —O—.

Amine compounds of formula (IIa), where Z is NH$_2$, are reacted with optionally unsubstituted aryl or heteroaryl halides of formula (III) in a nucleophilic aromatic substitution (SNAr) displacement reaction to provide intermediates of formula (VI), where Y is —NH— and X is hydrogen. For example, the amine (II) is reacted in an inert solvent such as EtOAc, THF or a protic solvent such as EtOH, in the presence of a base such as TEA, DIEA, and the like, at temperatures ranging from room temperature to the reflux temperature of the solvent.

Compounds of formula (VI), where R$^3$ is an aryl or heteroaryl ring substituted with a —Br, are prepared from nitro intermediates of formula (VI) in two steps. Reduction of nitro compounds of formula (VI) where R$^3$ is an aryl or heteroaryl ring substituted with a nitro with a suitable reducing agent such as iron, in a solvent such as AcOH/H$_2$O, provides the corresponding amine intermediate. Subsequent bromination employing Sandmeyer conditions, for example, reaction of an intermediate diazonium salt with CuBr$_2$, LiBr and the like, t-BuNO$_2$, in a solvent such as ACN, and the like, provides bromo intermediates of formula (VI) where R$^3$ is an aryl or heteroaryl ring substituted with a —Br.

Compounds of formula (VI), where Y is a bond, and X is —OH, are prepared by a Grignard reaction, for example, reaction of aryl or heteroaryl halide compounds of formula (III), where HAL is —I (iodine) and X is hydrogen, with an alkyl magnesium halide compound such as, isopropylmagnesium chloride, and the like, a suitable ketone of formula (IIb), in a solvent such as THF and the like, at temperatures ranging from −20 to 100° C., to provide compounds of formula (VI). Subsequent reaction of compounds of formula (VI), where X is —OH, with a fluorinating agent such as triethylamine trihydrofluoride, employing conditions known to one skilled in the art, provides compounds of formula (VI) where X is —F.

Removal of the tert-butylcarbamate (BOC) in compounds of formula (VI) is accomplished by using methods known to one skilled in the art, such as, HCl, TFA, or p-toluenesulfonic acid, in a solvent such as MeOH, dioxane, or DCM. In a preferred embodiment, a compound of formula (VI) is treated with TFA in DCM or HCl to afford a compound of formula (VII). Removal of the benzyl (Bn) or benzhydryl (Bh) in compounds of formula (VI) is accomplished by using methods known to one skilled in the art, such as, hydrogenolysis.

with a suitable carbonyl compound, such as cyclopentanone, and the like, a palladium catalyst such as Pd(OAc)$_2$, Pd$_2$(dba)$_3$, and the like, a ligand such as Xantphos®, S-Phos®,

SCHEME B

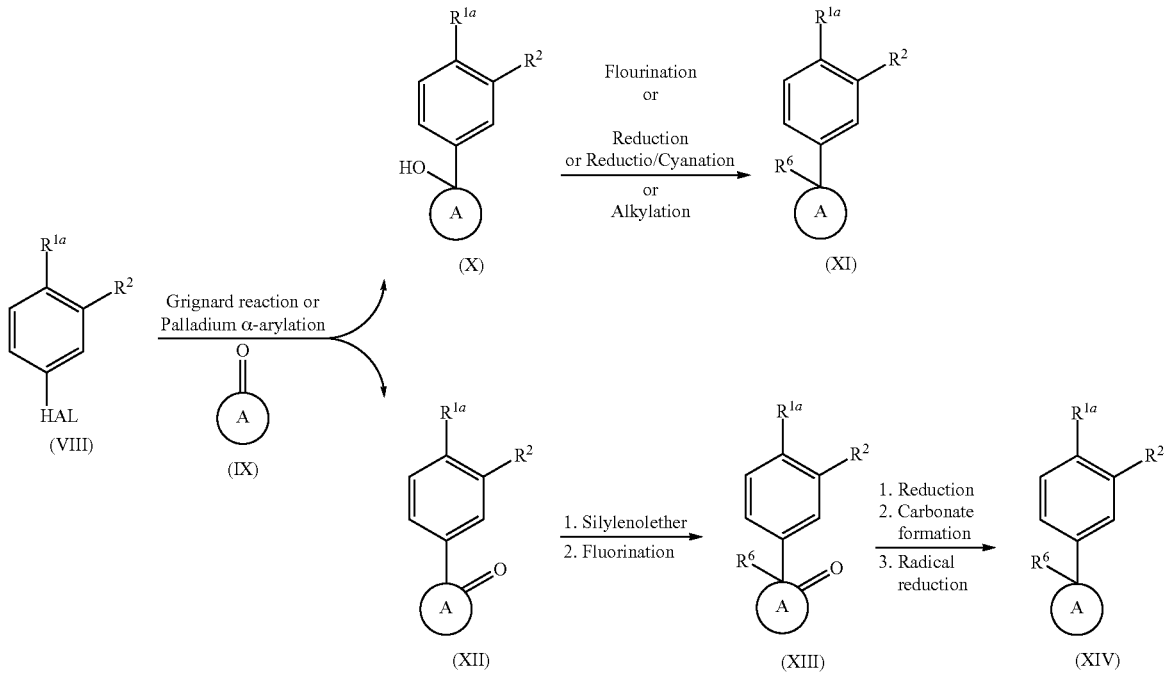

Intermediate compounds of formula (XI) are readily prepared according to Scheme B. Compounds of formula (X) are prepared by a Grignard reaction, for example, reaction of aryl halide compounds of formula (VIII), where $R^{1a}$ is —Br or —CN, $R^2$ is —F, and HAL is —I, with an alkyl magnesium halide compound such as, isopropylmagnesium chloride, and the like, a suitable ketone of formula (IX), where ring A is an optionally substituted —C$_{4-8}$ heterocycloalkyl or —C$_{4-8}$ cycloalkyl ring, in a solvent such as THF and the like, at temperatures ranging from −20 to 100° C., to provide compounds of formula (X). Fluoro compounds of formula (XI), where $R^6$ is —F, are prepared by reacting compounds of formula (X) with Deoxo-Fluor®, XtalFluor®, DAST, and the like, in an appropriate solvent such as DCM, and the like, at rt, for a period of 1 to 24 h. In the event that alkene by-products, which are difficult to separate from the desired product, are formed in the fluorination reaction, oxidation to the corresponding epoxides with an oxidizing agent such as m-CPBA facilitates separation from the desired fluoro compounds of formula (XI) where $R^6$ is —F.

Compounds of formula (XI), where $R^6$ is —H, are prepared by reduction of tertiary alcohol compounds of formula (X), where $R^{1a}$ is —Br or —CN and $R^2$ is —F, with an organosilane such as triethylsilane, triethylsilane-d, and the like, and a strong acid such as boron trifluoride diethyl etherate, and the like, at temperatures ranging from −78 to 0° C., to provide compounds of formula (XI), where $R^6$ is —H.

Alternately, aryl bromides of formula (VIII), where HAL is —Br, undergo a palladium-catalyzed α-arylation with carbonyl compounds of formula (IX) to provide compounds of formula (XII). For example, aryl bromide compounds of formula (VIII), where $R^1$ is —CN, $R^2$ is —F, are reacted BINAP, t-Bu$_3$PHBF$_4$, DPEphos, preferably Xantphos®, a suitable base such as NaOt-Bu, Cs$_2$CO$_3$, K$_3$PO$_4$, and the like, in a suitable solvent such as ACN, THF, toluene, and the like, a temperatures ranging from 60 to 90° C., for a period of 12 to 19 h, to provide compounds of formula (XII). One skilled in the art will recognize that suitable carbonyl compounds employed in the palladium-catalyzed α-arylation reaction may also include unsubstituted or substituted —C$_{5-8}$ cycloalkyl carbonyl and —C$_{6-10}$ alkyl carbonyl compounds. Silylenolether are prepared from compounds of formula (XII), by reaction with NaI, a base such as TEA, in a suitable solvent such as ACN, and a haloalkylsilane such as chlorotrimethylsilane. Subsequent fluorination of the silylenolether with a fluorinating agent such as Selectfluor®, in a suitable solvent such as DMF, provides fluoro compounds of formula (XIII), where $R^6$ is —F. Reduction of compounds of formula (XIII) with a reducing agent such as NaBH$_4$, and the like, in a suitable solvent such as MeOH, at temperatures ranging from 0 to 23° C., provides the corresponding alcohol. Compounds of formula (XIV) are prepared in two steps from the alcohol, first by formation of the thiocarbonate, second by a radical reduction. Thiocarbonate compounds are prepared employing methods known to one skilled in the art, for example, reaction of alcohol compounds with O-phenyl chlorothionoformate, in the presence of DMAP, in a solvent such as ACN, at temperatures ranging from 0 to 23° C. Radical reduction of thiocarbonate compounds with a reducing agent such as tributyltin hydride, a radical initiator such as AIBN, and the like, in a solvent such as toluene, employing microwave or conventional heating at temperatures ranging from 120 to 140° C., provides compounds of formula (XIV).

SCHEME C

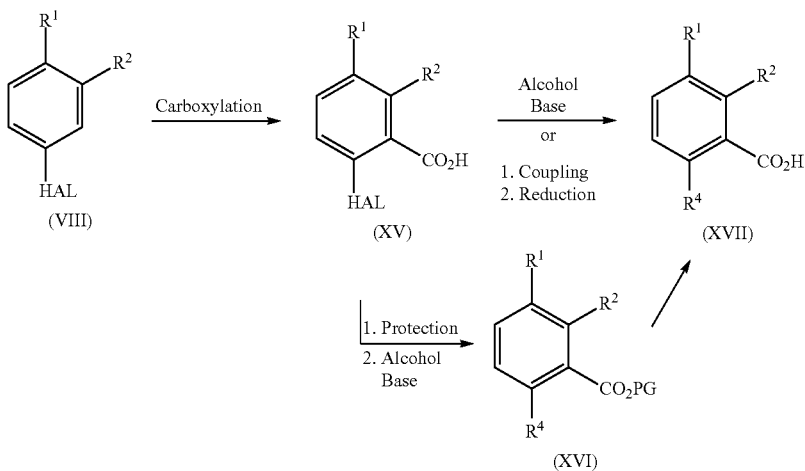

Carboxy compounds of formula (XV) shown in Scheme C are commercially available or are synthetically accessible. For example, compounds of formula (XV) are prepared from compounds of formula (VIII). Compounds of formula (VIII), where $R^1$ is —CN, $R^2$ is —Cl, —F, or —OCH$_3$, and HAL is —F, are reacted with an organolithium base such as lithium diisopropylamide, and the like, in the presence of a CO$_2$ source such as dry ice or CO$_2$ (g), in a solvent such as THF, at temperatures ranging from −78 to 30° C. to provide compounds of formula (XV). Subsequent aromatic nucleophilic substitution reaction with a commercially available or synthetically accessible suitable alcohol, a suitable base such as K$_2$CO$_3$, Cs$_2$CO$_3$, and the like, in a suitable solvent such as THF, dioxane, and the like, at temperatures ranging from 80 to 120° C., provides compounds of formula (XVII), where $R^4$ is —OC$_{1-6}$alkyl, —OC$_{1-6}$haloalkyl, —O(C$_{1-3}$alkyl)$_{0-1}$C$_{3-6}$cycloalkyl. Alternatively, compounds of formula (XV), are protected with an appropriate carboxy protecting group, for example benzyl, prior to aromatic nucleophilic substitution with an appropriate alcohol of formula $R^4$, where $R^4$ is defined above. Deprotection affords compounds of formula (XVII).

According to Scheme C, carboxy compounds of formula (XV), where $R^1$ is —CN, $R^2$ is —F or —OCH$_3$, and HAL is —Br, under Suzuki reaction conditions known to one skilled in the art, are reacted with commercially available or synthetically accessible boronic acids or esters, such as 2-(cyclopent-1-en-1-yl)-4,4,5,5-tetramethyl-1,3,2-dioxaborolane, in a solvent such as ACN, toluene, EtOH, H$_2$O, or a mixture thereof, in the presence of a base such as, KH$_2$PO$_4$, NaHCO$_3$, Na$_2$CO$_3$, K$_2$CO$_3$, Cs$_2$CO$_3$, and the like, and a palladium catalyst such as, Pd(dba)$_2$, Pd(dppf)$_2$, Pd(Ph$_3$)$_4$, and the like, using conventional or microwave heating, at temperatures ranging from 80 to 120° C. Subsequent reduction employing conditions known to one skilled in the art, for example, Pd/C, under a hydrogen atmosphere, provides compounds of formula (XVII) where $R^4$ is cyclopentyl.

SCHEME D

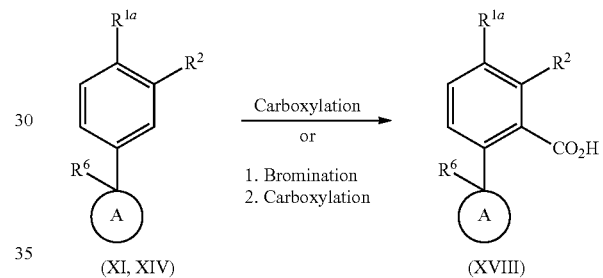

According to Scheme D, carboxylation of compounds of formula (XI), where $R^{1a}$ is —CN or —Br, and $R^2$ is —F, employing a lithiating agent such as n-BuLi, lithium diisopropylamide, and the like, a CO$_2$ source such as crushed solid CO$_2$, with or without a base such as diisopropylamine, 2,2,6,6-tetramethylpiperidine, and the like, in a solvent such as THF and the like, provides carboxy compounds of formula (XVIII).

Carboxylic acid compounds of formula (XVIII), where $R^{1a}$ is —Br and $R^2$ is —F, are suitably protected (preferably benzyl), shown by substitutent PG, under conditions known to one skilled in the art. Cyanation, employing methods known to one skilled in the art provides benzonitrile compounds of formula (XVIII). For example, reaction of compounds of formula (XVIII), where $R^{1a}$ is —Br and $R^2$ is —F, in the presence of a cyanide source such as, but not limited to KCN, NaCN, Zn(CN)$_2$, preferably Zn(CN)$_2$, a palladium catalyst such as Pd$_2$(dba)$_3$, Pd(PPh$_3$)$_4$, and the like, with or without the presence of additional ligand such as dppf, in a solvent such as DMF, ACN, THF, DMA, or a mixture thereof, at temperatures ranging from ambient temperature to 120° C., provides benzonitrile compounds of formula (XVIII) where $R^{1a}$ is —CN. Removal of the benzyl (Bn) protecting group (PG) is accomplished by using methods known to one skilled in the art, such as, hydrogenolysis. Employing methods previously described, additional aromatic nucleophilic substitution reactions on compounds of formula (XVIII), where $R^2$ is —F, under conditions known to one skilled in the art, provide compounds of formula (XVIII), where where $R^{1a}$ is —CN and $R^2$ is —OC$_{1-6}$alkyl.

SCHEME E

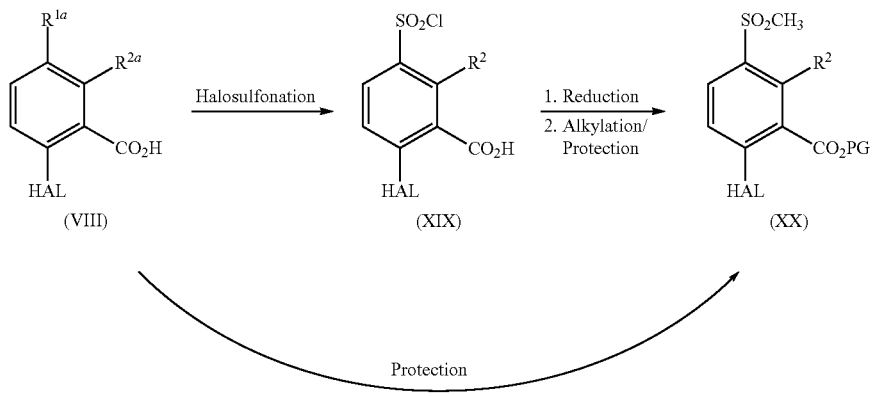

According to Scheme E, compounds of formula (XX) are prepared from commercially available or synthetically accessible substituted benzoic acids of formula (VIII). Esters of formula (XX) are prepared from commercially available or synthetically accessible compounds of formula (VIII), where $R^{1a}$ is —H, $R^{2a}$ is —F, and HAL is —F. Halosulfonation of compounds of formula (VIII), by treatment with chlorosulfonic acid, at temperatures ranging from 65 to 150° C., for a period of 1 to 6 h, provides compounds of formula (XIX). Reduction of sulfonyl chloride of formula (XIX) with an aq. solution of $Na_2SO_3$, for a period of 1 to 3 h, provides the corresponding sulfinic acid. Subsequent alkylation, employing an alkyl halide such as methyl iodide, a mild base such as $K_2CO_3$, and the like, in a solvent such as DMF, DMA, THF and the like, delivers compounds of formula (XX), where PG is —$CH_3$.

In an alternate method, the carboxylic acid moiety of compounds of formula (VIII), where $R^1$ is —$SO_2CH_3$, $R^{2a}$ is —H, and HAL is —Br, may be suitably protected by substitutent PG, under conditions known to one skilled in the art, to provide compounds of formula (XX). For example, compounds of formula (VIII), where HAL is —F, may be reacted with a catalytic amount of an acid such as $H_2SO_4$, in a solvent such as MeOH, at temperatures ranging from rt to the reflux temperature of the solvent, for a period of 24 to 72 h, to provide ester compounds of formula (XX), where PG is —$CH_3$. In an alternative method, compounds of formula (VIII), where HAL is —Br, may be alkylated, employing a base such as $K_2CO_3$ and the like, an alkyl halide such as iodomethane, in a suitable solvent such as DMF, to afford compounds of formula (XX), where PG is —$CH_3$.

SCHEME F

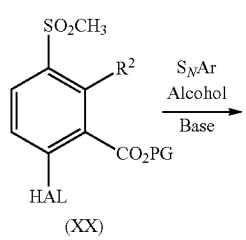

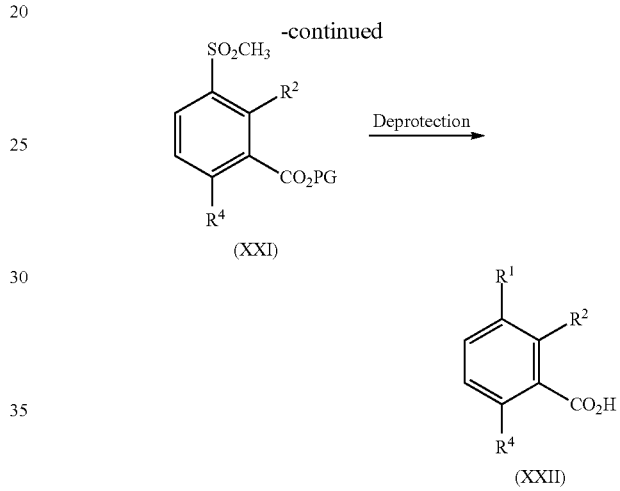

According to Scheme F, compounds of formula (XX), where $R^2$ is —F, HAL is —F, and compounds of formula (VIII, scheme B), where $R^1$ is —$SO_2CH_3$, and HAL is —F, are reacted with commercially available or synthetically accessible alcohol, in an aromatic nucleophilic substitution reaction ($S_NAr$). For example, compounds of formula (XX) are reacted with a racemic alcohol such as racemic 1,1,1-trifluoropropan-2-ol, in a suitable solvent such as THF, dioxane, DMF, and the like, a base such as $Cs_2CO_3$, and the like, at temperatures ranging from 0 to 25° C., for a period of 12 to 24 h, to provide racemic compounds of formula (XXI) where $R^4$ is —O—$C_{1-6}$haloalkyl. Additional aromatic nucleophilic substitution reactions on compounds of formula (XXI), where $R^2$ is —F, under conditions known to one skilled in the art, provides compounds of formula (XXI), where $R^2$ is —O—$C_{1-6}$alkyl. For example, reaction of compounds of formula (XXI) with a base such as $NaHCO_3$, $Na_2CO_3$, $K_2CO_3$, NaH, potassium tert-butoxide, $Cs_2CO_3$, preferably NaH, in a solvent such as DMF, DMA, THF, preferably THF, and a suitable alcohol such as MeOH, at temperatures ranging from 0° C. to rt, for a period of 5 min to 2 h, to afford compounds of formula (XXI), where $R^2$ is —$OCH_3$. Where chiral alcohol reagents are employed, chiral separation employing methods known to one skilled in the art, for example, supercritical fluid chromatography, affords the pure (R) and (S) enantiomers of compounds of formula (XXI).

Hydrolysis of the ester moiety of compounds of formula (XXI), with a base such as NaOH, LiOH, and the like, in a solvent such as MeOH, and the like, at temperatures ranging from 50 to 80° C., for a period of 1 to 12 h, affords substituted benzoic acid compounds of formula (XXII).

the compound of formula (X), or the activating agent is presented in the form of an acid addition salt), at from about 0° C. to rt, to provide compounds of Formula (I).

Compounds of Formula (I), where $R^3$ is substituted with a halogen, under Suzuki reaction conditions known to one

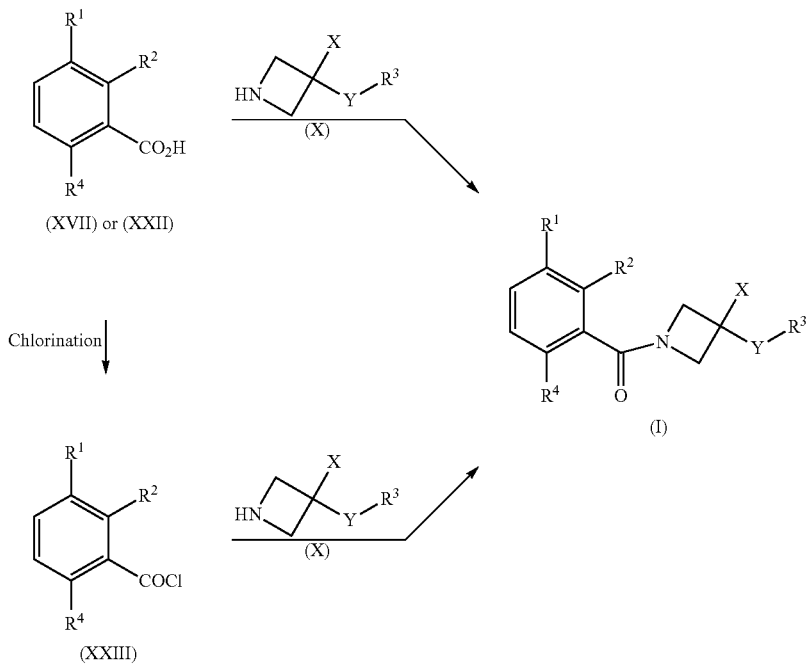

SCHEME G

According to Scheme G, compounds of Formula (I) are prepared by conventional amide bond forming techniques such as coupling reactions which are well known to those skilled in the art. Acid chloride derivatives of compounds of formula (XVII or XXII) are formed employing conditions known to one skilled in the art, for example, reaction of acid compounds of formula (XVII or XXII) with a chlorinating agent such as thionyl chloride, oxalyl chloride, and the like, with or without a catalyst such as DMF, neat or in a solvent such as DCM, and the like, at temperatures ranging from room temperature to 80° C. provides acyl halides of formula (XXIII). Acyl halides of formula (XXIII), are reacted with a compound of formula (X), in the presence of an excess of a tertiary amine, such as TEA, DIEA or pyridine, optionally in the presence of a suitable catalyst, such as DMAP, in a suitable solvent such as DCM or THF, at a temperature of about 0° C. to rt, to provide compounds of Formula (I).

A variety of other amino acid coupling methodologies are used to couple the compounds of formulae (XVII or XXII), with the compound of formula (X). For example, the acid of formulae (XVII or XXII) or a suitable salt thereof (e.g. sodium salt) are activated with an appropriate activating reagent, for example a carbodiimide, such as DCC or EDCI optionally in the presence of HOBt and/or a catalyst such as DMAP; a halotrisaminophosphonium salt such as PyBroP; a suitable pyridinium salt such as 2-chloro-1-methyl pyridinium chloride; or another suitable coupling agent such as HATU. Coupling reactions are conducted in a suitable solvent such as DCM, THF, DMF and the like, optionally in the presence of a tertiary amine such as N-methylmorpholine or N-ethyldiisopropylamine (for example when either skilled in the art, are reacted with commercially available or synthetically accessible aromatic, heteroaromatic, cycloalkyl or heterocycloalkyl boronic acids or esters, in a solvent such as ACN, toluene, EtOH, $H_2O$, or a mixture thereof, in the presence of a base such as, $NaHCO_3$, $Na_2CO_3$, $K_2CO_3$, $Cs_2CO_3$, and the like, and a palladium catalyst such as, $Pd(dppf)_2$, $Pd(Ph_3)_4$, and the like, using conventional or microwave heating, at temperatures ranging from 80 to 120° C., to provide compounds of Formula (I). Compounds of Formula (I), where $R^3$ is an unsubstituted or substituted cycloalkyl or hetercycloalkyl group optionally bearing a double bond are reduced employing conditions known to one skilled in the art, for example, by treatment with a palladium source such as Pd/C, in a solvent such as MeOH, EtOH, or a mixture thereof, under a hydrogen atmosphere at room temperature for a period of 2 to 18 h.

Compounds of Formula (I), where $R^2$ is —F, are reacted with a base such as sodium methoxide, and the like, and an alcohol such as MeOH, at temperatures ranging from rt to 50° C., for a period of 12 to 24 h, to provide compounds of Formula (I), where $R^2$ is —$OC_{1-4}$ alkyl.

Removal of the tert-butylcarbamate (BOC) in compounds with —NH—BOC or —N—BOC is accomplished by using methods known to one skilled in the art, such as, HCl, TFA, or p-toluenesulfonic acid, in a solvent such as $CH_3OH$, dioxane, or $CH_2Cl_2$. In a preferred embodiment, compounds with —NH—BOC or —N—BOC are treated with TFA in DCM or HCl to afford a compound with —$NH_2$— or —NH—. Removal of the benzyl (Bn) in compounds with —$CO_2$—Bn, and removal of the benzhydryl (Bh) in com-

EXAMPLES

Chemistry:

In obtaining the compounds described in the examples below, and the corresponding analytical data, the following experimental and analytical protocols were followed unless otherwise indicated.

Unless otherwise stated, reaction mixtures were magnetically stirred at rt (rt) under nitrogen atmosphere. Where solutions were "dried," they were generally dried over a drying agent such as $Na_2SO_4$ or $MgSO_4$. Where mixtures, solutions, and extracts were "concentrated," they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on $SiO_2$ ($SiO_2$) using packed or prepackaged cartridges, eluting with the indicated solvents.

LC/MS were obtained on a Waters 2695 Separations Unit, 2487 Dual Absorbance Detector, Micromass ZQ fitted with ESI Probe, or a Waters Acquity™ Ultra performance LC (UPLC) with PDA eλ and SQ detectors.

Preparative HPLC was performed on a Shimadzu SIL-10AP system using a Waters SunFire OBD 30 mm×100 mm×2.5 μm (particle size) $C^{18}$ column with a 15 minute gradient of 10-100% acetonitrile in water and 0.05% trifluoroacetic acid added as a modifier to both phases. Elution profiles were monitored by UV at 254 and 220 nm.

Nuclear magnetic resonance (NMR) spectra were obtained in a Varian 400 MHz or Bruker 400 MHz NMR. Samples were analyzed in either deuterated acetone ($(CD_3)_2CO$), chloroform ($CDCl_3$), MeOH-$d_4$ ($CD_3OD$), or dimethyl sulfoxide-$d_6$ (DMSO-$d_6$). For $CDCl_3$ samples, the residual central resonance peak at 7.26 for $^1H$ was used for chemical shift assignment for $^1H$ NMR spectra. For $CD_3OD$ the residual central resonance peak at 3.31 for $^1H$ was used for chemical shift assignment and for DMSO-$d_6$ the residual central resonance peak at 2.50 ppm for $^1H$ was used for chemical shift assignment. The format of the $^1H$ NMR data below is: chemical shift in ppm downfield the tetramethylsilane reference (multiplicity, coupling constant J in Hz, integration).

Chemical names were generated using ChemDraw Ultra 12.0 (CambridgeSoft Corp., Cambridge, Mass.) or ChemAxon.

Intermediate 1. N-(Azetidin-3-yl)-5-(trifluoromethyl)pyridin-2-amine hydrochloride

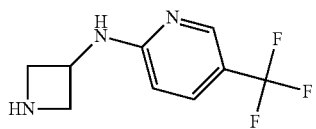 [SMILES: FC(F)(F)c1ccc(NC2CNC2)nc1]

Step 1. tert-Butyl 3-((5-(trifluoromethyl)pyridin-2-yl)amino)azetidine-1-carboxylate. To a solution of tert-butyl 3-aminoazetidine-1-carboxylate (200 mg, 1.16 mmol) in DMF (4 mL) was added DIEA (0.96 mL, 5.81 mmol) and 2-fluoro-5-(trifluoromethyl)pyridine (307 mg, 1.86 mmol). The reaction mixture was heated in a sealed vessel at 80° C. for 24 h. The reaction solvents were then evaporated to afford the title compound.

Step 2. N-(Azetidin-3-yl)-5-(trifluoromethyl)pyridin-2-amine hydrochloride. tert-Butyl 3-((5-(trifluoromethyl)pyridin-2-yl)amino)azetidine-1-carboxylate (from Step 1.) was treated with 4N hydrochloric acid in dioxane (4 mL, 4 mol/L, 16 mmol) for 1 h. The solvent was removed under reduced pressure and the resulting residue was taken up in minimum amount of MeOH and poured onto diethyl ether. The resulting white precipitate was collected and dried under reduced pressure to afford the title compound (83 mg, 85%), as an HCl salt.

Intermediate 2. 2-(Azetidin-3-yl)-3-fluoro-5-(trifluoromethyl)pyridine TFA salt

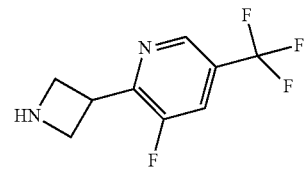 [SMILES: Fc1cc(C(F)(F)F)cnc1C1CNC1]

Step 1. tert-Butyl 3-(3-fluoro-5-(trifluoromethyl)pyridin-2-yl)azetidine-1-carboxylate. A solution of Zn dust (201 mg, 3.08 mmol) and 1,2 dibromoethane (72 mg, 0.38 mmol) in THF (1 mL) was vigorously stirred in a sealed vial. The suspension was then heated at 80° C. for 8 min and allowed to cool to rt. Trimethylsilyl chloride (39 mg, 0.36 mmol) was then added neat, in one portion, and the mixture was stirred at rt for 45 min. A solution of 3-iodo-azetidine-1-carboxylic acid tert-butyl ester (680 mg, 2.38 mmol) in THF (1 mL) was then added dropwise to the solution over a period of 15 min and the reaction mixture was stirred at rt for 2 h. $Pd_2(dba)_3$ (44 mg, 0.05 mmol) and P(2-furyl)$_3$ (33 mg, 3.08 mmol) were then added to the mixture, followed by 2-bromo-3-fluoro-5-(trifluoromethyl) pyridine (640 mg, 2.62 mmol). The reaction mixture was heated to 55° C. and stirred for 18 h. The reaction mixture was cooled to rt and quenched with brine and extracted with DCM (2× 40 mL). The combined organic layers were dried ($MgSO_4$), filtered, and concentrated under reduced pressure. Purification (FCC, $SiO_2$, 20% EtOAc/Hexanes) afforded the title compound as yellow oil.

Step 2. 2-(Azetidin-3-yl)-3-fluoro-5-(trifluoromethyl) pyridine TFA salt. A solution of tert-butyl 3-(3-fluoro-5-(trifluoromethyl)pyridin-2-yl)azetidine-1-carboxylate in 20% TFA solution in DCM (8 mL) was stirred at ambient temperature for 30 min. Concentration under reduced pressure afforded the title compound. [M+H]=221.06.

Intermediate 3. tert-Butyl 3-(difluoro(4-(trifluoromethyl)phenyl)methyl)azetidine-1-carboxylate

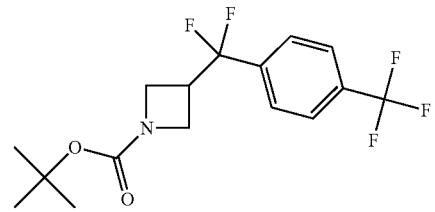 [SMILES: CC(C)(C)OC(=O)N1CC(C(F)(F)c2ccc(C(F)(F)F)cc2)C1]

Step 1. tert-Butyl 3-(4-(trifluoromethyl)benzoyl)azetidine-1-carboxylate. A solution of Zn dust (268 mg, 4.10 mmol) and 1,2 dibromoethane (96 mg, 0.51 mmol) in THF (2 mL) was vigorously stirred in a sealed vial. The suspension was then heated at 80° C. for 8 min and allowed to cool to rt. Trimethylsilyl chloride (52 mg, 0.48 mmol) was then added neat, in one portion, and the mixture stirred at rt for 45 min. A solution of 3-iodo-azetidine-1-carboxylic acid tert-butyl ester (900 mg, 3.18 mmol) in THF (1 mL) was then added dropwise to the solution over a period of 15 min and the reaction mixture stirred at rt for 2 h. Pd$_2$(dba)$_3$ (58 mg, 0.06 mmol) and P(2-furyl)$_3$ (44 mg, 0.19 mmol) were then added to the mixture, followed by 4-(trifluoromethyl) benzoyl chloride (730 mg, 3.50 mmol). The reaction mixture was heated to 55° C. and stirred for 18 h. The reaction mixture was cooled to rt and quenched with brine and extracted with DCM (2× 40 mL). The combined organic layers were dried (MgSO$_4$), filtered, and concentrated under reduced pressure. Purification (FCC, SiO$_2$, 10-40% EtOAc/Hexanes) afforded the title compound (0.564 g, 51%)

Step 2. tert-Butyl 3-(difluoro(4-(trifluoromethyl)phenyl) methyl)azetidine-1-carboxylate. A solution of tert-butyl 3-(4-(trifluoromethyl)benzoyl)azetidine-1-carboxylate (86 mg, 0.26 mmol) and Deoxofluor® (0.144 mL, 0.78 mmol) in DCM (1.00 mL) was stirred at rt for 2 h. EtOH (2 drops) was added and the reaction mixture was heated to 60° C. for 36 h. The reaction mixture was cooled, then poured onto DCM and washed with water then brine. The combined organics were dried (MgSO$_4$), filtered, and concentrated under reduced pressure. Purification (FCC, SiO$_2$, 10-60% EtOAc/hexanes) afforded the title compound (0.55 g, 58%).

Intermediate 4. tert-Butyl 3-(3-bromo-5-(trifluoromethyl)pyridin-2-yl)azetidine-1-carboxylate

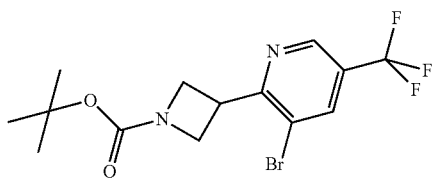 [SMILES: CC(C)(C)OC(=O)N1CC(c2ncc(C(F)(F)F)cc2Br)C1]

The title compound was prepared in a manner analogous to Intermediate 2, Step 1, with the appropriate starting material and reagent substitutions.

Intermediate 5. tert-Butyl 3-(5-aminopyridin-2-yl)azetidine-1-carboxylate

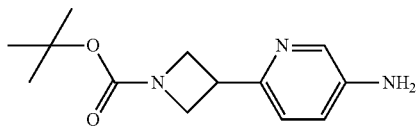 [SMILES: CC(C)(C)OC(=O)N1CC(c2ccc(N)cn2)C1]

Step 1. tert-Butyl 3-(5-nitropyridin-2-yl)azetidine-1-carboxylate. The title compound was prepared in a manner analogous to Intermediate 2, Step 1, with the appropriate starting material and reagent substitutions.

Step 2. tert-Butyl 3-(5-aminopyridin-2-yl)azetidine-1-carboxylate. To a solution of tert-butyl 3-(5-nitropyridin-2-yl) azetidine-1-carboxylate (816 mg, 2.92 mmol) in acetic acid (10 mL), was added iron powder (980 mg, 17.5 mmol) and 2 drops of water. The reaction mixture was heated to 60° C. for 3 h. The reaction mixture was cooled to rt and poured onto EtOAc and washed with water. The organic layer was carefully washed with aq. NaHCO$_3$, then brine. The combined combined organics were dried (Na$_2$SO$_4$), filtered and concentrated under reduced pressure to afford the title compound as pale brown oil (0.0261 g, 36%).

Intermediate 6. 2-(Azetidin-3-yl)-5-bromopyridine TFA salt

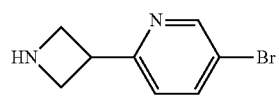

Step 1. tert-Butyl 3-(5-bromopyridin-2-yl)azetidine-1-carboxylate. To a chilled, 0° C., solution of tert-butyl 3-(5-aminopyridin-2-yl)azetidine-1-carboxylate (Intermediate 5, 261 mg, 1.05 mmol) in ACN (6 mL) was added tert-butyl nitrite (168 mg, 1.47 mmol) dropwise. The reaction mixture was stirred for 30 min at 0° C. Copper (II) bromide (269 mg, 1.20 mmol) was added and the mixture was warmed to rt and stirred for an additional 2 h. The reaction mixture was diluted with water and extracted with EtOAc. The combined organics were dried (Na$_2$SO$_4$), filtered and concentrated under reduced pressure. Purification (FCC, SiO$_2$, 10-80% EtOAc/hexanes) afforded the title compound as oil (0.182 g, 56%).

Step 2. 2-(Azetidin-3-yl)-5-bromopyridine. The title compound was prepared in a manner analogous to Intermediate 2, Step 2.

Intermediate 7. 3-(4-Chlorophenoxy)azetidine

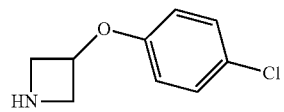

Step 1. tert-Butyl 3-(4-chlorophenoxy)azetidine-1-carboxylate. To a solution of tert-butyl 3-iodoazetidine-1-carboxylate (1.00 g, 3.53 mmol) in DMF (8 mL) was added 4-chlorophenol (0.52 g, 4.06 mmol) followed by K$_2$CO$_3$ (1.07 g, 7.77 mmol). The reaction mixture was stirred at 70° C. for 2 h. The reaction contents were then diluted with EtOAc and washed with water (2×), and brine (1×). The organic phase was concentrated under reduced pressure, providing a thick oil which was used crude in the next step without further purification.

Step 2. 3-(4-Chlorophenoxy)azetidine. tert-Butyl 3-(4-chlorophenoxy)azetidine-1-carboxylate was treated with 4N HCl in dioxane (5 mL, 4 mol/L, 20 mmol) and stirred for 1 h. The solvents were removed under reduced pressure and resulting oil was taken up in minimum amount of MeOH and dripped into vigorously stirring diethyl ether. Suspended solids were spun down in centrifuge tube, supernatant was poured off. Remaining solids were dried under high vacuum affording title compound (0.55 g, 60%).

Intermediate 8. 3-(p-Tolyloxy)azetidine

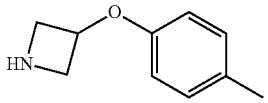

Step 1. 1-Benzhydryl-3-(p-tolyloxy)azetidine. To a slurry of NaH (60%, 93 mg, 2.31 mmol) in toluene (1.5 mL) was added a solution of p-cresol (250 mg, 2.31 mmol) in toluene (1 mL) and the solution bubbled upon addition. The reaction was heated to 60° C. and allowed to stir for 2 hours. Additional toluene was added then the solution was cooled to rt. A slurry of 1-benzhydrylazetidin-3-yl methanesulfonate (455 mg, 1.43 mmol) in toluene (5 mL) was added. The reaction was heated to 80° C. for 2 h then was cooled to rt. Water and EtOAc were added and the layers were separated. The organic layer was washed with 1N NaOH, then brine. The organic later was dried ($Na_2SO_4$), filtered, and concentrated under reduced pressure. Purification (FCC, $SiO_2$, 0-15% EtOAc/hexanes) afforded the title compound (250 mg, 96%) as a colorless oil. $^1$H NMR (400 MHz, $CDCl_3$) δ=7.51-7.45 (m, 4H), 7.33 (t, J=7.4 Hz, 4H), 7.25 (d, J=7.0 Hz, 2H), 7.16 (t, J=7.8 Hz, 1H), 6.80 (d, J=7.4 Hz, 1H), 6.65-6.58 (m, 2H), 4.84 (quin, J=5.8 Hz, 1H), 4.48 (s, 1H), 3.84-3.71 (m, 2H), 3.23-3.11 (m, 2H), 2.33 (s, 3H); [M+H]=330.28.

Step 2. 3-(p-Tolyloxy)azetidine. Palladium hydroxide was added to a solution of 1-benzhydryl-3-(p-tolyloxy)azetidine (100 mg, 0.30 mmol) and EtOH (1.5 mL). The mixture was put under 50 psi of hydrogen at rt for 24 h. Removal of solvent under reduced pressure gave the crude product, which was taken forward without any further purification. [M+H]=164.19.

Intermediate 9. 3-Fluoro-3-(4-(trifluoromethyl)phenyl)azetidine

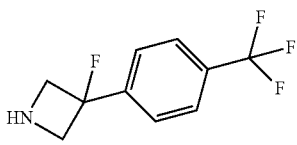 [SMILES: FC(F)(F)c1ccc(C2(F)CNC2)cc1]

Step 1. tert-Butyl 3-hydroxy-3-(4-(trifluoromethyl)phenyl)azetidine-1-carboxylate. To a solution of 1-iodo-4-(trifluoromethyl)benzene (6.36 g, 1.85 mmol) in THF (58.4 mL) at −78° C. was added a solution of i-PrMgCl (11.7 mL, 23.4 mmol, 2.0 M) dropwise. The solution was allowed to stir for several minutes then was warmed to 0° C. After 1 h, the reaction was cooled back to −78° C. then a solution of tert-butyl 3-oxoazetidine-1-carboxylate (2.0 g, 11.7 mmol) in THF (10 mL) was added dropwise. The reaction was stirred for 3.5 h at −78° C. then warmed to rt and allowed to stir overnight. The reaction was cooled to 0° C. and an aqueous solution of $NH_4Cl$ (sat) was added (100 mL) followed by EtOAc (100 mL). The layers were separated then the aqueous layer was extracted with EtOAc (100 mL). The combined organics were washed with brine, dried ($Na_2SO_4$) and concentrated under reduced pressure. Purification (FCC, $SiO_2$, 0-40% EtOAc/Hexanes) provided the title compound (3.2 g, 87%). $^1$H NMR (400 MHz, $CDCl_3$) δ=7.65 (s, 4H), 4.20 (s, 4H), 3.38 (s, 1H), 1.45 (s, 9H); [M−55]=262.25; [M+H]=318.25.

Step 2. tert-Butyl 3-fluoro-3-(4-(trifluoromethyl)phenyl)azetidine-1-carboxylate. (Diethylamino)difluorosulfonium tetrafluoroborate (XtalFluor-E®, 812 mg, 3.55 mmol) was transferred to a roundbottom flask and put under nitrogen, then DCM (10 mL) was added via syringe. The reaction mixture was cooled to 0° C. in an ice bath, then triethylamine trihydrofluoride (0.77 mL, 2.36 mmol) and TEA (0.33 mL, 2.36 mmol) were added via syringe. The reaction was stirred until all reagents had completely dissolved then the reaction was cooled to −78° C. in a dry ice/acetone bath. A solution of tert-butyl 3-hydroxy-3-(4-(trifluoromethyl)phenyl)azetidine-1-carboxylate (750 mg, 2.36 mmol) in DCM (10 mL) was added via syringe then the reaction was warmed back to 0° C. and allowed to stir for 1 hour. An aqueous solution of $NaHCO_3$ (3 mL, sat aq) was added and the reaction was stirred at rt until the evolution of gas ceased. Water and DCM were added and layers separated. The organic layer was washed with 10% aq chlorox, aq. $Na_2CO_3$, and brine. The organic layer was dried ($Na_2SO_4$), filtered, and concentrated under reduced pressure. Purification (FCC, $SiO_2$, 0-10, 10-20% EtOAc/Hexanes) provided the title compound (520 mg, 70%) as a white solid. $^1$H NMR (400 MHz, $CDCl_3$) δ=7.86-7.47 (m, 4H), 4.59-4.33 (m, 2H), 4.23 (dd, J=10.2, 18.4 Hz, 2H), 1.49 (s, 9H); [M+H]=320.28.

Step 3. 3-Fluoro-3-(4-(trifluoromethyl)phenyl)azetidine. To a solution of tert-butyl 3-fluoro-3-(4-(trifluoromethyl)phenyl)azetidine-1-carboxylate (250 mg, 0.78 mmol) in dioxane (4 mL) was added a solution of HCl in dioxane (0.59 mL, 4 mol/L, 2.35 mmol). The reaction mixture was stirred at rt then heated to 45° C. for 1 hour. More HCl in dioxane (0.98 mL, 4 mol/L, 3.90 mmol) was added and the resulting reaction mixture was heated to 60° C. for 2.5 h. The solvent was removed under reduced pressure to give the HCl salt of the title compound; [M+H]=220.19.

TABLE 2

Amine Intermediates

| $R^3$ | Y | X | Prepared analogous to INT # | $R^3$ | Y | X | Prepared analogous to INT # |
|---|---|---|---|---|---|---|---|
| —⟨phenyl⟩—$OCH_3$ | —O— | H | 8 | —⟨phenyl-NC⟩—F | Bond | H | 2, Step 1 |

TABLE 2-continued
Amine Intermediates
| R³ | Y | X | Prepared analogous to INT # | R³ | Y | X | Prepared analogous to INT # |
|---|---|---|---|---|---|---|---|
| 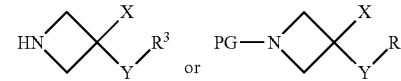 | Bond | H | 2, Step 1 |  | Bond | H | 2, Step 1 |
| 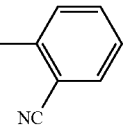 | Bond | H | 2, Step 1 | 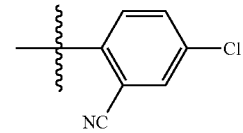 | Bond | H | 2, Step 1 |
| 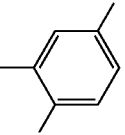 | Bond | H | 2, Step 1 | 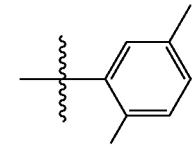 | Bond | H | 2, Step 1 |
| 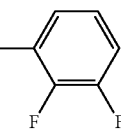 | Bond | H | 2, Step 1 | 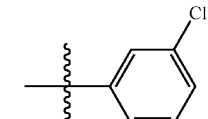 | Bond | H | 2, Step 1 |
| 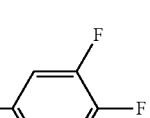 | Bond | H | 2, Step 1 | 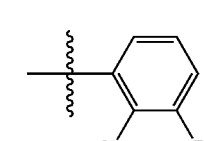 | Bond | H | 2, Step 1 |
| 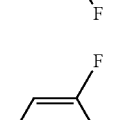 | Bond | H | 2, Step 1 | 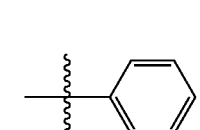 | Bond | H | 2, Step 1 |
| 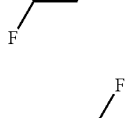 | Bond | H | 2, Step 1 | 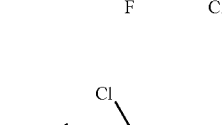 | Bond | H | 2, Step 1 |
| 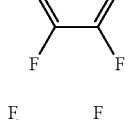 | Bond | H | 2, Step 1 | 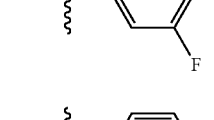 | —O— | H | 7 |

TABLE 2-continued

Amine Intermediates

| R³ | Y | X | Prepared analogous to INT # | R³ | Y | X | Prepared analogous to INT # |
|---|---|---|---|---|---|---|---|
| 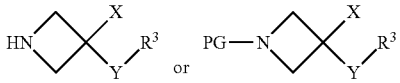 4-CN, 2-Cl phenyl | Bond | H | 2, Step 1 | 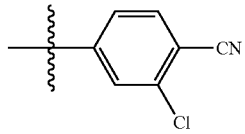 5-CF₃ pyridin-2-yl | Bond | H | 2, Step 1 |
| 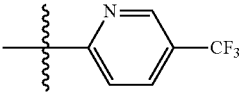 4-CN, 2-F phenyl | Bond | H | 2, Step 1 | 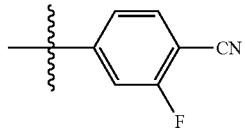 5-CHF₂ pyridin-2-yl | Bond | H | 2, Step 1 |
| 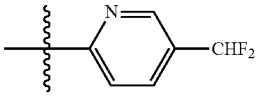 4-CN, 3-OMe phenyl | Bond | H | 2, Step 1 | 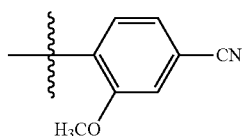 [SMILES: *c1ccc(C#N)cc1Cl] 3-Br, 5-CF₃ pyridin-2-yl | Bond | H | 2, Step 1 |
| 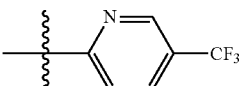 4-CN, 2-F, 3-Cl phenyl | Bond | H | 2 | 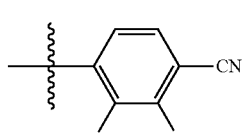 3-Cl pyridin-2-yl | Bond | H | 2, Step 1 |
| 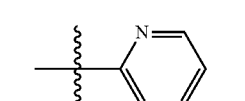 4-CF₃, 3-Cl phenyl | Bond | H | 2, Step 1 | 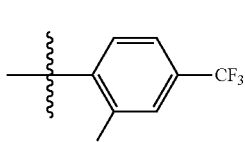 3-Cl, 5-CF₃ pyridin-2-yl | Bond | H | 2, Step 1 |
| 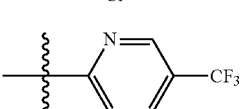 4-CF₃, 2-F phenyl | Bond | H | 2, Step 1 | 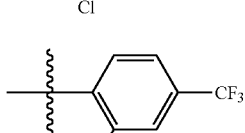 3-F, 5-CF₃ pyridin-2-yl | Bond | H | 2, Step 1 |
| | | | | | —NH— | H | 1 |
| 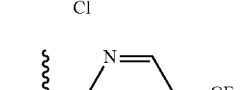 4-CF₃, 3-F phenyl | Bond | H | 2, Step 1 | 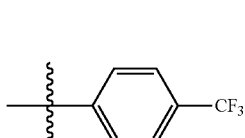 3-F, 5-F pyridin-2-yl | Bond | H | 2, Step 1 |
| 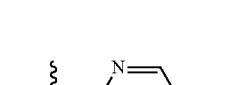 4-CF₃, 3-Me phenyl | Bond | H | 2, Step 1 | 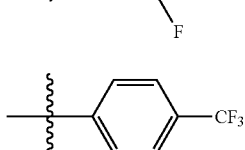 3,4-diF phenyl | Bond | F | 9 |
| 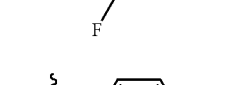 4-CHF₂, 3-F phenyl | Bond | H | 2, Step 1 | 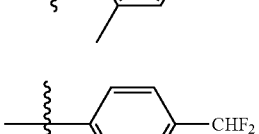 benzoxazol-6-yl | Bond | H | 2, Step 1 |

TABLE 2-continued

Amine Intermediates

HN△X/Y/R³  or  PG—N△X/Y/R³

| R³ | Y | X | Prepared analogous to INT # | R³ | Y | X | Prepared analogous to INT # |
|---|---|---|---|---|---|---|---|
| ⸺⟨phenyl with F and CHF₂⟩ | Bond | H | 2, Step 1 | ⸺⟨phenyl with Cl and CHF₂⟩ | Bond | H | 2, Step 1 |

Intermediate 10: (S)-2-Methoxy-3-(methylsulfonyl)-6-((1,1,1-trifluoropropan-2-yl)oxy)benzoic acid

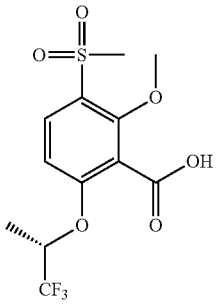 [SMILES: COc1c(S(C)(=O)=O)ccc(O[C@@H](C)C(F)(F)F)c1C(=O)O]

Step 1. 3-(Chlorosulfonyl)-2,6-difluorobenzoic acid. 2,6-Difluorobenzoic acid (230 g, 1.455 mol) in ClSO₃H (700 mL, 10.2 mol) was stirred at 120° C. for 2 h. The mixture was poured into ice and stirred for 20 minutes. The slurry was filtered. The filter cake was dissolved with DCM, dried (Na₂SO₄) and concentrated under reduced pressure to give the title compound (200 g, 54%) as a gray solid. ¹H NMR (400 MHz, CD₃OD) δ=8.192-8.247 (m, 1H), 7.34-7.42 (m, 1H).

Step 2. 2,6-Difluoro-3-hydrosulfonylbenzoic acid. 3-(Chlorosulfonyl)-2,6-difluorobenzoic acid (122 g, 0.476 mol) was added to a solution of Na₂SO₃ (1420 g, 3.33 mol) in water (2 L) and stirred for 3 hours. The clear reaction mixture was then cooled to 0° C. and acidified by the addition of 20% H₂SO₄ solution until reaching pH 2. Water was evaporated under vacuum, and then MeOH (60 mL) was added and stirred for 1 h. The suspension was filtered and the filtrate evaporated and dried under reduced pressure. The resulting title compound was used in the next step without further purification.

Step 3. Methyl 2,6-difluoro-3-(methylsulfonyl)benzoate. To a solution of crude 2,6-difluoro-3-hydrosulfonylbenzoic acid (174 g) in DMF (1.75 L) was added MeI (83 mL, 1.3 mol) and K₂CO₃ (156 g, 1.13 mol), and the reaction was stirred at rt overnight. The mixture was poured into ice-water and stirred for 10 minutes. The slurry was filtered, washed with water and dried overnight under vacuum to afford the title compound (54 g, 57%) as a white solid. ¹H NMR (400 MHz, CDCl₃) δ 8.09-8.10 (m, 1H), 7.13-7.18 (m, 1H), 3.99 (s, 3H), 3.23 (s, 3H).

Step 4. Methyl 2-fluoro-3-(methylsulfonyl)-6-((1,1,1-trifluoropropan-2-yl)oxy)benzoate. To a mixture of methyl 2,6-difluoro-3-(methylsulfonyl)benzoate (65 g, 0.26 mol) and Cs₂CO₃ (255 g, 0.78 mol) in THF (1.3 L) was added 1,1,1-trifluoropropan-2-ol (29.6 g, 0.26 mol) at 0° C. Then the resulting mixture was stirred at rt overnight. The mixture was poured into ice-water and extracted with EtOAc. The organic layers were separated and washed with brine, dried (Na₂SO₄), filtered, and concentrated under reduced pressure to give the crude product. Purification (FCC, SiO₂) afforded the title compound (20 g, 22.4%) as a brown oil. ¹H NMR (400 MHz, CDCl₃) δ=7.89-7.93 (m, 1H), 6.85-6.87 (d, J=8.8 Hz, 1H), 4.71-4.80 (m, 1H), 3.88 (s, 3H), 3.13 (s, 3H), 1.48-1.49 (d, J=6.0 Hz, 3H).

Step 5. Methyl 2-methoxy-3-(methylsulfonyl)-6-((1,1,1-trifluoropropan-2-yl)oxy)benzoate. To a mixture of methyl 2-fluoro-3-(methylsulfonyl)-6-((1,1,1-trifluoropropan-2-yl)oxy)benzoate (25 g, 72.61 mmol) and MeOH (3.25 g, 101.65 mmol) in THF (250 mL) was added NaH (7 g, 174.3 mmol) at 0° C. Then the resulting mixture was stirred at 0° C. for 5 min. The mixture was poured into ice-water and extracted with EtOAc, the organic layer was separated and collected. The collected organic layers were washed with brine, dried (Na₂SO₄), filtered, and concentrated to give the crude product. The crude material was purified (FCC, SiO₂) to afford the title compound (20 g, 77%) as a white solid. ¹H NMR (400 MHz, CDCl₃) δ=8.01-8.03 (d, J=8.8 Hz, 1H), 6.83-6.86 (d, J=8.8 Hz, 1H), 4.74-4.83 (m, 1H), 4.05 (s, 3H), 3.97 (s, 3H), 3.32 (s, 3H), 1.55-1.56 (d, J=6.4 Hz 3H). Note: Methyl 2-methoxy-3-(methylsulfonyl)-6-((1,1,1-trifluoropropan-2-yl)oxy)benzoate was separated by SFC to (S)-methyl 2-methoxy-3-(methylsulfonyl)-6-((1,1,1-trifluoropropan-2-yl)oxy)benzoate and (R)-methyl 2-methoxy-3-(methylsulfonyl)-6-((1,1,1-trifluoropropan-2-yl)oxy)benzoate.

Step 6. (S)-2-Methoxy-3-(methylsulfonyl)-6-((1,1,1-trifluoropropan-2-yl)oxy)benzoic acid. To a solution of (S)-methyl 2-methoxy-3-(methylsulfonyl)-6-((1,1,1-trifluoropropan-2-yl)oxy)benzoate (peak 2) (10 g, 28.1 mmol) in MeOH (100 mL) and H₂O (50 mL) was added LiOH aq. (140 mL, 140 mmol). Then the mixture was stirred and heated to reflux overnight. Then the mixture was extracted with EtOAc, the aqueous phase was separated and acidified by the addition of diluted hydrochloric acid to pH=~2. Then the mixture was extracted with EtOAc, the organic layer was separated and collected. The collected organic layers were washed with brine, dried (Na₂SO₄), filtered, and concentrated to give the title compound (7 g, 73%) as a white solid. ¹H NMR (400 MHz, CDCl₃) δ=8.03-8.05 (d, J=8.8 Hz, 1H), 6.86-6.89 (d, J=8.8 Hz, 1H), 4.77-4.86 (m, 1H), 4.11 (s, 3H), 3.22 (s, 3H), 1.56-1.57 (d, J=6.4 Hz, 3H).

Intermediate 11: (R)-2-Methoxy-3-(methylsulfonyl)-6-((1,1,1-trifluoropropan-2-yl)oxy)benzoic acid

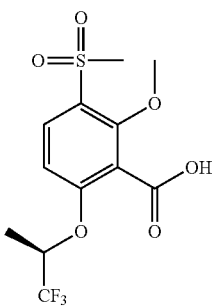 [SMILES: COc1c(S(C)(=O)=O)ccc(O[C@H](C)C(F)(F)F)c1C(=O)O]

The title compound was prepared in a manner analogous to Intermediate 10, employing (R)-2-methoxy-3-(methylsulfonyl)-6-((1,1,1-trifluoropropan-2-yl)oxy)benzoic acid (peak 1) in Step 6.

Intermediate 12: 3-Cyano-2-methoxy-6-(4-fluorotetrahydropyran-4-yl)benzoic acid

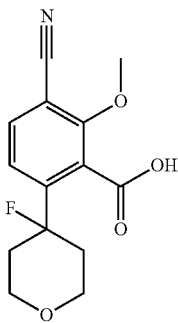

Step 1. 4-(4-Bromo-3-fluorophenyl)tetrahydro-2H-pyran-4-ol. To a solution of 4-bromo-3-fluoroiodobenzene (40 g, 133 mmol) in THF (400 mL) at −78° C. was added 2 M solution of i-PrMgCl in THF (73 mL, 146 mmol) and the mixture was stirred 40 min at −78° C. To this mixture was added via cannula needle over a period of about 5 minutes a solution of tetrahydro-4H-pyran-4-one (13.5 mL, 146 mmol) in THF (100 mL). The resulting mixture stirred for 30 min at −78° C. and then 1 h at 0° C. The resulting mixture was diluted with 1 M aq. NH$_4$Cl (200 mL) and extracted into EtOAc (2× 300 mL). The organic extract was washed with brine, dried (MgSO$_4$) and concentrated under reduced pressure. Purification (FCC, SiO$_2$, 10-40% EtOAc/hexane) provided the title compound (18.9 g, 52%) as a tan solid. $^1$H NMR (400 MHz, CDCl$_3$) δ=7.54 (dd, J=8.4, 7.2 Hz, 1H), 7.29 (dd, J=10, 2 Hz, 1H), 7.15 (dd, J=8.4, 2.4 Hz, 1H), 3.88-3.91 (m, 4H), 2.08-2.13 (m, 2H), 1.64 (dd, J=15, 1 Hz, 1H), 1.64 (s, 1H); $^{19}$F NMR (376 MHz, CDCl$_3$) δ=−106.76 (dd, J=10.2, 7.9 Hz, 1F).

Step 2. 4-(4-Bromo-3-fluorophenyl)-4-fluorotetrahydro-2H-pyran. To XtalFluor-E® (23.6 g, 103.1 mmol) in DCM (170 mL) at 0° C. was added triethylamine trihydrofluoride (22.5 mL, 137.4 mmol) and triethylamine (9.8 mL, 68.7 mmol) and the mixture stirred for 5 min at 0° C. when a homogeneous solution formed. This mixture was cooled to −78° C. and 4-(4-bromo-3-fluorophenyl)tetrahydro-2H-pyran-4-ol (18.9 g, 68.7 mmol) as a solution in DCM (170 mL) precooled to −78° C. was added via cannula needle. The resulting mixture was then stirred 1 h at 0° C. and then 1M aqueous NaHCO$_3$ (400 mL) was carefully added and stirred for 30 min until gas generation had ceased and pH was ≥6. The organic layer was separated and washed with 0.3 M NaClO$_4$ (400 mL) and brine (300 mL). The combined organics were dried (MgSO$_4$) and concentrated under reduced pressure to 300 mL. To this solution was added KHCO$_3$ (4.13 g, 41.2 mmol) and m-CPBA (5.93 g, 34.4 mmol) and the mixture stirred for 30 min at rt (conversion of alkene by-products to the corresponding epoxide for ease in purification). The mixture was washed with water, aqueous 1 M Na$_2$SO$_3$, and the combined organic layers were dried (MgSO$_4$), filtered, and concentrated under reduced pressure. Purification (FCC, SiO$_2$, 5-20% EtOAc/hexanes) provided the title compound (16.7 g, 88%) as a tan solid (HPLC purity 93%). $^1$H NMR (400 MHz, CDCl$_3$) δ=7.56 (dt, J=7.8, 0.6 Hz, 1H), 7.18 (dd, J=9.6, 2.0 Hz, 1H), 7.04 (dd, J=8.4, 2.4 Hz, 1H), 3.95 (dd, J=11.6, 6 Hz, 2H), 3.85 (td, J=12, 2 Hz, 2H), 2.10 (dtd, J=40, 12, 5 Hz, 2H), 1.88 (dd, J=12.8, 10.8 Hz, 2H); $^{19}$F NMR (376 MHz, CDCl$_3$) δ=−106.42 (t, J=8.3 Hz, 1F), −160.53 (tt, J=40, 9 Hz, 1F).

Step 3. 3-Bromo-2-fluoro-6-(4-fluorotetrahydro-2H-pyran-4-yl)benzoic acid. To a solution of diisopropylamine (10.2 mL, 72.2 mmol) in THF (100 mL) was added 2.4 M n-butyllithium (27.6 mL, 66.2 mmol), the mixture stirred 1 min at −78° C. To this mixture at −78° C. was added 4-(4-bromo-3-fluorophenyl)-4-fluorotetrahydro-2H-pyran (16.7 g, 60.2 mmol) in THF (180 mL) chilled to −78° C. over 2 min via cannula needle. The resulting mixture stirred for 20 min at −78° C. To the resulting solution at −78° C. was added crushed solid CO$_2$ (8 g, 182 mmol). The reaction mixture was stirred for 10 min at −78° C. The mixture was diluted with water (500 mL) and extracted with EtOAc (2× 400 mL). The aqueous layer was mixed with 4 N aq. HCl until pH 1 was obtained and then extracted EtOAc (2× 200 mL). The combined organic layers were washed with brine, dried (MgSO$_4$), filtered and concentrated under reduced pressure to provide the title compound (17.2 g, 89%). $^1$H NMR (400 MHz, CDCl$_3$) δ=7.63 (ddd, J=8.4, 7.2, 1.2 Hz, 1H), 6.99 (d, J=8.4 Hz, 1H), 4.00 (dd, J=11.6, 5.2 Hz, 2H), 3.88 (td, J=12, 2 Hz, 2H), 2.23 (dtd, J=40, 12, 5 Hz, 2H), 2.10 (dd, J=12.8, 10.8 Hz, 2H); $^{19}$F NMR (376 MHz, CDCl$_3$) δ=−108.39 (d, J=8.3 Hz, 1F), −156.43 (tt, J=40, 9 Hz, 1F).

Step 4. Benzyl 3-bromo-2-fluoro-6-(4-fluorotetrahydro-2H-pyran-4-yl)benzoate. A mixture of 3-bromo-2-fluoro-6-(4-fluorotetrahydro-2H-pyran-4-yl)benzoic acid (17.2 g, 53.6 mmol), benzyl bromide (8.3 mL, 69.7 mmol) and TEA (11.5 mL, 80.5 mmol) in dioxane (270 mL) was stirred at rt for 96 h, then at 90° C. for 10 h. Additional benzyl bromide (2.2 mL, 19 mmol) and TEA (3.8 mL, 27 mmol) were added and the mixture heated at 90° C. for 16 h. Additional benzyl bromide (2.2 mL, 19 mmol) and TEA (3.8 mL, 27 mmol) were added and the mixture heated at 90° C. for 3 h. The mixture was diluted with EtOAc (300 mL) and washed with water (2× 500 mL), and brine. The combined organics were dried (MgSO$_4$), filtered, and concentrated under reduced pressure. Purification (FCC, SiO$_2$, 10-33% EtOAc/hexanes) provided the title compound (18.7 g, 85%) as a white solid. $^1$H NMR (400 MHz, CDCl$_3$) δ=7.58 (ddd, J=8.4, 7.2, 1.6 Hz, 1H), 7.3-7.4 (m, 5H), 6.91 (dt, J=8.4, 1.2 Hz, 1H), 5.37 (s, 2H), 3.87 (dd, J=11.6, 5.6 Hz, 2H), 3.75 (td, J=12, 2.4 Hz, 2H), 2.12 (dtd, J=40, 12, 5 Hz, 2H), 2.00 (dd, J=12.8, 10.8 Hz, 2H); $^{19}$F NMR (376 MHz, CDCl$_3$) δ=−108.70 (d, J=6.4 Hz, 1F), −157.91 (tt, J=40, 9 Hz, 1F).

Step 5. Benzyl 3-cyano-2-fluoro-6-(4-fluorotetrahydro-2H-pyran-4-yl)benzoate. A mixture of benzyl 3-bromo-2-fluoro-6-(4-fluorotetrahydro-2H-pyran-4-yl)benzoate (18.7 g, 45.5 mmol), Zn(CN)$_2$ (5.87 g, 50.1 mmol), Pd$_2$(dba)$_3$ (2.09 g, 2.28 mmol), and dppf (2.52 g, 4.55 mmol) in DMF/ACN (3:1, 200 mL) was sparged with N$_2$ for 2 min, and then stirred for 16 h at 100° C. The mixture was diluted with EtOAc (300 mL) and water (1 L), and filtered. The organic layers were separated, and the aqueous layer extracted with EtOAc. The combined organic layers washed with brine, dried (MgSO$_4$), filtered, and concentrated under reduced pressure. Purification (FCC, SiO$_2$, 10-50% EtOAc/hexanes) provided the title compound (7.95 g, 49%) as a gum. $^1$H NMR (400 MHz, CDCl$_3$) δ=7.67 (ddd, 1H, J=8.4, 7.2, 1.6 Hz), 7.3-7.4 (m, 5H), 7.15 (dd, 1H, J=8.0, 0.4 Hz), 5.38 (s, 2H), 3.89 (dd, 2H, J=11.6, 5.6 Hz), 3.75 (td, 2H, J=12, 2.4 Hz), 2.12 (dtd, 2H, J=40, 12, 5 Hz), 1.99 (dd, 2H, J=12.8, 10.8 Hz); $^{19}$F NMR (376 MHz, CDCl$_3$) δ=−108.26 (d, 1F, J=6.4 Hz), −157.98 (tt, 1F, J=40, 7.5 Hz); [M+H]=358.3.

Step 6. 3-Cyano-2-fluoro-6-(4-fluorotetrahydro-2H-pyran-4-yl)benzoic acid. A mixture of benzyl 3-cyano-2-fluoro-6-(4-fluorotetrahydro-2H-pyran-4-yl)benzoate (7.95 g, 22.2 mmol) and 10% Pd/C (1.10 g) in EtOAc (90 mL) was subjected to 55 psi H$_2$ in a Parr shaker for 2.5 h. The resulting mixture was filtered through CELITE®, and the filtrate was concentrated under reduced pressure to provide (5.70 g, 96%) of the title compound as a white solid. $^1$H NMR (400 MHz, CDCl$_3$) δ=7.72 (ddd, J=8.4, 7.2, 1.6 Hz, 1H), 7.26 (t, J=8.4 Hz, 1H), 4.04 (dd, J=11.6, 5.6 Hz, 2H), 3.89 (td, J=12, 2.4 Hz, 2H), 2.30 (dtd, J=40, 12, 5 Hz, 2H), 2.09 (dd, J=12.8, 10.8 Hz, 2H); $^{19}$F NMR (376 MHz, CDCl$_3$) δ=−108.17 (d, J=6.4 Hz, 1F), −156.44 (tt, J=40, 7.5 Hz, 1F).

Step 7. Preparation of 3-Cyano-2-methoxy-6-(4-fluorotetrahydropyran-4-yl)benzoic acid. To a solution of 3-cyano-2-fluoro-6-(4-fluorotetrahydro-2H-pyran-4-yl)benzoic acid (5.70 g, 21.3 mmol) in MeOH (50 mL) was added sodium methoxide in MeOH (25 weight % solution, 58 mL, 213 mmol) and the resulting solution stirred for 13 h at 65° C. The resulting mixture was cooled by ice-bath and 4 N aq. HCl (60 mL, 240 mmol) was added. Then the mixture was diluted with water (200 mL) and extracted with EtOAc (3× 200 mL). The organic layers were combined, dried (MgSO$_4$), filtered, and concentrated under reduced pressure to provide the title compound (5.66 g, 95%) as a tan solid. $^1$H NMR (400 MHz, CDCl$_3$) δ=7.67 (dd, J=8, 1.6 Hz, 1H), 7.11 (dd, J=8, 1.6 Hz, 1H), 4.16 (s, 3H), 4.00 (dd, J=12, 5.2 Hz, 2H), 3.87 (td, J=12, 2.0 Hz, 2H), 2.13 (dtd, J=40, 12, 5 Hz, 2H), 2.08 (dd, J=12.8, 10.8 Hz, 2H); $^{19}$F NMR (376 MHz, CDCl$_3$) δ=−157.22 (tt, J=40, 10 Hz, 1F), [M−(HF)+H]=260.3.

Intermediate 13: 3-Cyano-2-methoxy-6-(1,4,4-trifluorocyclohexyl)benzoic acid

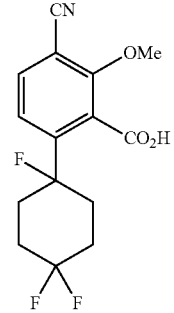 [SMILES: COc1c(C#N)ccc(C2(F)CCC(F)(F)CC2)c1C(=O)O]

The title compound was prepared in a manner analogous to Intermediate 12, Steps 1-7. $^1$H NMR (400 MHz, CDCl$_3$) δ=7.66 (dd, J=8.4, 1.6 Hz, 1H), 7.07 (dd, J=8.4, 0.8 Hz, 1H), 4.17 (s, 3H), 2.1-2.4 (m, 8H); $^{19}$F NMR (376 MHz, CDCl$_3$) δ=−93.49 (d, J=240 Hz, 1F), −104.91 (ddd, J=239, 21, 8 Hz, 1F), −158.66 (tt, J=40, 6 Hz, 1F), M−HF+H=294.3.

Intermediate 14: 3-Cyano-6-(1-fluorocyclobutyl)-2-methoxybenzoic acid

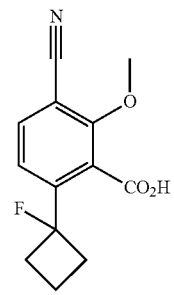 [SMILES: COc1c(C#N)ccc(C2(F)CCC2)c1C(=O)O]

The title compound was prepared in a manner analogous to Intermediate 12, Steps 1-3 and 7, substituting 2-fluoro-4-iodobenzonitrile and cyclobutanone in Step 1. $^1$H NMR (400 MHz, CDCl$_3$) δ=7.70 (dd, J=8, 1.6 Hz, 1H), 7.27 (dd, J=8.4, 1.2 Hz, 1H), 2.6-2.8 (m, 4H), 2.1-2.2 (m, 1H), 1.7-1.9 (m, 1H); $^{19}$F NMR (376 MHz, CDCl$_3$) δ=−126.83 (ddd, J=39, 22, 17 Hz, 1F); [M+H]=192.1.

Intermediate 15: 3-Cyano-2-fluoro-6-(1-fluorocyclopentyl)benzoic acid

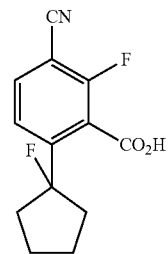 [SMILES: N#Cc1ccc(C2(F)CCCC2)c(C(=O)O)c1F]

Step 1. 2-Fluoro-4-(2-oxocyclopentyl)benzonitrile. A mixture of 4-bromo-2-fluorobenzonitrile (4.52 g, 22.6 mmol), cyclopentanone (8 mL, 90.4 mmol), Pd$_2$(dba)$_3$ (103 mg, 0.113 mmol), Xantphos® (144 mg, 0.249 mmol), K$_3$PO$_4$ (9.60 g, 45.2 mmol) in toluene (45 mL) was stirred at 80° C. for 19 h. The reaction mixture was diluted with EtOAc and water, layers separated and the organic layer washed with brine, dried (MgSO$_4$), filtered, and concentrated under reduced pressure. Purification (FCC, SiO$_2$, 10-40% EtOAc/hexanes) provided the title compound (1.90 g, 41%) as a white solid. $^1$H NMR (400 MHz, CDCl$_3$) δ=7.58 (dd, J=8, 6 Hz, 1H), 7.13 (dd, J=6, 2 Hz, 1H), 7.11 (dd, J=8, 2 Hz, 1H), 3.38 (dd, J=12, 8 Hz, 1H), 2.5-2.6 (m, 2H), 1.9-2.4 (m, 4H); [M+H]=204.1.

Step 2. 2-Fluoro-4-(2-((trimethylsilyl)oxy)cyclopent-1-en-1-yl)benzonitrile. To a mixture of NaI (2.07 g, 13.8 mmol) in ACN (5 mL) was added a solution of 2-fluoro-4-(2-oxocyclopentyl)benzonitrile (1.87 g, 9.2 mmol) in ACN (5 mL) and then TEA (2.0 mL, 13.8 mmol) was added. The mixture was chilled to 0° C. and chlorotrimethylsilane (1.77 mL, 13.8 mmol) added. After stirring at 0° C. for 10 min and 23° C. for 1 h, the reaction mixture was extracted with hexanes, and the hexane extract washed with ice-cold water and brine. The organics were dried (MgSO$_4$), filtered, and concentrated under reduced pressure to provide the title compound (2.1 g, 83%) as an oil. $^1$H NMR (400 MHz, CDCl$_3$) δ=7.48 (t, J=8 Hz, 1H), 7.50 (d, J=12 Hz, 1H), 7.37 (d, J=8 Hz, 1H), 2.5-2.6 (m, 4H), 1.96 (quin, J=7.5 Hz, 2H), 0.29 (s, 9H).

Step 3. 2-Fluoro-4-(1-fluoro-2-oxocyclopentyl)benzonitrile. To a solution of 2-fluoro-4-(2-((trimethylsilyl)oxy)cyclopent-1-en-1-yl)benzonitrile (2.10 g, 7.6 mmol) in DMF (25 mL) at 0° C. was added Selectfluor® (4.07 g, 11.5 mmol). The mixture stirred at 23° C. for 20 h. The reaction mixture was poured onto water, extracted with EtOAc, the organic extract washed with water, brine, dried (MgSO$_4$), filtered, and concentrated under reduced pressure. Purification (FCC, SiO$_2$, 10-40% EtOAc/hexanes) provided the title compound (950 mg, 57%) as a white crystalline solid. $^1$H NMR (400 MHz, CDCl$_3$) δ=7.66 (t, J=8 Hz, 1H), 7.27 (dd, J=10, 2 Hz, 1H), 7.22 (dd, J=8, 2 Hz, 1H), 2.5-2.8 (m, 2H), 2.2-2.5 (m, 3H), 2.1-2.2 (m, 1H); [M+H]=222.1.

Step 4. 2-Fluoro-4-(1-fluoro-2-hydroxycyclopentyl)benzonitrile. A mixture of 2-fluoro-4-(1-fluoro-2-oxocyclopentyl)benzonitrile (950 mg, 4.3 mmol) and NaBH$_4$ (163 mg, 4.3 mmol) was combined in MeOH (17 mL) at 0° C. and then stirred at 23° C. for 1 h. The reaction mixture was diluted with DCM, washed with water, brine, dried (MgSO$_4$) and under reduced pressure to provide the title compound (940 mg, 98%) as a white solid. $^1$H NMR (400 MHz, CDCl$_3$) δ=7.64 (t, J=8 Hz, 1H), 7.2-7.3 (m, 2H), 4.17 (dt, J=22, 7.6 Hz, 1H), 1.8-2.4 (m, 6H); [M+H]=224.1.

Step 5. O-(2-(4-Cyano-3-fluorophenyl)-2-fluorocyclopentyl) O-phenyl carbonothioate. To a solution of 2-fluoro-4-(1-fluoro-2-hydroxycyclopentyl)benzonitrile (940 mg, 4.22 mmol) and DMAP (1.031 g, 8.44 mmol) in ACN (21 mL) at 0° C. was added O-phenyl chlorothionoformate (0.64 mL, 4.64 mmol). The mixture stirred at 23° C. for 1.5 h. The reaction was diluted with EtOAc, washed with 1 M HCl, water, 1 M NaHCO$_3$, dried (MgSO$_4$), filtered, and concentrated under reduced pressure. Purification (FCC, SiO$_2$, 0-20% EtOAc/hexanes) provided the title compound (1.28 g, 85%) as a white solid. $^1$H NMR (400 MHz, CDCl$_3$) δ=7.66 (t, J=8 Hz, 1H), 7.3-7.4 (m, 5H), 7.01 (dd, J=8, 2 Hz, 2H), 5.72 (dt, J=22, 8 Hz, 1H), 2.5-2.6 (m, 1H), 2.1-2.4 (m, 4H), 1.9-2.0 (m, 1H); [M+H]=360.2.

Step 6. 2-Fluoro-4-(1-fluorocyclopentyl)benzonitrile. A mixture of o-(2-(4-cyano-3-fluorophenyl)-2-fluorocyclopentyl) o-phenyl carbonothioate (1230 mg, 3.42 mmol), tributyltin hydride (1.5 mL, 5.5 mmol) and 2,2'-azobis(2-methylpropionitrile) (112 mg, 0.68 mmol) in toluene (17 mL) was microwave heated to 140° C. for 10 min. The mixture was concentrated under reduced pressure and purified (FCC, SiO$_2$, 0-20% EtOAc/hexanes) to provide (603 mg, 82%) the title compound. $^1$H NMR (400 MHz, CDCl$_3$) δ=7.60 (t, J=8 Hz, 1H), 7.2-7.3 (m, 2H), 2.2-2.3 (m, 2H), 1.9-2.1 (m, 6H); [M+H]=208.1.

Step 7. 3-Cyano-2-fluoro-6-(1-fluorocyclopentyl)benzoic acid. The title compound was prepared in a manner analogous to Intermediate 12, Step 3, from 2-fluoro-4-(1-fluorocyclopentyl)benzonitrile. $^1$H NMR (400 MHz, CDCl$_3$) δ=7.67 (ddd, J=8, 6.4, 1.6 Hz, 1H), 7.19 (d, J=8 Hz, 1H), 5.09 (br s, 1H), 2.3-2.4 (m, 2H), 1.9-2.2 (m, 6H), [M−HF+H]=232.0.

Intermediate 16:
3-Cyano-6-fluoro-2-methoxybenzoic acid

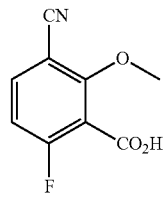

A solution of lithium diisopropylamide (18.20 mL, 36.39 mmol) in THF (25 mL) was stirred at −78° C. for ~10 minutes. A solution of 4-fluoro-2-methoxybenzonitrile (5.00 g, 33.08 mmol) in THF (15 mL) was added dropwise over 10 minutes and the resulting mixture was stirred at −78 for 1 h. The reaction mixture was poured over dry ice (excess) and then allowed to warm to rt over several hours. After all the dry ice had evaporated the crude product was dissolved in DCM (125 mL) and extracted with saturated aqueous NaHCO$_3$ (2× 70 mL). The combined aqueous extracts were acidified with conc. HCl to pH=~2, then extracted with DCM (2× 75 mL). The combined organic layers were dried (Na$_2$SO$_4$), filtered, and concentrated at reduced pressure to provide the product as a light yellow solid (4.5 g, 69%). $^1$H NMR (400 MHz, DMSO-d$_6$) δ=7.97 (dd, J=6.3, 8.6 Hz, 1H), 7.26 (t, J=8.8 Hz, 1H), 4.00 (s, 3H).

Intermediate 17: (S)-2-Chloro-3-cyano-6-((1,1,1-trifluoropropan-2-yl)oxy)benzoic acid

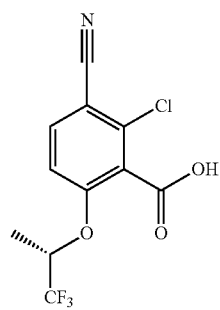 [SMILES: C[C@H](Oc1ccc(C#N)c(Cl)c1C(=O)O)C(F)(F)F]

Step 1. 2-Chloro-3-cyano-6-fluorobenzoic acid. To a solution of 2-chloro-4-fluorobenzonitrile (50 g, 0.32 mol) in THF (2000 mL) was added LDA (160 mL, 0.32 mol) at −78° C. under $N_2$ atmosphere, then stirred at this temperature for 30 min. $CO_2$ was bubbled into the mixture at −78° C. Then the mixture was stirred for another 30 min at −78° C. and at rt overnight. The mixture was poured into ice-water and acidified to pH=2 with 1 M HCl at 0° C. Then the mixture was extracted with EtOAc, the organic layer was separated and washed with brine, dried ($Na_2SO_4$), filtered, and concentrated under reduced pressure to give the title compound (47 g, 73.3%) as a white solid. $^1$H NMR (400 MHz, DMSO-$d_6$) δ=8.12-8.16 (m, 1H), 7.56-7.61 (m, 1H).

Step 2. Methyl 2-chloro-3-cyano-6-fluorobenzoate. To a solution of compound 2-chloro-3-cyano-6-fluorobenzoic acid (2 g, 0.01 mol) and $K_2CO_3$ (2.13 g, 0.015 mol) in DMF (50 mL) was added $CH_3I$ (0.62 mL, 0.015 mol) thereto at 0° C., the mixture was stirred at rt overnight. The mixture was poured into ice-water, the mixture was filtered and the filter cake was collected to give the title compound (2.14 g, 98.1%) as a white solid. $^1$H NMR (400 MHz, $CDCl_3$) δ=7.67-7.71 (m, 1H), 7.12-7.16 (m, 1H), 3.94 (s, 3H).

Step 3. Methyl 2-chloro-3-cyano-6-((1,1,1-trifluoropropan-2-yl)oxy)benzoate. To a mixture of methyl 2-chloro-3-cyano-6-fluorobenzoate (85 g, 0.40 mol) and $Cs_2CO_3$ (130.32 g, 0.40 mol) in THF (850 mL) was added 1,1,1-trifluoropropan-2-ol (45.5 g, 0.40 mol) at 0° C. Then the resulting mixture was stirred at rt overnight. The mixture was poured into ice-water, the mixture was filtered and the filter cake was collected to give the title compound (80 g, 68.3%) as a white solid. $^1$H NMR (400 MHz, $CDCl_3$) δ=7.67-7.69 (d, J=8.8 Hz, 1H), 6.97-6.99 (d, J=8.8 Hz, 1H), 4.74-4.77 (m, 1H), 3.93 (s, 3H), 1.51-1.52 (d, J=7.2 Hz, 3H).

Step 4. 2-Chloro-3-cyano-6-((1,1,1-trifluoropropan-2-yl)oxy)benzoic acid. A solution of methyl 2-chloro-3-cyano-6-((1,1,1-trifluoropropan-2-yl)oxy)benzoate (100 g, 0.33 mol) and LiI (174 g, 1.29 mol) in pyridine (1000 mL) was refluxed for 2 h. The solution was poured into ice-water and acidified to pH=2 with 1 M HCl at 0° C., then the mixture was extracted with EtOAc, the organic layer was separated and washed with brine, dried ($Na_2SO_4$), filtered, and concentrated under reduced pressure to give the title compound (87 g, 95%) as a white solid. $^1$H NMR (400 MHz, $CD_3OD$) δ=7.83-7.85 (d, J=8.8 Hz, 1H), 7.33-7.35 (d, J=9.2 Hz, 1H), 5.21-5.23 (m, 1H), 1.49-1.51 (d, J=6.4 Hz, 3H).

Step 5. Benzyl 2-chloro-3-cyano-6-((1,1,1-trifluoropropan-2-yl)oxy)benzoate. To a mixture of 2-chloro-3-cyano-6-((1,1,1-trifluoropropan-2-yl)oxy)benzoic acid (86 g, 0.29 mol) and $K_2CO_3$ (92.75 g, 0.59 mol) in DMF (1500 mL) was added BnBr (55.2 g, 0.32 mol) at 0° C., then the resulting mixture was stirred at rt overnight. The mixture was poured into ice-water and extracted with EtOAc, the organic layer was separated and washed with brine, dried ($Na_2SO_4$), filtered, concentrated to give the title compound (85 g, 74.7%) as brown oil. The title compound was separated by SFC to give (S)-benzyl 2-chloro-3-cyano-6-((1,1,1-trifluoropropan-2-yl)oxy)benzoate (Peak 1) (63 g) and compound (R)-benzyl 2-chloro-3-cyano-6-((1,1,1-trifluoropropan-2-yl)oxy)benzoate (Peak 2) (66 g).

Step 6. (S)-2-Chloro-3-cyano-6-((1,1,1-trifluoropropan-2-yl)oxy)benzoic acid. To a solution of compound (S)-benzyl 2-chloro-3-cyano-6-((1,1,1-trifluoropropan-2-yl)oxy)benzoate (10 g, 26 mmol) in EtOAc (600 mL) and conc. HCl (60 mL) was added Pd/C (1 g) under $N_2$ atmosphere. After the addition, the mixture was stirred under $H_2$ balloon at rt overnight. Then the mixture was filtered and the filtrate was concentrated under reduced pressure to give the title compound (6 g, 81%) as a brown oil. $^1$H NMR (400 MHz, $CDCl_3$) δ=7.65-7.67 (d, 1H), 6.92-6.95 (d, 1H), 4.66-4.74 (m, 1H), 1.44-1.51 (s, 3H).

Intermediate 18: (R)-2-Chloro-3-cyano-6-((1,1,1-trifluoropropan-2-yl)oxy)benzoic acid

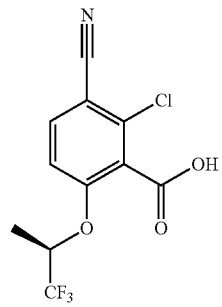 [SMILES: C[C@@H](Oc1ccc(C#N)c(Cl)c1C(=O)O)C(F)(F)F]

The title compound was prepared in a manner analogous to Intermediate 17, substituting (R)-benzyl 2-chloro-3-cyano-6-((1,1,1-trifluoropropan-2-yl)oxy)benzoate (Peak 2) in Step 6.

Intermediate 19: (S)-3-Cyano-2-methoxy-6-((1,1,1-trifluoropropan-2-yl)oxy)benzoic acid

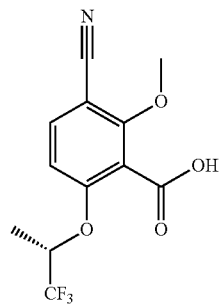 [SMILES: COc1c(C#N)ccc(O[C@@H](C)C(F)(F)F)c1C(=O)O]

Step 1. 3-Cyano-2,6-difluorobenzoic acid. To a solution of 2,4-difluorobenzonitrile (100 g, 0.718 mol) in THF (2000 mL) was added LDA (360 mL, 0.718 mol) at −78° C. under $N_2$ atmosphere, and then stirred at this temperature for 30 min. $CO_2$ was bubbled into the mixture at −78° C. Then the mixture was stirred at −78° C. for another 30 min and at rt overnight. The mixture was poured into ice-water and acidified to pH=~2 with 1 M HCl at 0° C. Then the mixture was extracted with EtOAc, the organic layer was separated and washed with brine, dried ($Na_2SO_4$), filtered, and concentrated under reduced pressure to give the title compound (84 g, 68%) as a white solid. $^1$H NMR (400 MHz, $CDCl_3$) δ=8.14-8.19 (m, 1H), 7.44-7.49 (m, 1H).

Step 3. Benzyl 3-cyano-2,6-difluorobenzoate. To a mixture of 3-cyano-2,6-difluorobenzoic acid (50 g, 0.27 mol) and $K_2CO_3$ (86 g, 0.54 mol) in DMF (1000 mL) was added BnBr (51 g, 0.29 mol) dropwise at 0° C. The resulting mixture was stirred at rt overnight. The mixture was poured into ice-water and extracted with EtOAc. The organic layers were combined and washed with brine and dried ($Na_2SO_4$), filtered, concentrated under reduced pressure to give the title compound (72 g, 97.7%) as a brown oil. $^1$H NMR (400

MHz, CDCl₃) δ=7.70-7.75 (m, 1H), 7.36-7.44 (m, 5H), 7.06-7.11 (m, 1H), 5.41 (s, 2H).

Step 3. Benzyl 3-cyano-2-fluoro-6-((1,1,1-trifluoropropan-2-yl)oxy)benzoate. To a mixture of benzyl 3-cyano-2,6-difluorobenzoate (350 g, 1.28 mol) and Cs₂CO₃ (1251 g, 3.84 mol) in THF (6000 mL) was added 1,1,1-trifluoropropan-2-ol (146 g, 1.28 mol) at 0° C. The resulting mixture was stirred at rt overnight. The mixture was poured into ice-water and extracted with EtOAc, the organic layer was separated and washed with brine, dried (Na₂SO₄), filtered, and concentrated to give the crude product. Purification (FCC, SiO₂) afforded the title compound (108 g, 37.9%) as a yellow oil. The title compound was separated by SFC to give (S)-benzyl 3-cyano-2-fluoro-6-((1,1,1-trifluoropropan-2-yl)oxy)benzoate (peak 1) (79 g) and (R)-benzyl 3-cyano-2-fluoro-6-((1,1,1-trifluoropropan-2-yl)oxy)benzoate (peak2) (81 g). ¹H NMR (400 MHz, CDCl₃) δ=7.65-7.69 (m, 1H), 7.39-7.44 (m, 5H), 6.86-6.88 (d, 1H), 5.40-5.41 (s, 2H), 4.75-4.78 (m, 1H), 1.47-1.49 (d, 3H).

Step 4. (S)-3-Cyano-2-fluoro-6-((1,1,1-trifluoropropan-2-yl)oxy)benzoic acid. To a solution of (S)-benzyl 3-cyano-2-fluoro-6-((1,1,1-trifluoropropan-2-yl)oxy)benzoate (peak 1) (10 g, 0.027 mol) in EtOAc (600 mL) was added Pd/C (1 g) under N₂ atmosphere. After the addition, the mixture was stirred under H₂ balloon at rt overnight. Then the mixture was filtered and the filtrate was concentrated under reduced pressure to give the title compound (6 g, 80%) as a brown oil. ¹H NMR (400 MHz, DMSO-d₆) δ=8.01-8.05 (m, 1H), 7.38-7.40 (d, 1H), 5.52-5.55 (m, 1H), 1.41-1.43 (d, 3H).

Step 5. (S)-3-Cyano-2-methoxy-6-((1,1,1-trifluoropropan-2-yl)oxy)benzoic acid. (S)-3-Cyano-2-fluoro-6-((1,1,1-trifluoropropan-2-yl)oxy)benzoic acid (12 g, 0.043 mol) and MeONa (46.8 g, 0.86 mol) was dissolved in ACN (120 mL) at rt for 5 min. Then the solution was poured into ice-water and acidified to pH=2 with 1 M HCl, and the mixture was extracted with EtOAc, the organic layer was separated and washed with brine, dried (Na₂SO₄) and concentrated under reduced pressure to give crude product. Purification (FCC, SiO₂) afforded the title compound (6.5 g, 52%) as a white solid: ¹H NMR (400 MHz, CDCl₃) δ=7.63-7.65 (d, J=8.8 Hz, 1H), 6.77-6.80 (d, J=8.8 Hz, 1H), 4.74-4.76 (m, 1H), 4.16 (s, 3H), 1.54-1.56 (d, J=6.4 Hz, 3H).

Intermediate 20: (R)-3-Cyano-2-methoxy-6-((1,1,1-trifluoropropan-2-yl)oxy)benzoic acid

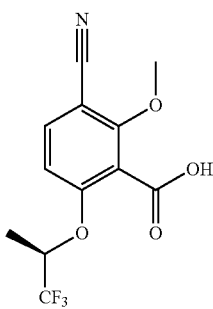

The title compound was prepared in a manner analogous to Intermediate 19, substituting (R)-benzyl 3-cyano-2-fluoro-6-((1,1,1-trifluoropropan-2-yl)oxy)benzoate (peak 2) in Step 4.

Intermediate 21: 3-Cyano-6-cyclopentyl-2-fluorobenzoic acid

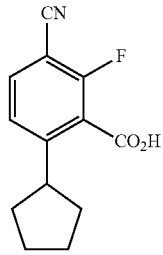 [SMILES: N#Cc1ccc(C2CCCC2)c(C(=O)O)c1F]

Step 1. 6-Bromo-3-cyano-2-fluorobenzoic acid. The title compound was prepared in a manner analogous to Intermediate 15, Step 1.

Step 2. 3-Cyano-6-(cyclopent-1-en-1-yl)-2-fluorobenzoic acid. To a 100 mL flask was added 6-bromo-3-cyano-2-fluorobenzoic acid (2.0 g, 8.2 mmol), 2-(cyclopent-1-en-1-yl)-4,4,5,5-tetramethyl-1,3,2-dioxaborolane (2.6 mL, 2.39 mmol), Pd(dba)₂ (0.375 g, 0.41 mmol), di-tert-butyl(methyl)phosphoniumtetrafluoroborate salt (0.36 g, 1.23 mmol), potassium phosphate (5.22 g, 24.6 mmol), and THF:H₂O (41 mL, 4:1). The mixture was heated to 80° C. and stirred at that temperature for 1 h. The reaction mixture was basicified with 1 M NaOH and washed with EtOAc (2× 100 mL). The aqueous layer was acidified with 1 M HCl and extracted with EtOAc (3× 25 mL). The organic layers were combined, dried (MgSO₄), filtered, and concentrated under reduced pressure. The title compound was used crude without further purification.

Step 3. 3-Cyano-6-cyclopentyl-2-fluorobenzoic acid. To a 150 mL pressure-vessel was added 3-cyano-6-(cyclopent-1-en-1-yl)-2-fluorobenzoic acid (1.89 g, 8.20 mmol), 10% Pd/C (0.38 g, 0.36 mmol), and 1:1 EtOAc:MeOH (82 mL). The reaction mixture was evacuate and backfilled with N₂ (3 times) and then evacuated and backfilled with H₂ (3 times). On the last refill, the hydrogen-pressure was adjusted to 30-35 psi. The mixture was shook under 40 psi of H₂ for 24 h. The crude material was used in the next step without further purification (0.67 g, 35%). [M+H]=234.1.

Intermediate 22: 3-Cyano-6-cyclopentyl-2-methoxy-benzoic acid

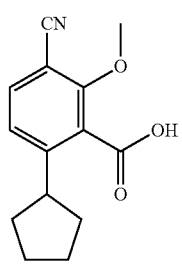 [SMILES: COc1c(C#N)ccc(C2CCCC2)c1C(=O)O]

Step 1. 6-Bromo-3-cyano-2-fluoro-benzoic acid. Diisopropylamine (5.25 mL, 37 mmol) was slowly added to a solution of n-BuLi 2.5M in hexanes (14 mL, 35 mmol) and dry THF (50 mL) at 0° C. The reaction mixture was stirred at 0° C. for 15 min. and cooled to −78° C. A solution of 4-bromo-2-fluoro-benzonitrile (5 g, 25 mmol) in THF (20 mL) was added dropwise to the reaction mixture. The reaction mixture was stirred for 15 min. Dry-ice pellets were charged into a separated flask that was capped with an unfolded septum. The sublimating $CO_2$ was passed through a drierite laboratory gas drying unit, then added subsurface to the reaction mixture (bubbling) while the temperature was slowly allowed to reach 0° C. The reaction mixture was then allowed to warm to ambient temperature and stirred for 2 h. The reaction was quenched with water (20 mL) and the product was extracted with a 0.5 M NaOH solution (4× 40 mL). The combined aqueous layers were washed with EtOAc (2× 50 mL). The separated aqueous layer was acidified to pH 1 using a 2M HCl solution. The product was extracted using EtOAc (3× 100 mL). The combined organic layers were washed with brine, dried ($Na_2SO_4$), filtered, and concentrated under reduced pressure to provide the title compound (5.02 g, 82%) as a solid. The product was used for the next step without further purification. NMR (300 MHz, DMSO-$d_6$) δ 7.96 (dd, J=8.4, J=7.0 Hz, 1H), 7.80 (dd, J=8.4, J=0.8 Hz, 1H).

Step 2. 6-Bromo-3-cyano-2-methoxy-benzoic acid. Sodium methoxide 25% in MeOH (40 mL, 175 mmol) was added to a solution of 6-bromo-3-cyano-2-fluoro-benzoic acid (5.02 g, 21 mmol) in MeOH (60 mL). The reaction mixture was heated to 65° C. and stirred for 18 h. The reaction mixture was allowed cool to ambient temperature and the solvent was concentrated under reduced pressure. The residue was recovered in HCl 0.5M (100 mL) and the mixture pH was adjusted to 1 using concentrated HCl. The product was extracted with EtOAc (3× 75 mL). The combined organic layers were washed with brine, dried ($Na_2SO_4$), filtered, and concentrated under reduced pressure to provide the title compound (4.65 g, 88%) as a solid. The product was used for the next step without further purification. $^1$H NMR (300 MHz, DMSO-$d_6$) δ 7.81 (d, J=8.4 Hz, 1H), 7.62 (d, J=8.4 Hz, 1H), 4.00 (s, 3H).

Step 3. 3-Cyano-6-(cyclopenten-1-yl)-2-methoxy-benzoic acid. Pd(OAc)$_2$ (0.48 g, 2.14 mmol) and PPh$_3$ (1.12 g, 4.29 mmol) were added to a degassed solution of DME (200 mL). The argon bubbling was continued for 30 min and the mixture was stirred until a dark-orange color appears (~20 min). Together was added 6-bromo-3-cyano-2-methoxy-benzoic acid (5.5 g, 21.4 mmol) and Cs$_2$CO$_3$ (17.5 g, 53.7 mmol) followed by degassed water (50 mL) and a solution of 2-(cyclopenten-1-yl)-4,4,5,5-tetramethyl-1,3,2-dioxaborolane (6.25 g, 32.2 mmol) in DME (3 mL). The reaction mixture was degassed with argon for 15 min. The reaction mixture was then heated to 88° C. for 3 h. The reaction mixture was allowed to cool to ambient temperature and partitioned between HCl 0.5 M (300 mL) and EtOAc (300 mL). The separated aqueous layer was washed with EtOAc (3× 100 mL). The combined organic layers were washed with brine, dried (Na$_2$SO$_4$), filtered and concentrated under reduced pressure. Purification (FCC, SiO$_2$, 1% AcOH/1% MeOH/DCM) afforded the title compound (3.70 g, 70%) as yellow gum. $^1$H NMR (300 MHz, CDCl$_3$) δ 7.59 (d, J=8.2 Hz, 1H), 7.15 (d, J=8.2 Hz, 1H), 6.15 (m, 1H), 4.13 (s, 3H), 2.70 (m, 2H), 2.54 (m, 2H), 2.02 (m, 2H); [M+H]$^+$=244.2.

Step 4. 3-Cyano-6-cyclopentyl-2-methoxy-benzoic acid. Hydrogen gas was passed through a stirred mixture of 10% Pd/C (710 mg, 0.66 mmol), EtOH (200 mL) and 3-cyano-6-(cyclopenten-1-yl)-2-methoxy-benzoic acid (3.70 g, 15.2 mmol) for 60 min. The reaction mixture was filtered over a CELITE® pad and the solvent was concentrated under reduced pressure. Purification (FCC, SiO$_2$, 1% AcOH/20% of EtOAc/hexanes) provided the title compound (3.09 g, 88%) as colorless gum. $^1$H NMR (300 MHz, CDCl$_3$) δ 7.60 (d, J=8.3 Hz, 1H), 7.17 (d, J=8.3 Hz, 1H), 4.13 (s, 3H), 3.13 (m, 1H), 2.12 (m, 2H), 1.83 (m, 2H), 1.71 (m, 2H), 1.58 (m, 2H); [M−OH]$^+$=228.2.

Intermediate 23. 3-Cyano-6-(4-fluorotetrahydro-2H-pyran-4-yl)-2-methoxybenzoyl chloride

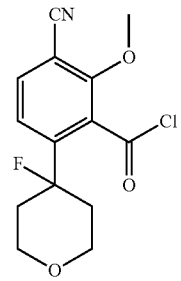 [SMILES: COc1c(C#N)ccc(C2(F)CCOCC2)c1C(=O)Cl]

To a solution of 3-cyano-6-(4-fluorotetrahydro-2H-pyran-4-yl)-2-methoxybenzoic acid (Intermediate 12, 60 mg, 0.21 mmol) in DCM (1 mL) was added oxalyl dichloride (22.5 μL, 0.26 mmol) followed by one drop of DMF. The reaction mixture was stirred at rt for 30 minutes. The reaction mixture was dried under reduced pressure and used crude without further purification (64 mg, 99%).

Intermediate 24. (S)-3-Cyano-2-methoxy-6-((1,1,1-trifluoropropan-2-yl)oxy)benzoyl chloride

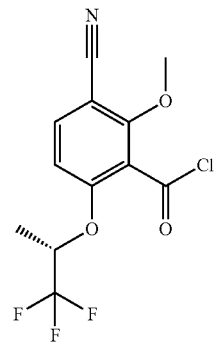

A solution of (S)-3-cyano-2-methoxy-6-((1,1,1-trifluoropropan-2-yl)oxy)benzoic acid (251 mg, 0.87 mmol) in thionyl chloride (0.32 mL, 4.34 mmol) was heated to 80° C. for 30 minutes. The reaction was cooled and concentrated under reduced pressure. The crude product was again diluted with EtOAc and concentrated under reduced pressure to afford the title compound which was used crude without further purification.

Intermediate 25. (S)-3-(3-Aminoazetidine-1-carbonyl)-2-methoxy-4-((1,1,1-trifluoropropan-2-yl)oxy)benzonitrile

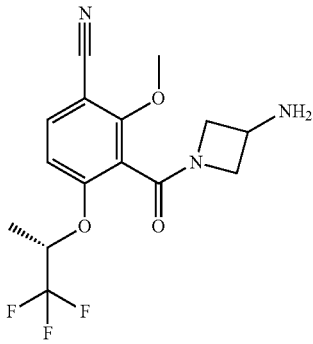 [SMILES: COc1c(C#N)ccc(O[C@@H](C)C(F)(F)F)c1C(=O)N1CC(N)C1]

Step 1. (S)-tert-Butyl (1-(3-cyano-2-methoxy-6-((1,1,1-trifluoropropan-2-yl)oxy)benzoyl)azetidin-3-yl)carbamate. To a cooled solution, 0° C., of tert-butyl azetidin-3-ylcarbamate HCl salt (217 mg, 1.04 mmol) in DCM was added DIEA (0.36 mL, 2.17 mmol). To the cooled reaction mixture was added a solution of (S)-3-cyano-2-methoxy-6-((1,1,1-trifluoropropan-2-yl)oxy)benzoyl chloride (Intermediate 24) in DCM (4 mL) and the reaction mixture was stirred at rt for an additional 3 h. The reaction mixture was washed with sat. aq. NaHCO₃. The organic layer was separated, dried (Na₂SO₄), filtered, and concentrated under reduced pressure. Purification (FCC, SiO₂, 10-90% EtOAc/hexanes) afforded the title compound which was used directly in the next step.

Step 2. (S)-3-(3-Amino azetidine-1-carbonyl)-2-methoxy-4-((1,1,1-trifluoropropan-2-yl)oxy)benzonitrile. (S)-tert-butyl (1-(3-cyano-2-methoxy-6-((1,1,1-trifluoropropan-2-yl)oxy)benzoyl)azetidin-3-yl)carbamate (product from the previous step) was treated with 4N HCl/dioxane (5 mL) and stirred at rt for 1 hour. Solvent was removed under reduced pressure to provide the title compound which was used crude without further purification.

Intermediate 26. (S)-3-(3-(5-Bromopyridin-2-yl)azetidine-1-carbonyl)-2-methoxy-4-((1,1,1-trifluoropropan-2-yl)oxy)benzonitrile

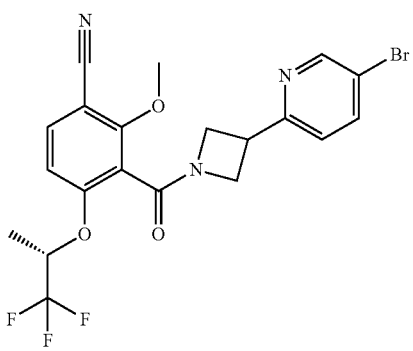 [SMILES: COc1c(C#N)ccc(O[C@@H](C)C(F)(F)F)c1C(=O)N1CC(c2ccc(Br)cn2)C1]

The title compound was prepared in a manner analogous to Intermediate 25 Step 1, with the appropriate starting material substitutions.

Intermediate 27. 6-Isopropoxy-2-methoxy-3-methylsulfonyl-benzoic acid

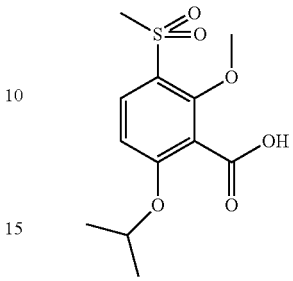

Step 1. Methyl 2-fluoro-6-isopropoxy-3-methylsulfonyl-benzoate. The title compound was prepared in a manner analogous to Intermediate 10, Steps 1-3.

Step 2. Methyl 2-fluoro-6-isopropoxy-3-methylsulfonyl-benzoate. Sodium hydride (2.55 g, 64 mmol, 60% suspension in oil) was added to isopropanol (1.3 L) under an argon atmosphere. The mixture was stirred for 1 hr. DIPEA (11.1 mL, 64 mmol) and methyl 2,6-difluoro-3-methylsulfonyl-benzoate (16 g, 64 mmol) were then added successively. The reaction mixture was vigorously stirred until a clear solution was obtained (1.5 h) and the mixture was concentrated. The residue was diluted with 0.1M HCl (400 mL) and the product was extracted with EtOAc (4× 100 mL). The combined organic layers were washed with water then brine, dried (MgSO₄), filtered and concentrated under reduced pressure to provide a mixture of title compound and isopropyl 2-fluoro-6-isopropoxy-3-methylsulfonyl-benzoate. The product was used in the next step without further purification. $[M+H]^+=291.2$, and isopropyl 2-fluoro-6-isopropoxy-3-methylsulfonyl-benzoate $[M+H]^+=319.1$.

Step 3. Methyl 6-isopropoxy-2-methoxy-3-methylsulfonyl-benzoate. Sodium methoxide 25% w/w in MeOH (161 mL, 0.70 mol) was added to a solution of methyl 2-fluoro-6-isopropoxy-3-methylsulfonyl-benzoate and isopropyl 2-fluoro-6-isopropoxy-3-methylsulfonyl-benzoate (19.4 g, 64 mmol) in MeOH (400 mL). The reaction mixture was stirred for 18 h and then concentrated under reduced pressure. The residue was diluted in cold 1M HCl (800 mL). The product was extracted with EtOAc (4× 150 mL). The combined organic layers were washed with brine, dried (MgSO₄), filtered, and concentrated under reduced pressure. Purification (MPLC, SiO₂) provided a mixture of title compound and isopropyl 6-isopropoxy-2-methoxy-3-methylsulfonyl-benzoate (20.2 g, 64 mmol (100% yield of a 1:1 mixture assumed for the next step)) as a solid. $[M+H]^+=303.1$ and isopropyl 6-isopropoxy-2-methoxy-3-methylsulfonyl-benzoate $[M+H]^+=331.1$.

Step 4. 6-Isopropoxy-2-methoxy-3-methylsulfonyl-benzoic acid. A 2.5M aqueous solution of LiOH (128 mL, 320 mmol) was added to a solution of methyl 6-isopropoxy-2-methoxy-3-methylsulfonyl-benzoate and isopropyl 6-isopropoxy-2-methoxy-3-methylsulfonyl-benzoate (20.2 g, 64 mmol) in DMSO (150 mL). The reaction mixture was heated to 105° C. and stirred for 3 h. The reaction mixture was allowed to cool to ambient temperature. The reaction mixture was poured into cold 1M HCl (800 mL). The product was extracted with DCM (4× 150 mL). The combined organic layers were washed with brine, dried (Na₂SO₄), filtered, and concentrated under reduced pressure. Purification (MPLC, SiO$_2$, 40% EtOAc/hexane, 1% AcOH) provided the title compound (7.15 g, 38% over three steps) as a solid. $^1$H NMR (300 MHz, CDCl$_3$) 7.99 (d, J=9.0 Hz, 1H), 6.83 (d, J=9.1 Hz, 1H), 4.72 (sep, J=6.1 Hz, 1H), 4.08 (s, 3H), 3.22 (s, 3H), 1.40 (d, J=6.1 Hz, 6H). [M−OiPr]$^+$=229.0.

TABLE 3

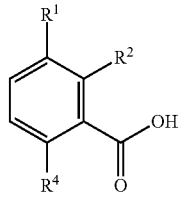

| R$^4$ | R$^1$ | R$^2$ | Prepared analogous to INT # |
|---|---|---|---|
| 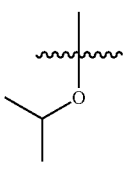 | —CN<br>SO$_2$CH$_2$CH$_3$ | —OCH$_3$<br>—OCH$_3$ | 16, 19 Step 3<br>27 |
| 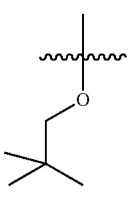 [SMILES: *OCC(C)(C)C] | —OS$_2$CH$_3$ | —OCH$_3$ | 27 |
| 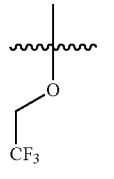 | —CN<br>—CN<br>—SO$_2$CH$_3$ | —OCH$_3$<br>—Cl<br>—OCH$_3$ | 19<br>17<br>27 |
| 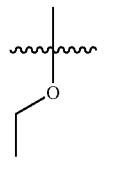 | —CN | —OCH$_3$ | 19 |
| 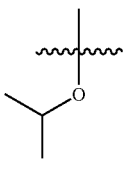 [SMILES: *OC(C)C] | —CN<br>—CN<br>—SO$_2$CH$_3$ | —Cl<br>—OCH$_3$<br>—OCH$_3$ | 17<br>19<br>10 |

TABLE 3-continued

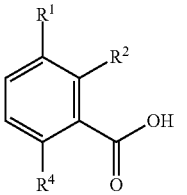

| R$^4$ | R$^1$ | R$^2$ | Prepared analogous to INT # |
|---|---|---|---|
| 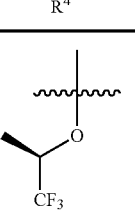 | —CN<br>—SO$_2$CH$_3$<br>—CN | —OCH$_3$<br>—OCH$_3$<br>—Cl | 19<br>10<br>17 |
| 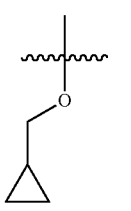 | —CN | —OCH$_3$ | 16, 19 Step 3 |
| 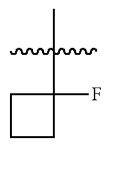 [SMILES: *C1(F)CCC1] | —CN | —OCH$_3$ | 12, Steps 1-3 and 7 |
| 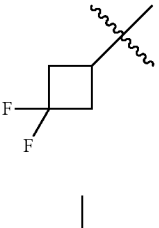 | —CN | —OCH$_3$ | 12 |
| 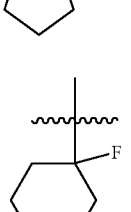 | —CN | —F | 15 |
|  | —CN | —OCH$_3$ | 12, Steps 1-7 |

CHEMISTRY EXAMPLES

Example 1. 4-(4-Fluorotetrahydro-2H-pyran-4-yl)-2-methoxy-3-(3-((5-(trifluoromethyl)pyridin-2-yl)amino)azetidine-1-carbonyl)benzonitrile

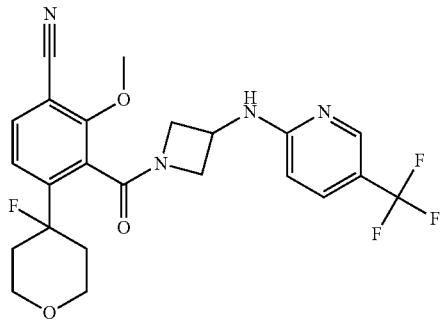 [SMILES: COc1c(C#N)ccc(C2(F)CCOCC2)c1C(=O)N1CC(Nc2ccc(C(F)(F)F)cn2)C1]

Step 1. tert-Butyl (1-(3-cyano-6-(4-fluorotetrahydro-2H-pyran-4-yl)-2-methoxybenzoyl)azetidin-3-yl)carbamate. To a chilled solution, 0° C., of tert-butyl azetidin-3-ylcarbamate (183 mg, 0.88 mmol) in DCM (5.00 mL), was added DIEA (0.58 mL, 3.51 mmol) followed by 3-cyano-6-(4-fluorotetrahydro-2H-pyran-4-yl)-2-methoxybenzoyl chloride (Intermediate 23, 261 mg, 0.88 mmol). The reaction mixture was stirred for 18 h at rt. The reaction mixture was then washed with water then brine. The combined organic layers were isolated, dried (MgSO$_4$), filtered and concentrated under reduced pressure. The resulting residue was purified (FCC, SiO$_2$, 40-100% EtOAc/Hexanes) to afford the title compound.

Step 2. 3-(3-Aminoazetidine-1-carbonyl)-4-(4-fluorotetrahydro-2H-pyran-4-yl)-2-methoxybenzonitrile. tert-Butyl (1-(3-cyano-6-(4-fluorotetrahydro-2H-pyran-4-yl)-2-methoxybenzoyl)azetidin-3-yl)carbamate (from Step 1.) was combined with 4N hydrochloric acid in dioxane (5 mL, 4 mol/L, 20 mmol) for 1 h. The solvents were removed under reduced pressure and resulting residue was taken up in minimum amount of MeOH and poured onto diethyl ether. The resulting white precipitate was collected and dried under reduced pressure to afford the title compound (210 mg, 69%).

Step 3. To a solution of 3-(3-aminoazetidine-1-carbonyl)-4-(4-fluorotetrahydro-2H-pyran-4-yl)-2-methoxybenzonitrile (55 mg, 0.15 mmol) in DMF (1 mL), was added DIEA (0.12 mL, 0.74 mmol) and 2-fluoro-5-(trifluoromethyl)pyridine (120 mg, 0.74 mmol). The reaction mixture was stirred in sealed vessel at 80° C. for 90 minutes. The reaction mixture was cooled and the solvent was removed under reduced pressure. Purification (FCC, SiO$_2$, 10-80% EtOAc/hexanes) afforded the title compound as a white solid (16 mg, 22%). $^1$H NMR (400 MHz, DMSO-d$_6$) δ=8.27 (s, 1H), 8.07-7.94 (m, 1H), 7.87 (d, J=8.2 Hz, 1H), 7.67 (d, J=8.6 Hz, 1H), 7.41 (t, J=8.4 Hz, 1H), 6.61 (dd, J=4.7, 8.6 Hz, 1H), 4.61 (dd, J=5.7, 11.9 Hz, 1H), 4.40-4.28 (m, 1H), 4.05-3.75 (m, 7H), 3.72-3.53 (m, 3H), 2.60-2.51 (m, 1H), 2.13-1.95 (m, 2H), 1.94-1.67 (m, 2H); [M+H]=479.34.

Example 2. (S)-2-Methoxy-3-(3-((5-(trifluoromethyl)pyridin-2-yl)amino)azetidine-1-carbonyl)-4-((1,1,1-trifluoropropan-2-yl)oxy)benzonitrile

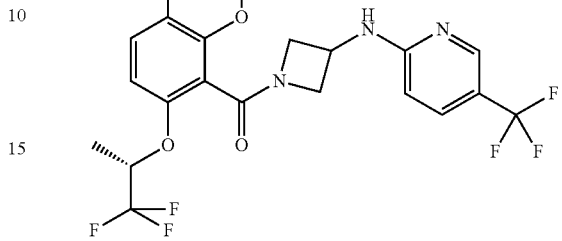

To a solution of N-(azetidin-3-yl)-5-(trifluoromethyl)pyridin-2-amine hydrochloride (Intermediate 1, 26 mg, 0.1 mmol) in DCM (1.00 mL) was added DIEA (0.067 mL, 0.41 mmol) and cooled to 0° C. (S)-3-Cyano-2-methoxy-6-((1,1,1-trifluoropropan-2-yl)oxy)benzoyl chloride (Intermediate 24, 0.336 mL, 0.31 mol/L, 0.1 mmol) was then added as a solution in DCM (1 mL). The reaction mixture was stirred at rt for 18 h. The solvent was removed under reduced pressure. Purification (FCC, SiO$_2$, 10% MeOH/DCM) afforded title compound as off-white semi-solid (29 mg, 55%). $^1$H NMR (400 MHz, DMSO-d$_6$) δ=8.28 (br s, 1H), 8.05-7.91 (m, 1H), 7.85 (br s, 1H), 7.68 (d, J=8.6 Hz, 1H), 7.24-7.09 (m, 1H), 6.60 (d, J=8.6 Hz, 1H), 5.57-5.34 (m, 1H), 4.64-4.25 (m, 1H), 4.18-3.83 (m, 6H), 3.70 (br s, 1H), 1.53-1.31 (m, 4H); [M+H]=489.

Example 3. 4-(1-Fluorocyclobutyl)-2-methoxy-3-({3-[4-(trifluoromethyl)phenyl]azetidin-1-yl}carbonyl)benzonitrile

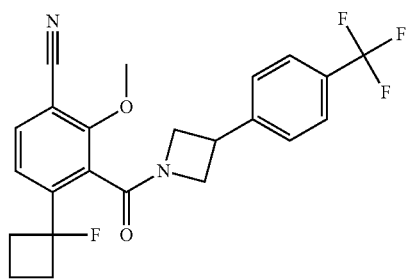 [SMILES: COc1c(C#N)ccc(C2(F)CCC2)c1C(=O)N1CC(c2ccc(C(F)(F)F)cc2)C1]

A mixture of 3-cyano-6-(1-fluorocyclobutyl)-2-methoxybenzoic acid (19 mg, 0.076 mmol), 3-(4-(trifluoromethyl)phenyl)azetidine hydrochloride (20 mg, 0.084 mmol), HATU (32 mg, 0.084 mmol), and TEA (0.027 mL, 0.191 mmol) in DMF (0.4 mL) was stirred for 2 h at rt. The reaction mixture was diluted with EtOAc, washed with water, then brine. The organics were dried (MgSO$_4$) and concentrated under reduced pressure. Purification (preparative TLC, SiO$_2$, 2:1 hexane/acetone) provided the title compound (7.4 mg, 39%) as a solid: $^1$H NMR (400 MHz, CDCl$_3$) δ=7.73-7.56 (m, 3H), 7.46 (t, J=8.8 Hz, 2H), 7.31-7.15 (m, 1H), 4.70-4.52 (m, 1H), 4.33-4.17 (m, 2H), 4.13 (d, J=10.2 Hz, 3H), 3.98-3.78 (m, 2H), 2.88-2.51 (m, 4H), 2.28-2.10 (m, 1H), 1.86-1.71 (m, 1H); LCMS: found [M+H]= 433.2.

Example 4. (S)-3-(3-(difluoro(4-(trifluoromethyl)phenyl)methyl)azetidine-1-carbonyl)-2-methoxy-4-((1,1,1-trifluoropropan-2-yl)oxy)benzonitrile

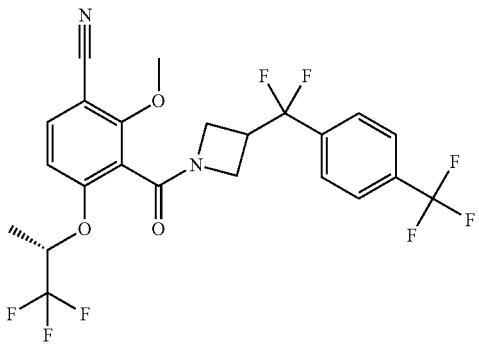 [SMILES: COc1c(C#N)ccc(O[C@@H](C)C(F)(F)F)c1C(=O)N1CC(C(F)(F)c2ccc(C(F)(F)F)cc2)C1]

Step 1. 3-(Difluoro(4-(trifluoromethyl)phenyl)methyl)azetidine. A solution of tert-butyl 3-(difluoro(4-(trifluoromethyl)phenyl)methyl)azetidine-1-carboxylate (Intermediate 3, 54 mg, 0.15 mmol) in DCM (1 mL) was treated with 50% TFA in DCM (1 mL). The reaction mixture was stirred at ambient temperature for 45 min. The reaction mixture was concentrated under reduced pressure to afford the title compound, which was used without further purification in the next step.

Step 2. (S)-3-(3-(Difluoro(4-(trifluoromethyl)phenyl)methyl)azetidine-1-carbonyl)-2-methoxy-4-((1,1,1-trifluoropropan-2-yl)oxy)benzonitrile. 3-(Difluoro(4-(trifluoromethyl)phenyl)methyl)azetidine was diluted with DCM (2 mL), treated with DIEA (0.11 mL, 0.77 mmol) and cooled to 0° C. (S)-3-Cyano-2-methoxy-6-((1,1,1-trifluoropropan-2-yl)oxy)benzoyl chloride (Intermediate 24, 0.37 mL, 0.42 mol/L, 0.15 mmol) was added, and the resulting mixture was stirred at ambient temperature for 3 h. The reaction mixture was diluted with DCM, washed with water, then brine. The organic phase was dried (Na$_2$SO$_4$), filtered, and concentrated under reduced pressure. Purification (FCC, SiO$_2$, 10-80% EtOAc/hexanes) afforded the title compound (0.047 g, 56%). $^1$H NMR (400 MHz, DMSO-d$_6$) δ=7.86 (d, J=8.6 Hz, 3H), 7.82-7.69 (m, 2H), 7.21 (d, J=9.0 Hz, 1H), 5.48 (br s, 1H), 4.17-3.76 (m, 6H), 1.48-1.34 (m, 3H); [M+H]= 523.14.

Example 5. (S)-3-(3-(3-Fluoro-5-(trifluoromethyl)pyridin-2-yl)azetidine-1-carbonyl)-2-methoxy-4-((1,1,1-trifluoropropan-2-yl)oxy)benzonitrile

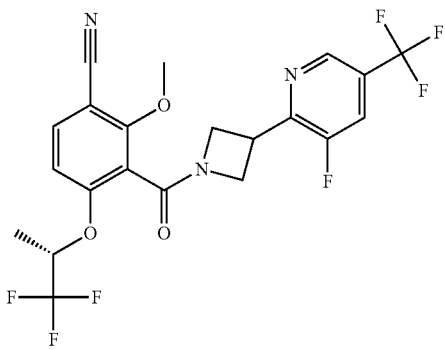 [SMILES: COc1c(C#N)ccc(O[C@@H](C)C(F)(F)F)c1C(=O)N1CC(c2ncc(C(F)(F)F)cc2F)C1]

To a cooled, 0° C., solution of 2-(azetidin-3-yl)-3-fluoro-5-(trifluoromethyl)pyridine (Intermediate 2, 35 mg, 0.1 mmol) in DCM (1 mL), was added DIEA (0.069 mL, 0.42 mmol). (S)-3-Cyano-2-methoxy-6-((1,1,1-trifluoropropan-2-yl)oxy)benzoyl chloride (Intermediate 24, 0.343 mL, 0.31 mol/L, 0.10 mmol) was then added and the reaction mixture was stirred at rt for 2 h. The solvent was removed under reduced pressure and the residue was reconstituted in DMSO (1 mL). Purification (HPLC (mass trigger): 15 min method: 30%-95% ACN:H$_2$O) afforded the title compound, which was diluted with EtOAc and washed with saturated sodium bicarbonate. The organic layers were isolated, dried (MgSO$_4$), filtered, and concentrated under reduced pressure to afford the title compound as a white solid (0.036 g, 67%). $^1$H NMR (400 MHz, DMSO-d$_6$) δ=8.92-8.78 (m, 1H), 8.28 (d, J=9.8 Hz, 1H), 7.86 (d, J=8.6 Hz, 1H), 7.24-7.12 (m, 1H), 5.58-5.35 (m, 1H), 4.45-4.06 (m, 5H), 3.96 (d, J=7.8 Hz, 3H), 1.53-1.19 (m, 3H); [M+H]=492.09.

Example 6. 2-methoxy-3-(3-(4-(tetrahydro-2H-pyran-4-yl)phenyl)azetidine-1-carbonyl)-4-((1,1,1-trifluoropropan-2-yl)oxy)benzonitrile

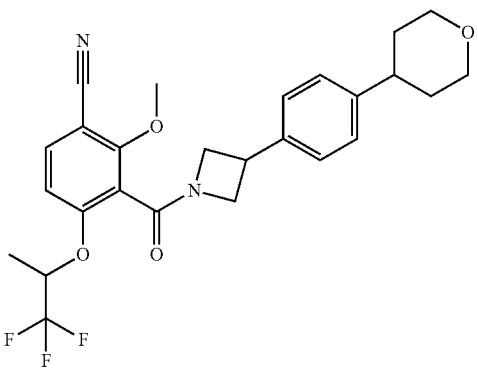 [SMILES: COc1c(C#N)ccc(OC(C)C(F)(F)F)c1C(=O)N1CC(c2ccc(C3CCOCC3)cc2)C1]

Step 1. 3-(3-(4-Bromophenyl)azetidine-1-carbonyl)-2-methoxy-4-((1,1,1-trifluoropropan-2-yl)oxy)benzonitrile. The title compound was prepared in a manner analogous to Example 2 with the appropriate starting material substitutions.

Step 2. 3-(3-(4-(3,6-Dihydro-2H-pyran-4-yl)phenyl)azetidine-1-carbonyl)-2-methoxy-4-((1,1,1-trifluoropropan-2-yl)oxy)benzonitrile. A solution of 3-(3-(4-bromophenyl)azetidine-1-carbonyl)-2-methoxy-4-((1,1,1-trifluoropropan-2-yl)oxy)benzonitrile (82 mg, 0.17 mmol), tetrakis(triphenylphosphine)palladium(0) (16 mg, 0.01 mmol), K$_2$CO$_3$ (170 mL, 2 mol/L, 0.34 mmol), 2-(3,6-dihydro-2H-pyran-4-yl)-4,4,5,5-tetramethyl-1,3,2-dioxaborolane (43 mg, 0.2 mmol) in dioxane (3 mL) was heated employing microwave irradiation at 150° C. for 15 minutes. The reaction mixture was cooled to rt, diluted with EtOAc and washed with water. The organic phase was isolated, dried (Na$_2$SO$_4$), filtered, and concentrated under reduced pressure. Purification (FCC, SiO$_2$, 10-80% EtOAc/hexanes) afforded the title compound (0.060 g, 70%).

Step 3. 3-(3-(4-(3,6-Dihydro-2H-pyran-4-yl)phenyl)azetidine-1-carbonyl)-2-methoxy-4-((1,1,1-trifluoropropan-2-yl)oxy)benzonitrile (46 mg, 0.09 mmol) was diluted with MeOH (25 mL), sparged with nitrogen and treated with Pd/C (50 mg, 0.47 mmol). The reaction atmosphere was sparged with hydrogen and pressurized to 30 PSI and shaken for 2 h. The reaction mixture was filtered and concentrated under reduced pressure. Purification (FCC, SiO$_2$, 10% EtOAc/hexanes-90% EtOAc/hexanes) afforded the title compound (0.003 g, 6%). $^1$H NMR (400 MHz, CDCl$_3$) δ=7.58 (d, J=8.6 Hz, 1H), 7.28 (br s, 1H), 7.23 (d, J=4.3 Hz, 2H), 6.77 (d, J=8.6 Hz, 1H), 4.83-4.72 (m, 1H), 4.58 (t, J=9.4 Hz, 1H), 4.22 (d, J=8.2 Hz, 2H), 4.17-4.04 (m, 5H), 3.97-3.80 (m, 2H), 3.53 (t, J=11.2 Hz, 2H), 2.82-2.71 (m, 1H), 2.02 (dd, J=1.6, 15.3 Hz, 1H), 1.85-1.71 (m, 4H); [M+H]=489.28.

Example 7. (S)-3-(3-(3-ethynyl-5-(trifluoromethyl)pyridin-2-yl)azetidine-1-carbonyl)-2-methoxy-4-((1,1,1-trifluoropropan-2-yl)oxy)benzonitrile

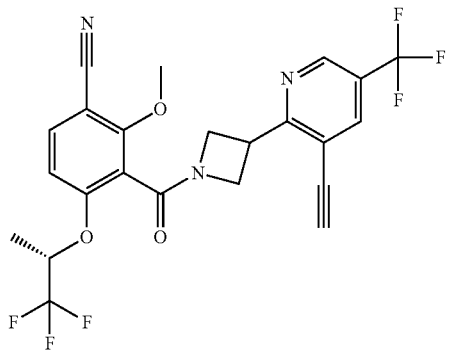 [SMILES: C#Cc1cc(C(F)(F)F)cnc1C1CN(C(=O)c2c(O[C@@H](C)C(F)(F)F)ccc(C#N)c2OC)C1]

Step 1. (S)-3-(3-(3-Bromo-5-(trifluoromethyl)pyridin-2-yl)azetidine-1-carbonyl)-2-methoxy-4-((1,1,1-trifluoropropan-2-yl)oxy)benzonitrile. The title compound was prepared in a manner analogous to Example 5, with the appropriate starting material substitutions.

Step 2. (S)-2-Methoxy-3-(3-(5-(trifluoromethyl)-3-((trimethylsilyl)ethynyl)pyridin-2-yl)azetidine-1-carbonyl)-4-((1,1,1-trifluoropropan-2-yl)oxy)benzonitrile. To a solution of (S)-3-(3-(3-bromo-5-(trifluoromethyl)pyridin-2-yl)azetidine-1-carbonyl)-2-methoxy-4-((1,1,1-trifluoropropan-2-yl)oxy)benzonitrile (150 mg, 0.27 mmol) in THF (2 mL) was added trans-dichlorobis(triphenylphosphine)palladium (II) (10 mg, 0.01 mmol), triphenyl phosphine (3 mg, 0.01 mmol), TEA (41 mg, 0.41 mmol), and ethynyltrimethylsilane (67 mg, 0.68 mmol). The reaction was was stirred under a nitrogen atmosphere for 10 minutes then treated with CuI (3 mg, 0.01 mmol). The mixture was stirred for an additional 2 h and poured onto EtOAc and washed with water. The organic layers were dried (Na$_2$SO$_4$), filtered, and concentrated under reduced pressure. Purification (FCC, SiO$_2$, 10-80% EtOAc/hexanes) afforded the TMS-protected title compound as white solid.

Step 3. (S)-3-(3-(3-Ethynyl-5-(trifluoromethyl)pyridin-2-yl)azetidine-1-carbonyl)-2-methoxy-4-((1,1,1-trifluoropropan-2-yl)oxy)benzonitrile. A solution of (S)-2-methoxy-3-(3-(5-(trifluoromethyl)-3-((trimethylsilyl)ethynyl)pyridin-2-yl)azetidine-1-carbonyl)-4-((1,1,1-trifluoropropan-2-yl)oxy)benzonitrile (product from step 2) in 1:1 DCM/MeOH (10 mL) was treated with K$_2$CO$_3$ (100 mg) for 2 h. The reaction mixture was diluted DCM, washed with water, and the combined organics were dried (Na$_2$SO$_4$), filtered, and concentrated under reduced pressure to afford the title compound as white foam (0.119 g, 85%). $^1$H NMR (400 MHz, DMSO-d$_6$) δ=9.03-8.92 (m, 1H), 8.34 (d, J=1.6 Hz, 1H), 7.89-7.82 (m, 1H), 7.25-7.13 (m, 1H), 5.58-5.37 (m, 1H), 4.87-4.79 (m, 1H), 4.59-4.20 (m, 4H), 4.17-4.06 (m, 1H), 4.00-3.90 (m, 3H), 1.54-1.26 (m, 3H); [M+H]=498.28.

Example 8. (S)-3-(3-(3-ethyl-5-(trifluoromethyl)pyridin-2-yl)azetidine-1-carbonyl)-2-methoxy-4-((1,1,1-trifluoropropan-2-yl)oxy)benzonitrile

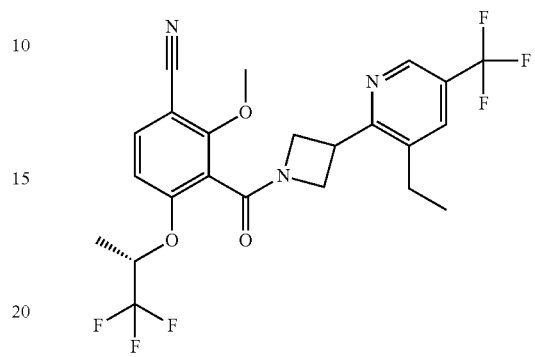

Step 1. (S)-3-(3-(3-Bromo-5-(trifluoromethyl)pyridin-2-yl)azetidine-1-carbonyl)-2-methoxy-4-((1,1,1-trifluoropropan-2-yl)oxy)benzonitrile. The title compound was prepared in a manner analogous to Example 5, with the appropriate starting material substitutions.

Step 2. (S)-3-(3-(3-Ethyl-5-(trifluoromethyl)pyridin-2-yl)azetidine-1-carbonyl)-2-methoxy-4-((1,1,1-trifluoropropan-2-yl)oxy)benzonitrile. To a solution of (S)-3-(3-(3-bromo-5-(trifluoromethyl)pyridin-2-yl)azetidine-1-carbonyl)-2-methoxy-4-((1,1,1-trifluoropropan-2-yl)oxy)benzonitrile (84 mg, 0.15 mmol) in THF (2 mL) was added tri(furan-2-yl)phosphine (2 mg, 0.01 mmol), and Pd$_2$(dba)$_3$ (3 mg, 0.01 mmol). Diethyl zinc (0.152 mL, 1.00 mol/L, 0.15 mmol) was added and the reaction temperature was increased to 60° C. for 16 h. The reaction contents were poured onto DCM (20 mL) and washed with water. The organic layer was isolated, dried (Na$_2$SO$_4$), filtered, and concentrated under reduced pressure. Purification (FCC, SiO$_2$, 10% EtOAc/hexanes-70% EtOAc/hexanes) afforded the title compound as a white solid (0.018 g, 24%). $^1$H NMR (400 MHz, DMSO-d$_6$) δ=8.89-8.73 (m, 1H), 7.99 (br s, 1H), 7.93-7.84 (m, 1H), 7.26-7.15 (m, 1H), 5.59-5.38 (m, 1H), 4.46-4.09 (m, 5H), 3.99 (d, J=6.7 Hz, 3H), 2.71-2.55 (m, 2H), 1.57-1.31 (m, 3H), 1.20-1.09 (m, 3H); [M+H]=502.31.

Example 9. (S)-2-methoxy-3-(3-(3-methoxy-5-(trifluoromethyl)pyridin-2-yl)azetidine-1-carbonyl)-4-((1,1,1-trifluoropropan-2-yl)oxy)benzonitrile

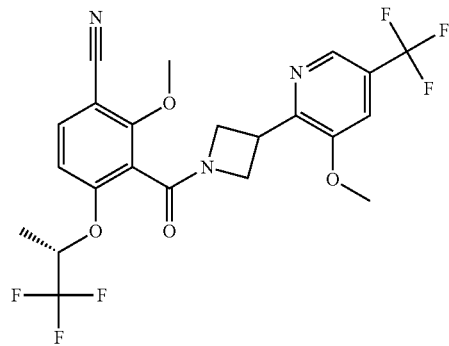 [SMILES: COc1cc(C(F)(F)F)cnc1C1CN(C(=O)c2c(O[C@@H](C)C(F)(F)F)ccc(C#N)c2OC)C1]

A solution of (S)-3-(3-(3-fluoro-5-(trifluoromethyl)pyridin-2-yl)azetidine-1-carbonyl)-2-methoxy-4-((1,1,1-trifluoropropan-2-yl)oxy)benzonitrile (Example 5, 81.2 mg, 0.17 mmol) in MeOH (2 mL) was treated with sodium methoxide solution (71 mg, 25% w/w, 0.33 mmol) and heated at 60° C. for 16 h. The reaction mixture was poured onto EtOAc (20 mL) and washed with water. The organic layer was dried (Na$_2$SO$_4$), filtered, and concentrated under reduced pressure. Purification (FCC, SiO$_2$, 10% EtOAc/hexanes-90% EtOAc/hexanes) afforded the title compound as white solid (0.059 g, 71%). $^1$H NMR (400 MHz, DMSO-d$_6$) δ=8.55-8.46 (m, 1H), 7.86 (d, J=3.9 Hz, 1H), 7.70 (s, 1H), 7.23-7.12 (m, 1H), 5.55-5.36 (m, 1H), 4.52-4.04 (m, 5H), 3.97 (d, J=2.0 Hz, 1H), 3.92-3.83 (m, 3H), 1.53-1.22 (m, 3H); [M+H]=504.14.

Example 10. 1-(3-Methanesulfonyl-2-methoxy-6-{[(2S)-1,1,1-trifluoropropan-2-yl]oxy}benzoyl)-3-[3-(trifluoromethyl)phenyl]azetidine

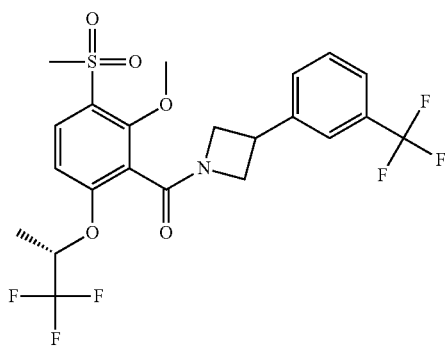 [SMILES: COc1c(S(C)(=O)=O)ccc(O[C@@H](C)C(F)(F)F)c1C(=O)N1CC(c2cccc(C(F)(F)F)c2)C1]

Step 1. (S)-2-methoxy-3-(methylsulfonyl)-6-((1,1,1-trifluoropropan-2-yl)oxy)benzoyl chloride. A solution of (S)-2-methoxy-3-(methylsulfonyl)-6-((1,1,1-trifluoropropan-2-yl)oxy)benzoic acid (50 mg, 0.15 mmol) in thionyl chloride (1 mL) was heated at 60° C. for 2 h. The reaction mixture was cooled and concentrated under reduced pressure. The title compound was used crude in the next step without further purification.

Step 2. 1-(3-Methanesulfonyl-2-methoxy-6-{[(2S)-1,1,1-trifluoropropan-2-yl]oxy}benzoyl)-3-[3-(trifluoromethyl)phenyl]azetidine. To a solution of (S)-2-methoxy-3-(methylsulfonyl)-6-((1,1,1-trifluoropropan-2-yl)oxy)benzoyl chloride in DCM (0.5 mL), was added N-ethyl-N-isopropylpropan-2-amine (0.13 mL, 0.73 mmol) followed by 3-(3-(trifluoromethyl)phenyl)azetidine (59 mg, 0.29 mmol). The reaction stirred at rt for 1 h, then poured into a saturated solution of ammonium chloride (10 mL), and extracted with DCM (3×10 mL). The combined organics were dried (Na$_2$SO$_4$), filtered, and concentrated under reduced pressure. Purification (LCMS, eluting with CH$_3$CN:H$_2$O) afforded the title compound (59 mg, 76%). $^1$H NMR (400 MHz, CDCl$_3$) δ=7.90-8.06 (m, 1H) 7.42-7.62 (m, 4H) 6.73-6.92 (m, 1H) 4.76-4.91 (m, 1H) 4.57-4.71 (m, 1H) 4.19-4.39 (m, 2H) 4.10 (s, 3H) 3.87-4.05 (m, 2H) 3.15-3.22 (m, 3H) 1.47-1.62 (m, 3H); [M+H]=526.11.

Example 11. 2-Methoxy-3-({3-[3-methyl-5-(trifluoromethyl)pyridin-2-yl]azetidin-1-yl}carbonyl)-4-{[(2S)-1,1,1-trifluoropropan-2-yl]oxy}benzonitrile

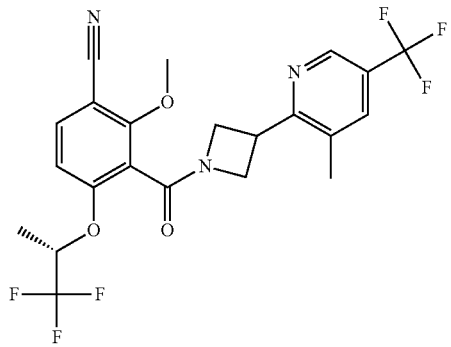 [SMILES: COc1c(C#N)ccc(O[C@@H](C)C(F)(F)F)c1C(=O)N1CC(c2ncc(C(F)(F)F)cc2C)C1]

To a solution of (S)-3-(3-(3-bromo-5-(trifluoromethyl)pyridin-2-yl)azetidine-1-carbonyl)-2-methoxy-4-((1,1,1-trifluoropropan-2-yl)oxy)benzonitrile in dioxane (2 mL) was added Pd(PPh$_3$)$_4$ (19 mg, 0.02 mmol), K$_2$CO$_3$ (214 µL, 0.43 mmol), methylboronic acid (19 mg, 0.32 mmol). The reaction mixture was heated to 150° C. for 15 minutes employing microwave heating. Additional Pd(PPh$_3$)$_4$ (19 mg, 0.02 mmol), and methylboronic acid (25 mg, 0.41 mmol) were added and the reaction was heated to 150° C. for 30 minutes employing microwave heating. The reaction mixture was cooled, diluted with EtOAc, and washed with water. The organic layer was separated, dried (Na$_2$SO$_4$), filtered, and concentrated under reduced pressure. Purification (FCC, SiO$_2$, 10-80% EtOAc/hexanes) afforded the title compound (77 mg, 74%). $^1$H NMR (400 MHz, DMSO-d$_6$) δ=8.82-8.69 (m, 1H), 8.01 (s, 1H), 7.90-7.82 (m, 1H), 7.26-7.11 (m, 1H), 5.57-5.33 (m, 1H), 4.58-4.07 (m, 5H), 4.00-3.89 (m, 3H), 2.30-2.20 (m, 3H), 1.54-1.26 (m, 3H); [M+H]=488.0.

Example 12. 4-Cyclopentyl-2-methoxy-3-{3-[5-(trifluoromethyl)pyridin-2-yl]azetidine-1-carbonyl}benzonitrile

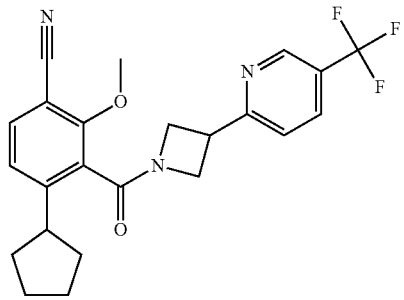 [SMILES: COc1c(C#N)ccc(C2CCCC2)c1C(=O)N1CC(c2ccc(C(F)(F)F)cn2)C1]

To a solution of 2-(azetidin-3-yl)-5-(trifluoromethyl)pyridine TFA salt (55 mg, 0.17 mmol) in DCM (2 mL) was added TEA (0.15 mL, 1.05 mmol), followed by 3-cyano-6-cyclopentyl-2-methoxybenzoyl chloride in DCM (2 mL). The reaction mixture was stirred at rt for 3 h. The solvent was removed under reduced pressure. Purification (HPLC, 30-95% ACN:H2O, 0.1% TFA as modifier) afforded the title compound (47 mg, 67%). $^1$H NMR (400 MHz, DMSO-d$_6$) δ=9.05-8.90 (m, 1H), 8.18 (dt, J=2.2, 8.5 Hz, 1H), 7.75 (d, J=8.2 Hz, 1H), 7.57 (t, J=7.6 Hz, 1H), 7.29 (dd, J=3.3, 8.4 Hz, 1H), 4.50-4.40 (m, 1H), 4.28-4.02 (m, 3H), 3.90-3.77 (m, 1H), 3.01 (quin, J=8.6 Hz, 1H), 2.12-1.89 (m, 2H), 1.85-1.71 (m, 2H), 1.71-1.41 (m, 4H); [M+H]=430.46.

Example 13. 5-Chloro-6-{1-[(3-cyano-2-methoxy-6-{[(2S)-1,1,1-trifluoropropan-2-yl]oxy}phenyl)carbonyl]azetidin-3-yl}pyridine-3-carbonitrile

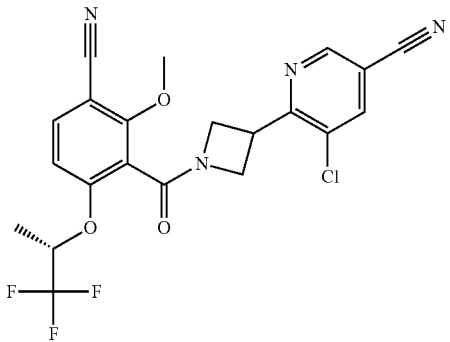

To a solution of (S)-3-(3-(5-bromo-3-chloropyridin-2-yl)azetidine-1-carbonyl)-2-methoxy-4-((1,1,1-trifluoropropan-2-yl)oxy)benzonitrile (119 mg, 0.23 mmol) in DMF (2 mL) was added dicyanozinc (32 mg, 0.28 mmol). Nitrogen was bubbled through the reaction mixture followed by the addition of Pd(PPh$_3$)$_4$ (26.5 mg, 0.02 mmol). The reaction mixture was heated at 100° C. for 16 h. The reaction mixture was cooled, diluted with EtOAc, and washed with water. The organic layer was separated, dried (Na$_2$SO$_4$), filtered, and concentrated under reduced pressure. Purification (FCC, SiO$_2$, 10-80% EtOAc/hexanes) afforded the title compound (84 mg, 78%). $^1$H NMR (400 MHz, DMSO-d$_6$) δ=8.99-8.87 (m, 1H), 8.58 (br s, 1H), 7.86 (d, J=9.0 Hz, 1H), 7.25-7.15 (m, 1H), 5.58-5.40 (m, 1H), 4.39 (br s, 2H), 4.31-4.04 (m, 3H), 3.97 (d, J=9.0 Hz, 3H), 1.54-1.31 (m, 3H); [M+H]=465.11.

Example 14. 3-[(3-{[3-Fluoro-5-(trifluoromethyl)pyridin-2-yl]amino}azetidin-1-yl)carbonyl]-2-methoxy-4-{[(2S)-1,1,1-trifluoropropan-2-yl]oxy}benzonitrile

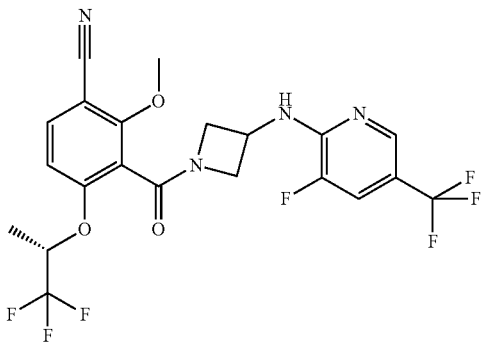 [SMILES: COc1c(C#N)ccc(O[C@@H](C)C(F)(F)F)c1C(=O)N1CC(Nc2ncc(C(F)(F)F)cc2F)C1]

The title compound was prepared in a manner analogous to Example 1, Step 3. $^1$H NMR (400 MHz, DMSO-d$_6$) δ=8.22-8.00 (m, 2H), 7.90-7.77 (m, 2H), 7.24-7.12 (m, 1H), 5.57-5.38 (m, 1H), 4.78-4.53 (m, 1H), 4.42-4.25 (m, 1H), 4.21-3.98 (m, 2H), 3.95 (s, 3H), 3.90-3.82 (m, 1H), 3.76-3.58 (m, 1H), 1.52-1.19 (m, 3H); [M+H]=507.07.

Example 15-Example 16 were prepared in a manner analogous to Example 1 with the appropriate starting material substitutions.

Example 15. 3-(3,4-Difluorophenyl)-1-({3-methanesulfonyl-2-methoxy-6-[(1,1,1-trifluoropropan-2-yl)oxy]phenyl}carbonyl)azetidine

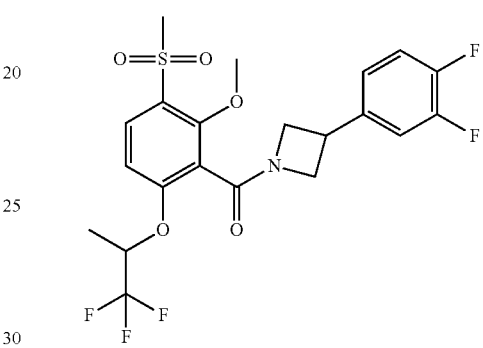

$^1$H NMR (400 MHz, CDCl$_3$) δ=1.55 (qd, J=15.85, 6.46 Hz, 3H) 3.20 (d, J=7.04 Hz, 3H) 4.03-4.24 (m, 5H) 4.27-4.41 (m, 2H) 4.55-4.73 (m, 1H) 4.82 (ddd, J=18.78, 12.52, 6.26 Hz, 1H) 6.78-6.87 (m, 1H) 7.01-7.17 (m, 3H) 8.00 (d, J=9.00 Hz, 1H); [M+H]=494.14.

Example 16. 3-(4-Fluorophenoxy)-1-({3-methanesulfonyl-2-methoxy-6-[(1,1,1-trifluoropropan-2-yl)oxy]phenyl}carbonyl)azetidine

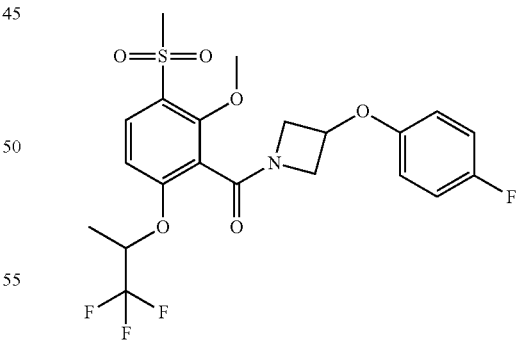

$^1$H NMR (400 MHz, CDCl$_3$) δ=1.47-1.66 (m, 3H) 3.19 (d, J=3.91 Hz, 3H) 3.96-4.10 (m, 4H) 4.21-4.34 (m, 2H) 4.53-4.67 (m, 1H) 4.74-5.01 (m, 2H) 6.69 (dt, J=8.80, 4.21 Hz, 2H) 6.81 (d, J=9.00 Hz, 1H) 6.98 (t, J=8.61 Hz, 2H) 8.00 (dd, J=9.00, 1.96 Hz, 1H); [M+H]=491.52.

Example 17-Example 62 were prepared in a manner analogous to Example 2, with the appropriate starting material substitutions.

Example 17. 3-({3-Fluoro-3-[4-(trifluoromethyl)phenyl]azetidin-1-yl}carbonyl)-4-(4-fluorooxan-4-yl)-2-methoxybenzonitrile

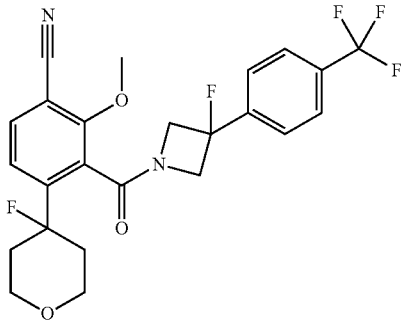 [SMILES: COc1c(C#N)ccc(C2(F)CCOCC2)c1C(=O)N1CC(F)(c2ccc(C(F)(F)F)cc2)C1]

$^1$H NMR (400 MHz, CDCl$_3$) δ=7.81-7.52 (m, 5H), 7.22-7.02 (m, 1H), 4.87-4.23 (m, 3H), 4.21-4.14 (m, 3H), 4.12-3.77 (m, 5H), 2.63-2.30 (m, 2H), 2.14-1.75 (m, 2H); [M+H]=481.3.

Example 18. 3-{[3-(3,4-Difluorophenyl)-3-fluoroazetidin-1-yl]carbonyl}-4-(4-fluorooxan-4-yl)-2-methoxybenzonitrile

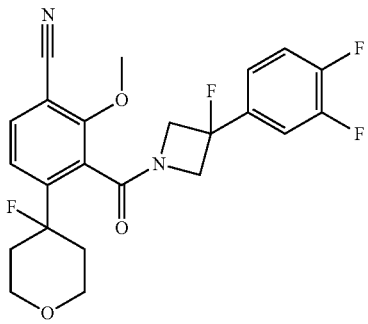 [SMILES: COc1c(C#N)ccc(C2(F)CCOCC2)c1C(=O)N1CC(F)(c2ccc(F)c(F)c2)C1]

$^1$H NMR (400 MHz, CDCl$_3$) δ=7.65 (dd, J=4.5, 7.6 Hz, 1H), 7.44-7.29 (m, 1H), 7.24-7.01 (m, 2H), 4.77-4.20 (m, 3H), 4.17-4.12 (m, 3H), 4.11-3.75 (m, 6H), 2.60-2.28 (m, 2H), 2.11-1.74 (m, 2H); [M+H]=449.3.

Example 19. 3-{[3-(3,5-Difluorophenyl)azetidin-1-yl]carbonyl}-4-(4-fluorooxan-4-yl)-2-methoxybenzonitrile

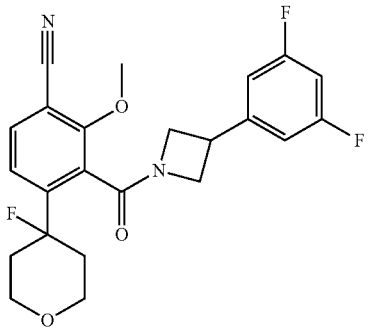 [SMILES: COc1c(C#N)ccc(C2(F)CCOCC2)c1C(=O)N1CC(c2cc(F)cc(F)c2)C1]

$^1$H NMR (400 MHz, DMSO-d$_6$) δ=7.87 (d, J=8.2 Hz, 1H), 7.46-7.31 (m, 2H), 7.15-7.03 (m, 2H), 4.48-4.36 (m, 1H), 4.27-4.14 (m, 2H), 4.11-3.92 (m, 5H), 3.90-3.75 (m, 3H), 3.74-3.53 (m, 2H), 2.14-1.67 (m, 3H); [M+H]=431.2.

Example 20. 3-{[3-(4-Chlorophenyl)azetidin-1-yl]carbonyl}-4-(4-fluorooxan-4-yl)-2-methoxybenzonitrile

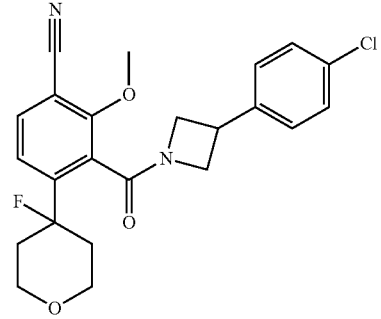 [SMILES: COc1c(C#N)ccc(C2(F)CCOCC2)c1C(=O)N1CC(c2ccc(Cl)cc2)C1]

$^1$H NMR (400 MHz, DMSO-d$_6$) δ=7.87 (d, J=8.2 Hz, 1H), 7.46-7.31 (m, 5H), 4.46-4.36 (m, 1H), 4.11 (t, J=8.8 Hz, 1H), 4.03-3.75 (m, 7H), 3.73-3.57 (m, 3H), 2.46-2.36 (m, 1H), 2.13-1.87 (m, 2H), 1.85-1.70 (m, 1H); [M+H]=429.32.

Example 21. 3-{[3-(3,4-Difluorophenyl)azetidin-1-yl]carbonyl}-4-(4-fluorooxan-4-yl)-2-methoxybenzonitrile

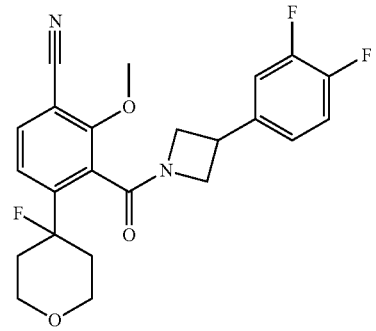 [SMILES: COc1c(C#N)ccc(C2(F)CCOCC2)c1C(=O)N1CC(c2ccc(F)c(F)c2)C1]

$^1$H NMR (400 MHz, DMSO-d$_6$) δ=7.88 (d, J=8.2 Hz, 1H), 7.42 (t, J=8.2 Hz, 1H), 7.36-7.18 (m, 3H), 4.44 (q, J=8.7 Hz, 1H), 4.21-4.03 (m, 3H), 3.97 (d, J=14.9 Hz, 3H), 3.91-3.53 (m, 6H), 2.53 (d, J=14.1 Hz, 1H), 2.14-1.71 (m, 3H); [M+H]=431.35.

Example 22. 4-(4-Fluorooxan-4-yl)-3-{[3-(4-fluorophenyl)azetidin-1-yl]carbonyl}-2-methoxybenzonitrile

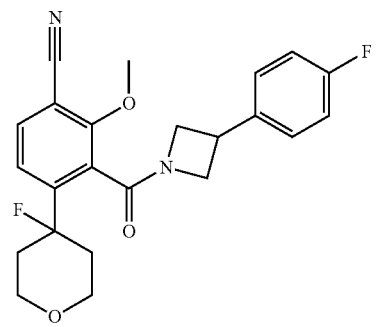 [SMILES: COc1c(C#N)ccc(C2(F)CCOCC2)c1C(=O)N1CC(c2ccc(F)cc2)C1]

$^1$H NMR (400 MHz, DMSO-d$_6$) δ=7.88 (d, J=8.6 Hz, 1H), 7.46-7.32 (m, 3H), 7.19 (td, J=8.7, 12.3 Hz, 2H), 4.44-4.36 (m, 1H), 4.11 (t, J=8.6 Hz, 1H), 4.01-3.93 (m, 5H), 3.91-3.75 (m, 3H), 3.73-3.57 (m, 3H), 2.14-1.99 (m, 2H), 1.98-1.71 (m, 2H); [M+H]=413.37.

Example 23. 4-(4-Fluorooxan-4-yl)-2-methoxy-3-({3-[3-(trifluoromethyl)phenyl]azetidin-1-yl}carbonyl)benzonitrile

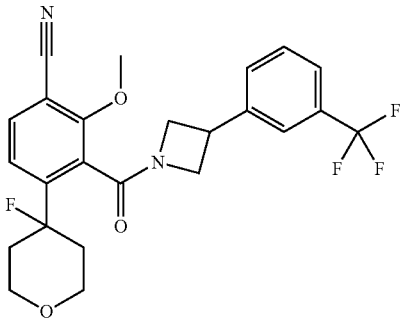 [SMILES: COc1c(C#N)ccc(C2(F)CCOCC2)c1C(=O)N1CC(c2cccc(C(F)(F)F)c2)C1]

¹H NMR (400 MHz, DMSO-d₆) δ=7.88 (d, J=8.6 Hz, 1H), 7.70 (d, J=6.7 Hz, 2H), 7.65-7.56 (m, 3H), 7.42 (t, J=8.8 Hz, 1H), 4.48-4.40 (m, 1H), 4.20-4.12 (m, 1H), 4.07-4.00 (m, 1H), 3.98 (s, 3H), 3.91-3.81 (m, 3H), 3.81-3.71 (m, 2H), 3.70-3.57 (m, 2H), 2.54 (dd, J=5.3, 13.5 Hz, 1H), 2.14-2.01 (m, 1H), 2.01-1.87 (m, 1H), 1.86-1.72 (m, 1H); [M+H]=463.32.

Example 24. 4-(4-Fluorooxan-4-yl)-2-methoxy-3-({3-[4-(trifluoromethyl)phenoxy]azetidin-1-yl}carbonyl)benzonitrile

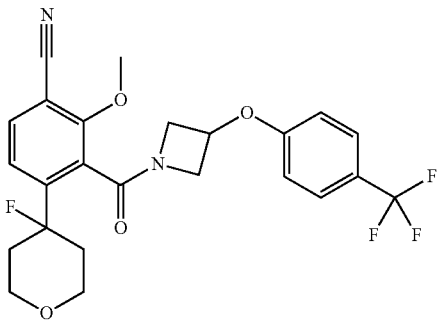 [SMILES: COc1c(C#N)ccc(C2(F)CCOCC2)c1C(=O)N1CC(Oc2ccc(C(F)(F)F)cc2)C1]

¹H NMR (400 MHz, DMSO-d₆) δ=7.88 (d, J=8.2 Hz, 1H), 7.62 (d, J=7.0 Hz, 2H), 7.41 (t, J=8.4 Hz, 1H), 7.04 (dd, J=4.1, 8.4 Hz, 2H), 5.23-5.10 (m, 1H), 4.50 (dt, J=6.7, 11.7 Hz, 1H), 4.26-4.15 (m, 1H), 4.03-3.91 (m, 4H), 3.91-3.53 (m, 5H), 2.52 (br s, 1H), 2.12-1.95 (m, 2H), 1.94-1.65 (m, 2H); [M+H]=479.30.

Example 25. 3-{[3-(3,4-Difluorophenoxy)azetidin-1-yl]carbonyl}-4-(4-fluorooxan-4-yl)-2-methoxybenzonitrile

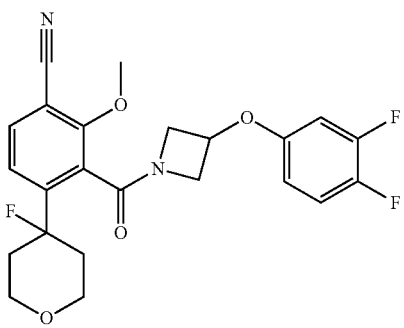 [SMILES: COc1c(C#N)ccc(C2(F)CCOCC2)c1C(=O)N1CC(Oc2ccc(F)c(F)c2)C1]

¹H NMR (400 MHz, DMSO-d₆) δ=7.88 (d, J=8.2 Hz, 1H), 7.41 (t, J=7.8 Hz, 1H), 7.37-7.27 (m, 1H), 7.01 (ddd, J=3.5, 6.4, 9.3 Hz, 1H), 6.73-6.66 (m, 1H), 5.11-5.00 (m, 1H), 4.46 (dt, J=6.7, 11.7 Hz, 1H), 4.22-4.12 (m, 1H), 3.95 (d, J=13.7 Hz, 4H), 3.90-3.74 (m, 2H), 3.72-3.54 (m, 3H), 2.59-2.50 (m, 1H), 2.11-1.69 (m, 3H); [M+H]=447.33.

Example 26. 4-(4-Fluorooxan-4-yl)-3-{[3-(4-fluorophenoxy)azetidin-1-yl]carbonyl}-2-methoxybenzonitrile

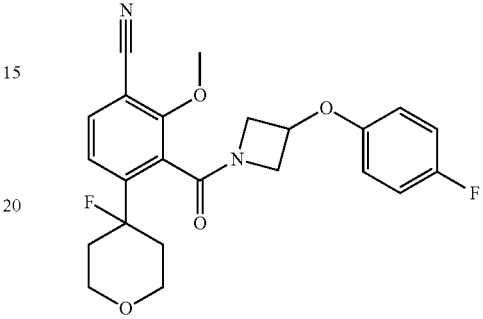

¹H NMR (400 MHz, DMSO-d₆) δ=7.88 (d, J=8.2 Hz, 1H), 7.41 (t, J=7.8 Hz, 1H), 7.37-7.27 (m, 1H), 7.01 (ddd, J=3.5, 6.4, 9.3 Hz, 1H), 6.73-6.66 (m, 1H), 5.11-5.00 (m, 1H), 4.46 (dt, J=6.7, 11.7 Hz, 1H), 4.22-4.12 (m, 1H), 3.95 (d, J=13.7 Hz, 4H), 3.90-3.74 (m, 2H), 3.72-3.54 (m, 3H), 2.59-2.50 (m, 1H), 2.11-1.69 (m, 3H); [M+H]=429.32.

Example 27. 4-(4-Fluorooxan-4-yl)-2-methoxy-3-({3-[6-(trifluoromethyl)pyridin-3-yl]azetidin-1-yl}carbonyl)benzonitrile

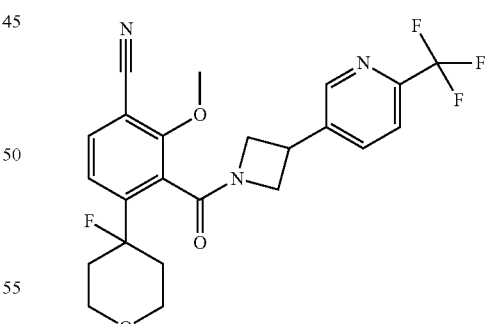

¹H NMR (400 MHz, DMSO-d₆) δ=8.72 (d, J=14.9 Hz, 1H), 8.13-8.00 (m, 1H), 7.98-7.85 (m, 2H), 7.42 (t, J=9.0 Hz, 1H), 4.49-4.42 (m, 1H), 4.21-4.06 (m, 3H), 3.99 (d, J=2.3 Hz, 3H), 3.92-3.76 (m, 4H), 3.73-3.56 (m, 2H), 2.53 (br s, 1H), 2.14-1.98 (m, 2H), 1.97-1.73 (m, 2H); [M+H]=464.33.

Example 28. 3-{[3-(4-Chlorophenoxy)azetidin-1-yl]carbonyl}-4-(4-fluorooxan-4-yl)-2-methoxybenzonitrile

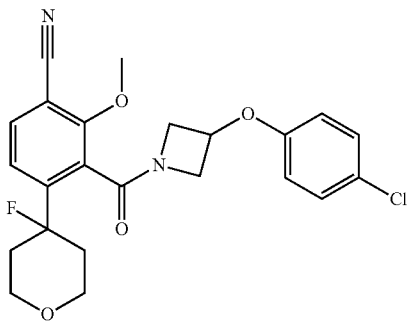 [SMILES: COc1c(C#N)ccc(C2(F)CCOCC2)c1C(=O)N1CC(Oc2ccc(Cl)cc2)C1]

¹H NMR (400 MHz, DMSO-d₆) δ=7.88 (d, J=8.2 Hz, 1H), 7.41 (t, J=8.0 Hz, 1H), 7.30 (dd, J=2.3, 8.6 Hz, 2H), 6.91-6.84 (m, 2H), 5.12-4.99 (m, 1H), 4.46 (dt, J=6.7, 11.7 Hz, 1H), 4.21-4.12 (m, 1H), 3.95 (d, J=14.5 Hz, 4H), 3.89-3.73 (m, 2H), 3.71-3.55 (m, 3H), 2.59-2.50 (m, 1H), 2.10-1.94 (m, 2H), 1.92-1.67 (m, 2H); [M+H]=445.26.

Example 29. 3-{[3-(4-Chlorophenoxy)azetidin-1-yl]carbonyl}-2-methoxy-4-{[(2S)-1,1,1-trifluoropropan-2-yl]oxyl}benzonitrile

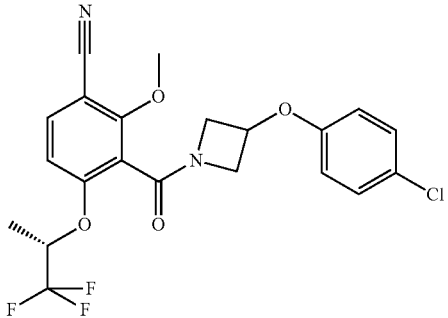 [SMILES: COc1c(C#N)ccc(O[C@@H](C)C(F)(F)F)c1C(=O)N1CC(Oc2ccc(Cl)cc2)C1]

¹H NMR (400 MHz, DMSO-d₆) δ=7.87 (d, J=9.0 Hz, 1H), 7.34-7.27 (m, 2H), 7.24-7.13 (m, 1H), 6.90-6.78 (m, 2H), 5.47 (d, J=5.5 Hz, 1H), 5.06 (br s, 1H), 4.51-4.42 (m, 1H), 4.33-4.09 (m, 1H), 3.99-3.89 (m, 4H), 3.86-3.62 (m, 1H), 1.52-1.31 (m, 3H); [M+H]=455.3.

Example 30. 2-Methoxy-3-({3-[4-(trifluoromethyl)phenoxy]azetidin-1-yl}carbonyl)-4-{[(2S)-1,1,1-trifluoropropan-2-yl]oxy}benzonitrile

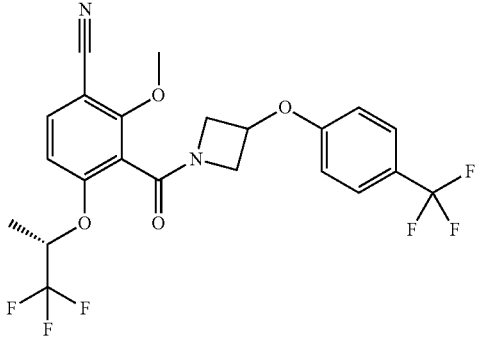 [SMILES: COc1c(C#N)ccc(O[C@@H](C)C(F)(F)F)c1C(=O)N1CC(Oc2ccc(C(F)(F)F)cc2)C1]

¹H NMR (400 MHz, DMSO-d₆) δ=7.87 (d, J=8.6 Hz, 1H), 7.64 (dd, J=2.7, 8.6 Hz, 2H), 7.25-7.14 (m, 1H), 7.07-6.94 (m, 2H), 5.47 (d, J=5.9 Hz, 1H), 5.17 (br s, 1H), 4.49 (d, J=5.9 Hz, 1H), 4.32 (br s, 1H), 4.24 (br s, 1H), 4.01-3.90 (m, 4H), 3.89-3.64 (m, 1H), 1.53-1.31 (m, 3H); [M+H]=489.09.

Example 31. 2-Methoxy-3-({3-[6-(trifluoromethyl)pyridin-3-yl]azetidin-1-yl}carbonyl)-4-{[(2S)-1,1,1-trifluoropropan-2-yl]oxy}benzonitrile

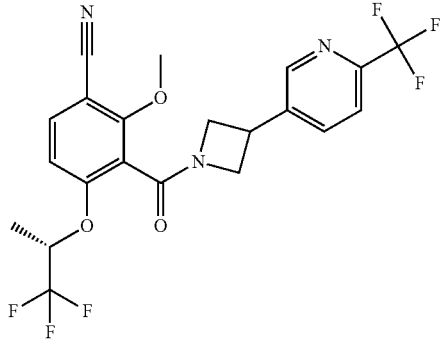 [SMILES: COc1c(C#N)ccc(O[C@@H](C)C(F)(F)F)c1C(=O)N1CC(c2ccc(C(F)(F)F)nc2)C1]

¹H NMR (400 MHz, DMSO-d₆) δ=8.76-8.64 (m, 1H), 8.14-7.95 (m, 1H), 7.94-7.83 (m, 2H), 7.25-7.15 (m, 1H), 5.49 (td, J=5.7, 10.9 Hz, 1H), 4.46 (q, J=9.7 Hz, 1H), 4.35-4.25 (m, 1H), 4.21-4.04 (m, 2H), 3.97 (s, 3H), 3.87-3.68 (m, 1H), 1.54-1.28 (m, 3H); [M+H]=474.23.

Example 32. 3-{[3-(4-Chlorophenyl)azetidin-1-yl]carbonyl}-2-methoxy-4-{[(2S)-1,1,1-trifluoropropan-2-yl]oxy}benzonitrile

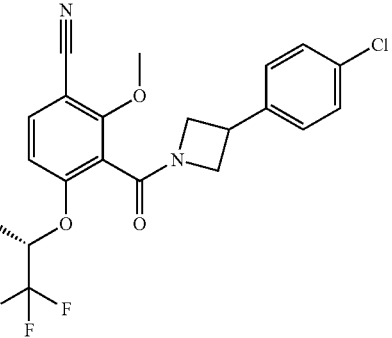

¹H NMR (400 MHz, DMSO-d₆) δ=7.87 (d, J=8.6 Hz, 1H), 7.44-7.28 (m, 4H), 7.24-7.15 (m, 1H), 5.56-5.43 (m, 1H), 4.46-4.36 (m, 1H), 4.28-4.18 (m, 1H), 4.03-3.64 (m, 6H), 1.51-1.32 (m, 3H); [M+H]=439.23.

Example 33. 3-{[3-(4-Fluorophenoxy)azetidin-1-yl]carbonyl}-2-methoxy-4-{[(2S)-1,1,1-trifluoropropan-2-yl]oxy}benzonitrile

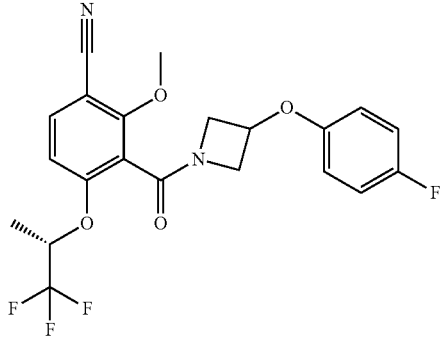 [SMILES: COc1c(C#N)ccc(O[C@@H](C)C(F)(F)F)c1C(=O)N1CC(Oc2ccc(F)cc2)C1]

¹H NMR (400 MHz, DMSO-d₆) δ=7.86 (d, J=8.6 Hz, 1H), 7.18 (d, J=8.6 Hz, 1H), 7.10 (dt, J=3.5, 8.8 Hz, 2H), 6.90-6.77 (m, 2H), 5.48 (d, J=5.5 Hz, 1H), 5.08-4.94 (m, 1H), 4.44 (d, J=5.9 Hz, 1H), 4.27 (d, J=8.2 Hz, 1H), 3.99-3.64 (m, 5H), 1.53-1.31 (m, 3H); [M+H]=438.7.

Example 34. 2-Methoxy-3-({3-[5-(trifluoromethyl)pyridin-2-yl]azetidin-1-yl}carbonyl)-4-{[(2S)-1,1,1-trifluoropropan-2-yl]oxy}benzonitrile

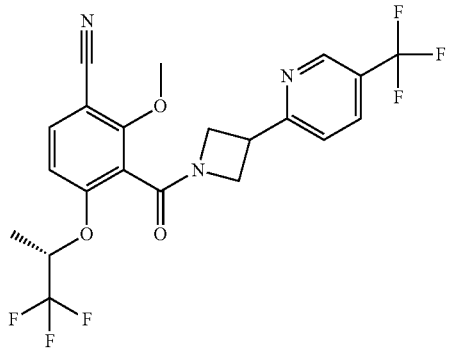 [SMILES: COc1c(C#N)ccc(O[C@@H](C)C(F)(F)F)c1C(=O)N1CC(c2ccc(C(F)(F)F)cn2)C1]

¹H NMR (400 MHz, DMSO-d₆) δ=9.03-8.86 (m, 1H), 8.17 (d, J=6.7 Hz, 1H), 7.85 (d, J=9.0 Hz, 1H), 7.62-7.50 (m, 1H), 7.26-7.09 (m, 1H), 5.56-5.37 (m, 1H), 4.44-4.30 (m, 1H), 4.17 (d, J=9.8 Hz, 2H), 4.10-3.86 (m, 5H), 1.54-1.27 (m, 3H); [M+H]=474.20.

Example 35. 2-Methoxy-3-{[3-(pyridin-4-yloxy)azetidin-1-yl]carbonyl}-4-{[(2S)-1,1,1-trifluoropropan-2-yl]oxy}benzonitrile

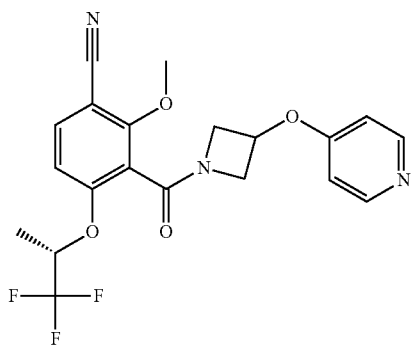 [SMILES: COc1c(C#N)ccc(O[C@@H](C)C(F)(F)F)c1C(=O)N1CC(Oc2ccncc2)C1]

¹H NMR (400 MHz, DMSO-d₆) δ=8.38 (d, J=4.3 Hz, 2H), 7.87 (d, J=9.0 Hz, 1H), 7.26-7.13 (m, 1H), 6.85 (d, J=6.3 Hz, 2H), 5.54-5.41 (m, 1H), 5.16 (br s, 1H), 4.49 (d, J=5.9 Hz, 1H), 4.33 (br s, 1H), 3.99-3.89 (m, 4H), 3.76-3.64 (m, 1H), 1.55-1.20 (m, 3H); [M+H]=422.02.

Example 36. 2-Methoxy-3-({3-[5-(trifluoromethyl)pyridin-2-yl]azetidin-1-yl}carbonyl)-4-[(1,1,1-trifluoropropan-2-yl)oxy]benzonitrile

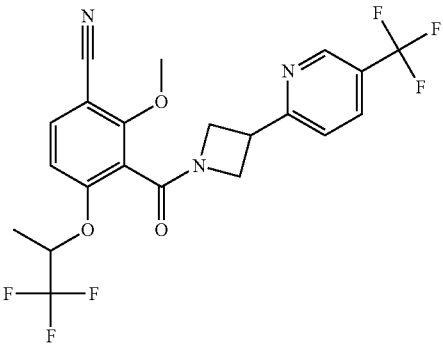 [SMILES: COc1c(C#N)ccc(OC(C)C(F)(F)F)c1C(=O)N1CC(c2ccc(C(F)(F)F)cn2)C1]

¹H NMR (400 MHz, DMSO-d₆) δ=9.02-8.86 (m, 1H), 8.16 (d, J=7.4 Hz, 1H), 7.85 (d, J=8.2 Hz, 1H), 7.58 (br s, 1H), 7.18 (br s, 1H), 5.55-5.37 (m, 1H), 4.37 (br s, 1H), 4.17 (d, J=8.6 Hz, 4H), 3.97 (d, J=3.1 Hz, 3H), 1.52-1.27 (m, 3H); [M+H]=473.97.

Example 37. 3-({3-[(4-Fluorophenyl)methyl]azetidin-1-yl}carbonyl)-2-methoxy-4-{[(2S)-1,1,1-trifluoropropan-2-yl]oxy}benzonitrile

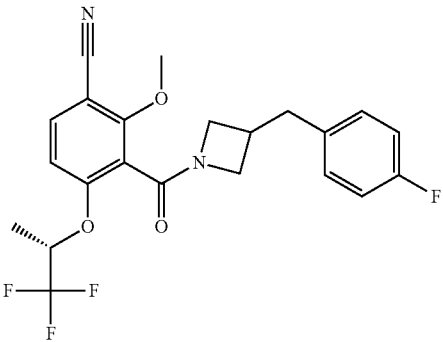 [SMILES: COc1c(C#N)ccc(O[C@@H](C)C(F)(F)F)c1C(=O)N1CC(Cc2ccc(F)cc2)C1]

¹H NMR (400 MHz, DMSO-d₆) δ=7.87 (d, J=8.9 Hz, 1H), 7.30-7.06 (m, 5H), 5.52 (ddd, J=6.5, 12.8, 19.6 Hz, 1H), 4.13-4.01 (m, 1H), 3.96-3.92 (m, 3H), 3.91-3.62 (m, 2H), 3.57-3.38 (m, 1H), 2.95-2.76 (m, 3H), 1.51-1.38 (m, 3H); [M+H]=437.03.

Example 38. 3-{[3-(3-Chloropyridin-2-yl)azetidin-1-yl]carbonyl}-2-methoxy-4-{[(2S)-1,1,1-trifluoropropan-2-yl]oxy}benzonitrile

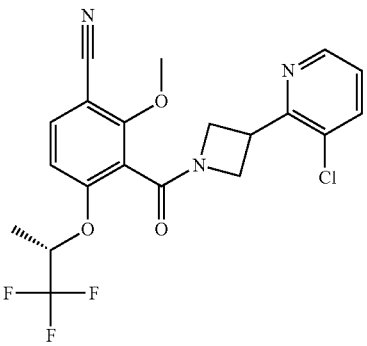 [SMILES: COc1c(C#N)ccc(O[C@@H](C)C(F)(F)F)c1C(=O)N1CC(c2ncccc2Cl)C1]

¹H NMR (400 MHz, DMSO-d₆) δ=8.54 (dd, J=4.1, 16.2 Hz, 1H), 7.95-7.89 (m, 1H), 7.85 (dd, J=3.5, 9.0 Hz, 1H), 7.41-7.33 (m, 1H), 7.24-7.12 (m, 1H), 5.58-5.35 (m, 1H), 4.55-4.23 (m, 3H), 4.18-4.06 (m, 1H), 4.02-3.88 (m, 3H), 1.53-1.26 (m, 3H); [M+H]=440.0.

Example 39. 3-[(4-Fluorophenyl)methyl]-1-(3-methanesulfonyl-2-methoxy-6-{[(2R)-1,1,1-trifluoropropan-2-yl]oxy}benzoyl)azetidine

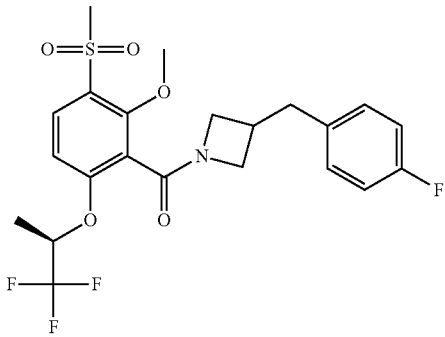 [SMILES: COc1c(S(C)(=O)=O)ccc(O[C@H](C)C(F)(F)F)c1C(=O)N1CC(Cc2ccc(F)cc2)C1]

¹H NMR (400 MHz, DMSO-d₆) δ=7.83-7.78 (m, 1H), 7.28-7.13 (m, 3H), 7.13-7.04 (m, 2H), 5.56-5.39 (m, 1H), 4.12-4.02 (m, 1H), 3.95-3.81 (m, 4H), 3.80-3.64 (m, 2H), 3.59-3.36 (m, 2H), 3.24-3.19 (m, 3H), 1.51-1.36 (m, 3H); [M+H]=490.34.

Example 40. 1-(3-Methanesulfonyl-2-methoxy-6-{[(2S)-1,1,1-trifluoropropan-2-yl]oxy}benzoyl)-3-[2-methyl-4-(trifluoromethyl)phenyl]azetidine

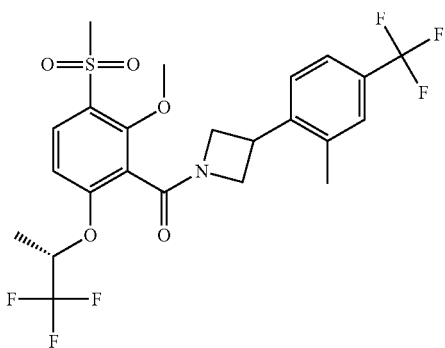

¹H NMR (400 MHz, DMSO-d₆) δ=7.85 (td, J=2.6, 8.9 Hz, 1H), 7.65 (dd, J=7.8, 12.7 Hz, 1H), 7.46-7.24 (m, 3H), 5.57-5.46 (m, 1H), 4.52-4.44 (m, 1H), 4.36-4.16 (m, 1H), 4.16-3.99 (m, 2H), 3.99-3.95 (m, 3H), 3.28-3.22 (m, 3H), 2.44 (s, 3H), 1.56-1.35 (m, 3H); [M+H]=540.20

Example 41. 3-(2,5-Difluorophenyl)-1-(3-methanesulfonyl-2-methoxy-6-{[(2S)-1,1,1-trifluoropropan-2-yl]oxy}benzoyl)azetidine

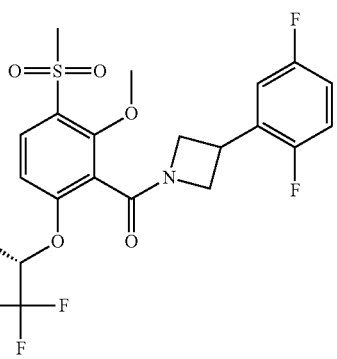

¹H NMR (400 MHz, DMSO-d₆) δ=7.91-7.81 (m, 1H), 7.44-7.13 (m, 4H), 5.60-5.42 (m, 1H), 4.51-4.40 (m, 1H), 4.36-4.05 (m, 3H), 4.00-3.90 (m, 3H), 3.89-3.77 (m, 1H), 3.28-3.20 (m, 3H), 1.57-1.33 (m, 3H); [M+H]=494.15.

Example 42. 3-(2-Fluoro-5-methylphenyl)-1-(3-methanesulfonyl-2-methoxy-6-{[(2S)-1,1,1-trifluoropropan-2-yl]oxy}benzoyl)azetidine

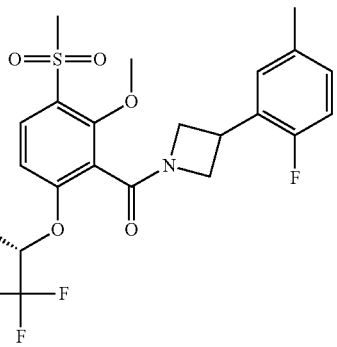

¹H NMR (400 MHz, DMSO-d₆) δ=7.85 (td, J=2.6, 8.9 Hz, 1H), 7.33-7.19 (m, 2H), 7.17-7.02 (m, 2H), 5.59-5.44 (m, 1H), 4.50-4.40 (m, 1H), 4.33-4.01 (m, 3H), 4.00-3.83 (m, 4H), 3.27-3.20 (m, 3H), 2.29 (s, 3H), 1.57-1.33 (m, 3H); [M+H]=490.16.

Example 43. 3-(4-Fluoro-3-methylphenoxy)-1-(3-methanesulfonyl-2-methoxy-6-{[(2S)-1,1,1-trifluoropropan-2-yl]oxy}benzoyl)azetidine

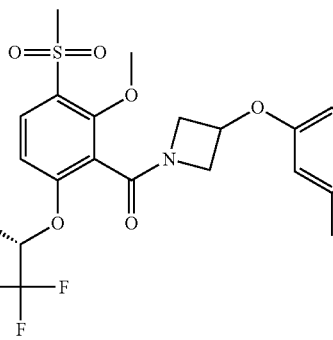

¹H NMR (400 MHz, DMSO-d$_6$) δ=7.87-7.79 (m, 1H), 7.31-7.18 (m, 1H), 7.02 (dt, J=3.9, 9.2 Hz, 1H), 6.81-6.69 (m, 1H), 6.69-6.57 (m, 1H), 5.54-5.41 (m, 1H), 5.08-4.93 (m, 1H), 4.48 (dd, J=6.7, 10.6 Hz, 1H), 4.37-4.19 (m, 1H), 4.18-3.95 (m, 1H), 3.94-3.88 (m, 3H), 3.87-3.81 (m, 1H), 3.76-3.66 (m, 1H), 3.26-3.17 (m, 3H), 2.17 (d, J=1.6 Hz, 3H), 1.56-1.35 (m, 3H); [M+H]=506.15

Example 44. 1-(3-Methanesulfonyl-2-methoxy-6-{[(2S)-1,1,1-trifluoropropan-2-yl]oxy}benzoyl)-3-[3-(trifluoromethyl)phenoxy]azetidine

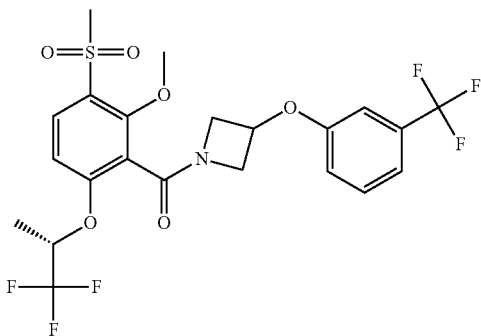 [SMILES: COc1c(S(C)(=O)=O)ccc(O[C@@H](C)C(F)(F)F)c1C(=O)N1CC(Oc2cccc(C(F)(F)F)c2)C1]

¹H NMR (400 MHz, DMSO-d$_6$) δ=7.86-7.80 (m, 1H), 7.57-7.49 (m, 1H), 7.33 (d, J=7.0 Hz, 1H), 7.29-7.07 (m, 3H), 5.47 (dt, J=6.8, 12.4 Hz, 1H), 5.25-5.13 (m, 1H), 4.52 (dd, J=6.3, 11.3 Hz, 1H), 4.43-4.24 (m, 1H), 4.00 (br s, 1H), 3.95-3.88 (m, 3H), 3.74 (t, J=10.2 Hz, 1H), 3.26-3.18 (m, 3H), 1.55-1.32 (m, 3H); [M+H]=542.07.

Example 45. 3-(2,6-Dimethylphenoxy)-1-(3-methanesulfonyl-2-methoxy-6-{[(2S)-1,1,1-trifluoropropan-2-yl]oxy}benzoyl)azetidine

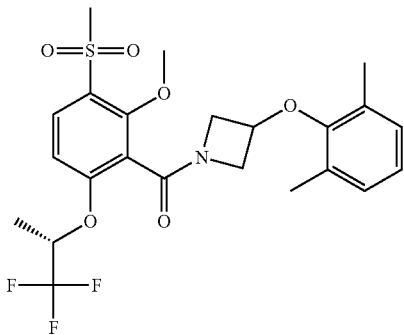 [SMILES: COc1c(S(C)(=O)=O)ccc(O[C@@H](C)C(F)(F)F)c1C(=O)N1CC(Oc2c(C)cccc2C)C1]

¹H NMR (400 MHz, DMSO-d$_6$) δ=7.84 (d, J=9.0 Hz, 1H), 7.31-7.22 (m, 1H), 7.04-6.97 (m, 2H), 6.94-6.87 (m, 1H), 5.58-5.42 (m, 1H), 4.77-4.64 (m, 1H), 4.45-4.35 (m, 1H), 4.24-4.15 (m, 1H), 4.14-3.97 (m, 2H), 3.97-3.85 (m, 3H), 3.26-3.18 (m, 3H), 2.17-2.10 (m, 6H), 1.54-1.37 (m, 3H); [M+H]=502.16.

Example 46. 3-(2-Chlorophenoxy)-1-(3-methanesulfonyl-2-methoxy-6-{[(2S)-1,1,1-trifluoropropan-2-yl]oxy}benzoyl)azetidine

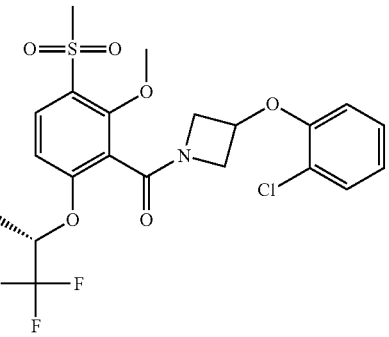

¹H NMR (400 MHz, DMSO-d$_6$) δ=7.87-7.80 (m, 1H), 7.48-7.41 (m, 1H), 7.30-7.20 (m, 2H), 7.03-6.82 (m, 2H), 5.54-5.41 (m, 1H), 5.20-5.08 (m, 1H), 4.54 (dd, J=6.1, 10.4 Hz, 1H), 4.41-4.24 (m, 1H), 4.06-3.94 (m, 1H), 3.94-3.88 (m, 3H), 3.83-3.73 (m, 1H), 3.26-3.16 (m, 3H), 1.55-1.34 (m, 3H); [M+H]=508.09.

Example 47. 1-(3-Methanesulfonyl-2-methoxy-6-{[(2S)-1,1,1-trifluoropropan-2-yl]oxy}benzoyl)-3-(3-methylphenoxy)azetidine

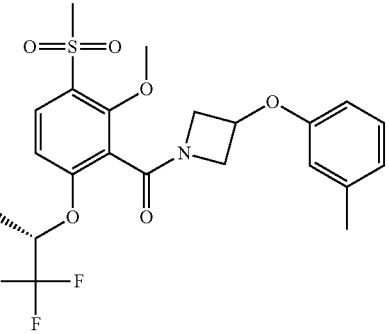

¹H NMR (400 MHz, DMSO-d$_6$) δ=7.86-7.80 (m, 1H), 7.30-7.19 (m, 1H), 7.18-7.09 (m, 1H), 6.82-6.74 (m, 1H), 6.68-6.55 (m, 2H), 5.54-5.42 (m, 1H), 5.09-4.96 (m, 1H), 4.49 (dd, J=6.5, 10.8 Hz, 1H), 4.38-4.21 (m, 1H), 4.20-3.80 (m, 5H), 3.76-3.67 (m, 1H), 3.27-3.16 (m, 3H), 2.24 (s, 3H), 1.55-1.35 (m, 3H); [M+H]=488.07.

Example 48. 1-(3-Methanesulfonyl-2-methoxy-6-{[(2S)-1,1,1-trifluoropropan-2-yl]oxy}benzoyl)-3-(2-methylphenoxy)azetidine

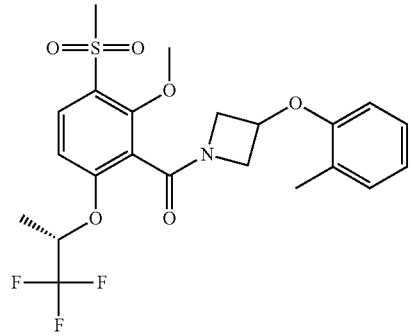 [SMILES: COc1c(S(C)(=O)=O)ccc(O[C@@H](C)C(F)(F)F)c1C(=O)N1CC(Oc2ccccc2C)C1]

¹H NMR (400 MHz, DMSO-d₆) δ=7.87-7.79 (m, 1H), 7.30-7.19 (m, 1H), 7.19-7.03 (m, 2H), 6.90-6.82 (m, 1H), 6.70-6.59 (m, 1H), 5.47 (qd, J=6.5, 13.0 Hz, 1H), 5.14-4.98 (m, 1H), 4.51 (dd, J=6.5, 10.8 Hz, 1H), 4.38-4.23 (m, 1H), 4.22-3.81 (m, 5H), 3.80-3.69 (m, 1H), 3.27-3.18 (m, 3H), 2.15 (s, 3H), 1.57-1.33 (m, 3H); [M+H]=488.18.

Example 49. 1-(3-Methanesulfonyl-2-methoxy-6-{[(2S)-1,1,1-trifluoropropan-2-yl]oxy}benzoyl)-3-phenylazetidine

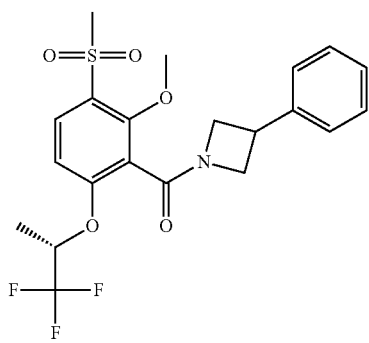 [SMILES: COc1c(S(C)(=O)=O)ccc(O[C@@H](C)C(F)(F)F)c1C(=O)N1CC(c2ccccc2)C1]

¹H NMR (400 MHz, DMSO-d₆) δ=7.86-7.80 (m, 1H), 7.39-7.22 (m, 6H), 5.55-5.43 (m, 1H), 4.45 (t, J=9.2 Hz, 1H), 4.32-4.20 (m, 1H), 4.19-3.83 (m, 6H), 3.80-3.73 (m, 1H), 3.26-3.19 (m, 3H), 1.55-1.36 (m, 3H); [M+H]=548.23.

Example 50. 2-Methoxy-3-(3-phenylazetidine-1-carbonyl)-4-{[(2S)-1,1,1-trifluoropropan-2-yl]oxy}benzonitrile

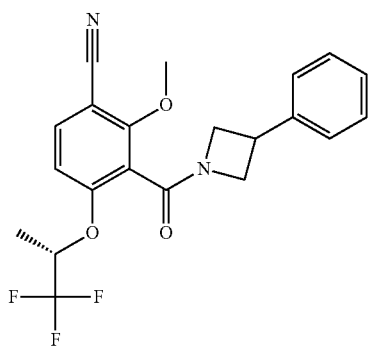 [SMILES: COc1c(C#N)ccc(O[C@@H](C)C(F)(F)F)c1C(=O)N1CC(c2ccccc2)C1]

¹H NMR (400 MHz, CDCl₃) δ=7.58 (d, J=8.6 Hz, 1H), 7.41-7.26 (m, 5H), 6.80-6.69 (m, 1H), 4.82-4.74 (m, 1H), 4.63-4.56 (m, 1H), 4.29-4.19 (m, 2H), 4.16-4.12 (m, 3H), 3.98-3.79 (m, 2H), 1.60-1.49 (m, 3H); [M+H]=405.03.

Example 51. 3-[3-(3,4-Difluorophenyl)azetidine-1-carbonyl]-2-methoxy-4-{[(2S)-1,1,1-trifluoropropan-2-yl]oxy}benzonitrile

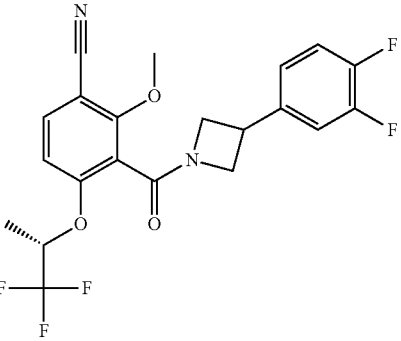

¹H NMR (400 MHz, CDCl₃) δ=7.58 (d, J=9.0 Hz, 1H), 7.17-7.05 (m, 3H), 6.76 (d, J=9.0 Hz, 1H), 4.77 (dd, J=6.1, 11.9 Hz, 1H), 4.66-4.55 (m, 1H), 4.35-4.21 (m, 2H), 4.20-4.06 (m, 4H), 4.05-3.91 (m, 1H), 1.54 (dd, J=6.3, 13.3 Hz, 3H); [M+H]=440.94.

Example 52. 3-[3-(4-Fluorophenyl)azetidine-1-carbonyl]-2-methoxy-4-{[(2S)-1,1,1-trifluoropropan-2-yl]oxy}benzonitrile

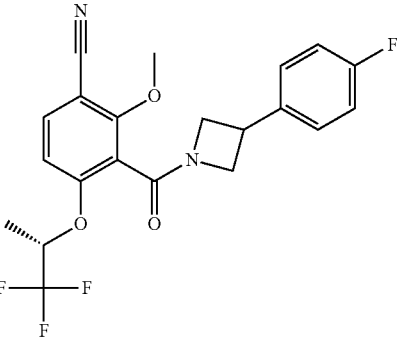

¹H NMR (400 MHz, CDCl₃) δ=7.58 (d, J=8.6 Hz, 1H), 7.28 (dd, J=5.3, 8.8 Hz, 2H), 7.09-7.00 (m, 2H), 6.77 (d, J=8.6 Hz, 1H), 4.78 (td, J=6.0, 12.3 Hz, 1H), 4.59 (dd, J=8.2, 10.2 Hz, 1H), 4.30-4.08 (m, 5H), 3.92-3.75 (m, 2H), 1.59-1.49 (m, 3H); [M+H]=423.12

Example 53. 3-[3-(3,5-Difluorophenyl)azetidine-1-carbonyl]-2-methoxy-4-{[(2S)-1,1,1-trifluoropropan-2-yl]oxy}benzonitrile

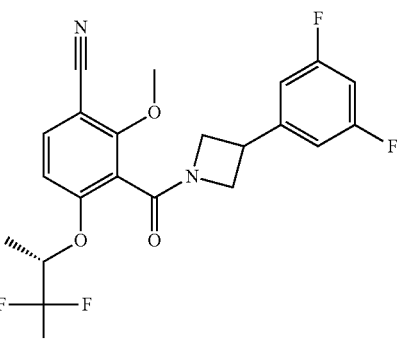

¹H NMR (400 MHz, CDCl₃) δ=7.57 (d, J=9.0 Hz, 1H), 7.26-7.17 (m, 1H), 6.95-6.84 (m, 2H), 6.80-6.68 (m, 1H), 4.83-4.71 (m, 1H), 4.62-4.42 (m, 2H), 4.29-4.16 (m, 3H), 4.13 (s, 3H), 1.55 (t, J=6.3 Hz, 3H); [M+H]=440.56.

Example 54. 2-Chloro-3-(3-phenylazetidine-1-carbonyl)-4-{[(2S)-1,1,1-trifluoropropan-2-yl]oxy}benzonitrile

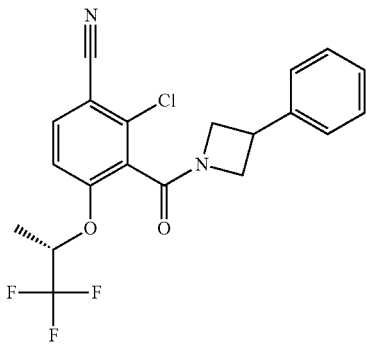 [SMILES: C[C@H](Oc1ccc(C#N)c(Cl)c1C(=O)N1CC(c2ccccc2)C1)C(F)(F)F]

¹H NMR (400 MHz, CDCl₃) δ=7.71-7.65 (m, 1H), 7.41-7.27 (m, 5H), 7.03-6.92 (m, 1H), 4.81 (quind, J=6.0, 12.2 Hz, 1H), 4.67-4.59 (m, 1H), 4.35-4.20 (m, 2H), 3.95-3.78 (m, 2H), 1.61-1.51 (m, 3H); [M+H]=409.02.

Example 55. 2-Chloro-3-[3-(3,4-difluorophenyl)azetidine-1-carbonyl]-4-{[(2S)-1,1,1-trifluoropropan-2-yl]oxy}benzonitrile

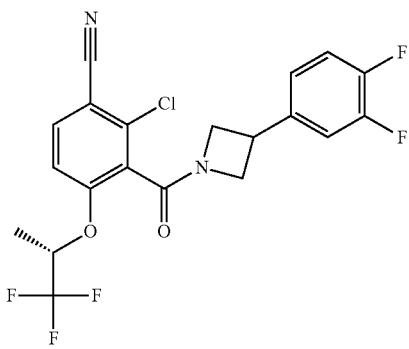 [SMILES: C[C@H](Oc1ccc(C#N)c(Cl)c1C(=O)N1CC(c2ccc(F)c(F)c2)C1)C(F)(F)F]

¹H NMR (400 MHz, CDCl₃) δ=7.71-7.66 (m, 1H), 7.17-7.07 (m, 3H), 7.04-6.93 (m, 1H), 4.80 (tt, J=6.2, 12.0 Hz, 1H), 4.69-4.60 (m, 1H), 4.42-4.12 (m, 3H), 4.01-3.86 (m, 1H), 1.62-1.48 (m, 3H); [M+H]=444.59.

Example 56. 2-Chloro-3-[3-(4-fluorophenyl)azetidine-1-carbonyl]-4-{[(2S)-1,1,1-trifluoropropan-2-yl]oxy}benzonitrile

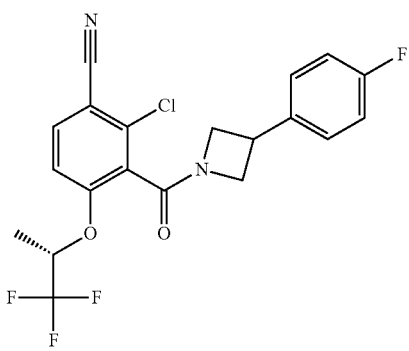 [SMILES: C[C@H](Oc1ccc(C#N)c(Cl)c1C(=O)N1CC(c2ccc(F)cc2)C1)C(F)(F)F]

¹H NMR (400 MHz, CDCl₃) δ=7.72-7.65 (m, 1H), 7.29 (ddd, J=3.3, 5.3, 8.6 Hz, 2H), 7.12-6.92 (m, 3H), 4.87-4.76 (m, 1H), 4.67-4.58 (m, 1H), 4.31-4.18 (m, 2H), 3.92-3.74 (m, 2H), 1.61-1.50 (m, 3H); [M+H]=426.96.

Example 57. 2-Chloro-3-[3-(3,5-difluorophenyl)azetidine-1-carbonyl]-4-{[(2S)-1,1,1-trifluoropropan-2-yl]oxy}benzonitrile

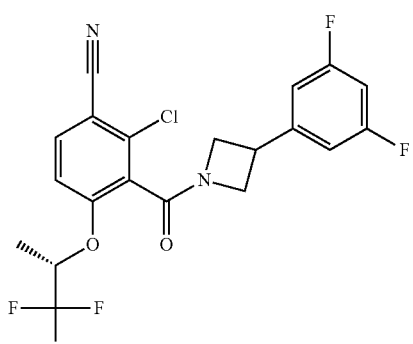

¹H NMR (400 MHz, CDCl₃) δ=7.68 (dd, J=1.6, 8.6 Hz, 1H), 7.26-7.18 (m, 1H), 7.04-6.86 (m, 3H), 4.79 (tdd, J=6.0, 12.2, 14.6 Hz, 1H), 4.65-4.47 (m, 2H), 4.34-4.14 (m, 3H), 1.61-1.53 (m, 3H); [M+H]=445.01.

Example 58. 3-(4-Fluoro-2-methylphenoxy)-1-(3-methanesulfonyl-2-methoxy-6-{[(2S)-1,1,1-trifluoropropan-2-yl]oxy}benzoyl)azetidine

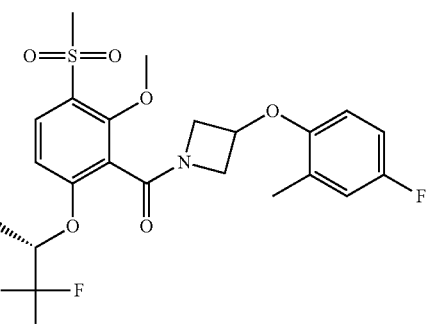

¹H NMR (400 MHz, DMSO-d₆) δ=7.88-7.79 (m, 1H), 7.30-7.18 (m, 1H), 7.04 (dd, J=3.1, 9.0 Hz, 1H), 6.98-6.83 (m, 1H), 6.75-6.58 (m, 1H), 5.55-5.41 (m, 1H), 5.12-4.94 (m, 1H), 4.49 (dd, J=6.5, 10.4 Hz, 1H), 4.37-3.96 (m, 2H), 3.95-3.81 (m, 4H), 3.73 (dt, J=3.7, 9.1 Hz, 1H), 3.26-3.13 (m, 3H), 2.15 (s, 3H), 1.57-1.33 (m, 3H); [M+H]=506.15.

Example 59. 1-(3-Methanesulfonyl-2-methoxy-6-
{[(2S)-1,1,1-trifluoropropan-2-yl]oxy}benzoyl)-3-(2,
4,6-trifluorophenoxy)azetidine

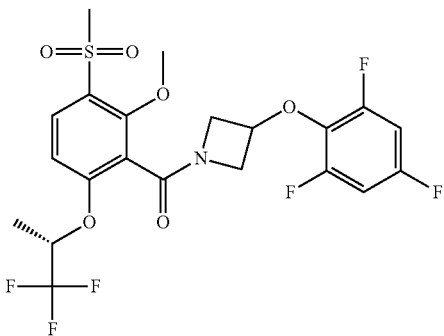

$^1$H NMR (400 MHz, DMSO-d$_6$) δ=7.83 (d, J=9.0 Hz, 1H), 7.35-7.22 (m, 3H), 5.49 (dd, J=5.7, 11.9 Hz, 1H), 5.10-4.95 (m, 1H), 4.37 (dd, J=6.5, 11.2 Hz, 1H), 4.25-3.85 (m, 6H), 3.22 (d, J=5.9 Hz, 3H), 1.51-1.36 (m, 3H); [M+H]=528.08.

Example 60. 1-(3-Methanesulfonyl-2-methoxy-6-
{[(2S)-1,1,1-trifluoropropan-2-yl]oxy}benzoyl)-3-(2,
4,5-trifluorophenoxy)azetidine

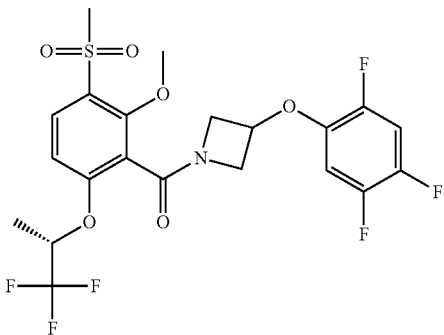 [SMILES: COc1c(S(C)(=O)=O)ccc(O[C@@H](C)C(F)(F)F)c1C(=O)N1CC(Oc2cc(F)c(F)cc2F)C1]

$^1$H NMR (400 MHz, DMSO-d$_6$) δ=7.88-7.79 (m, 1H), 7.71-7.58 (m, 1H), 7.34-7.11 (m, 2H), 5.52-5.41 (m, 1H), 5.18-5.05 (m, 1H), 4.51 (dd, J=6.7, 10.6 Hz, 1H), 4.40-4.23 (m, 1H), 4.21-3.86 (m, 5H), 3.82-3.70 (m, 1H), 3.26-3.18 (m, 3H), 1.55-1.36 (m, 3H); [M+H]=528.04.

Example 61. 2-{[1-(3-Methanesulfonyl-2-methoxy-
6-{[(2S)-1,1,1-trifluoropropan-2-yl]oxy}benzoyl)
azetidin-3-yl]oxy}-5-(trifluoromethyl)pyridine

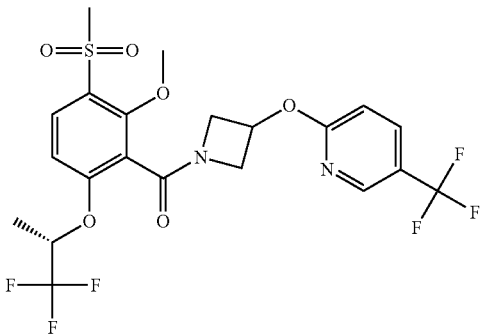 [SMILES: COc1c(S(C)(=O)=O)ccc(O[C@@H](C)C(F)(F)F)c1C(=O)N1CC(Oc2ccc(C(F)(F)F)cn2)C1]

$^1$H NMR (400 MHz, DMSO-d$_6$) δ=8.11 (d, J=11.3 Hz, 1H), 7.95-7.86 (m, 1H), 7.68 (dd, J=2.5, 9.6 Hz, 1H), 7.30 (dd, J=5.3, 9.2 Hz, 1H), 6.58 (dd, J=2.9, 9.6 Hz, 1H), 5.45 (td, J=6.7, 13.6 Hz, 1H), 5.06-4.96 (m, 1H), 4.42 (ddd, J=3.7, 10.5, 14.0 Hz, 1H), 4.18-3.95 (m, 2H), 3.91-3.75 (m, 3H), 3.23 (s, 3H), 1.47-1.32 (m, 3H); [M+H]=543.48.

Example 62. 4-{[1-(3-Methanesulfonyl-2-methoxy-
6-{[(2S)-1,1,1-trifluoropropan-2-yl]oxy}benzoyl)
azetidin-3-yl]oxy}pyridine

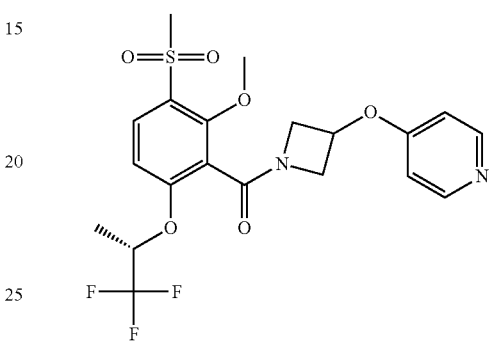

$^1$H NMR (400 MHz, DMSO-d$_6$) δ=8.74-8.66 (m, 2H), 7.84 (d, J=9.0 Hz, 1H), 7.44-7.21 (m, 3H), 5.54-5.35 (m, 2H), 4.64-4.39 (m, 2H), 4.36-3.98 (m, 2H), 3.96-3.87 (m, 3H), 3.87-3.75 (m, 1H), 3.27-3.19 (m, 3H), 1.56-1.34 (m, 3H); [M+H]=475.72.

Example 63-Example 113 were prepared in a manner analogous to Example 3, with the appropriate starting material substitutions.

Example 63. 2-Chloro-3-({3-[4-(trifluoromethyl)
phenyl]azetidin-1-yl}carbonyl)-4-[(1,1,1-trifluoro-
propan-2-yl)oxy]benzonitrile

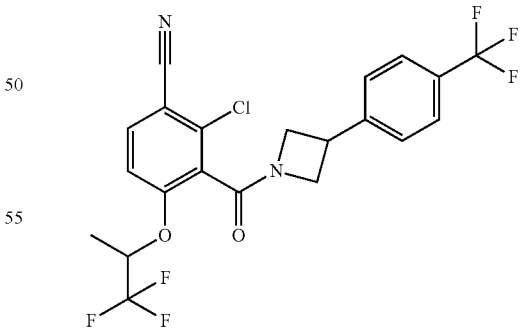

$^1$H NMR (400 MHz, CDCl$_3$) δ=7.69 (d, J=8.6 Hz, 1H), 7.66-7.57 (m, 2H), 7.52-7.39 (m, 2H), 7.07-6.89 (m, 1H), 4.92-4.73 (m, 1H), 4.73-4.57 (m, 1H), 4.43-4.18 (m, 2H), 4.04-3.84 (m, 2H), 1.68-1.48 (m, 3H); [M+H]=477.26.

Example 64. 3-({3-Hydroxy-3-[4-(trifluoromethyl)phenyl]azetidin-1-yl}carbonyl)-2-methoxy-4-[(1,1,1-trifluoropropan-2-yl)oxy]benzonitrile

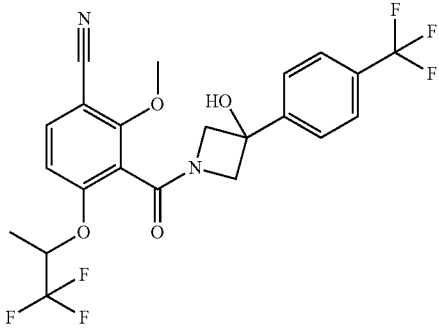 [SMILES: COc1c(C#N)ccc(OC(C)C(F)(F)F)c1C(=O)N1CC(O)(c2ccc(C(F)(F)F)cc2)C1]

The title compound was prepared in a manner analogous to Example 3, using the product from Intermediate 9, Step 1. ¹H NMR (400 MHz, CDCl₃) δ=7.85-7.49 (m, 5H), 6.91-6.62 (m, 1H), 4.78 (td, J=6.0, 12.3 Hz, 1H), 4.60-4.45 (m, 1H), 4.45-4.33 (m, 1H), 4.20-4.05 (m, 5H), 3.36 (br s, 0.5H), 3.19-2.84 (m, 0.5H), 1.69-1.44 (m, 3H); [M+H]=489.30.

Example 65. 3-{[3-(5-Fluoropyridin-2-yl)azetidin-1-yl]carbonyl}-2-methoxy-4-[(1,1,1-trifluoropropan-2-yl)oxy]benzonitrile

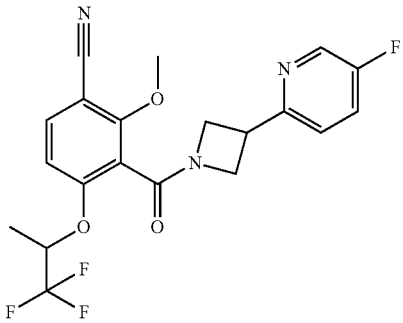 [SMILES: COc1c(C#N)ccc(OC(C)C(F)(F)F)c1C(=O)N1CC(c2ccc(F)cn2)C1]

¹H NMR (400 MHz, CDCl₃) δ=8.43 (br s, 2H), 7.58 (d, J=9.0 Hz, 1H), 7.30 (t, J=5.3 Hz, 1H), 6.75 (d, J=9.0 Hz, 1H), 4.77 (dt, J=5.7, 11.6 Hz, 1H), 4.60 (t, J=9.6 Hz, 1H), 4.40-4.19 (m, 2H), 4.18-4.04 (m, 4H), 4.03-3.82 (m, 1H), 1.64-1.41 (m, 3H); [M+H]=424.27.

Example 66. 2-Chloro-3-{[3-(5-fluoropyridin-2-yl)azetidin-1-yl]carbonyl}-4-[(1,1,1-trifluoropropan-2-yl)oxy]benzonitrile

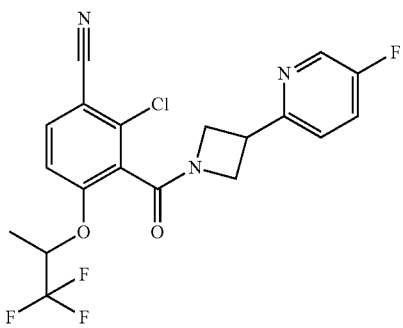 [SMILES: CC(Oc1ccc(C#N)c(Cl)c1C(=O)N1CC(c2ccc(F)cn2)C1)C(F)(F)F]

¹H NMR (400 MHz, CDCl₃) δ=8.55-8.17 (m, 2H), 7.66 (d, J=8.6 Hz, 1H), 7.36-7.20 (m, 1H), 7.07-6.92 (m, 1H), 4.99-4.70 (m, 1H), 4.65-4.46 (m, 1H), 4.38-4.17 (m, 2H), 4.17-4.00 (m, 1H), 4.00-3.77 (m, 1H), 1.51-1.36 (m, 3H); [M+H]=428.26.

Example 67. 3-{[3-(3,4-Difluorophenoxy)azetidin-1-yl]carbonyl}-2-methoxy-4-[(1,1,1-trifluoropropan-2-yl)oxy]benzonitrile

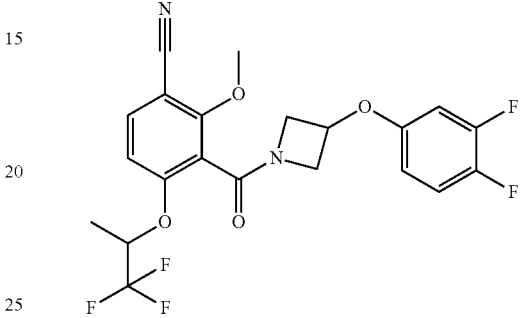

¹H NMR (400 MHz, CDCl₃) δ=7.58 (d, J=8.6 Hz, 1H), 7.17-6.95 (m, 1H), 6.74 (d, J=7.4 Hz, 1H), 6.58 (tdd, J=2.4, 6.5, 11.3 Hz, 1H), 6.48-6.32 (m, 1H), 4.91 (d, J=4.3 Hz, 1H), 4.76 (td, J=5.6, 11.8 Hz, 1H), 4.55 (dd, J=6.5, 11.2 Hz, 1H), 4.30-4.14 (m, 2H), 4.10 (s, 3H), 4.00-3.82 (m, 1H), 1.53 (t, J=5.5 Hz, 3H); [M+H]=457.26.

Example 68. 2-Chloro-3-{[3-(3,4-difluorophenoxy)azetidin-1-yl]carbonyl}-4-[(1,1,1-trifluoropropan-2-yl)oxy]benzonitrile

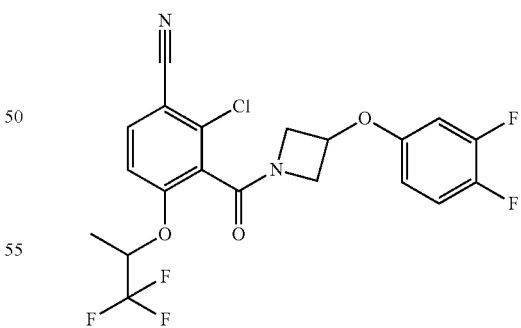

¹H NMR (400 MHz, CDCl₃) δ=7.69 (dd, J=1.8, 8.8 Hz, 1H), 7.15-7.02 (m, 1H), 7.02-6.91 (m, 1H), 6.66-6.52 (m, 1H), 6.43 (d, J=9.0 Hz, 1H), 5.04-4.88 (m, 1H), 4.87-4.69 (m, 1H), 4.66-4.49 (m, 1H), 4.37-4.10 (m, 2H), 3.93 (ddd, J=4.3, 9.9, 14.4 Hz, 1H), 1.67-1.45 (m, 3H); [M+H]=461.24.

Example 69. 3-({3-Fluoro-3-[4-(trifluoromethyl)phenyl]azetidin-1-yl}carbonyl)-2-methoxy-4-{[(2S)-1,1,1-trifluoropropan-2-yl]oxy}benzonitrile

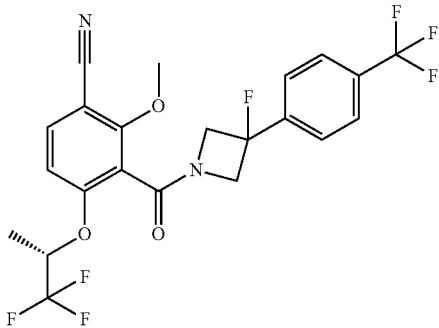 [SMILES: COc1c(C#N)ccc(O[C@@H](C)C(F)(F)F)c1C(=O)N1CC(F)(c2ccc(C(F)(F)F)cc2)C1]

$^1$H NMR (400 MHz, CDCl$_3$) δ=7.71-7.58 (m, 2H), 7.58-7.45 (m, 3H), 6.71 (d, J=9.0 Hz, 1H), 4.73 (td, J=5.9, 12.0 Hz, 1H), 4.65-4.39 (m, 2H), 4.39-4.21 (m, 1H), 4.16-3.95 (m, 4H), 1.57-1.36 (m, 3H); [M+H]=491.21.

Example 70. 3-{[3-(3,4-Difluorophenyl)-3-fluoroazetidin-1-yl]carbonyl}-2-methoxy-4-{[(2S)-1,1,1-trifluoropropan-2-yl]oxy}benzonitrile

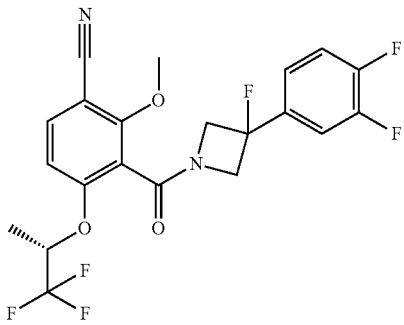 [SMILES: COc1c(C#N)ccc(O[C@@H](C)C(F)(F)F)c1C(=O)N1CC(F)(c2ccc(F)c(F)c2)C1]

$^1$H NMR (400 MHz, CDCl$_3$) δ=7.51 (d, J=9.0 Hz, 1H), 7.29-6.96 (m, 3H), 6.77-6.58 (m, 1H), 4.71 (td, J=5.9, 12.0 Hz, 1H), 4.60-4.45 (m, 1H), 4.45-4.33 (m, 1H), 4.26 (dd, J=9.0, 20.0 Hz, 1H), 4.12-3.92 (m, 4H), 1.46 (br s, 3H); [M+H]=459.29.

Example 71. 2-Chloro-3-{[3-(pyridin-3-yl)azetidin-1-yl]carbonyl}-4-[(1,1,1-trifluoropropan-2-yl)oxy]benzonitrile

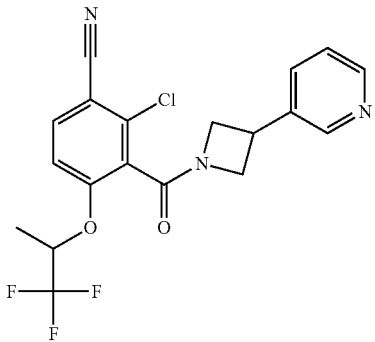

$^1$H NMR (400 MHz, CDCl$_3$) δ=8.59-8.50 (m, 2H), 7.79-7.66 (m, 2H), 7.39-7.30 (m, 1H), 7.03-6.97 (m, 1H), 4.95-4.76 (m, 1H), 4.72-4.60 (m, 1H), 4.39-4.21 (m, 2H), 3.99-3.85 (m, 2H), 1.63-1.53 (m, 3H); [M+H]=410.17.

Example 72. 2-Chloro-3-{[3-(pyridin-4-yl)azetidin-1-yl]carbonyl}-4-[(1,1,1-trifluoropropan-2-yl)oxy]benzonitrile

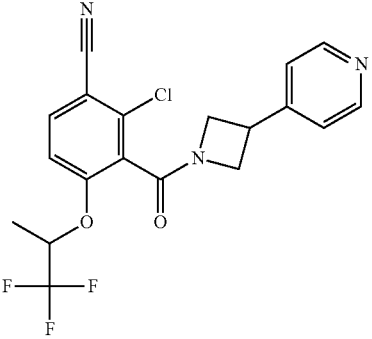 [SMILES: CC(Oc1ccc(C#N)c(Cl)c1C(=O)N1CC(c2ccncc2)C1)C(F)(F)F]

$^1$H NMR (400 MHz, CDCl$_3$) δ=8.61 (t, J=5.9 Hz, 2H), 7.70 (d, J=9.0 Hz, 1H), 7.26-7.20 (m, 2H), 7.00 (d, J=8.6 Hz, 1H), 4.82 (td, J=6.1, 12.1 Hz, 1H), 4.69-4.61 (m, 1H), 4.36-4.23 (m, 2H), 3.96-3.80 (m, 2H), 1.58 (dd, J=3.7, 6.5 Hz, 3H); [M+H]=410.20.

Example 73. 2-Chloro-3-{[3-(4-fluorophenoxy)azetidin-1-yl]carbonyl}-4-[(1,1,1-trifluoropropan-2-yl)oxy]benzonitrile

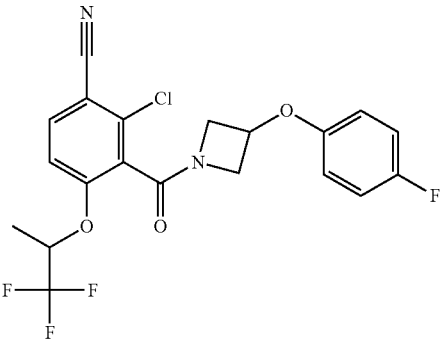 [SMILES: CC(Oc1ccc(C#N)c(Cl)c1C(=O)N1CC(Oc2ccc(F)cc2)C1)C(F)(F)F]

$^1$H NMR (400 MHz, CDCl$_3$) δ=7.69 (d, J=9.0 Hz, 1H), 7.02-6.93 (m, 3H), 6.69 (ddd, J=1.6, 4.1, 8.8 Hz, 2H), 5.02-4.92 (m, 1H), 4.79 (td, J=6.0, 16.9 Hz, 1H), 4.63-4.55 (m, 1H), 4.31-4.15 (m, 2H), 3.94 (ddd, J=4.1, 9.7, 14.0 Hz, 1H), 1.59-1.53 (t, J=8 Hz, 3H); [M+H]=443.18.

Example 74. 3-{[3-(4-Fluorophenoxy)azetidin-1-yl]carbonyl}-2-methoxy-4-[(1,1,1-trifluoropropan-2-yl)oxy]benzonitrile

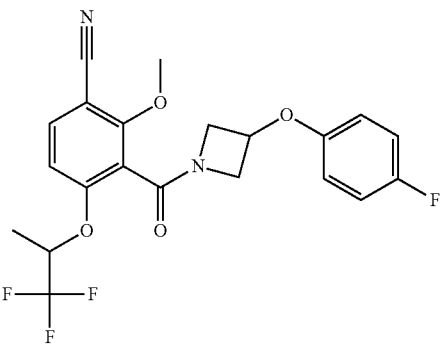 [SMILES: COc1c(C#N)ccc(OC(C)C(F)(F)F)c1C(=O)N1CC(Oc2ccc(F)cc2)C1]

¹H NMR (400 MHz, CDCl₃) δ=7.59 (d, J=8.6 Hz, 1H), 6.98 (t, J=8 Hz, 2H), 6.75 (dd, J=4.5, 8.4 Hz, 1H), 6.71-6.64 (m, 2H), 4.94 (br s, 1H), 4.76 (tt, J=6.1, 11.9 Hz, 1H), 4.60-4.52 (m, 1H), 4.27-4.16 (m, 2H), 4.12 (s, 3H), 4.01-3.89 (m, 1H), 1.55 (t, J=6.3 Hz, 3H); [M+H]=439.23

Example 75. 2-Methoxy-3-{[3-(pyridin-4-yl)azetidin-1-yl]carbonyl}-4-[(1,1,1-trifluoropropan-2-yl)oxy]benzonitrile

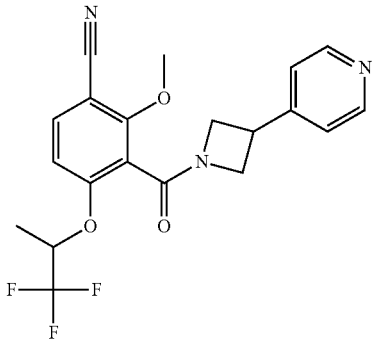 [SMILES: COc1c(C#N)ccc(OC(C)C(F)(F)F)c1C(=O)N1CC(c2ccncc2)C1]

¹H NMR (400 MHz, CDCl₃) δ=8.60 (br s, 2H), 7.59 (d, J=9.0 Hz, 1H), 7.24 (br s, 2H), 6.77 (d, J=9.0 Hz, 1H), 4.85-4.73 (m, 1H), 4.61 (t, J=9.4 Hz, 1H), 4.34-4.18 (m, 2H), 4.14 (s, 3H), 3.97-3.86 (m, 1H), 3.86-3.75 (m, 1H), 1.59-1.52 (m, 3H); [M+H]=406.22.

Example 76. 2-Chloro-3-[(3-phenoxyazetidin-1-yl)carbonyl]-4-[(1,1,1-trifluoropropan-2-yl)oxy]benzonitrile

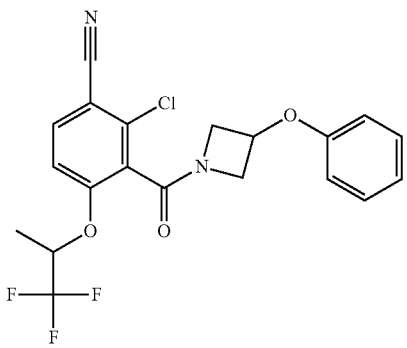 [SMILES: CC(Oc1ccc(C#N)c(Cl)c1C(=O)N1CC(Oc2ccccc2)C1)C(F)(F)F]

[M+H]=425.16.

Example 77. 2-Chloro-3-{[3-(4-methylphenoxy)azetidin-1-yl]carbonyl}-4-[(1,1,1-trifluoropropan-2-yl)oxy]benzonitrile

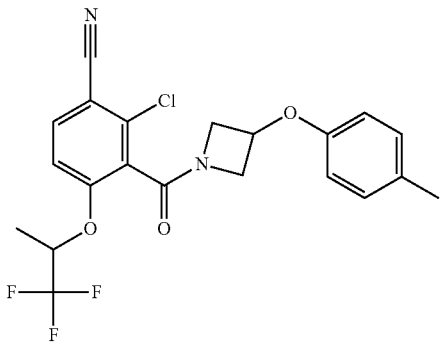 [SMILES: Cc1ccc(OC2CN(C(=O)c3c(OC(C)C(F)(F)F)ccc(C#N)c3Cl)C2)cc1]

¹H NMR (400 MHz, CDCl₃) δ=7.69 (d, J=9.0 Hz, 1H), 7.17 (t, J=7.8 Hz, 1H), 6.98 (d, J=8.2 Hz, 1H), 6.83 (d, J=7.8 Hz, 1H), 6.57 (s, 1H), 6.52 (d, J=7.0 Hz, 1H), 5.08-4.95 (m, 1H), 4.88-4.72 (m, 1H), 4.60 (td, J=5.7, 11.3 Hz, 1H), 4.34-4.24 (m, 1H), 4.24-4.14 (m, 1H), 3.95 (dt, J=3.7, 10.3 Hz, 1H), 2.32 (s, 3H), 1.60-1.56 (m, 3H); [M+H]=439.16.

Example 78. 2-Methoxy-3-{[3-(4-methylphenoxy)azetidin-1-yl]carbonyl}-4-[(1,1,1-trifluoropropan-2-yl)oxy]benzonitrile

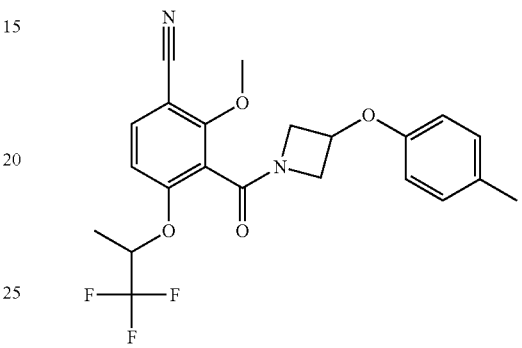

¹H NMR (400 MHz, CDCl₃) δ=7.58 (d, J=8.6 Hz, 1H), 7.16 (t, J=7.8 Hz, 1H), 6.81 (d, J=7.4 Hz, 1H), 6.77-6.71 (m, 1H), 6.56 (br s, 1H), 6.54-6.47 (m, 1H), 4.96 (d, J=6.7 Hz, 1H), 4.84-4.67 (m, 1H), 4.56 (dd, J=6.7, 11.0 Hz, 1H), 4.27-4.15 (m, 2H), 4.11 (d, J=2.3 Hz, 3H), 3.99-3.90 (m, 1H), 2.31 (s, 3H), 1.54 (t, J=7.0 Hz, 3H); [M+H]=435.22.

Example 79. 2-Chloro-3-{[3-(4-cyanophenyl)azetidin-1-yl]carbonyl}-4-[(1,1,1-trifluoropropan-2-yl)oxy]benzonitrile

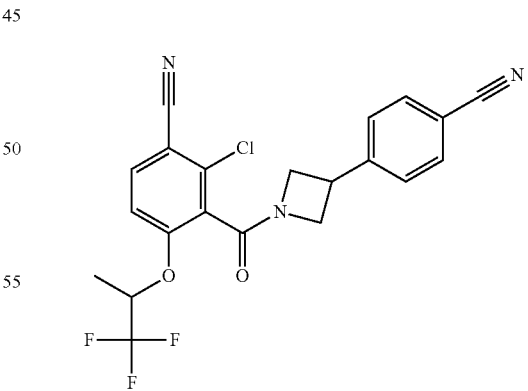

¹H NMR (400 MHz, CDCl₃) δ=7.72-7.64 (m, 3H), 7.48-7.41 (m, 2H), 7.00 (d, J=8.6 Hz, 1H), 4.87-4.76 (m, 1H), 4.70-4.61 (m, 1H), 4.36-4.21 (m, 2H), 3.99-3.83 (m, 2H), 1.57 (dd, J=3.1, 6.7 Hz, 3H); [M+H]=434.19.

Example 80. 2-Chloro-3-{[3-(4-methoxyphenyl)azetidin-1-yl]carbonyl}-4-[(1,1,1-trifluoropropan-2-yl)oxy]benzonitrile

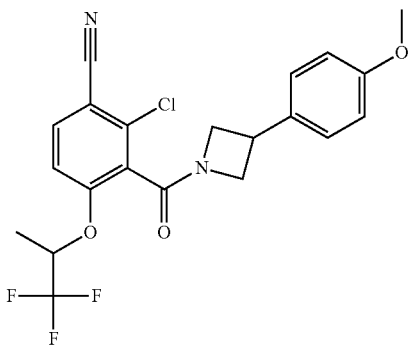 [SMILES: COc1ccc(C2CN(C(=O)c3c(OC(C)C(F)(F)F)ccc(C#N)c3Cl)C2)cc1]

[M+H]=439.16.

Example 81. 2-Chloro-3-{[3-(3,4-difluorophenyl)azetidin-1-yl]carbonyl}-4-[(1,1,1-trifluoropropan-2-yl)oxy]benzonitrile

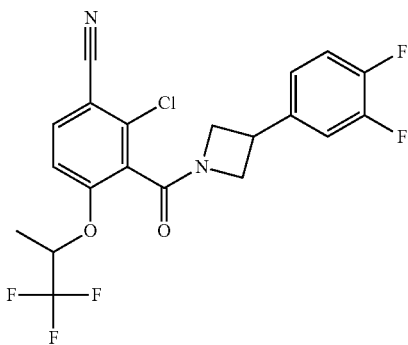 [SMILES: CC(Oc1ccc(C#N)c(Cl)c1C(=O)N1CC(c2ccc(F)c(F)c2)C1)C(F)(F)F]

$^1$H NMR (400 MHz, CDCl$_3$) δ=7.69 (d, J=9.0 Hz, 1H), 7.15-7.10 (m, 3H), 6.99 (dd, J=2.7, 8.6 Hz, 1H), 4.79 (td, J=5.8, 11.9 Hz, 1H), 4.68-4.61 (m, 1H), 4.38-4.30 (m, 1H), 4.30-4.10 (m, 2H), 3.97 (dt, J=6.3, 8.8 Hz, 1H), 1.57 (dd, J=4, 8 Hz, 3H); [M+H]=445.13.

Example 82. 2-Chloro-3-{[3-(3,5-difluorophenyl)azetidin-1-yl]carbonyl}-4-[(1,1,1-trifluoropropan-2-yl)oxy]benzonitrile

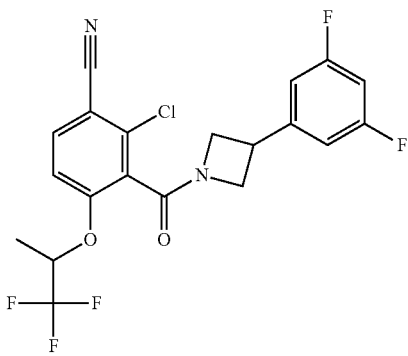 [SMILES: CC(Oc1ccc(C#N)c(Cl)c1C(=O)N1CC(c2cc(F)cc(F)c2)C1)C(F)(F)F]

$^1$H NMR (400 MHz, CDCl$_3$) δ=7.70-7.65 (m, 1H), 7.25-7.18 (m, 1H), 7.02-6.96 (m, 1H), 6.93-6.87 (m, 2H), 4.79 (qd, J=6.5, 13.0 Hz, 1H), 4.66-4.57 (m, 1H), 4.52 (dt, J=6.8, 9.9 Hz, 1H), 4.34-4.15 (m, 3H), 1.61-1.55 (m, 3H); [M+H]=445.13.

Example 83. 2-Chloro-3-{[3-(4-chlorophenyl)azetidin-1-yl]carbonyl}-4-[(1,1,1-trifluoropropan-2-yl)oxy]benzonitrile

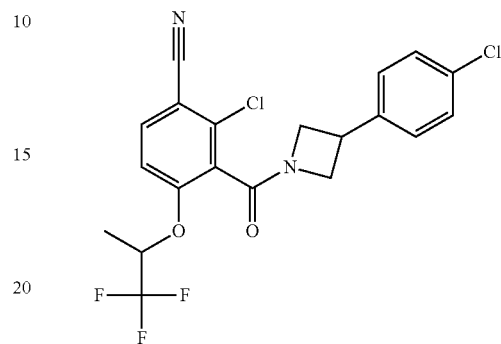

[M+H]=443.07.

Example 84. 2-Chloro-3-({3-[2-(trifluoromethyl)phenyl]azetidin-1-yl}carbonyl)-4-[(1,1,1-trifluoropropan-2-yl)oxy]benzonitrile

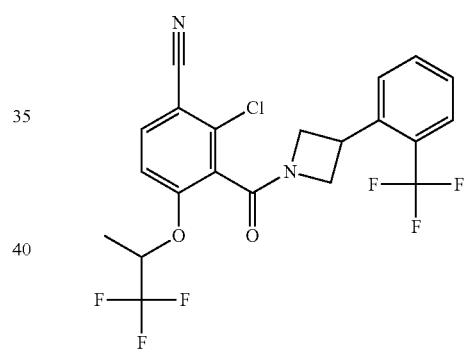

[M+H]=477.11.

Example 85. 2-Chloro-3-({3-[3-(trifluoromethyl)phenyl]azetidin-1-yl}carbonyl)-4-[(1,1,1-trifluoropropan-2-yl)oxy]benzonitrile

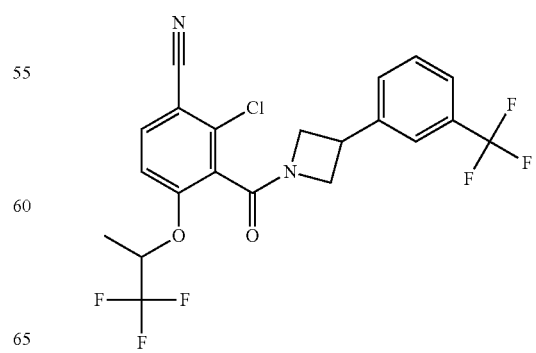

¹H NMR (400 MHz, CDCl₃) δ=7.70 (d, J=8.6 Hz, 1H), 7.59-7.50 (m, 4H), 7.00 (d, J=8.6 Hz, 1H), 4.85-4.76 (m, 1H), 4.72-4.63 (m, 1H), 4.34-4.25 (m, 2H), 4.01-3.88 (m, 2H), 1.62-1.57 (m, 3H); [M+H]=477.11.

Example 86. 2-Chloro-3-{[3-(4-fluorophenyl)azetidin-1-yl]carbonyl}-4-[(1,1,1-trifluoropropan-2-yl)oxy]benzonitrile

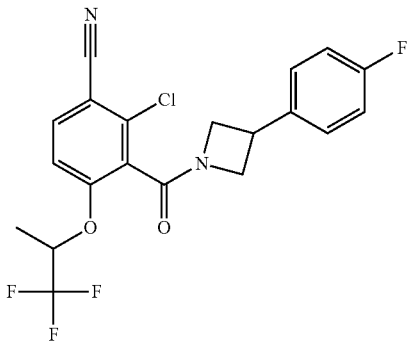 [SMILES: CC(Oc1ccc(C#N)c(Cl)c1C(=O)N1CC(c2ccc(F)cc2)C1)C(F)(F)F]

¹H NMR (400 MHz, CDCl₃) δ=7.68 (d, J=8.6 Hz, 1H), 7.29 (ddd, J=3.1, 5.2, 8.5 Hz, 2H), 7.09-7.02 (m, 2H), 7.00 (dd, J=1.4, 8.8 Hz, 1H), 4.86-4.77 (m, 1H), 4.67-4.58 (m, 1H), 4.31-4.17 (m, 2H), 3.91-3.81 (m, 2H), 1.57 (d, J=6.3 Hz, 3H); [M+H]=427.12.

Example 87. 2-Chloro-3-{[3-(2-fluorophenyl)azetidin-1-yl]carbonyl}-4-[(1,1,1-trifluoropropan-2-yl)oxy]benzonitrile

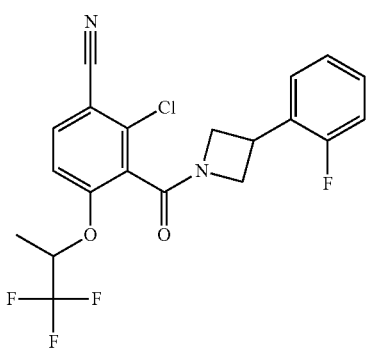 [SMILES: CC(Oc1ccc(C#N)c(Cl)c1C(=O)N1CC(c2ccccc2F)C1)C(F)(F)F]

¹H NMR (400 MHz, CDCl₃) δ=7.64-7.57 (m, 1H), 7.32-7.25 (m, 1H), 7.24-7.19 (m, 1H), 7.15-7.07 (m, 1H), 7.03-6.95 (m, 1H), 6.95-6.85 (m, 1H), 4.79-4.66 (m, 1H), 4.61-4.52 (m, 1H), 4.36-4.25 (m, 1H), 4.23-4.01 (m, 2H), 3.97-3.88 (m, 1H), 1.57-1.47 (m, 3H); [M+H]=427.15.

Example 88. 2-Chloro-3-{[3-(pyridin-2-yl)azetidin-1-yl]carbonyl}-4-[(1,1,1-trifluoropropan-2-yl)oxy]benzonitrile

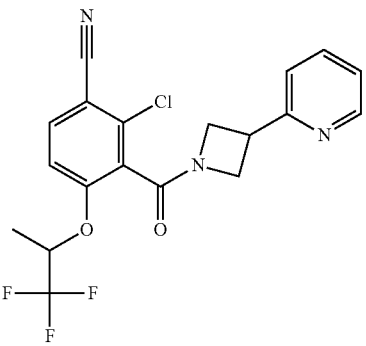 [SMILES: CC(Oc1ccc(C#N)c(Cl)c1C(=O)N1CC(c2ccccn2)C1)C(F)(F)F]

¹H NMR (400 MHz, CDCl₃) δ=8.66-8.44 (m, 1H), 7.76-7.61 (m, 2H), 7.25-7.16 (m, 2H), 6.98 (d, J=9.0 Hz, 1H), 4.87-4.72 (m, 1H), 4.66-4.54 (m, 1H), 4.50-4.39 (m, 1H), 4.26-4.11 (m, 2H), 4.09-3.94 (m, 1H), 1.57 (dd, J=6.5, 8.8 Hz, 3H); [M+H]=410.17.

Example 89. 2-Chloro-3-{[3-(4-methoxyphenoxy)azetidin-1-yl]carbonyl}-4-[(1,1,1-trifluoropropan-2-yl)oxy]benzonitrile

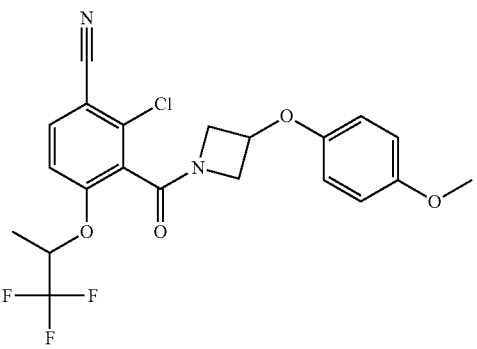 [SMILES: COc1ccc(OC2CN(C(=O)c3c(OC(C)C(F)(F)F)ccc(C#N)c3Cl)C2)cc1]

[M+H]=455.12.

Example 90. 2-Methoxy-3-({3-[2-(trifluoromethyl)phenyl]azetidin-1-yl}carbonyl)-4-[(1,1,1-trifluoropropan-2-yl)oxy]benzonitrile

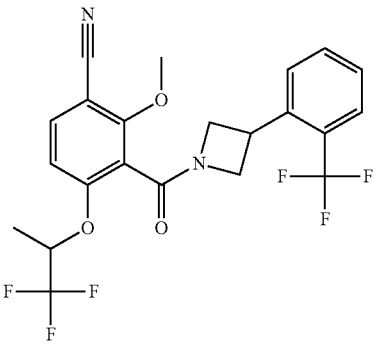 [SMILES: COc1c(C#N)ccc(OC(C)C(F)(F)F)c1C(=O)N1CC(c2ccccc2C(F)(F)F)C1]

¹H NMR (400 MHz, CDCl₃) δ=7.72 (dd, J=4.3, 7.4 Hz, 1H), 7.68-7.61 (m, 2H), 7.59 (d, J=8.6 Hz, 1H), 7.45-7.36 (m, 1H), 6.75 (d, J=8.6 Hz, 1H), 4.78 (td, J=6.0, 12.3 Hz, 1H), 4.64-4.54 (m, 1H), 4.34-4.22 (m, 3H), 4.15 (d, J=3.9 Hz, 3H), 3.91-3.83 (m, 1H), 1.56 (t, J=6.5 Hz, 3H); [M+H]= 473.20.

Example 91. 3-{[3-(4-Fluorophenyl)azetidin-1-yl]carbonyl}-2-methoxy-4-[(1,1,1-trifluoropropan-2-yl)oxy]benzonitrile

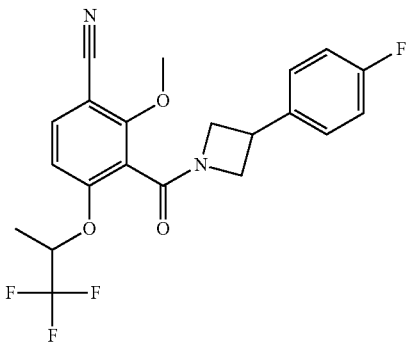

¹H NMR (400 MHz, CDCl₃) δ=7.62-7.54 (m, 1H), 7.32-7.26 (m, 2H), 7.11-6.99 (m, 2H), 6.76 (dd, J=2.0, 9.0 Hz, 1H), 4.79 (td, J=6.1, 12.1 Hz, 1H), 4.59 (dd, J=8.2, 10.2 Hz, 1H), 4.29-4.17 (m, 2H), 4.14 (d, J=3.5 Hz, 3H), 3.94-3.74 (m, 2H), 1.56 (d, J=6.3 Hz, 3H); [M+H]=423.21.

Example 92. 3-{[3-(2-Fluorophenyl)azetidin-1-yl]carbonyl}-2-methoxy-4-[(1,1,1-trifluoropropan-2-yl)oxy]benzonitrile

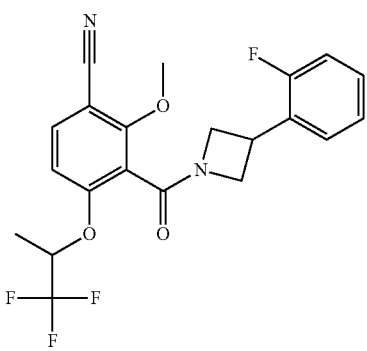 [SMILES: COc1c(C#N)ccc(OC(C)C(F)(F)F)c1C(=O)N1CC(c2ccccc2F)C1]

¹H NMR (400 MHz, CDCl₃) δ=7.58 (d, J=8.6 Hz, 1H), 7.40-7.26 (m, 2H), 7.20-7.13 (m, 1H), 7.10-6.99 (m, 1H), 6.75 (d, J=9.0 Hz, 1H), 4.77 (td, J=6.4, 12.6 Hz, 1H), 4.63-4.53 (m, 1H), 4.37-4.28 (m, 1H), 4.28-4.19 (m, 1H), 4.13 (d, J=10.2 Hz, 3H), 4.09-3.94 (m, 2H), 1.55 (dd, J=6.7, 13.7 Hz, 3H); [M+H]=423.21.

Example 93. 2-Methoxy-3-{[3-(pyridin-2-yl)azetidin-1-yl]carbonyl}-4-[(1,1,1-trifluoropropan-2-yl)oxy]benzonitrile

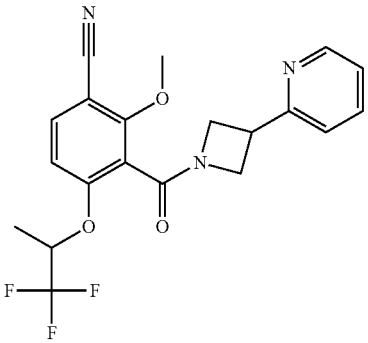 [SMILES: COc1c(C#N)ccc(OC(C)C(F)(F)F)c1C(=O)N1CC(c2ccccn2)C1]

¹H NMR (400 MHz, CDCl₃) δ=8.62-8.38 (m, 1H), 7.71-7.62 (m, 1H), 7.58-7.51 (m, 1H), 7.25-7.15 (m, 2H), 6.79-6.66 (m, 1H), 4.84-4.70 (m, 1H), 4.60-4.49 (m, 1H), 4.41-4.31 (m, 1H), 4.26-4.14 (m, 1H), 4.13-4.07 (m, 3H), 4.07-3.87 (m, 2H), 1.50 (dd, J=6.5, 12.7 Hz, 3H); [M+H]=406.19.

Example 94. 2-Methoxy-3-{[3-(4-methoxyphenoxy)azetidin-1-yl]carbonyl}-4-[(1,1,1-trifluoropropan-2-yl)oxy]benzonitrile

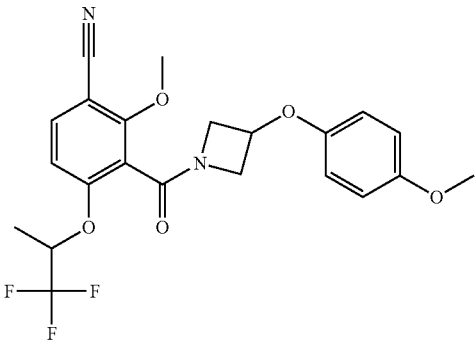 [SMILES: COc1ccc(OC2CN(C(=O)c3c(OC(C)C(F)(F)F)ccc(C#N)c3OC)C2)cc1]

¹H NMR (400 MHz, CDCl₃) δ=7.57 (d, J=8.6 Hz, 1H), 6.82 (d, J=9.0 Hz, 2H), 6.77-6.71 (m, 1H), 6.70-6.64 (m, 2H), 4.91 (d, J=7.0 Hz, 1H), 4.76 (tdd, J=6.0, 12.2, 18.4 Hz, 1H), 4.53 (dd, J=6.5, 10.8 Hz, 1H), 4.20 (ddd, J=4.7, 10.6, 15.3 Hz, 2H), 4.13-4.09 (m, 3H), 3.97-3.89 (m, 1H), 3.75 (s, 3H), 1.54 (t, J=5.5 Hz, 3H); [M+H]=451.14.

Example 95. 3-{[3-(4-Cyanophenyl)azetidin-1-yl]carbonyl}-2-methoxy-4-[(1,1,1-trifluoropropan-2-yl)oxy]benzonitrile

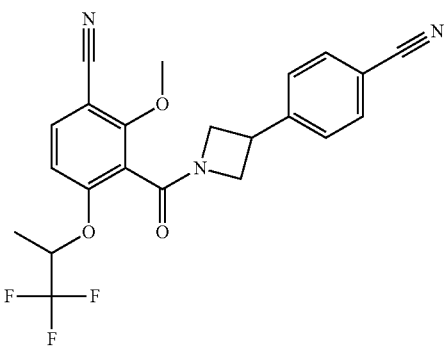 [SMILES: COc1c(C#N)ccc(OC(C)C(F)(F)F)c1C(=O)N1CC(c2ccc(C#N)cc2)C1]

¹H NMR (400 MHz, CDCl₃) δ=7.69-7.64 (m, 2H), 7.60 (d, J=8.6 Hz, 1H), 7.43 (d, J=8.2 Hz, 2H), 6.77 (d, J=8.6 Hz, 1H), 4.84-4.75 (m, 1H), 4.67-4.58 (m, 1H), 4.34-4.17 (m, 2H), 4.14 (d, J=2.0 Hz, 3H), 3.95-3.83 (m, 2H), 1.56 (d, J=6.7 Hz, 3H); [M+H]=430.14.

Example 96. 2-Methoxy-3-{[3-(4-methoxyphenyl)azetidin-1-yl]carbonyl}-4-[(1,1,1-trifluoropropan-2-yl)oxy]benzonitrile

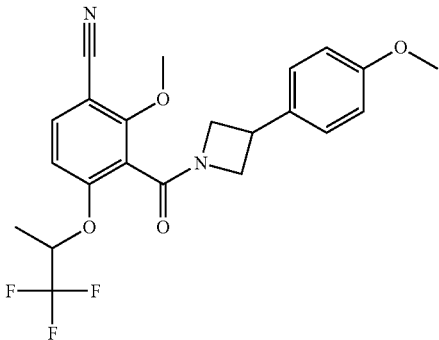 [SMILES: COc1ccc(C2CN(C(=O)c3c(OC(C)C(F)(F)F)ccc(C#N)c3OC)C2)cc1]

¹H NMR (400 MHz, CDCl₃) δ=7.57 (d, J=8.6 Hz, 1H), 7.25-7.21 (m, 2H), 6.89 (dd, J=5.9, 8.2 Hz, 2H), 6.76 (dd, J=4.5, 8.8 Hz, 1H), 4.78 (td, J=6.2, 12.2 Hz, 1H), 4.57 (t, J=9.4 Hz, 1H), 4.26-4.17 (m, 2H), 4.14 (d, J=4.7 Hz, 3H), 3.86 (td, J=6.2, 14.7 Hz, 1H), 3.80 (s, 3H), 3.78 (d, J=5.9 Hz, 1H), 1.56 (d, J=6.3 Hz, 3H); [M+H]=435.18.

Example 97. 3-{[3-(4-Chlorophenyl)azetidin-1-yl]carbonyl}-2-methoxy-4-[(1,1,1-trifluoropropan-2-yl)oxy]benzonitrile

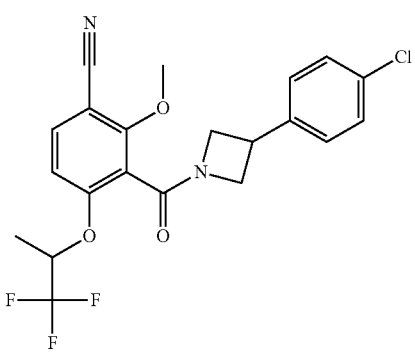 [SMILES: COc1c(C#N)ccc(OC(C)C(F)(F)F)c1C(=O)N1CC(c2ccc(Cl)cc2)C1]

¹H NMR (400 MHz, CDCl₃) δ=7.58 (d, J=8.6 Hz, 1H), 7.38-7.30 (m, 2H), 7.26-7.20 (m, 2H), 6.76 (dd, J=2.9, 8.8 Hz, 1H), 4.79 (td, J=6.1, 12.1 Hz, 1H), 4.59 (dd, J=8.6, 10.2 Hz, 1H), 4.28-4.16 (m, 2H), 4.14 (d, J=2.7 Hz, 3H), 3.94-3.74 (m, 2H), 1.56 (d, J=6.3 Hz, 3H); [M+H]=439.16.

Example 98. 2-Methoxy-3-({3-[4-(trifluoromethyl)phenyl]azetidin-1-yl}carbonyl)-4-[(1,1,1-trifluoropropan-2-yl)oxy]benzonitrile

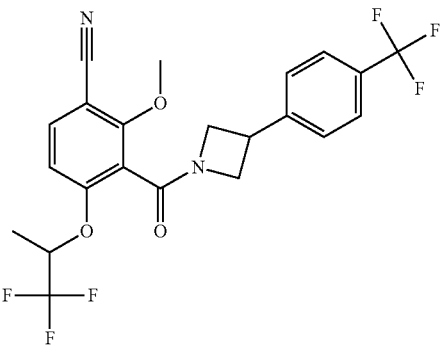 [SMILES: COc1c(C#N)ccc(OC(C)C(F)(F)F)c1C(=O)N1CC(c2ccc(C(F)(F)F)cc2)C1]

¹H NMR (400 MHz, DMSO-d₆) δ=7.82 (d, J=9.0 Hz, 1H), 7.70-7.61 (m, 2H), 7.56-7.43 (m, 2H), 7.20-7.11 (m, 1H), 5.44 (dd, J=6.1, 12.3 Hz, 1H), 4.40 (d, J=7.8 Hz, 1H), 4.28-3.96 (m, 3H), 3.93 (s, 3H), 3.87-3.64 (m, 1H), 1.49-1.26 (m, 3H); [M+H]=473.2.

Example 99. 2-Methoxy-3-({3-[3-(trifluoromethyl)phenyl]azetidin-1-yl}carbonyl)-4-[(1,1,1-trifluoropropan-2-yl)oxy]benzonitrile

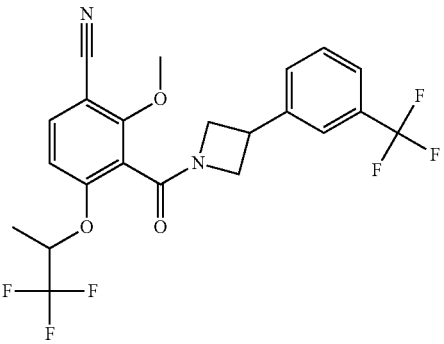 [SMILES: COc1c(C#N)ccc(OC(C)C(F)(F)F)c1C(=O)N1CC(c2cccc(C(F)(F)F)c2)C1]

¹H NMR (400 MHz, CDCl₃) δ=7.62-7.46 (m, 5H), 6.77 (d, J=8.6 Hz, 1H), 4.84-4.73 (m, 1H), 4.63 (dd, J=8.2, 10.2 Hz, 1H), 4.32-4.21 (m, 2H), 4.15 (d, J=8.2 Hz, 3H), 3.98-3.87 (m, 2H), 1.56 (d, J=6.3 Hz, 3H); [M+H]=473.17.

Example 100. 3-{[3-(3,5-Difluorophenyl)azetidin-1-yl]carbonyl}-2-methoxy-4-[(1,1,1-trifluoropropan-2-yl)oxy]benzonitrile

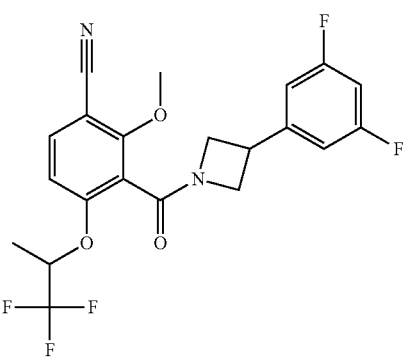 [SMILES: COc1c(C#N)ccc(OC(C)C(F)(F)F)c1C(=O)N1CC(c2cc(F)cc(F)c2)C1]

¹H NMR (400 MHz, CDCl₃) δ=7.57 (d, J=8.6 Hz, 1H), 7.25-7.18 (m, 1H), 6.94-6.86 (m, 2H), 6.80-6.70 (m, 1H), 4.83-4.70 (m, 1H), 4.62-4.53 (m, 1H), 4.52-4.42 (m, 1H), 4.26-4.17 (m, 3H), 4.14 (s, 3H), 1.58-1.52 (m, 3H); [M+H]=441.15.

Example 101. 3-{[3-(3,4-Difluorophenyl)azetidin-1-yl]carbonyl}-2-methoxy-4-[(1,1,1-trifluoropropan-2-yl)oxy]benzonitrile

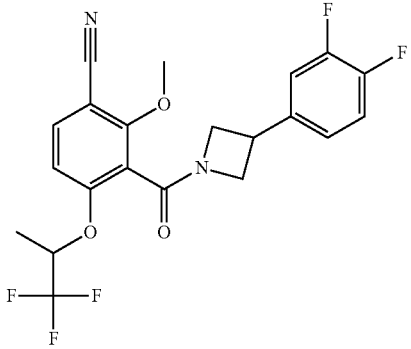 [SMILES: COc1c(C#N)ccc(OC(C)C(F)(F)F)c1C(=O)N1CC(c2ccc(F)c(F)c2)C1]

[M+H]=441.15.

Example 102. 2-Methoxy-3-{[3-(pyridin-3-yloxy)azetidin-1-yl]carbonyl}-4-[(1,1,1-trifluoropropan-2-yl)oxy]benzonitrile

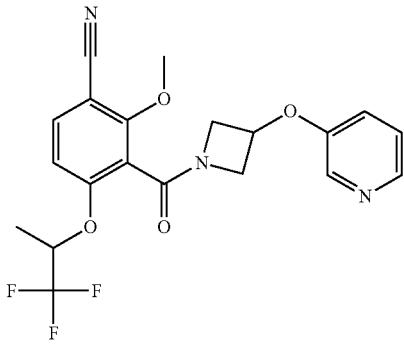 [SMILES: COc1c(C#N)ccc(OC(C)C(F)(F)F)c1C(=O)N1CC(Oc2cccnc2)C1]

¹H NMR (400 MHz, CDCl₃) δ=8.27 (d, J=4.3 Hz, 1H), 8.15 (d, J=2.7 Hz, 1H), 7.58 (d, J=9.0 Hz, 1H), 7.23 (dd, J=4.7, 8.6 Hz, 1H), 7.04 (dd, J=1.8, 7.6 Hz, 1H), 6.74 (d, J=8.6 Hz, 1H), 5.10-4.94 (m, 1H), 4.84-4.70 (m, 1H), 4.58 (dd, J=6.5, 11.2 Hz, 1H), 4.29-4.20 (m, 2H), 4.10 (s, 3H), 4.02-3.87 (m, 1H), 1.53 (t, J=7.2 Hz, 3H); [M+H]=422.21.

Example 103. 2-Chloro-3-{[3-(pyridin-3-yloxy)azetidin-1-yl]carbonyl}-4-[(1,1,1-trifluoropropan-2-yl)oxy]benzonitrile

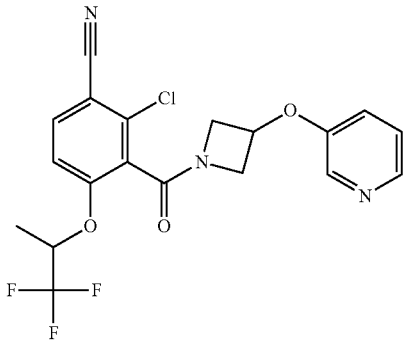 [SMILES: CC(Oc1ccc(C#N)c(Cl)c1C(=O)N1CC(Oc2cccnc2)C1)C(F)(F)F]

¹H NMR (400 MHz, CDCl₃) δ=8.28 (dd, J=1.4, 4.5 Hz, 1H), 8.16 (dd, J=2.9, 5.3 Hz, 1H), 7.69 (dd, J=2.0, 8.6 Hz, 1H), 7.23 (ddd, J=2.3, 4.3, 6.3 Hz, 1H), 7.10-7.03 (m, 1H), 6.98 (dd, J=5.1, 8.6 Hz, 1H), 5.12-4.99 (m, 1H), 4.79 (tdd, J=6.1, 12.2, 18.3 Hz, 1H), 4.67-4.58 (m, 1H), 4.34-4.19 (m, 2H), 4.03-3.88 (m, 1H), 1.55 (dd, J=6.7, 9.4 Hz, 3H); [M+H]=426.16.

Example 104. 3-{[3-(4-Cyanophenyl)azetidin-1-yl]carbonyl}-4-(1-fluorocyclobutyl)-2-methoxybenzonitrile

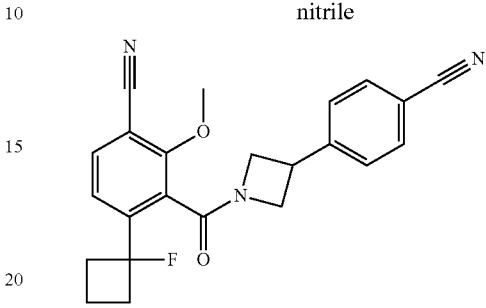

¹H NMR (400 MHz, CDCl₃) δ=7.75-7.59 (m, 3H), 7.45 (t, J=9.0 Hz, 2H), 7.27-7.20 (m, 1H), 4.71-4.49 (m, 1H), 4.30-4.15 (m, 2H), 4.12 (d, J=8.6 Hz, 3H), 3.97-3.75 (m, 2H), 2.92-2.48 (m, 4H), 2.28-2.09 (m, 1H), 1.93-1.71 (m, 1H); [M+H]=390.3.

Example 105. 2-Chloro-4-(2,2,2-trifluoroethoxy)-3-({3-[4-(trifluoromethyl)phenyl]azetidin-1-yl}carbonyl)benzonitrile

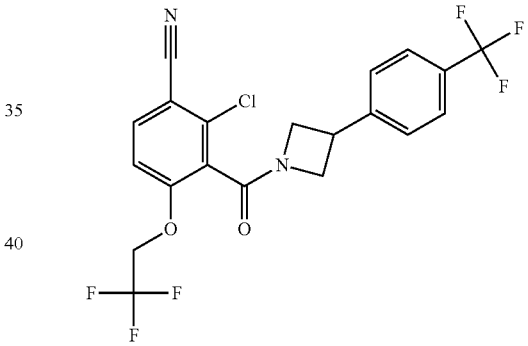

¹H NMR (400 MHz, CDCl₃) δ=7.74-7.69 (m, 1H), 7.68-7.58 (m, 2H), 7.45 (d, J=7.8 Hz, 2H), 6.96 (dd, J=4.9, 8.8 Hz, 1H), 4.67 (t, J=9.6 Hz, 1H), 4.53 (q, J=7.2 Hz, 2H), 4.37-4.25 (m, 2H), 3.99-3.84 (m, 2H); [M+H]=463.19.

Example 106. 2-Chloro-3-{[3-(4-cyanophenyl)azetidin-1-yl]carbonyl}-4-(2,2,2-trifluoroethoxy)benzonitrile

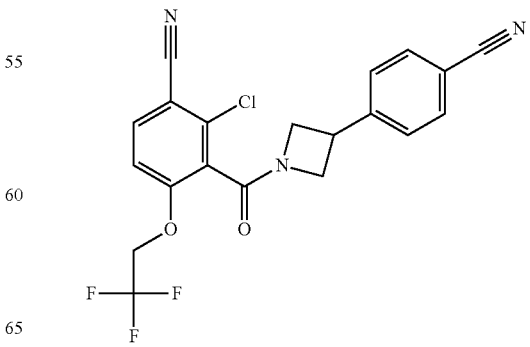

¹H NMR (400 MHz, CDCl₃) δ=7.75-7.63 (m, 3H), 7.44 (d, J=8.2 Hz, 2H), 7.00-6.92 (m, 1H), 4.68 (t, J=10.0 Hz, 1H), 4.53 (q, J=7.7 Hz, 2H), 4.38-4.22 (m, 2H), 4.00-3.80 (m, 2H); [M+H]=420.29.

Example 107. 2-Chloro-3-({3-[4-(trifluoromethyl)phenyl]azetidin-1-yl}carbonyl)-4-{[(2S)-1,1,1-trifluoropropan-2-yl]oxy}benzonitrile

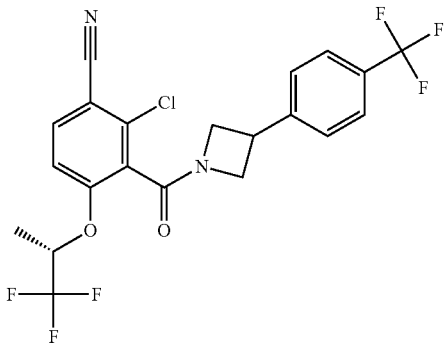 [SMILES: C[C@H](Oc1ccc(C#N)c(Cl)c1C(=O)N1CC(c2ccc(C(F)(F)F)cc2)C1)C(F)(F)F]

¹H NMR (400 MHz, CDCl₃) δ=7.71-7.67 (m, 1H), 7.66-7.59 (m, 2H), 7.44 (dd, J=3.1, 8.2 Hz, 2H), 7.01 (dd, J=1.6, 9.0 Hz, 1H), 4.82 (quin, J=6.2 Hz, 1H), 4.70-4.61 (m, 1H), 4.34-4.21 (m, 2H), 3.98-3.87 (m, 2H), 1.58 (dd, J=1.6, 6.3 Hz, 3H); [M+H]=477.22.

Example 108. 3-{[3-(4-Cyanophenyl)azetidin-1-yl]carbonyl}-2-methoxy-4-{[(2S)-1,1,1-trifluoropropan-2-yl]oxy}benzonitrile

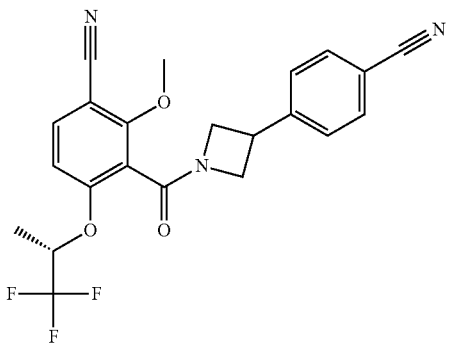 [SMILES: COc1c(C#N)ccc(O[C@@H](C)C(F)(F)F)c1C(=O)N1CC(c2ccc(C#N)cc2)C1]

¹H NMR (400 MHz, CDCl₃) δ=7.65 (t, J=7.6 Hz, 2H), 7.59 (d, J=9.0 Hz, 1H), 7.42 (d, J=8.2 Hz, 2H), 6.77 (d, J=8.6 Hz, 1H), 4.79 (td, J=6.0, 12.3 Hz, 1H), 4.61 (dd, J=8.4, 10.0 Hz, 1H), 4.33-4.16 (m, 2H), 4.12 (s, 3H), 3.94-3.83 (m, 2H), 1.55 (d, J=6.7 Hz, 3H); [M+H]=430.29.

Example 109. 2-Chloro-3-{[3-(4-cyanophenyl)azetidin-1-yl]carbonyl}-4-{[(2S)-1,1,1-trifluoropropan-2-yl]oxy}benzonitrile

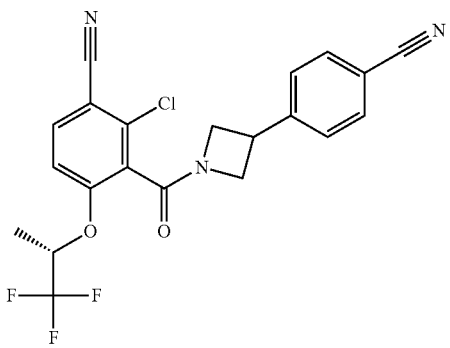 [SMILES: C[C@H](Oc1ccc(C#N)c(Cl)c1C(=O)N1CC(c2ccc(C#N)cc2)C1)C(F)(F)F]

¹H NMR (400 MHz, CDCl₃) δ=7.72-7.63 (m, 3H), 7.48-7.41 (m, 2H), 7.00 (d, J=8.6 Hz, 1H), 4.87-4.76 (m, 1H), 4.71-4.61 (m, 1H), 4.36-4.20 (m, 2H), 3.98-3.83 (m, 2H), 1.57 (dd, J=3.1, 6.7 Hz, 3H); [M+H]=434.28.

Example 110. 2-Chloro-3-{[3-(5-methylpyridin-3-yl)azetidin-1-yl]carbonyl}-4-[(1,1,1-trifluoropropan-2-yl)oxy]benzonitrile

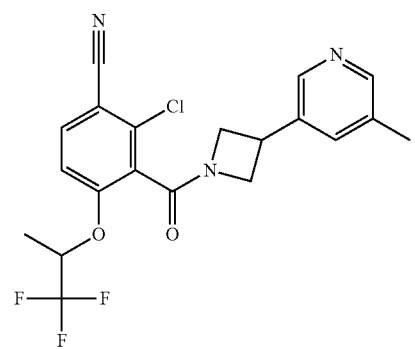 [SMILES: Cc1cncc(C2CN(C(=O)c3c(OC(C)C(F)(F)F)ccc(C#N)c3Cl)C2)c1]

¹H NMR (400 MHz, CDCl₃) δ=8.38 (s, 1H), 8.33 (dd, J=2.2, 6.8 Hz, 1H), 7.73-7.66 (m, 1H), 7.52 (d, J=9.4 Hz, 1H), 7.00 (dd, J=2.3, 8.6 Hz, 1H), 4.86-4.77 (m, 1H), 4.69-4.60 (m, 1H), 4.32-4.21 (m, 2H), 3.93-3.85 (m, 2H), 2.36 (d, J=3.5 Hz, 3H), 1.58 (d, J=6.7 Hz, 3H); [M+H]=424.27.

Example 111. 2-Methoxy-3-{[3-(5-methylpyridin-3-yl)azetidin-1-yl]carbonyl}-4-[(1,1,1-trifluoropropan-2-yl)oxy]benzonitrile

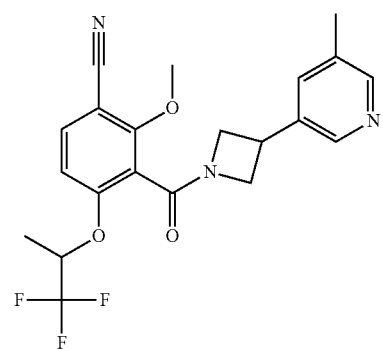 [SMILES: COc1c(C#N)ccc(OC(C)C(F)(F)F)c1C(=O)N1CC(c2cncc(C)c2)C1]

¹H NMR (400 MHz, CDCl₃) δ=8.43-8.27 (m, 2H), 7.59 (d, J=9.0 Hz, 1H), 7.52 (br s, 1H), 6.76 (d, J=9.0 Hz, 1H), 4.85-4.72 (m, 1H), 4.61 (dd, J=8.6, 10.2 Hz, 1H), 4.31-4.18 (m, 2H), 4.15 (d, J=7.0 Hz, 3H), 3.95-3.77 (m, 2H), 2.36 (d, J=6.7 Hz, 3H), 1.57 (d, J=6.7 Hz, 3H); [M+H]=420.33.

Example 112. 2-Chloro-3-({3-[6-(trifluoromethyl)pyridin-3-yl]azetidin-1-yl}carbonyl)-4-[(1,1,1-trifluoropropan-2-yl)oxy]benzonitrile

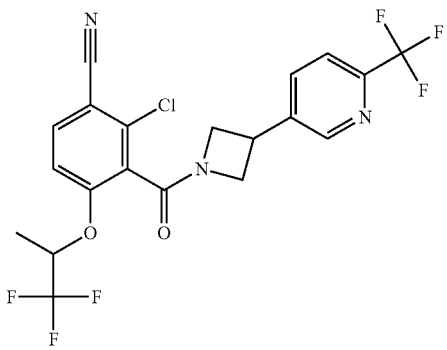 [SMILES: CC(Oc1ccc(C#N)c(Cl)c1C(=O)N1CC(c2ccc(C(F)(F)F)nc2)C1)C(F)(F)F]

¹H NMR (400 MHz, CDCl₃) δ=8.73-8.57 (m, 1H), 7.90 (dt, J=2.2, 5.2 Hz, 1H), 7.79-7.65 (m, 2H), 7.01 (d, J=8.6 Hz, 1H), 4.83 (td, J=6.1, 12.1 Hz, 1H), 4.70 (dt, J=3.1, 9.6 Hz, 1H), 4.41-4.22 (m, 2H), 4.07-3.96 (m, 1H), 3.95-3.81 (m, 1H), 1.57 (dd, J=4.1, 6.5 Hz, 3H); [M+H]=478.16.

Example 113. 2-Methoxy-3-({3-[6-(trifluoromethyl)pyridin-3-yl]azetidin-1-yl}carbonyl)-4-[(1,1,1-trifluoropropan-2-yl)oxy]benzonitrile

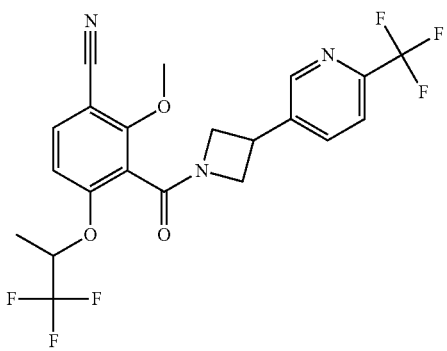 [SMILES: COc1c(C#N)ccc(OC(C)C(F)(F)F)c1C(=O)N1CC(c2ccc(C(F)(F)F)nc2)C1]

¹H NMR (400 MHz, CDCl₃) δ=8.73-8.51 (m, 1H), 7.90 (dd, J=2.2, 8.0 Hz, 1H), 7.76-7.68 (m, 1H), 7.59 (d, J=8.6 Hz, 1H), 6.77 (d, J=9.0 Hz, 1H), 4.85-4.74 (m, 1H), 4.71-4.61 (m, 1H), 4.38-4.29 (m, 1H), 4.22 (dd, J=5.9, 10.2 Hz, 1H), 4.16-4.11 (m, 3H), 4.02-3.81 (m, 2H), 1.55 (d, J=6.3 Hz, 3H); [M+H]=474.26.

Example 114-Example 157 were prepared in a manner analogous to Example 4, with the appropriate starting material substitutions.

Example 114. 3-({3-[3-Chloro-5-(trifluoromethyl)pyridin-2-yl]azetidin-1-yl}carbonyl)-2-methoxy-4-{[(2S)-1,1,1-trifluoropropan-2-yl]oxy}benzonitrile

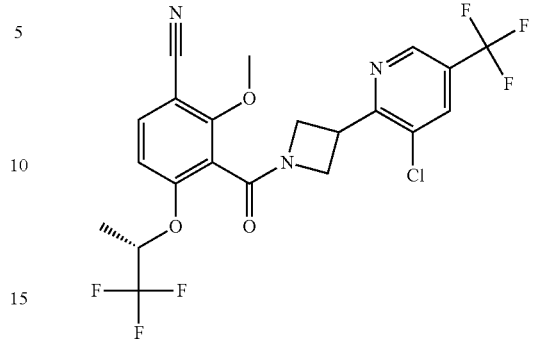

¹H NMR (400 MHz, DMSO-d₆) δ=9.10-8.97 (m, 1H), 8.55 (br s, 1H), 7.94 (dd, J=4.1, 8.0 Hz, 1H), 7.35-7.18 (m, 1H), 5.67-5.40 (m, 1H), 4.53-4.36 (m, 3H), 4.29-4.13 (m, 1H), 4.10-3.96 (m, 3H), 3.63 (s, 2H), 1.62-1.31 (m, 3H); [M+H]=508.09.

Example 115. 3-({3-[5-(Difluoromethyl)pyridin-2-yl]azetidin-1-yl}carbonyl)-2-methoxy-4-{[(2S)-1,1,1-trifluoropropan-2-yl]oxy}benzonitrile

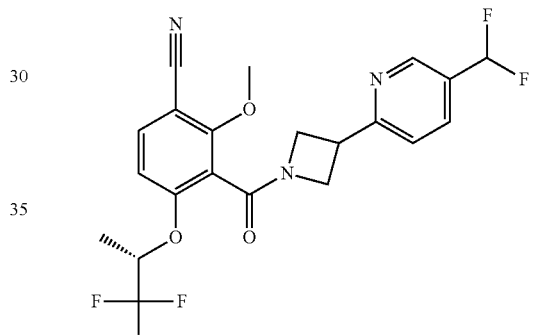

¹H NMR (400 MHz, DMSO-d₆) δ=8.82-8.70 (m, 1H), 7.95 (d, J=7.8 Hz, 1H), 7.85 (d, J=8.6 Hz, 1H), 7.54-7.41 (m, 1H), 7.31-6.96 (m, 2H), 5.57-5.38 (m, 1H), 4.44-4.01 (m, 5H), 3.98 (s, 3H), 1.54-1.31 (m, 3H); [M+H]=455.99.

Example 116. 3-{[3-(4-Cyano-3-fluorophenyl)azetidin-1-yl]carbonyl}-2-methoxy-4-{[(2S)-1,1,1-trifluoropropan-2-yl]oxy}benzonitrile

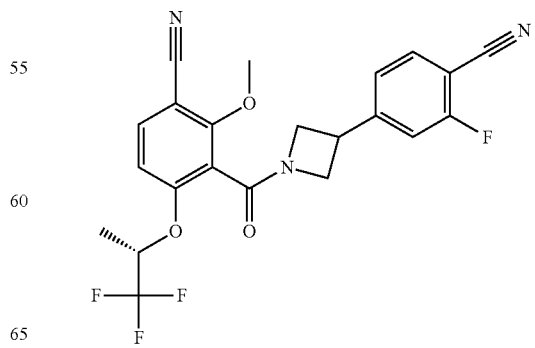

¹H NMR (400 MHz, DMSO-d6) δ=7.96-7.81 (m, 2H), 7.57-7.27 (m, 2H), 7.21 (d, J=8.6 Hz, 1H), 5.48 (d, J=5.9 Hz, 1H), 4.43 (d, J=8.2 Hz, 1H), 4.30-3.64 (m, 7H), 1.53-1.29 (m, 3H); [M+H]=448.01.

Example 117. 3-({3-[3-Chloro-5-(trifluoromethyl)pyridin-2-yl]azetidin-1-yl}carbonyl)-4-(4-fluorooxan-4-yl)-2-methoxybenzonitrile

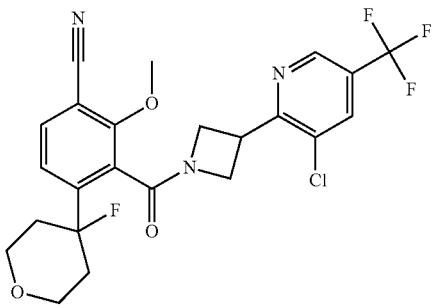 [SMILES: COc1c(C#N)ccc(C2(F)CCOCC2)c1C(=O)N1CC(c2ncc(C(F)(F)F)cc2Cl)C1]

¹H NMR (400 MHz, DMSO-d₆) δ=9.03-8.92 (m, 1H), 8.45 (br s, 1H), 7.87 (dd, J=2.0, 8.2 Hz, 1H), 7.41 (t, J=9.0 Hz, 1H), 4.48-4.29 (m, 3H), 4.19-3.58 (m, 8H), 3.53-3.40 (m, 1H), 2.16-1.64 (m, 4H); [M+H]=498.14.

Example 118. 3-{[3-(2-Chloro-4-cyanophenyl)azetidin-1-yl]carbonyl}-2-methoxy-4-{[(2S)-1,1,1-trifluoropropan-2-yl]oxy}benzonitrile

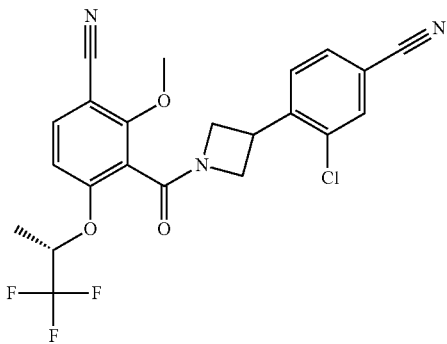 [SMILES: COc1c(C#N)ccc(O[C@@H](C)C(F)(F)F)c1C(=O)N1CC(c2ccc(C#N)cc2Cl)C1]

¹H NMR (400 MHz, DMSO-d₆) δ=8.08 (d, J=1.5 Hz, 1H), 7.90 (dd, J=1.6, 8.0 Hz, 2H), 7.82-7.65 (m, 1H), 7.27-7.16 (m, 1H), 5.61-5.40 (m, 1H), 4.52-4.41 (m, 1H), 4.38-4.16 (m, 3H), 4.04-3.75 (m, 4H), 1.55-1.23 (m, 3H); [M+H]=464.12.

Example 119. 3-({3-[3-Chloro-5-(trifluoromethyl)pyridin-2-yl]azetidin-1-yl}carbonyl)-2-methoxy-4-(2,2,2-trifluoroethoxy)benzonitrile

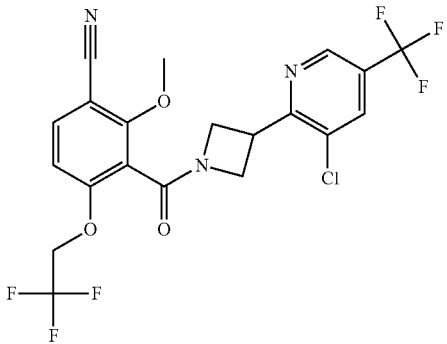 [SMILES: COc1c(C#N)ccc(OCC(F)(F)F)c1C(=O)N1CC(c2ncc(C(F)(F)F)cc2Cl)C1]

¹H NMR (400 MHz, DMSO-d₆) δ=8.97 (br s, 1H), 8.49 (d, J=1.5 Hz, 1H), 7.92 (d, J=8.9 Hz, 1H), 7.13 (d, J=8.9 Hz, 1H), 4.74 (br s, 2H), 4.50-4.32 (m, 4H), 4.30-4.12 (m, 2H), 3.90 (s, 3H); [M+H]=494.18.

Example 120. 2-Chloro-3-({3-[5-(trifluoromethyl)pyridin-2-yl]azetidin-1-yl}carbonyl)-4-{[(2S)-1,1,1-trifluoropropan-2-yl]oxy}benzonitrile

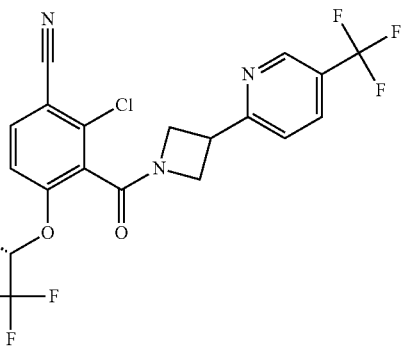

Rotamers observed: ¹H NMR (400 MHz, DMSO-d₆) δ=9.02-8.87 (m, 1H), 8.17 (dd, J=2.7, 8.2 Hz, 1H), 8.11-8.03 (m, 1H), 7.63-7.46 (m, 2H), 5.64-5.45 (m, 1H), 4.46-4.33 (m, 1H), 4.29-3.86 (m, 4H), 1.54-1.33 (m, 3H); [M+H]=478.07.

Example 121. 3-{[3-(3,5-Difluoropyridin-2-yl)azetidin-1-yl]carbonyl}-2-methoxy-4-{[(2S)-1,1,1-trifluoropropan-2-yl]oxy}benzonitrile

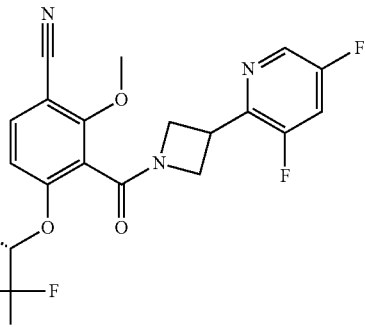

¹H NMR (400 MHz, DMSO-d₆) δ=8.58-8.45 (m, 1H), 7.98-7.82 (m, 2H), 7.24-7.14 (m, 1H), 5.56-5.37 (m, 1H), 4.43-4.05 (m, 5H), 3.96 (d, J=9.8 Hz, 3H), 1.53-1.31 (m, 3H); [M+H]=442.01.

Example 122. 3-{[3-(3-Chloro-4-cyanophenyl)azetidin-1-yl]carbonyl}-2-methoxy-4-{[(2S)-1,1,1-trifluoropropan-2-yl]oxy}benzonitrile

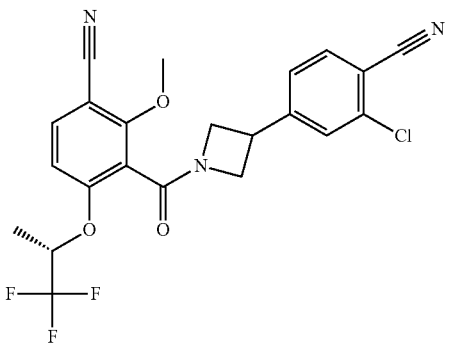 [SMILES: COc1c(C#N)ccc(O[C@@H](C)C(F)(F)F)c1C(=O)N1CC(c2ccc(C#N)c(Cl)c2)C1]

¹H NMR (400 MHz, DMSO-d₆) δ=8.00-7.93 (m, 1H), 7.87 (d, J=9.0 Hz, 1H), 7.75-7.63 (m, 1H), 7.54-7.41 (m, 1H), 7.26-7.16 (m, 1H), 5.57-5.42 (m, 1H), 4.49-4.38 (m, 1H), 4.30-4.02 (m, 3H), 4.00-3.95 (m, 3H), 3.80-3.66 (m, 1H), 1.52-1.34 (m, 3H); [M+H]=464.12.

Example 123. 3-{[3-(2-Cyanophenyl)azetidin-1-yl]carbonyl}-2-methoxy-4-{[(2S)-1,1,1-trifluoropropan-2-yl]oxy}benzonitrile

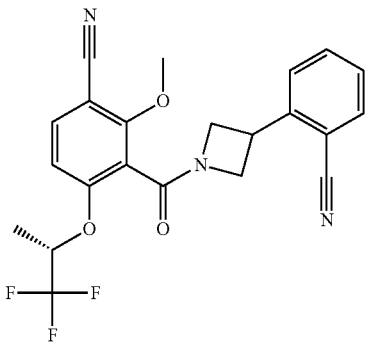 [SMILES: COc1c(C#N)ccc(O[C@@H](C)C(F)(F)F)c1C(=O)N1CC(c2ccccc2C#N)C1]

¹H NMR (400 MHz, DMSO-d₆) δ=7.88 (d, J=9.0 Hz, 1H), 7.81 (d, J=7.4 Hz, 1H), 7.79-7.60 (m, 2H), 7.47 (dt, J=1.4, 7.5 Hz, 1H), 7.25-7.17 (m, 1H), 5.47 (dd, J=6.1, 11.9 Hz, 1H), 4.55-4.44 (m, 1H), 4.40-4.14 (m, 3H), 4.01-3.92 (m, 3H), 3.85-3.76 (m, 1H), 1.53-1.28 (m, 3H); [M+H]=430.08.

Example 124. 3-Chloro-4-{1-[(3-cyano-2-methoxy-6-{[(2S)-1,1,1-trifluoropropan-2-yl]oxy}phenyl)carbonyl]azetidin-3-yl}-2-fluorobenzonitrile

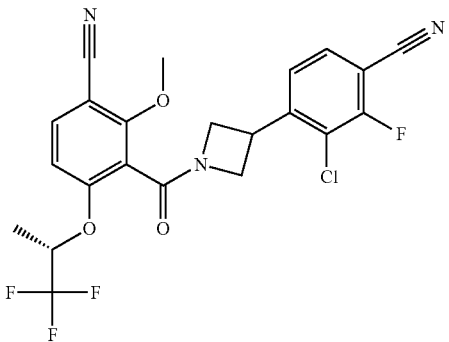 [SMILES: COc1c(C#N)ccc(O[C@@H](C)C(F)(F)F)c1C(=O)N1CC(c2ccc(C#N)c(F)c2Cl)C1]

¹H NMR (400 MHz, DMSO-d₆) δ=8.02-7.94 (m, 1H), 7.87 (d, J=9.0 Hz, 1H), 7.65-7.49 (m, 1H), 7.26-7.15 (m, 1H), 5.58-5.40 (m, 1H), 4.46 (d, J=6.7 Hz, 1H), 4.38-4.14 (m, 3H), 4.06-3.74 (m, 4H), 1.53-1.21 (m, 4H); [M+H]=482.14.

Example 125. 2-Methoxy-4-(2,2,2-trifluoroethoxy)-3-({3-[5-(trifluoromethyl)pyridin-2-yl]azetidin-1-yl}carbonyl)benzonitrile

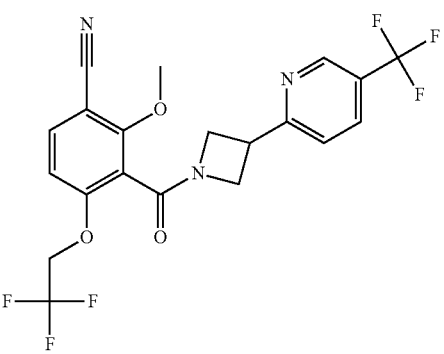 [SMILES: COc1c(C#N)ccc(OCC(F)(F)F)c1C(=O)N1CC(c2ccc(C(F)(F)F)cn2)C1]

¹H NMR (400 MHz, DMSO-d₆) δ=9.03-8.89 (m, 1H), 8.21-8.14 (m, 1H), 7.89 (d, J=8.6 Hz, 1H), 7.57 (br s, 1H), 7.10 (d, J=7.8 Hz, 1H), 5.05-4.83 (m, 2H), 4.39 (br s, 1H), 4.32-4.01 (m, 4H), 4.01-3.93 (m, 3H); [M+H]=460.13.

Example 126. 3-{[3-(4-Chloro-2-cyanophenyl)azetidin-1-yl]carbonyl}-2-methoxy-4-{[(2S)-1,1,1-trifluoropropan-2-yl]oxy}benzonitrile

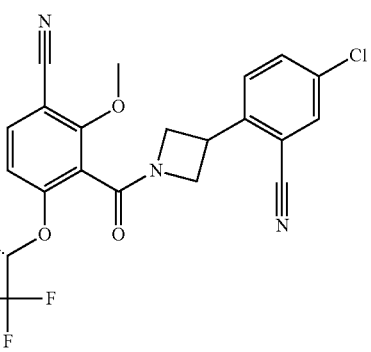

¹H NMR (400 MHz, DMSO-d₆) δ=8.02 (d, J=2.3 Hz, 1H), 7.88 (d, J=9.0 Hz, 1H), 7.85-7.57 (m, 2H), 7.20 (d, J=9.0 Hz, 1H), 5.46 (br s, 1H), 4.48 (d, J=8.6 Hz, 1H), 4.38-4.13 (m, 3H), 4.02-3.93 (m, 3H), 3.83-3.72 (m, 1H), 1.53-1.29 (m, 3H); [M+H]=464.12.

Example 127. 3-{[3-(2-Cyano-4-fluorophenyl)azetidin-1-yl]carbonyl}-2-methoxy-4-{[(2S)-1,1,1-trifluoropropan-2-yl]oxy}benzonitrile

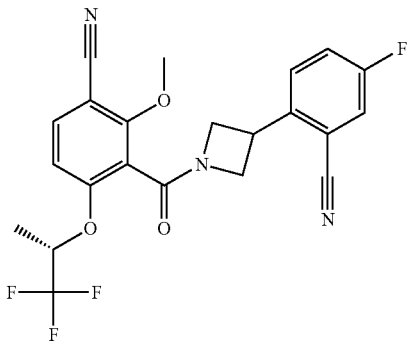 [SMILES: COc1c(C#N)ccc(O[C@@H](C)C(F)(F)F)c1C(=O)N1CC(c2ccc(F)cc2C#N)C1]

$^{1}$H NMR (400 MHz, DMSO-d$_{6}$) δ=7.91-7.82 (m, 2H), 7.81-7.61 (m, 2H), 7.21 (br s, 1H), 5.49 (br s, 1H), 4.48 (d, J=8.6 Hz, 1H), 4.38-4.13 (m, 3H), 4.01-3.93 (m, 3H), 3.76 (br s, 1H), 1.54-1.28 (m, 3H); [M+H]=448.20.

Example 128. 3-{[3-(4-Cyano-2-methoxyphenyl)azetidin-1-yl]carbonyl}-2-methoxy-4-{[(2S)-1,1,1-trifluoropropan-2-yl]oxy}benzonitrile

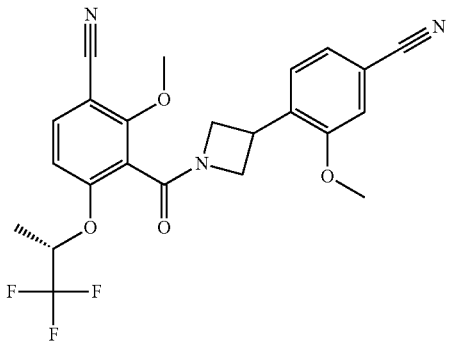 [SMILES: COc1cc(C#N)ccc1C1CN(C(=O)c2c(O[C@@H](C)C(F)(F)F)ccc(C#N)c2OC)C1]

$^{1}$H NMR (400 MHz, DMSO-d$_{6}$) δ=7.86 (d, J=9.0 Hz, 1H), 7.53-7.38 (m, 3H), 7.19 (ddd, J=3.7, 9.1, 16.5 Hz, 1H), 5.56-5.38 (m, 1H), 4.42-4.31 (m, 1H), 4.25-4.05 (m, 2H), 3.98-3.68 (m, 6H), 1.53-1.20 (m, 3H); [M+H]=460.13.

Example 129. 2-Methoxy-3-({3-[2-methoxy-4-(trifluoromethyl)phenyl]azetidin-1-yl}carbonyl)-4-{[(2S)-1,1,1-trifluoropropan-2-yl]oxy}benzonitrile

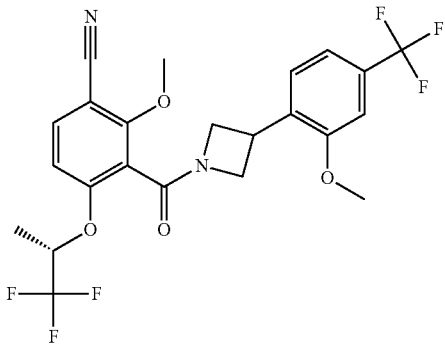 [SMILES: COc1cc(C(F)(F)F)ccc1C1CN(C(=O)c2c(O[C@@H](C)C(F)(F)F)ccc(C#N)c2OC)C1]

$^{1}$H NMR (400 MHz, DMSO-d$_{6}$) δ=7.86 (d, J=9.0 Hz, 1H), 7.55-7.41 (m, 1H), 7.35-7.14 (m, 3H), 5.57-5.38 (m, 1H), 4.44-4.31 (m, 1H), 4.27-4.03 (m, 2H), 3.99-3.70 (m, 6H), 1.54-1.19 (m, 3H); [M+H]=503.15.

Example 130. 3-{[3-(1,3-Benzoxazol-6-yl)azetidin-1-yl]carbonyl}-2-methoxy-4-{[(2S)-1,1,1-trifluoropropan-2-yl]oxy}benzonitrile

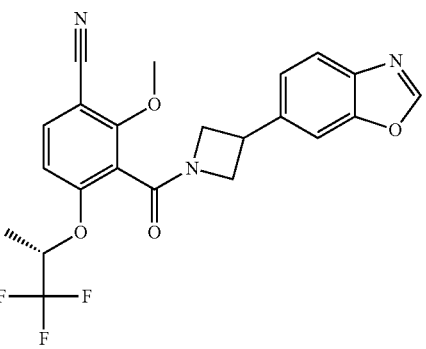

$^{1}$H NMR (400 MHz, DMSO-d$_{6}$) δ=8.73-8.70 (m, 1H), 7.88 (d, J=9.0 Hz, 1H), 7.81-7.67 (m, 2H), 7.41-7.30 (m, 1H), 7.26-7.18 (m, 1H), 5.57-5.44 (m, 1H), 4.53-4.43 (m, 1H), 4.35-4.23 (m, 1H), 4.07 (d, J=5.9 Hz, 3H), 4.00-3.96 (m, 3H), 3.78 (d, J=5.9 Hz, 1H), 1.53-1.32 (m, 3H); [M+H]=455.81.

Example 131. 2-Chloro-3-{[3-(2-chloro-4-cyanophenyl)azetidin-1-yl]carbonyl}-4-{[(2S)-1,1,1-trifluoropropan-2-yl]oxy}benzonitrile

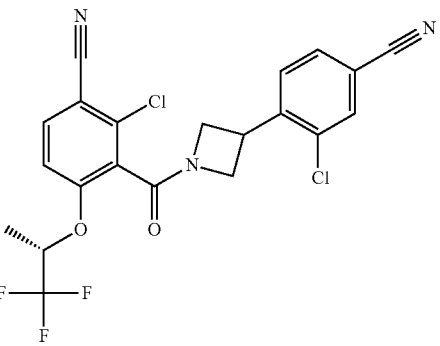

$^{1}$H NMR (400 MHz, DMSO-d$_{6}$) δ=8.11-8.05 (m, 2H), 7.90-7.85 (m, 1H), 7.78-7.63 (m, 1H), 7.56-7.47 (m, 1H), 5.64-5.46 (m, 1H), 4.52-4.25 (m, 3H), 4.24-4.10 (m, 1H), 4.02-3.70 (m, 2H), 1.54-1.21 (m, 3H); [M+H]=469.98.

Example 132. 3-{[3-(2-Chloro-4-cyanophenyl)azetidin-1-yl]carbonyl}-4-(4-fluorooxan-4-yl)-2-methoxybenzonitrile

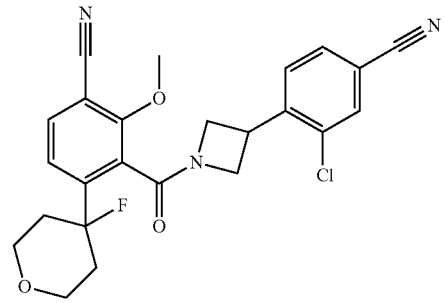 [SMILES: COc1c(C#N)ccc(C2(F)CCOCC2)c1C(=O)N1CC(c2ccc(C#N)cc2Cl)C1]

¹H NMR (400 MHz, DMSO-d₆) δ=8.05 (dd, J=1.8, 5.3 Hz, 1H), 7.94-7.86 (m, 2H), 7.80-7.67 (m, 1H), 7.42 (ddd, J=1.4, 8.5, 11.2 Hz, 1H), 4.46 (q, J=9.3 Hz, 1H), 4.30-4.09 (m, 3H), 3.90-3.78 (m, 2H), 3.77-3.55 (m, 2H), 2.15-1.68 (m, 4H); [M+H]=453.98.

Example 133. 3-{[3-(2-Chloro-4-cyanophenyl)azetidin-1-yl]carbonyl}-2-methoxy-4-(1,4,4-trifluorocyclohexyl)benzonitrile

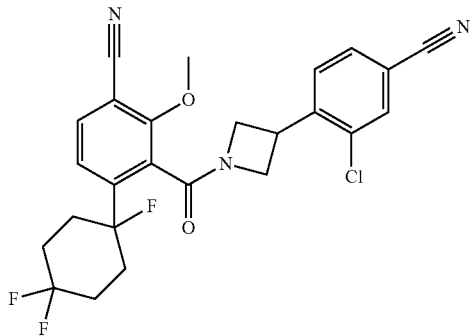 [SMILES: COc1c(C#N)ccc(C2(F)CCC(F)(F)CC2)c1C(=O)N1CC(c2ccc(C#N)cc2Cl)C1]

¹H NMR (400 MHz, DMSO-d₆) δ=8.06 (dd, J=1.6, 4.3 Hz, 1H), 7.94-7.86 (m, 2H), 7.80-7.66 (m, 1H), 7.42 (ddd, J=1.2, 8.2, 12.1 Hz, 1H), 4.51-4.39 (m, 1H), 4.31-4.06 (m, 3H), 3.88-3.81 (m, 1H), 2.46-2.23 (m, 2H), 2.21-1.85 (m, 6H); [M+H]=488.14.

Example 134. 3-{[3-(2-Chloro-4-cyanophenyl)azetidin-1-yl]carbonyl}-4-(1-fluorocyclobutyl)-2-methoxybenzonitrile

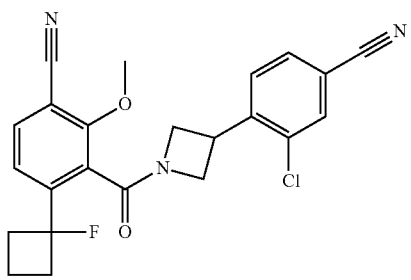

¹H NMR (400 MHz, DMSO-d₆) δ=8.05 (dd, J=1.6, 5.1 Hz, 1H), 7.95-7.85 (m, 2H), 7.79-7.62 (m, 1H), 7.45 (dt, J=2.0, 7.8 Hz, 1H), 4.51-4.39 (m, 1H), 4.31-4.08 (m, 3H), 3.90-3.74 (m, 1H), 2.93-2.51 (m, 3H), 2.46-2.29 (m, 2H), 2.14-1.91 (m, 2H), 1.80-1.61 (m, 2H); [M+H]=424.15.

Example 135. 2-Methoxy-3-{3-[5-(trifluoromethyl)pyridin-2-yl]azetidine-1-carbonyl}-4-{[(2R)-1,1,1-trifluoropropan-2-yl]oxy}benzonitrile

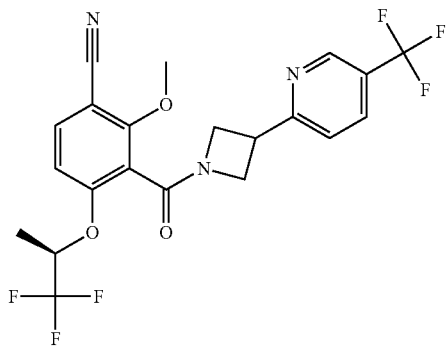

¹H NMR (400 MHz, DMSO-d₆) δ=9.02-8.88 (m, 1H), 8.17 (dd, J=1.6, 8.2 Hz, 1H), 7.86 (d, J=9.0 Hz, 1H), 7.63-7.52 (m, 1H), 7.25-7.14 (m, 1H), 5.57-5.38 (m, 1H), 4.28-4.13 (m, 2H), 4.11-4.02 (m, 1H), 4.45-4.01 (m, 1H), 4.01-3.93 (m, 3H), 1.53-1.31 (m, 3H); [M+H]=474.27.

Example 136. 3-{3-[3-Chloro-5-(trifluoromethyl)pyridin-2-yl]azetidine-1-carbonyl}-2-methoxy-4-{[(2R)-1,1,1-trifluoropropan-2-yl]oxy}benzonitrile

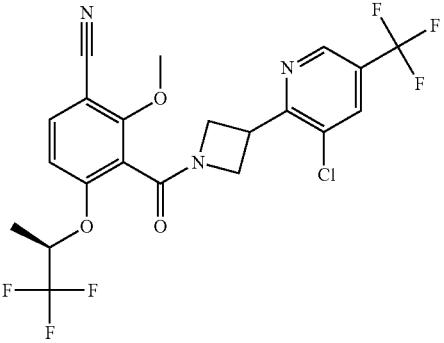 [SMILES: COc1c(C#N)ccc(O[C@H](C)C(F)(F)F)c1C(=O)N1CC(c2ncc(C(F)(F)F)cc2Cl)C1]

¹H NMR (400 MHz, DMSO-d₆) δ=9.01-8.89 (m, 1H), 8.46 (br s, 1H), 7.85 (br s, 1H), 7.26-7.12 (m, 1H), 5.59-5.33 (m, 1H), 4.64-4.07 (m, 5H), 4.03-3.87 (m, 3H), 1.55-1.24 (m, 3H); [M+H]=508.24.

Example 137. 3-{3-[5-(Difluoromethyl)pyridin-2-yl]azetidine-1-carbonyl}-2-methoxy-4-{[(2R)-1,1,1-trifluoropropan-2-yl]oxy}benzonitrile

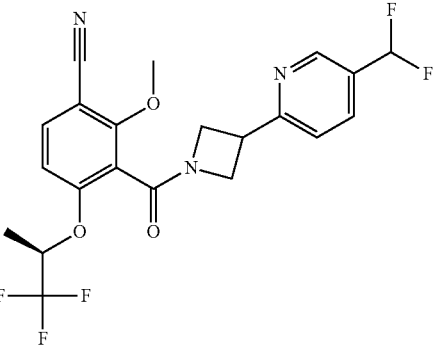

¹H NMR (400 MHz, DMSO-d₆) δ=8.83-8.69 (m, 1H), 7.96 (d, J=7.8 Hz, 1H), 7.86 (d, J=9.0 Hz, 1H), 7.53-7.42 (m, 1H), 7.30-6.97 (m, 2H), 5.56-5.39 (m, 1H), 4.43-4.33 (m, 1H), 4.32-4.01 (m, 4H), 3.98 (s, 3H), 1.53-1.31 (m, 3H); [M+H]=456.03.

Example 138. 3-[2-Fluoro-4-(trifluoromethyl)phenyl]-1-(3-methanesulfonyl-2-methoxy-6-{[(2R)-1,1,1-trifluoropropan-2-yl]oxy}benzoyl)azetidine

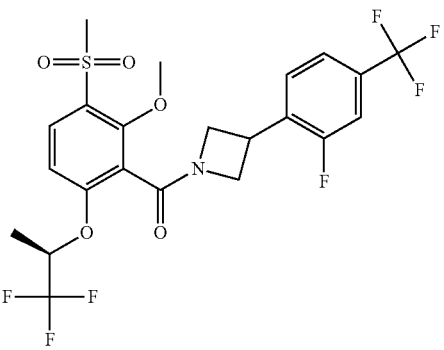 [SMILES: COc1c(S(C)(=O)=O)ccc(O[C@H](C)C(F)(F)F)c1C(=O)N1CC(c2ccc(C(F)(F)F)cc2F)C1]

¹H NMR (400 MHz, DMSO-d₆) δ=7.86-7.80 (m, 1H), 7.75-7.56 (m, 3H), 7.31-7.19 (m, 1H), 5.56-5.39 (m, 1H), 4.52-4.43 (m, 1H), 4.36-4.04 (m, 4H), 3.98-3.89 (m, 3H), 3.26-3.19 (m, 3H), 1.55-1.28 (m, 3H); [M+H]=544.19.

Example 139. 3-[2-Fluoro-4-(trifluoromethyl)phenyl]-1-(3-methanesulfonyl-2-methoxy-6-{[(2S)-1,1,1-trifluoropropan-2-yl]oxy}benzoyl)azetidine

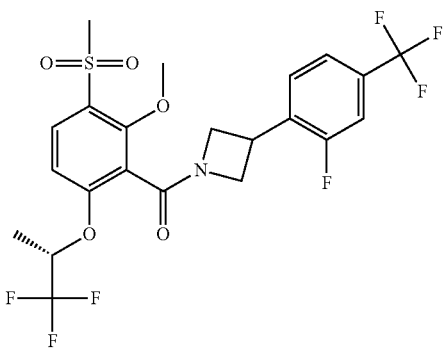 [SMILES: COc1c(S(C)(=O)=O)ccc(O[C@@H](C)C(F)(F)F)c1C(=O)N1CC(c2ccc(C(F)(F)F)cc2F)C1]

¹H NMR (400 MHz, DMSO-d₆) δ=7.86-7.81 (m, 1H), 7.75-7.56 (m, 3H), 7.30-7.21 (m, 1H), 5.55-5.39 (m, 1H), 4.52-4.42 (m, 1H), 4.36-4.03 (m, 4H), 3.97-3.89 (m, 3H), 3.26-3.19 (m, 3H), 1.54-1.29 (m, 3H); [M+H]=544.12.

Example 140. 3-[3-Fluoro-4-(trifluoromethyl)phenyl]-1-(3-methanesulfonyl-2-methoxy-6-{[(2R)-1,1,1-trifluoropropan-2-yl]oxy}benzoyl)azetidine

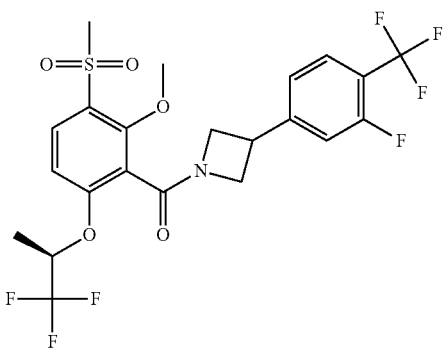 [SMILES: COc1c(S(C)(=O)=O)ccc(O[C@H](C)C(F)(F)F)c1C(=O)N1CC(c2ccc(C(F)(F)F)c(F)c2)C1]

¹H NMR (400 MHz, DMSO-d₆) δ=7.87-7.81 (m, 1H), 7.80-7.71 (m, 1H), 7.56-7.23 (m, 3H), 5.54-5.41 (m, 1H), 4.51-4.42 (m, 1H), 4.37-4.28 (m, 1H), 4.26-3.96 (m, 3H), 3.96-3.91 (m, 3H), 3.83-3.71 (m, 1H), 3.25-3.19 (m, 3H), 1.54-1.33 (m, 3H); [M+H]=543.70.

Example 141. 3-[3-Fluoro-4-(trifluoromethyl)phenyl]-1-(3-methanesulfonyl-2-methoxy-6-{[(2S)-1,1,1-trifluoropropan-2-yl]oxy}benzoyl)azetidine

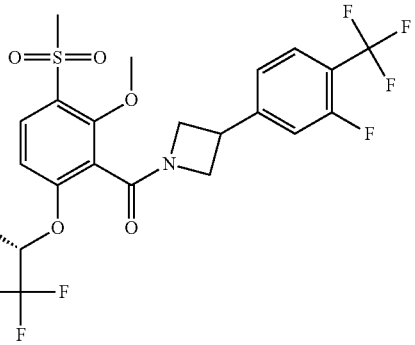

¹H NMR (400 MHz, DMSO-d₆) δ=7.86-7.81 (m, 1H), 7.79-7.71 (m, 1H), 7.56-7.23 (m, 3H), 5.55-5.41 (m, 1H), 4.50-4.42 (m, 1H), 4.35-4.28 (m, 1H), 4.26-3.97 (m, 3H), 3.96-3.91 (m, 3H), 3.82-3.70 (m, 1H), 3.25-3.20 (m, 3H), 1.54-1.34 (m, 3H); [M+H]=544.12.

Example 142. 3-[4-(Difluoromethyl)-3-fluorophenyl]-1-(3-methanesulfonyl-2-methoxy-6-{[(2S)-1,1,1-trifluoropropan-2-yl]oxy}benzoyl)azetidine

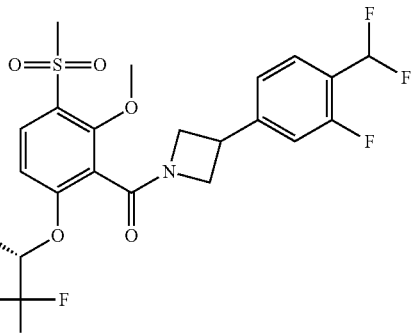

¹H NMR (400 MHz, DMSO-d₆) δ=7.86-7.80 (m, 1H), 7.65-7.57 (m, 1H), 7.42-7.16 (m, 4H), 5.48 (td, J=6.3, 12.5 Hz, 1H), 4.50-4.40 (m, 1H), 4.30 (dt, J=3.7, 8.5 Hz, 1H), 4.24-4.03 (m, 2H), 4.01 (br s, 1H), 3.96-3.91 (m, 3H), 3.80-3.70 (m, 1H), 3.26-3.19 (m, 3H), 1.54-1.34 (m, 3H); [M+H]=526.18.

Example 143. 3-[4-(Difluoromethyl)-2-fluorophenyl]-1-(3-methanesulfonyl-2-methoxy-6-{[(2S)-1,1,1-trifluoropropan-2-yl]oxy}benzoyl)azetidine

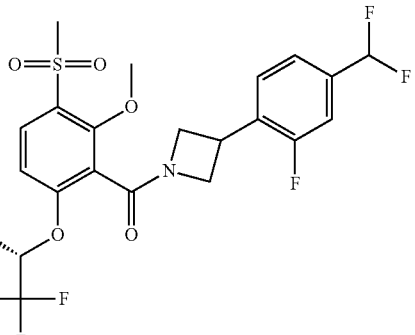

¹H NMR (400 MHz, DMSO-d₆) δ=7.83 (td, J=2.5, 9.0 Hz, 1H), 7.67-7.52 (m, 1H), 7.43 (d, J=8.2 Hz, 2H), 7.29-6.86 (m, 3H), 5.55-5.40 (m, 1H), 4.50-4.41 (m, 1H), 4.33-4.27 (m, 1H), 4.25-4.03 (m, 3H), 3.97-3.88 (m, 3H), 3.88-3.81 (m, 1H), 3.26-3.19 (m, 3H), 1.54-1.29 (m, 3H); [M+H]=526.14.

Example 144. 1-(3-Methanesulfonyl-2-methoxy-6-{[(2S)-1,1,1-trifluoropropan-2-yl]oxy}benzoyl)-3-[3-methoxy-4-(trifluoromethyl)phenyl]azetidine

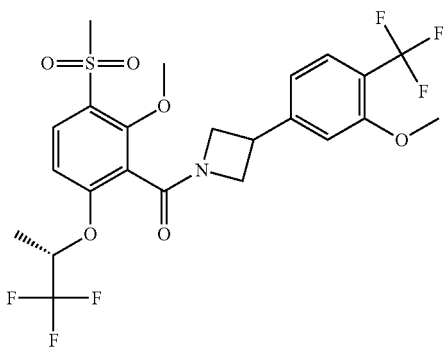 [SMILES: COc1cc(C2CN(C(=O)c3c(O[C@@H](C)C(F)(F)F)ccc(S(C)(=O)=O)c3OC)C2)ccc1C(F)(F)F]

¹H NMR (400 MHz, DMSO-d₆) δ=7.83 (td, J=2.5, 9.0 Hz, 1H), 7.61-7.54 (m, 1H), 7.31-7.22 (m, 1H), 7.19-6.99 (m, 2H), 5.55-5.43 (m, 1H), 4.50-4.42 (m, 1H), 4.33-4.22 (m, 1H), 4.19-4.12 (m, 1H), 4.06-3.97 (m, 1H), 3.97-3.91 (m, 3H), 3.87 (d, J=3.5 Hz, 3H), 3.84-3.75 (m, 1H), 3.26-3.19 (m, 3H), 1.54-1.31 (m, 3H); [M+H]=556.28.

Example 145. 3-(2-Chloro-4-fluorophenyl)-1-(3-methanesulfonyl-2-methoxy-6-{[(2S)-1,1,1-trifluoropropan-2-yl]oxy}benzoyl)azetidine

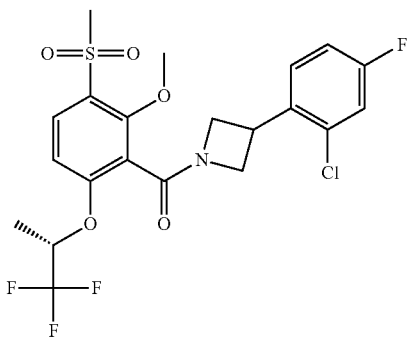 [SMILES: COc1c(S(C)(=O)=O)ccc(O[C@@H](C)C(F)(F)F)c1C(=O)N1CC(c2ccc(F)cc2Cl)C1]

Rotamers observed: ¹H NMR (400 MHz, DMSO-d₆) δ=7.86-7.80 (m, 1H), 7.63-7.43 (m, 2H), 7.30-7.19 (m, 2H), 5.58-5.37 (m, 1H), 4.48-4.40 (m, 1H), 4.31 (dt, J=3.7, 8.3 Hz, 1H), 4.25-3.97 (m, 3H), 3.95 (d, J=2.3 Hz, 2H), 3.86 (d, J=1.6 Hz, 1H), 3.84-3.72 (m, 1H), 3.26-3.19 (m, 3H), 1.54-1.23 (m, 3H); [M+H]=510.

Example 146. 3-[2-Chloro-4-(trifluoromethyl)phenyl]-1-(3-methanesulfonyl-2-methoxy-6-{[(2S)-1,1,1-trifluoropropan-2-yl]oxy}benzoyl)azetidine

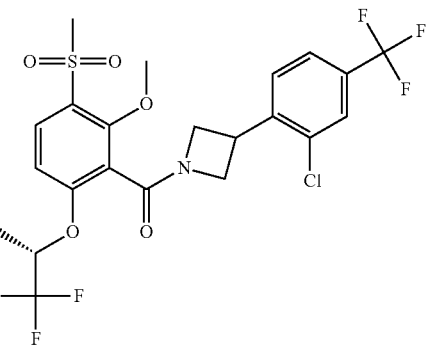

Rotamers observed: ¹H NMR (400 MHz, DMSO-d₆) δ=7.91-7.67 (m, 4H), 7.31-7.18 (m, 1H), 5.59-5.36 (m, 1H), 4.53-4.44 (m, 1H), 4.41-4.03 (m, 4H), 3.99-3.84 (m, 3H), 3.78 (dd, J=5.7, 8.4 Hz, 1H), 3.28-3.18 (m, 3H), 1.59-1.20 (m, 3H); [M+H]=560.

Example 147. 3-[2-Chloro-4-(difluoromethyl)phenyl]-1-(3-methanesulfonyl-2-methoxy-6-{[(2S)-1,1,1-trifluoropropan-2-yl]oxy}benzoyl)azetidine

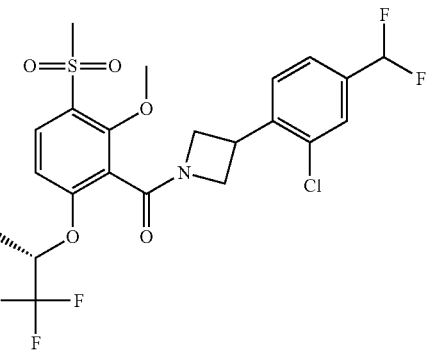

Rotamers observed: ¹H NMR (400 MHz, DMSO-d₆) δ=7.87-7.80 (m, 1H), 7.75-7.54 (m, 3H), 7.30-7.16 (m, 1H), 7.05-6.87 (m, 1H), 5.59-5.37 (m, 1H), 4.54-4.43 (m, 1H), 4.40-3.99 (m, 4H), 3.98-3.85 (m, 3H), 3.85-3.75 (m, 1H), 3.26-3.19 (m, 3H), 1.55-1.21 (m, 3H); [M+H]=5428.

Example 148. 1-(3-Methanesulfonyl-2-methoxy-6-{[(2S)-1,1,1-trifluoropropan-2-yl]oxy}benzoyl)-3-(4-nitrophenyl)azetidine

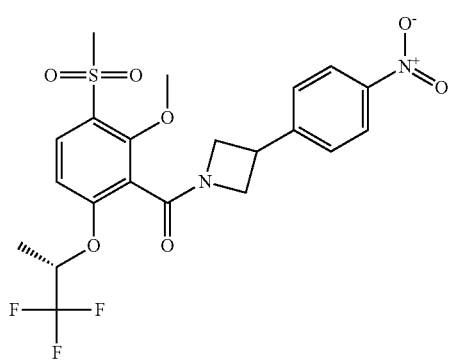 [SMILES: COc1c(S(C)(=O)=O)ccc(O[C@@H](C)C(F)(F)F)c1C(=O)N1CC(c2ccc([N+](=O)[O-])cc2)C1]

Rotamers observed: ¹H NMR (400 MHz, DMSO-d6) δ=8.26-8.17 (m, 2H), 7.87-7.81 (m, 1H), 7.67-7.54 (m, 2H), 7.30-7.22 (m, 1H), 5.57-5.43 (m, 1H), 4.55-4.45 (m, 1H), 4.38-3.98 (m, 4H), 3.97-3.92 (m, 3H), 3.85-3.76 (m, 1H), 3.26-3.20 (m, 3H), 1.55-1.35 (m, 3H); [M+H]=503.

Example 149. 1-(3-Methanesulfonyl-2-methoxy-6-{[(2R)-1,1,1-trifluoropropan-2-yl]oxy}benzoyl)-3-{[4-(trifluoromethyl)phenyl]methyl}azetidine

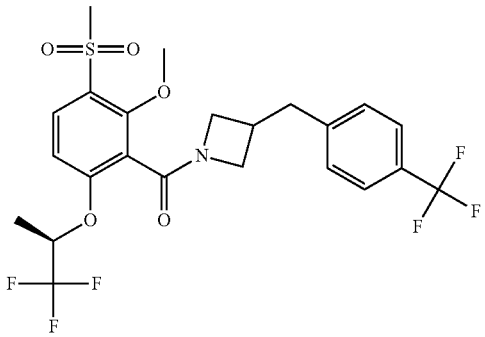 [SMILES: COc1c(S(C)(=O)=O)ccc(O[C@H](C)C(F)(F)F)c1C(=O)N1CC(Cc2ccc(C(F)(F)F)cc2)C1]

¹H NMR (400 MHz, DMSO-d₆) δ=7.84-7.78 (m, 1H), 7.67-7.59 (m, 2H), 7.48-7.33 (m, 2H), 7.28-7.18 (m, 1H), 5.56-5.40 (m, 1H), 4.15-4.04 (m, 1H), 3.98-3.68 (m, 5H), 3.61-3.35 (m, 2H), 3.25-3.18 (m, 3H), 3.03-2.85 (m, 3H), 1.50-1.36 (m, 3H); [M+H]=540.09.

Example 150. 1-(3-Methanesulfonyl-2-methoxy-6-{[(2S)-1,1,1-trifluoropropan-2-yl]oxy}benzoyl)-3-(3,4,5-trifluorophenyl)azetidine

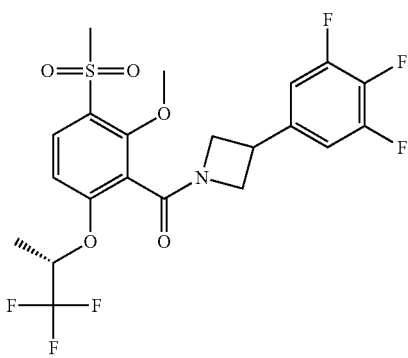 [SMILES: COc1c(S(C)(=O)=O)ccc(O[C@@H](C)C(F)(F)F)c1C(=O)N1CC(c2cc(F)c(F)c(F)c2)C1]

¹H NMR (400 MHz, DMSO-d₆) δ=7.86-7.81 (m, 1H), 7.39-7.20 (m, 3H), 5.47 (tt, J=6.3, 13.1 Hz, 1H), 4.46-4.37 (m, 1H), 4.27 (dt, J=2.3, 8.8 Hz, 1H), 4.15-3.95 (m, 2H), 3.95-3.89 (m, 4H), 3.77-3.66 (m, 1H), 3.26-3.19 (m, 3H), 1.54-1.36 (m, 3H); [M+H]=512.08.

Example 151. 4-(3,3-Difluorocyclobutyl)-2-methoxy-3-{3-[5-(trifluoromethyl)pyridin-2-yl]azetidine-1-carbonyl}benzonitrile

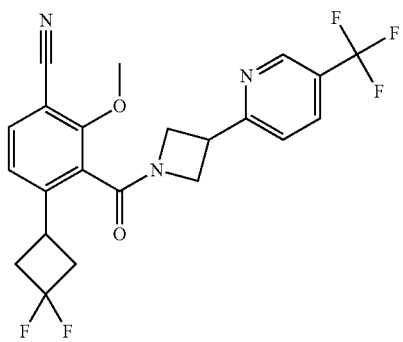 [SMILES: COc1c(C#N)ccc(C2CC(F)(F)C2)c1C(=O)N1CC(c2ccc(C(F)(F)F)cn2)C1]

¹H NMR (400 MHz, DMSO-d₆) δ=9.06-8.88 (m, 1H), 8.18 (d, J=7.4 Hz, 1H), 7.86 (d, J=8.2 Hz, 1H), 7.57 (d, J=8.2 Hz, 1H), 7.38 (d, J=8.2 Hz, 1H), 4.52-4.41 (m, 1H), 4.29-4.04 (m, 3H), 3.98 (s, 2H), 3.91-3.43 (m, 2H), 3.08-2.87 (m, 2H), 2.79 (br s, 2H); [M+H]=452.

Example 152. 3-{3-[3-Chloro-5-(trifluoromethyl)pyridin-2-yl]azetidine-1-carbonyl}-4-(3,3-difluorocyclobutyl)-2-methoxybenzonitrile

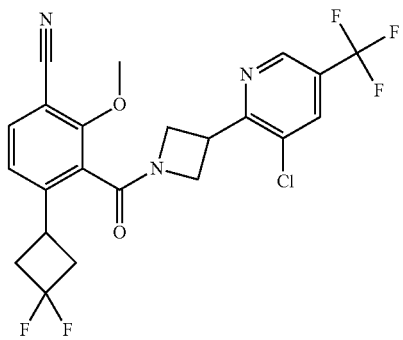 [SMILES: COc1c(C#N)ccc(C2CC(F)(F)C2)c1C(=O)N1CC(c2ncc(C(F)(F)F)cc2Cl)C1]

¹H NMR (400 MHz, DMSO-d₆) δ=9.06-8.86 (m, 1H), 8.47 (br s, 1H), 7.86 (d, J=8.2 Hz, 1H), 7.37 (d, J=8.2 Hz, 1H), 4.54-4.37 (m, 2H), 4.36-4.13 (m, 2H), 4.09-3.84 (m, 3H), 3.57-3.35 (m, 1H), 3.13-2.66 (m, 4H); [M+H]=486.17.

Example 153. 4-(3,3-Difluorocyclobutyl)-3-{3-[3-fluoro-5-(trifluoromethyl)pyridin-2-yl]azetidine-1-carbonyl}-2-methoxybenzonitrile

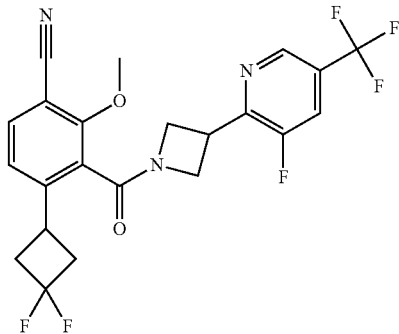 [SMILES: COc1c(C#N)ccc(C2CC(F)(F)C2)c1C(=O)N1CC(c2ncc(C(F)(F)F)cc2F)C1]

¹H NMR (400 MHz, DMSO-d₆) δ=8.97-8.76 (m, 1H), 8.29 (d, J=9.8 Hz, 1H), 7.86 (d, J=8.2 Hz, 1H), 7.38 (d, J=7.8 Hz, 1H), 4.52-4.43 (m, 1H), 4.41-4.22 (m, 2H), 4.20-3.87 (m, 4H), 3.60-3.42 (m, 1H), 3.13-2.65 (m, 4H); [M+H]= 470.17.

Example 154. 1-(3-Methanesulfonyl-2-methoxy-6-{[(2S)-1,1,1-trifluoropropan-2-yl]oxy}benzoyl)-3-(2,4,5-trifluorophenyl)azetidine

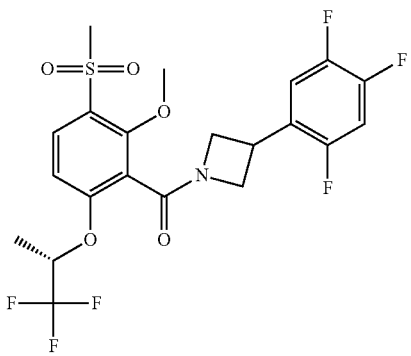 [SMILES: COc1c(S(C)(=O)=O)ccc(O[C@@H](C)C(F)(F)F)c1C(=O)N1CC(c2cc(F)c(F)cc2F)C1]

¹H NMR (400 MHz, DMSO-d₆) δ=7.83 (td, J=2.2, 9.0 Hz, 1H), 7.68-7.45 (m, 2H), 7.29-7.21 (m, 1H), 5.55-5.42 (m, 1H), 4.46-4.38 (m, 1H), 4.32-3.97 (m, 4H), 3.96-3.89 (m, 3H), 3.86-3.74 (m, 1H), 3.25-3.19 (m, 3H), 1.54-1.33 (m, 3H); [M+H]=512.12.

Example 155. 1-(3-Methanesulfonyl-2-methoxy-6-{[(2S)-1,1,1-trifluoropropan-2-yl]oxy}benzoyl)-3-(2,3,4-trifluorophenyl)azetidine

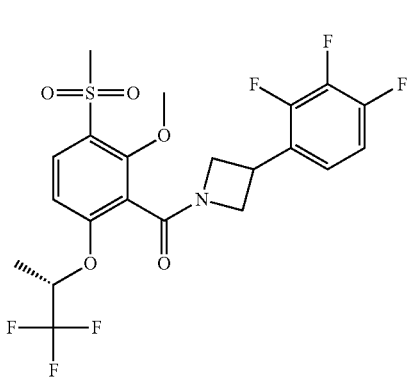 [SMILES: COc1c(S(C)(=O)=O)ccc(O[C@@H](C)C(F)(F)F)c1C(=O)N1CC(c2ccc(F)c(F)c2F)C1]

¹H NMR (400 MHz, DMSO-d₆) δ 7.83 (td, J=2.5, 9.0 Hz, 1H), 7.37-7.21 (m, 3H), 5.54-5.42 (m, 1H), 4.48-4.40 (m, 1H), 4.32-4.25 (m, 1H), 4.22-4.01 (m, 3H), 3.96-3.89 (m, 3H), 3.89-3.78 (m, 1H), 3.25-3.19 (m, 3H), 1.54-1.33 (m, 3H); [M+H]=512.12.

Example 156. 1-(3-Methanesulfonyl-2-methoxy-6-{[(2S)-1,1,1-trifluoropropan-2-yl]oxy}benzoyl)-3-(2,3,5-trifluorophenyl)azetidine

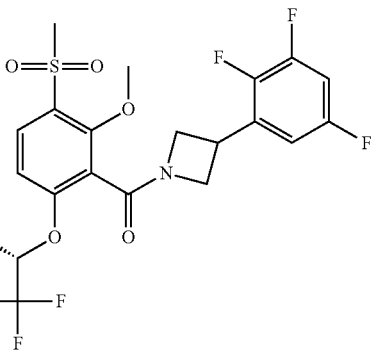

¹H NMR (400 MHz, DMSO-d₆) δ=7.83 (td, J=2.2, 8.9 Hz, 1H), 7.51-7.40 (m, 1H), 7.30-7.22 (m, 1H), 7.21-7.09 (m, 1H), 5.56-5.42 (m, 1H), 4.49-4.39 (m, 1H), 4.35-4.26 (m, 1H), 4.25-4.06 (m, 3H), 3.97-3.89 (m, 3H), 3.89-3.77 (m, 1H), 3.25-3.19 (m, 3H), 1.54-1.33 (m, 3H); [M+H]= 511.55.

Example 157. 3-(2,3-Difluorophenyl)-1-(3-methanesulfonyl-2-methoxy-6-{[(2S)-1,1,1-trifluoropropan-2-yl]oxy}benzoyl)azetidine

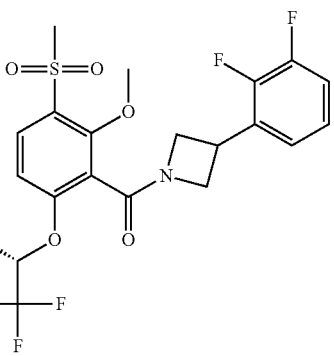

¹H NMR (400 MHz, DMSO-d₆) δ=7.86-7.80 (m, 1H), 7.40-7.18 (m, 4H), 5.56-5.40 (m, 1H), 4.51-4.41 (m, 1H), 4.31 (t, J=8.2 Hz, 1H), 4.23-4.02 (m, 3H), 3.98-3.89 (m, 3H), 3.85 (dt, J=5.7, 9.5 Hz, 1H), 3.26-3.18 (m, 3H), 1.54-1.32 (m, 3H); [M+H]=493.65.

Example 158-Example 168 were prepared in a manner analogous to Example 6, with the appropriate starting material substitutions.

Example 158. 2-Methoxy-3-{3-[4-(oxan-4-yl)phenyl]azetidine-1-carbonyl}-4-{[(2S)-1,1,1-trifluoropropan-2-yl]oxy}benzonitrile

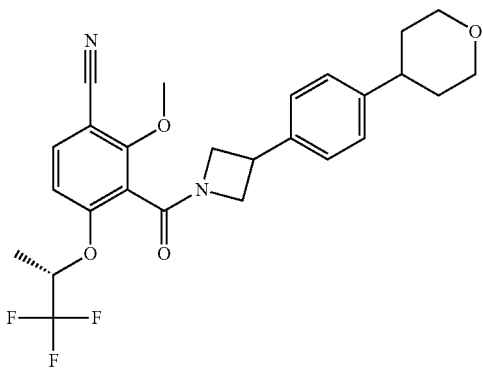

¹H NMR (400 MHz, DMSO-d₆) δ=7.87 (d, J=8.6 Hz, 1H), 7.36-7.16 (m, 5H), 5.51 (dd, J=5.7, 11.9 Hz, 1H), 4.45-4.36 (m, 1H), 4.21 (d, J=7.4 Hz, 1H), 4.08 (d, J=8.2 Hz, 1H), 4.01-3.95 (m, 3H), 3.92 (dd, J=2.5, 10.4 Hz, 2H), 3.87-3.79 (m, 1H), 3.76-3.66 (m, 1H), 3.45-3.34 (m, 2H), 2.73 (br s, 1H), 1.65 (dd, J=3.3, 8.4 Hz, 3H), 1.49 (d, J=6.3 Hz, 1H), 1.44-1.33 (m, 3H); [M+H]=489.24.

Example 159. 2-Methoxy-3-{3-[5-(oxan-4-yl)pyridin-2-yl]azetidine-1-carbonyl}-4-{[(2S)-1,1,1-trifluoropropan-2-yl]oxy}benzonitrile

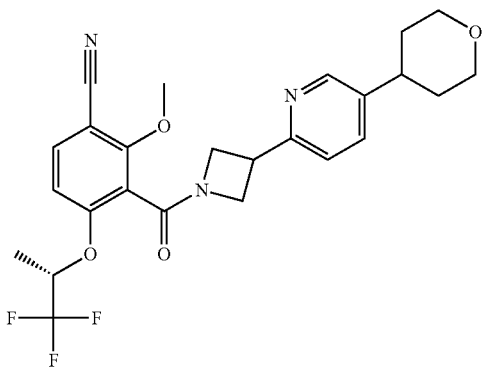

¹H NMR (400 MHz, DMSO-d₆) δ=8.53-8.41 (m, 1H), 7.85 (d, J=9.0 Hz, 1H), 7.63 (dd, J=2.3, 7.8 Hz, 1H), 7.30-7.15 (m, 2H), 5.56-5.38 (m, 1H), 4.39-4.29 (m, 1H), 4.27-4.07 (m, 2H), 4.07-3.86 (m, 7H), 3.47-3.35 (m, 2H), 2.87-2.75 (m, 1H), 1.66 (br s, 4H), 1.53-1.31 (m, 3H); [M+H]=490.31.

Example 160. 3-{3-[4-(2,2-Dimethyloxan-4-yl)phenyl]azetidine-1-carbonyl}-2-methoxy-4-{[(2S)-1,1,1-trifluoropropan-2-yl]oxy}benzonitrile

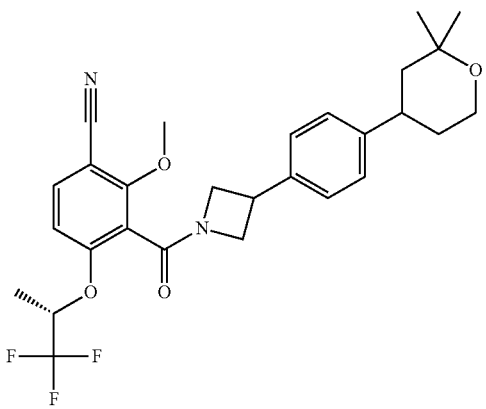 [SMILES: COc1c(C#N)ccc(O[C@@H](C)C(F)(F)F)c1C(=O)N1CC(c2ccc(C3CCOC(C)(C)C3)cc2)C1]

¹H NMR (400 MHz, DMSO-d₆) δ=7.86 (d, J=8.6 Hz, 1H), 7.29-7.17 (m, 5H), 5.50 (dd, J=5.9, 12.1 Hz, 1H), 4.46-4.34 (m, 2H), 4.28-4.07 (m, 5H), 4.04-3.89 (m, 5H), 3.84 (d, J=5.9 Hz, 2H), 3.75-3.68 (m, 1H), 3.68-3.60 (m, 2H), 2.98-2.87 (m, 1H), 1.65-1.35 (m, 7H), 1.22 (s, 3H), 1.14 (s, 3H).

Example 161. 2-Methoxy-3-{3-[4-(oxan-4-yl)phenyl]azetidine-1-carbonyl}-4-{[(2R)-1,1,1-trifluoropropan-2-yl]oxy}benzonitrile

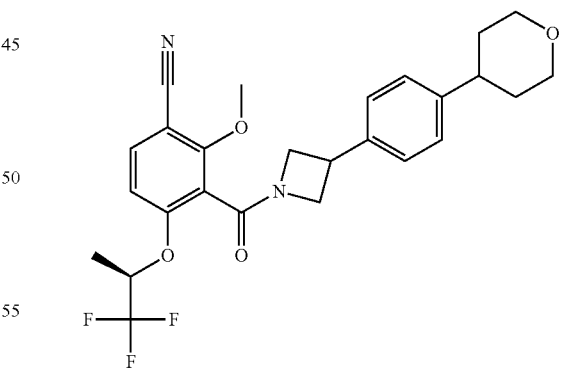

¹H NMR (400 MHz, DMSO-d₆) δ=7.86 (d, J=8.6 Hz, 1H), 7.29-7.17 (m, 5H), 5.50 (dd, J=5.9, 11.7 Hz, 1H), 4.45-4.35 (m, 1H), 4.26-4.14 (m, 1H), 4.00-3.96 (m, 3H), 3.94-3.88 (m, 2H), 3.87-3.66 (m, 3H), 3.44-3.36 (m, 3H), 2.79-2.69 (m, 1H), 1.70-1.58 (m, 4H), 1.52-1.35 (m, 3H); [M+H]=489.32.

Example 162. 4-(1-Fluorocyclobutyl)-2-methoxy-3-{3-[5-(oxan-4-yl)pyridin-2-yl]azetidine-1-carbonyl}benzonitrile

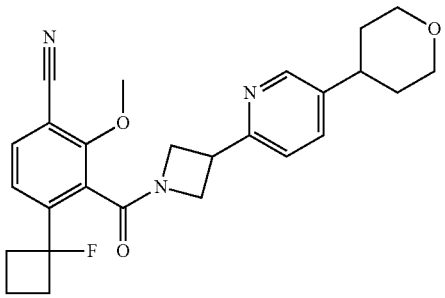 [SMILES: COc1c(C#N)ccc(C2(F)CCC2)c1C(=O)N1CC(c2ccc(C3CCOCC3)cn2)C1]

¹H NMR (400 MHz, DMSO-d₆) δ=8.48 (dd, J=2.2, 19.8 Hz, 1H), 7.90 (td, J=1.6, 8.2 Hz, 1H), 7.68-7.50 (m, 3H), 7.42 (ddd, J=2.0, 6.3, 8.2 Hz, 1H), 7.25 (dd, J=8.0, 11.9 Hz, 1H), 4.42-4.28 (m, 1H), 4.21-4.10 (m, 1H), 4.07-3.89 (m, 7H), 3.47-3.36 (m, 2H), 2.89-2.74 (m, 2H), 2.60-2.50 (m, 2H), 2.12-2.00 (m, 1H), 1.77-1.62 (m, 4H); [M+H]=450.03.

Example 163. 3-{3-[3-Fluoro-4-(oxan-4-yl)phenyl]azetidine-1-carbonyl}-2-methoxy-4-{[(2S)-1,1,1-trifluoropropan-2-yl]oxy}benzonitrile

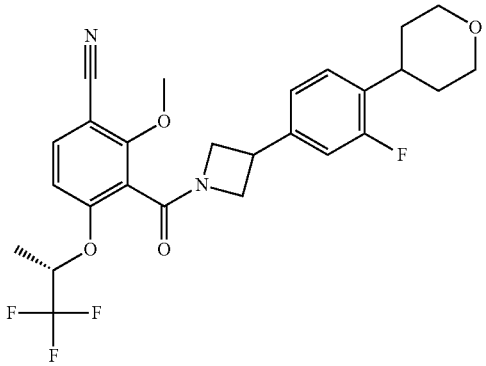 [SMILES: COc1c(C#N)ccc(O[C@@H](C)C(F)(F)F)c1C(=O)N1CC(c2ccc(C3CCOCC3)c(F)c2)C1]

¹H NMR (400 MHz, DMSO-d₆) δ=7.87 (d, J=9.0 Hz, 1H), 7.30 (td, J=8.2, 16.1 Hz, 1H), 7.25-7.17 (m, 1H), 7.17-7.04 (m, 2H), 5.55-5.45 (m, 1H), 4.45-4.35 (m, 1H), 4.26-4.17 (m, 1H), 4.16-4.03 (m, 1H), 4.02-3.80 (m, 7H), 3.73-3.66 (m, 1H), 3.43 (dt, J=2.2, 11.6 Hz, 2H), 3.02 (tt, J=3.9, 11.8 Hz, 1H), 1.77-1.57 (m, 4H), 1.51-1.35 (m, 3H); [M+H]=507.29.

Example 164. 1-(3-Methanesulfonyl-2-methoxy-6-{[(2R)-1,1,1-trifluoropropan-2-yl]oxy}benzoyl)-3-[4-(oxan-4-yl)phenyl]azetidine

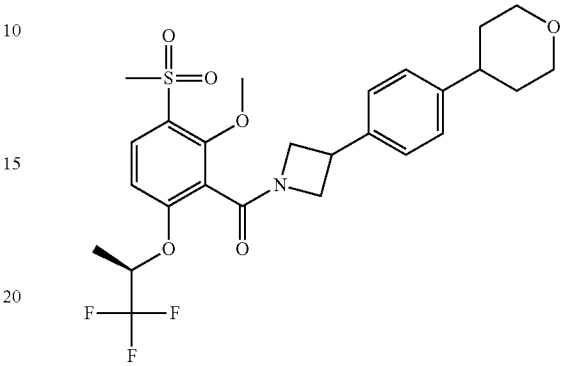

¹H NMR (400 MHz, CDCl₃) δ=7.93-8.04 (m, 1H) 7.25 (d, J=7.43 Hz, 4H) 6.76-6.90 (m, 1H) 4.77-4.90 (m, 1H) 4.56-4.70 (m, 1H) 4.22-4.36 (m, 2H) 4.10 (s, 4H) 3.82-4.05 (m, 2H) 3.48-3.51 (m, 1H) 3.54 (s, 4H) 3.20 (s, 3H) 2.71-2.83 (m, 1H) 1.74-1.86 (m, 3H) 1.51-1.63 (m, 3H); [M+H]=542.22.

Example 165. 4-Ethoxy-2-methoxy-3-{3-[5-(oxan-4-yl)pyridin-2-yl]azetidine-1-carbonyl}benzonitrile

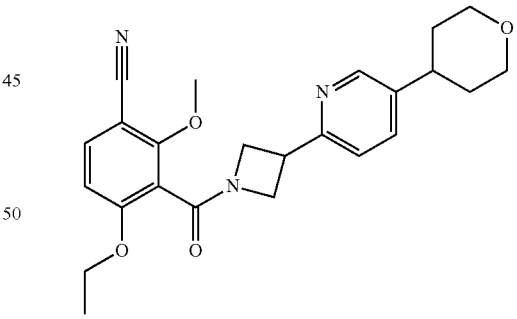

The title compound was prepared from 4-fluoro-2-methoxy-3-(3-(5-(tetrahydro-2H-pyran-4-yl)pyridin-2-yl)azetidine-1-carbonyl)benzonitrile employing conditions analogous to Example 6. ¹H NMR (400 MHz, DMSO-d₆) δ=8.49 (d, J=2.0 Hz, 1H), 7.77 (d, J=8.6 Hz, 1H), 7.68-7.62 (m, 1H), 7.26 (d, J=7.8 Hz, 1H), 6.95 (d, J=8.2 Hz, 1H), 4.39-4.30 (m, 1H), 4.25-4.07 (m, 4H), 4.02-3.89 (m, 5H), 3.46-3.37 (m, 2H), 2.81 (br s, 2H), 1.67 (dt, J=3.9, 9.0 Hz, 3H), 1.42-1.20 (m, 3H); [M+H]=422.17.

Example 166. 2-Methoxy-3-{3-[5-(oxan-4-yl)pyridin-2-yl]azetidine-1-carbonyl}-4-(propan-2-yloxy)benzonitrile

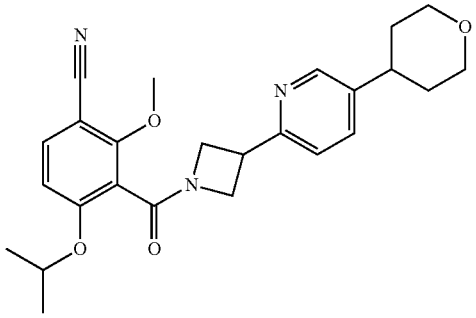 [SMILES: COc1c(C#N)ccc(OC(C)C)c1C(=O)N1CC(c2ccc(C3CCOCC3)cn2)C1]

$^1$H NMR (400 MHz, DMSO-d$_6$) δ=8.48 (br s, 1H), 7.74 (d, J=9.0 Hz, 1H), 7.64 (d, J=6.3 Hz, 1H), 7.26 (d, J=8.2 Hz, 1H), 6.95 (d, J=8.6 Hz, 1H), 4.71 (br s, 2H), 4.32 (br s, 1H), 4.27-4.06 (m, 3H), 4.02-3.88 (m, 6H), 3.47-3.37 (m, 2H), 2.81 (br s, 1H), 1.72-1.62 (m, 4H), 1.37-1.11 (m, 6H); [M+H]=436.04

Example 167. 3-[4-(4,4-Difluorocyclohexyl)phenyl]-1-(3-methanesulfonyl-2-methoxy-6-{[(2R)-1,1,1-trifluoropropan-2-yl]oxy}benzoyl)azetidine

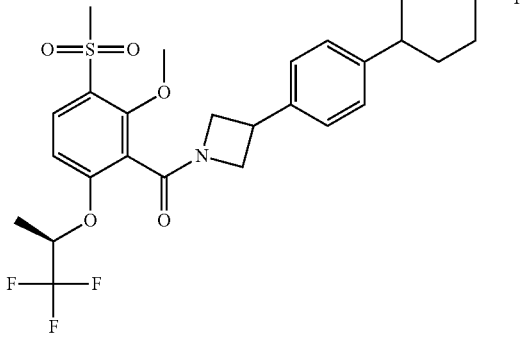

$^1$H NMR (400 MHz, DMSO-d$_6$) δ=7.86-7.80 (m, 1H), 7.31-7.18 (m, 5H), 5.55-5.43 (m, 1H), 4.42 (t, J=9.4 Hz, 1H), 4.30-4.17 (m, 1H), 4.06-3.97 (m, 1H), 3.96-3.92 (m, 3H), 3.92-3.85 (m, 1H), 3.80-3.71 (m, 1H), 3.57 (br s, 2H), 3.25-3.19 (m, 3H), 2.74-2.62 (m, 1H), 2.14-1.96 (m, 3H), 1.94-1.78 (m, 3H), 1.63 (q, J=13.3 Hz, 2H), 1.53-1.35 (m, 3H); [M+H]=576.15.

Example 168. 1-(3-Methanesulfonyl-2-methoxy-6-{[(2S)-1,1,1-trifluoropropan-2-yl]oxy}benzoyl)-3-[4-(oxan-4-yl)phenyl]azetidine

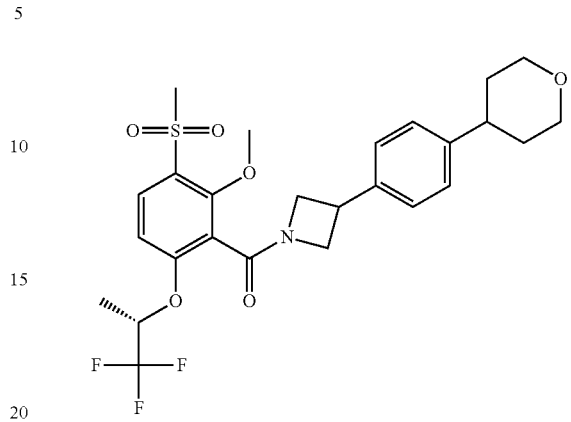

$^1$H NMR (400 MHz, DMSO-d$_6$) δ=7.86-7.80 (m, 1H), 7.31-7.19 (m, 5H), 5.49 (td, J=6.8, 13.7 Hz, 1H), 4.43 (t, J=9.2 Hz, 1H), 4.30-4.08 (m, 2H), 4.05-3.81 (m, 8H), 3.80-3.70 (m, 1H), 3.40 (dt, J=3.7, 10.9 Hz, 3H), 3.26-3.19 (m, 2H), 2.73 (dd, J=4.5, 9.6 Hz, 1H), 1.68-1.59 (m, 4H), 1.54-1.37 (m, 3H); [M+H]=542.44.

Example 169. 2-Chloro-3-{3-[5-(oxan-4-yl)pyridin-2-yl]azetidine-1-carbonyl}-4-{[(2S)-1,1,1-trifluoropropan-2-yl]oxy}benzonitrile

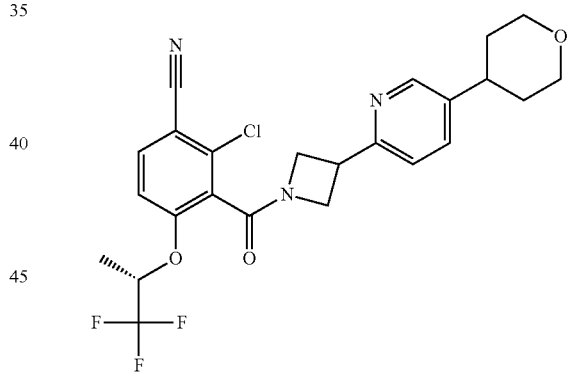

Step 1. tert-Butyl 3-(5-(3,6-dihydro-2H-pyran-4-yl)pyridin-2-yl)azetidine-1-carboxylate. In a 25 mL microwave vial was combined Intermediate 6, product from Step 1 (1.98 g, 6.3 mmol), Pd(PPh$_3$)$_4$ (0.584 mg, 0.51 mmol), K$_2$CO$_3$ (6.3 mL, 2.00 mol/L, 12.6 mmol), 2-(3,6-dihydro-2H-pyran-4-yl)-4,4,5,5-tetramethyl-1,3,2-dioxaborolane (1.59 g, 7.59 mmol) and dioxane (13 mL). The reaction was heated under microwave conditions at 150° C. for 15 minutes. The reaction was cooled to room temperature, diluted with EtOAc and washed with water. The organic phase was isolated, dried (Na$_2$SO$_4$), filtered, and concentrated under reduced pressure. Purification (FCC, SiO$_2$, 10-100% EtOAc/hexanes) afforded title compound (1.55 g, 77%).

Step 2. tert-Butyl 3-(5-(tetrahydro-2H-pyran-4-yl)pyridin-2-yl)azetidine-1-carboxylate. tert-Butyl 3-(5-(3,6-dihydro-2H-pyran-4-yl)pyridin-2-yl)azetidine-1-carboxylate (1.55 g, 4.9 mmol) was diluted with MeOH (15 mL), EtOH (15 mL), sparged with nitrogen and treated with Pd/C (0.52 g, 0.49 mmol). The reaction atmosphere was replaced with hydrogen and pressurized to 35 PSI and shaken for 4 h. The hydrogen atmosphere was removed and reaction contents were filtered and concentrated under reduced pressure to afford the title compound as colorless oil (1.5 g, 96%).

Step 3. 2-Chloro-3-{3-[5-(oxan-4-yl)pyridin-2-yl]azetidine-1-carbonyl}-4-{[(2S)-1,1,1-trifluoropropan-2-yl]oxy}benzonitrile. The title compound was prepared in a manner analogous to Example 4. $^1$H NMR (400 MHz, DMSO-$d_6$) δ=8.50 (d, J=2.0 Hz, 1H), 8.49-8.42 (m, 1H), 8.10-8.04 (m, 1H), 7.64 (dd, J=2.2, 8.0 Hz, 1H), 7.55-7.47 (m, 1H), 7.31-7.21 (m, 1H), 5.63-5.48 (m, 1H), 4.42-4.32 (m, 1H), 4.30-4.07 (m, 2H), 4.04-3.85 (m, 3H), 3.47-3.36 (m, 2H), 2.86-2.77 (m, 1H), 1.71-1.63 (m, 3H), 1.53-1.33 (m, 3H); [M+H]=494.15.

Example 170-Example 172 were prepared in a manner analogous to Example 169, with the appropriate starting material substitutions.

Example 170. 2-Chloro-3-{3-[5-(oxan-4-yl)pyridin-2-yl]azetidine-1-carbonyl}-4-{[(2R)-1,1,1-trifluoropropan-2-yl]oxy}benzonitrile

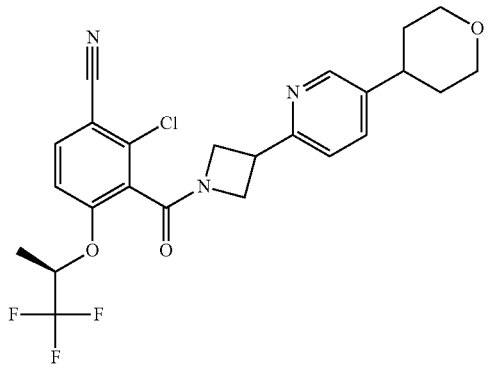 [SMILES: C[C@@H](Oc1ccc(C#N)c(Cl)c1C(=O)N1CC(c2ccc(C3CCOCC3)cn2)C1)C(F)(F)F]

$^1$H NMR (400 MHz, DMSO-$d_6$) δ=8.52-8.42 (m, 1H), 8.10-8.04 (m, 1H), 7.67-7.61 (m, 1H), 7.55-7.47 (m, 1H), 7.31-7.21 (m, 1H), 5.62-5.47 (m, 1H), 4.41-4.33 (m, 1H), 4.28-4.07 (m, 2H), 4.07-3.85 (m, 4H), 3.46-3.37 (m, 2H), 2.86-2.77 (m, 1H), 1.71-1.62 (m, 3H), 1.54-1.35 (m, 3H); [M+H]=494.22.

Example 171. 3-{3-[5-(4,4-Difluorocyclohexyl)pyridin-2-yl]azetidine-1-carbonyl}-2-methoxy-4-{[(2S)-1,1,1-trifluoropropan-2-yl]oxy}benzonitrile

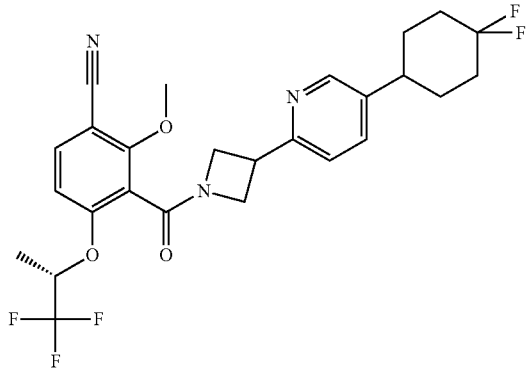 [SMILES: COc1c(C#N)ccc(O[C@@H](C)C(F)(F)F)c1C(=O)N1CC(c2ccc(C3CCC(F)(F)CC3)cn2)C1]

$^1$H NMR (400 MHz, DMSO-$d_6$) δ=8.52-8.41 (m, 1H), 8.33 (s, 1H), 7.85 (d, J=9.0 Hz, 1H), 7.63 (dd, J=2.0, 8.2 Hz, 1H), 7.30-7.15 (m, 2H), 5.56-5.41 (m, 1H), 4.39-4.29 (m, 1H), 4.28-4.08 (m, 2H), 4.07-3.87 (m, 5H), 2.75 (t, J=11.9 Hz, 1H), 2.16-1.97 (m, 3H), 1.97-1.79 (m, 3H), 1.74-1.59 (m, 2H), 1.52-1.31 (m, 3H); [M+H]=524.24.

Example 172. 3-{3-[5-(4,4-Difluorocyclohexyl)pyridin-2-yl]azetidine-1-carbonyl}-2-methoxy-4-{[(2R)-1,1,1-trifluoropropan-2-yl]oxy}benzonitrile

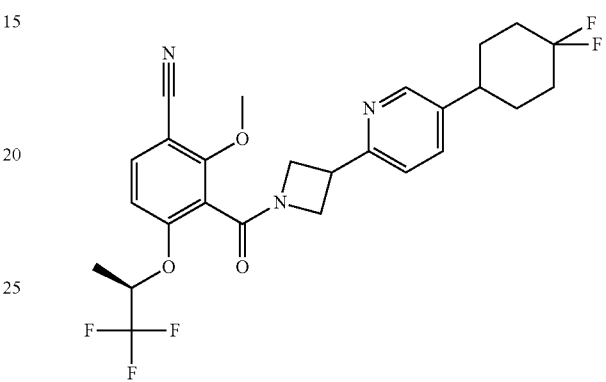

$^1$H NMR (400 MHz, DMSO-$d_6$) δ=8.51-8.42 (m, 1H), 8.40 (s, 2H), 7.85 (d, J=9.0 Hz, 1H), 7.63 (dd, J=2.2, 8.0 Hz, 1H), 7.29-7.16 (m, 2H), 5.56-5.40 (m, 1H), 4.38-4.29 (m, 1H), 4.27-4.07 (m, 2H), 4.06-3.85 (m, 4H), 2.75 (t, J=11.9 Hz, 1H), 2.15-1.92 (m, 3H), 1.91-1.79 (m, 2H), 1.66 (q, J=12.3 Hz, 2H), 1.53-1.30 (m, 3H); [M+H]=524.24.

Example 173-Example 177 were prepared in a manner analogous to Example 9, with the appropriate starting material substitutions.

Example 173. 3-{[3-(4-Cyanophenyl)azetidin-1-yl]carbonyl}-4-(cyclopropylmethoxy)-2-methoxybenzonitrile

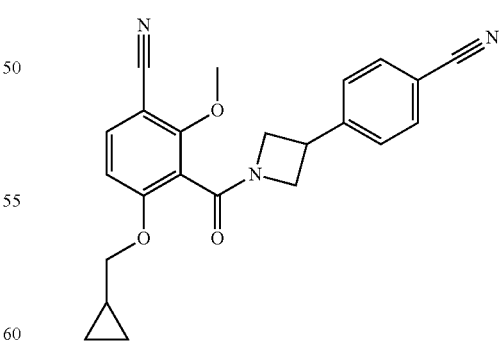

$^1$H NMR (400 MHz, CDCl$_3$) δ=7.66 (d, J=8.2 Hz, 2H), 7.54 (d, J=8.6 Hz, 1H), 7.46 (d, J=7.8 Hz, 2H), 6.69 (d, J=9.0 Hz, 1H), 4.64 (t, J=9.2 Hz, 1H), 4.36-4.28 (m, 1H), 4.25 (br s, 1H), 4.11 (s, 3H), 3.96-3.87 (m, 4H), 1.25 (s, 1H), 0.65 (d, J=7.8 Hz, 2H), 0.36 (br s, 2H); [M+H]=388.27.

Example 174. 3-{[3-(4-Cyano-3-methoxyphenyl)azetidin-1-yl]carbonyl}-2-methoxy-4-{[(2S)-1,1,1-trifluoropropan-2-yl]oxy}benzonitrile

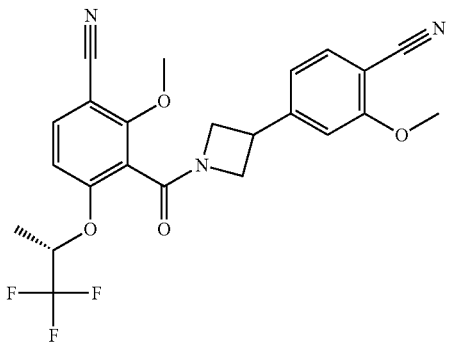 [SMILES: COc1cc(C2CN(C(=O)c3c(O[C@@H](C)C(F)(F)F)ccc(C#N)c3OC)C2)ccc1C#N]

$^1$H NMR (400 MHz, DMSO-d$_6$) δ=7.87 (d, J=8.6 Hz, 1H), 7.71 (d, J=7.8 Hz, 1H), 7.26-7.00 (m, 3H), 5.48 (d, J=6.3 Hz, 1H), 4.48-4.39 (m, 1H), 4.29-4.17 (m, 1H), 4.11 (d, J=6.7 Hz, 1H), 4.00-3.94 (m, 3H), 3.90 (d, J=5.1 Hz, 3H), 1.52-1.32 (m, 3H); [M+H]=460.13.

Example 175. 3-Chloro-4-{1-[(3-cyano-2-methoxy-6-{[(2S)-1,1,1-trifluoropropan-2-yl]oxy}phenyl)carbonyl]azetidin-3-yl}-2-methoxybenzonitrile

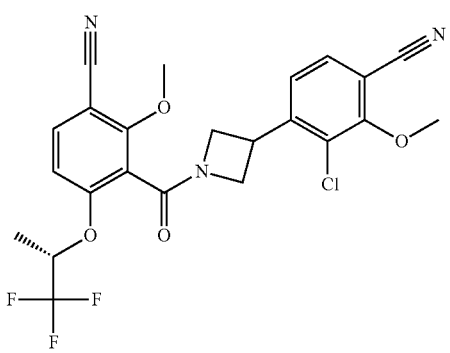 [SMILES: COc1c(C#N)ccc(C2CN(C(=O)c3c(O[C@@H](C)C(F)(F)F)ccc(C#N)c3OC)C2)c1Cl]

The title compound was prepared in a manner analogous to Example 9, using (S)-3-chloro-4-(1-(3-cyano-2-methoxy-6-((1,1,1-trifluoropropan-2-yl)oxy)benzoyl)azetidin-3-yl)-2-fluorobenzonitrile. $^1$H NMR (400 MHz, DMSO-d$_6$) δ=7.92-7.81 (m, 2H), 7.54-7.37 (m, 1H), 7.27-7.13 (m, 1H), 5.59-5.39 (m, 1H), 4.45 (br s, 1H), 4.36-4.12 (m, 3H), 4.03-3.86 (m, 5H), 3.86-3.70 (m, 1H), 1.54-1.20 (m, 3H); [M+H]=494.15.

Example 176. 3-Chloro-4-[1-(3-cyano-2-methoxy-6-{[(2S)-1,1,1-trifluoropropan-2-yl]oxy}benzoyl)azetidin-3-yl]-2-ethoxybenzonitrile

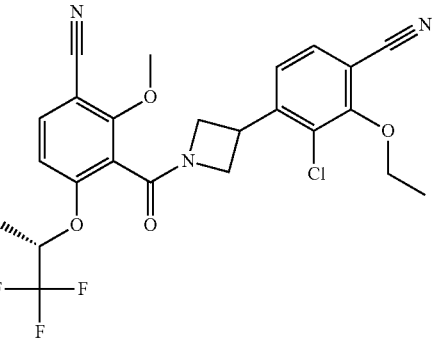

The title compound was prepared in a manner analogous to Example 9, using (S)-3-chloro-4-(1-(3-cyano-2-methoxy-6-((1,1,1-trifluoropropan-2-yl)oxy)benzoyl)azetidin-3-yl)-2-fluorobenzonitrile. $^1$H NMR (400 MHz, DMSO-d$_6$) δ=7.90-7.81 (m, 2H), 7.53-7.38 (m, 1H), 7.26-7.15 (m, 1H), 5.57-5.40 (m, 1H), 4.49-4.40 (m, 1H), 4.34-4.11 (m, 5H), 4.01-3.88 (m, 3H), 3.85-3.70 (m, 1H), 1.53-1.21 (m, 6H); [M+H]=508.2.

Example 177. 3-[3-(4-Cyano-3-methoxyphenyl)azetidine-1-carbonyl]-2-methoxy-4-{[(2R)-1,1,1-trifluoropropan-2-yl]oxy}benzonitrile

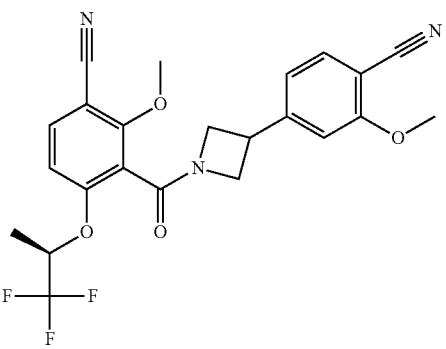 [SMILES: COc1cc(C2CN(C(=O)c3c(O[C@H](C)C(F)(F)F)ccc(C#N)c3OC)C2)ccc1C#N]

$^1$H NMR (400 MHz, DMSO-d$_6$) δ=7.87 (d, J=9.0 Hz, 1H), 7.73-7.67 (m, 1H), 7.25-7.19 (m, 1H), 7.18-6.98 (m, 2H), 5.57-5.43 (m, 1H), 4.48-4.39 (m, 1H), 4.29-4.17 (m, 1H), 4.11 (d, J=7.0 Hz, 1H), 4.00-3.94 (m, 3H), 3.90 (d, J=5.1 Hz, 3H), 3.75 (br s, 1H), 1.52-1.30 (m, 3H); [M+H]=460.2.

Example 178-Example 207 were prepared in a manner analogous to Example 10, with the appropriate starting material substitutions.

Example 178. 2-Methoxy-3-({3-[4-(trifluoromethyl)phenyl]azetidin-1-yl}carbonyl)-4-{[(2S)-1,1,1-trifluoropropan-2-yl]oxy}benzonitrile

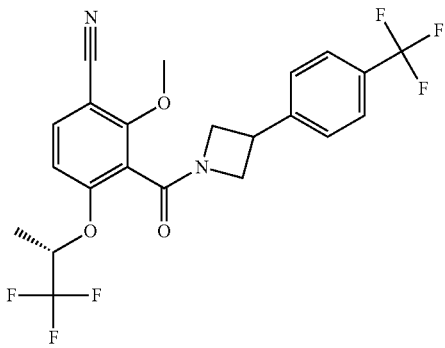 [SMILES: COc1c(C#N)ccc(O[C@@H](C)C(F)(F)F)c1C(=O)N1CC(c2ccc(C(F)(F)F)cc2)C1]

¹H NMR (400 MHz, DMSO-d₆) δ=7.87 (d, J=9.0 Hz, 1H), 7.76-7.67 (m, 2H), 7.59-7.49 (m, 2H), 7.25-7.18 (m, 1H), 5.55-5.45 (m, 1H), 4.45 (d, J=7.8 Hz, 1H), 4.27 (t, J=8.6 Hz, 1H), 4.21-4.02 (m, 2H), 4.00-3.95 (m, 3H), 3.79-3.69 (m, 1H), 1.52-1.33 (m, 3H); [M+H]=473.17.

Example 179. 1-({3-Methanesulfonyl-2-methoxy-6-[(1,1,1-trifluoropropan-2-yl)oxy]phenyl}carbonyl)-3-[4-(trifluoromethyl)phenyl]azetidine

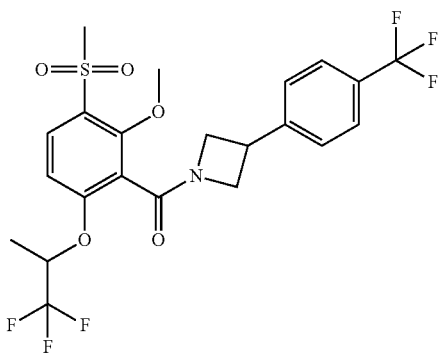 [SMILES: COc1c(S(C)(=O)=O)ccc(OC(C)C(F)(F)F)c1C(=O)N1CC(c2ccc(C(F)(F)F)cc2)C1]

¹H NMR (400 MHz, CDCl₃) δ=1.47-1.64 (m, 3H) 3.14-3.23 (m, 3H) 3.87-4.05 (m, 2H) 4.10 (s, 3H) 4.22-4.41 (m, 2H) 4.56-4.75 (m, 1H) 4.76-4.91 (m, 1H) 6.75-6.90 (m, 1H) 7.37-7.50 (m, 2H) 7.59-7.69 (m, 2H) 7.99 (d, J=9.00 Hz, 1H); [M+H]=526.1.

Example 180. 3-(3,4-Difluorophenoxy)-1-({3-methanesulfonyl-2-methoxy-6-[(1,1,1-trifluoropropan-2-yl)oxy]phenyl}carbonyl)azetidine

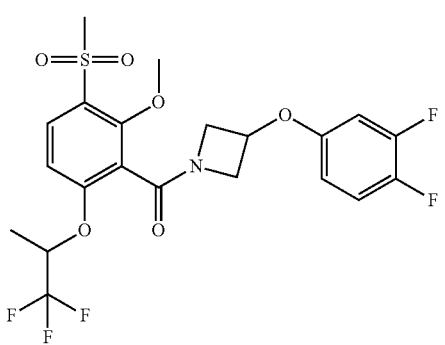 [SMILES: COc1c(S(C)(=O)=O)ccc(OC(C)C(F)(F)F)c1C(=O)N1CC(Oc2ccc(F)c(F)c2)C1]

¹H NMR (400 MHz, CDCl₃) δ=1.55 (d, J=6.65 Hz, 3H) 3.20 (d, J=3.91 Hz, 3H) 3.94-4.04 (m, 1H) 4.07 (s, 3H) 4.18-4.35 (m, 2H) 4.51-4.66 (m, 1H) 4.72-5.01 (m, 2H) 6.42 (br s, 1H) 6.54-6.64 (m, 1H) 6.81 (d, J=8.61 Hz, 1H) 7.08 (q, J=9.13 Hz, 1H) 8.00 (d, J=8.61 Hz, 1H); [M+H]=510.20.

Example 181. 2-Methoxy-3-[(3-{[4-(trifluoromethyl)phenyl]methyl}azetidin-1-yl)carbonyl]-4-{[(2S)-1,1,1-trifluoropropan-2-yl]oxy}benzonitrile

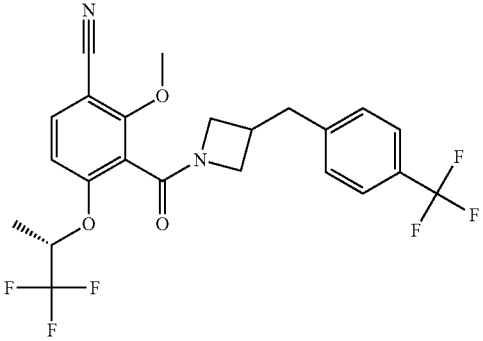 [SMILES: COc1c(C#N)ccc(O[C@@H](C)C(F)(F)F)c1C(=O)N1CC(Cc2ccc(C(F)(F)F)cc2)C1]

¹H NMR (400 MHz, CDCl₃) δ=1.53 (dd, J=15.06, 6.46 Hz, 3H) 2.85-3.08 (m, 3H) 3.49-3.65 (m, 1H) 3.86-4.01 (m, 2H) 4.06-4.15 (m, 3H) 4.26-4.36 (m, 1H) 4.67-4.88 (m, 1H) 6.73 (t, J=8.02 Hz, 1H) 7.17-7.31 (m, 2H) 7.50-7.63 (m, 3H); [M+H]=487.23.

Example 182. 3-(3,5-Difluorophenyl)-1-({3-methanesulfonyl-2-methoxy-6-[(1,1,1-trifluoropropan-2-yl)oxy]phenyl}carbonyl)azetidine

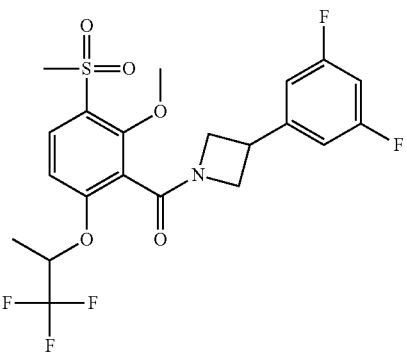 [SMILES: COc1c(S(C)(=O)=O)ccc(OC(C)C(F)(F)F)c1C(=O)N1CC(c2cc(F)cc(F)c2)C1]

¹H NMR (400 MHz, CDCl₃) δ=1.48-1.64 (m, 3H) 3.20 (d, J=3.52 Hz, 3H) 4.11 (s, 3H) 4.19-4.32 (m, 3H) 4.41-4.67 (m, 2H) 4.75-4.89 (m, 1H) 6.75-6.96 (m, 3H) 7.19-7.25 (m, 1H) 7.97 (d, J=9.00 Hz, 1H); [M+H]=494.20.

Example 183. 1-(3-Methanesulfonyl-2-methoxy-6-{[(2R)-1,1,1-trifluoropropan-2-yl]oxy}benzoyl)-3-[4-(trifluoromethyl)phenyl]azetidine

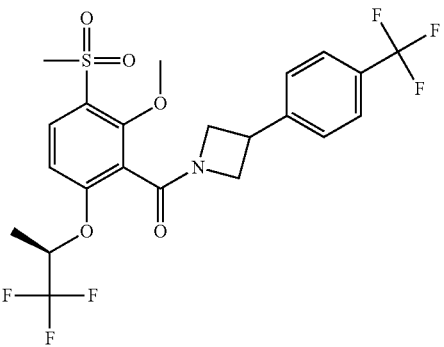 [SMILES: COc1c(S(C)(=O)=O)ccc(O[C@H](C)C(F)(F)F)c1C(=O)N1CC(c2ccc(C(F)(F)F)cc2)C1]

¹H NMR (400 MHz, CDCl₃) δ=7.92-8.06 (m, 1H) 7.59-7.67 (m, 2H) 7.38-7.49 (m, 2H) 6.76-6.88 (m, 1H) 4.76-4.90 (m, 1H) 4.57-4.71 (m, 1H) 4.20-4.38 (m, 2H) 4.10 (s, 3H) 3.88-4.02 (m, 2H) 3.16-3.23 (m, 3H) 1.50-1.60 (m, 3H); [M+H]=526.13.

Example 184. 2-[1-(3-Methanesulfonyl-2-methoxy-6-{[(2R)-1,1,1-trifluoropropan-2-yl]oxy}benzoyl)azetidin-3-yl]-5-(trifluoromethyl)pyridine

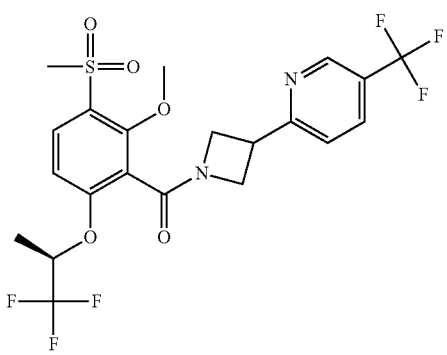 [SMILES: COc1c(S(C)(=O)=O)ccc(O[C@H](C)C(F)(F)F)c1C(=O)N1CC(c2ccc(C(F)(F)F)cn2)C1]

¹H NMR (400 MHz, CDCl₃) δ=8.82-8.90 (m, 1H) 7.85-8.03 (m, 2H) 7.28-7.45 (m, 1H) 6.75-6.88 (m, 1H) 4.04-4.87 (m, 9H) 3.20 (d, J=3.52 Hz, 3H) 1.50-1.63 (m, 3H); [M+H]=527.51.

Example 185. 5-(Difluoromethyl)-2-[1-(3-methanesulfonyl-2-methoxy-6-{[(2R)-1,1,1-trifluoropropan-2-yl]oxy}benzoyl)azetidin-3-yl]pyridine

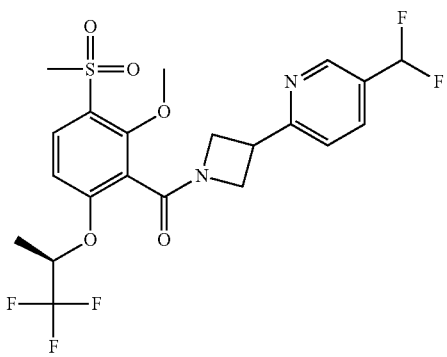 [SMILES: COc1c(S(C)(=O)=O)ccc(O[C@H](C)C(F)(F)F)c1C(=O)N1CC(c2ccc(C(F)F)cn2)C1]

¹H NMR (400 MHz, CDCl₃) δ=8.77-8.90 (m, 1H) 7.97-8.07 (m, 1H) 8.02 (d, J=9.00 Hz, 2H) 7.44-7.78 (m, 1H) 6.59-6.98 (m, 2H) 4.05-4.93 (m, 9H) 3.19 (d, J=8.61 Hz, 3H) 1.49-1.66 (m, 3H); [M+H]=509.61.

Example 186. 3-Chloro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine

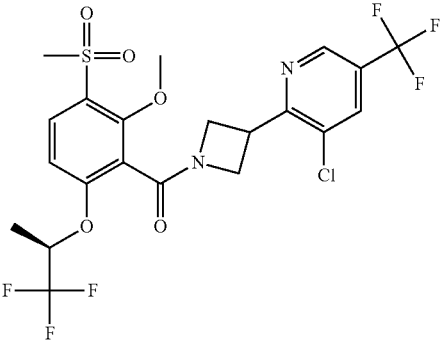 [SMILES: COc1c(S(C)(=O)=O)ccc(O[C@H](C)C(F)(F)F)c1C(=O)N1CC(c2ncc(C(F)(F)F)cc2Cl)C1]

¹H NMR (400 MHz, CDCl₃) δ=8.71-8.81 (m, 1H) 7.88-8.04 (m, 2H) 6.74-6.87 (m, 1H) 4.26-4.90 (m, 6H) 4.06 (s, 3H) 3.18 (s, 3H) 1.44-1.64 (m, 3H); [M+H]=561.06.

Example 187. 1-(3-Methanesulfonyl-2-methoxy-6-{[(2S)-1,1,1-trifluoropropan-2-yl]oxy}benzoyl)-3-[4-(trifluoromethyl)phenyl]azetidine

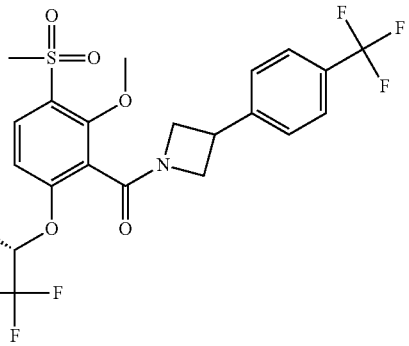

¹H NMR (400 MHz, CDCl₃) δ=7.87-8.01 (m, 1H) 7.55-7.66 (m, 2H) 7.34-7.49 (m, 2H) 6.76-6.91 (m, 1H) 4.78-4.92 (m, 1H) 4.53-4.71 (m, 1H) 4.19-4.39 (m, 2H) 4.08 (s, 3H) 3.84-4.02 (m, 2H) 3.18 (s, 3H) 1.54 (s, 3H); [M+H]=525.90.

Example 188. 3-(4-Fluorophenoxy)-1-(3-methanesulfonyl-2-methoxy-6-{[(2R)-1,1,1-trifluoropropan-2-yl]oxy}benzoyl)azetidine

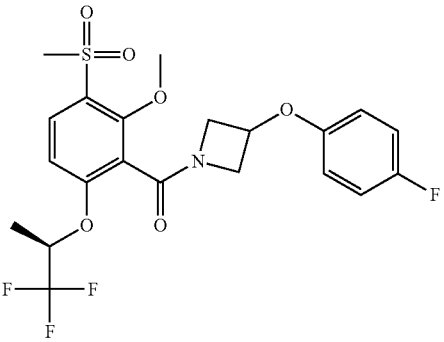 [SMILES: COc1c(S(C)(=O)=O)ccc(O[C@H](C)C(F)(F)F)c1C(=O)N1CC(Oc2ccc(F)cc2)C1]

¹H NMR (400 MHz, CDCl₃) δ=7.90-7.98 (m, 1H) 6.90-7.01 (m, 2H) 6.76-6.86 (m, 1H) 6.60-6.72 (m, 2H) 4.75-4.99 (m, 2H) 4.48-4.61 (m, 1H) 4.15-4.29 (m, 2H) 4.04 (s, 3H) 3.90-4.01 (m, 1H) 3.13-3.20 (m, 3H) 1.47-1.59 (m, 3H); [M+H]=491.98.

Example 189. 3-Fluoro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine

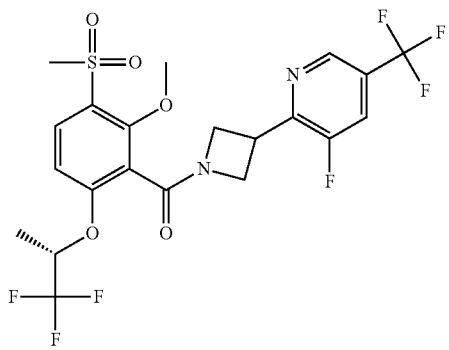 [SMILES: COc1c(S(C)(=O)=O)ccc(O[C@@H](C)C(F)(F)F)c1C(=O)N1CC(c2ncc(C(F)(F)F)cc2F)C1]

¹H NMR (400 MHz, CDCl₃) δ=8.62-8.71 (m, 1H) 7.89-7.99 (m, 1H) 7.55-7.65 (m, 1H) 6.72-6.87 (m, 1H) 4.26-4.89 (m, 6H) 4.08 (d, J=2.35 Hz, 3H) 3.12-3.22 (m, 3H) 1.45-1.62 (m, 3H) 1.18-1.26 (m, 1H); [M+H]=545.75.

Example 190. 3-Chloro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine

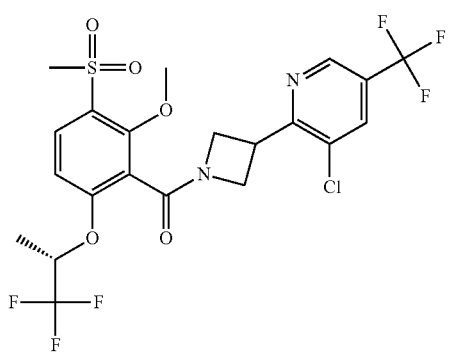 [SMILES: COc1c(S(C)(=O)=O)ccc(O[C@@H](C)C(F)(F)F)c1C(=O)N1CC(c2ncc(C(F)(F)F)cc2Cl)C1]

¹H NMR (400 MHz, DMSO-d₆) δ=8.96 (d, J=14.5 Hz, 1H), 8.51-8.45 (m, 1H), 7.86-7.79 (m, 1H), 7.29-7.16 (m, 1H), 5.58-5.33 (m, 1H), 4.65-4.26 (m, 4H), 4.23-4.10 (m, 1H), 3.99-3.86 (m, 3H), 3.22 (d, J=13.7 Hz, 3H), 1.57-1.25 (m, 3H).

Example 191. 3-Ethynyl-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine

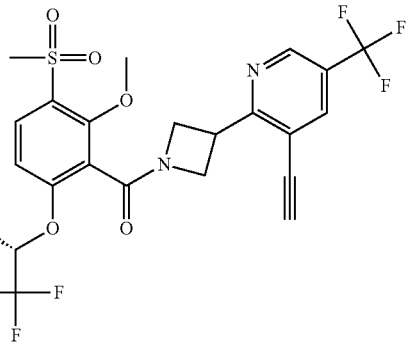

¹H NMR (400 MHz, CDCl₃) δ=8.71-8.88 (m, 1H) 7.88-8.09 (m, 2H) 6.73-6.87 (m, 1H) 4.09-4.89 (m, 8H) 3.48-3.55 (m, 1H) 3.48-3.55 (m, 1H) 3.20 (d, J=5.09 Hz, 3H) 3.17-3.23 (m, 3H) 1.47-1.65 (m, 3H); [M+H]=550.91.

Example 192. 3-(4-Fluorophenoxy)-1-(3-methanesulfonyl-2-methoxy-6-{[(2S)-1,1,1-trifluoropropan-2-yl]oxy}benzoyl)azetidine

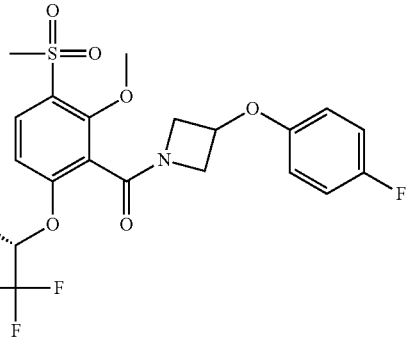

¹H NMR (400 MHz, DMSO-d₆) δ=7.77-7.87 (m, 1H) 7.20-7.29 (m, 1H) 7.07-7.14 (m, 2H) 6.79-6.90 (m, 2H) 5.40-5.53 (m, 1H) 4.97-5.10 (m, 1H) 4.44-4.52 (m, 1H) 3.92 (s, 6H) 3.20-3.29 (m, 3H) 1.33-1.54 (m, 3H); [M+H]= 492.37.

Example 193. 4-(1-Fluorocyclopentyl)-2-methoxy-3-{3-[5-(trifluoromethyl)pyridin-2-yl]azetidine-1-carbonyl}benzonitrile

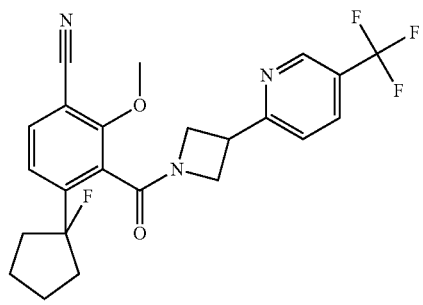 [SMILES: COc1c(C#N)ccc(C2(F)CCCC2)c1C(=O)N1CC(c2ccc(C(F)(F)F)cn2)C1]

¹H NMR (400 MHz, CDCl₃) δ=8.78-8.92 (m, 1H) 7.85-7.97 (m, 1H) 7.52-7.62 (m, 1H) 7.33-7.45 (m, 1H) 7.08-7.21 (m, 1H) 4.52-4.66 (m, 1H) 4.30-4.44 (m, 1H) 4.12 (d, J=4.70 Hz, 6H) 2.00 (s, 8H); [M+H]=447.99.

Example 194. 1-(3-Methanesulfonyl-2-methoxy-6-{[(2S)-1,1,1-trifluoropropan-2-yl]oxy}benzoyl)-3-phenoxyazetidine

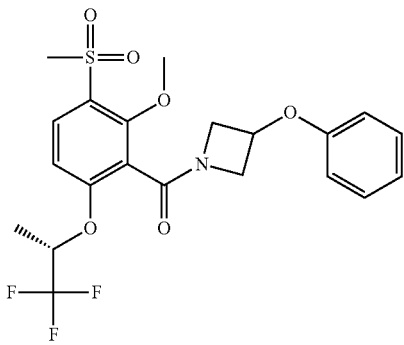 [SMILES: COc1c(S(C)(=O)=O)ccc(O[C@@H](C)C(F)(F)F)c1C(=O)N1CC(Oc2ccccc2)C1]

¹H NMR (400 MHz, CDCl₃) δ=7.92-8.03 (m, 1H) 7.26 (s, 2H) 6.94-7.06 (m, 1H) 6.77-6.84 (m, 1H) 6.70-6.77 (m, 2H) 4.95-5.06 (m, 1H) 4.72-4.90 (m, 1H) 4.51-4.66 (m, 1H) 4.19-4.34 (m, 2H) 4.07 (s, 4H) 3.18 (s, 3H) 1.55 (d, J=6.65 Hz, 3H); [M+H]=474.11.

Example 195. 3-(3,4-Difluorophenoxy)-1-(3-methanesulfonyl-2-methoxy-6-{[(2S)-1,1,1-trifluoropropan-2-yl]oxy}benzoyl)azetidine

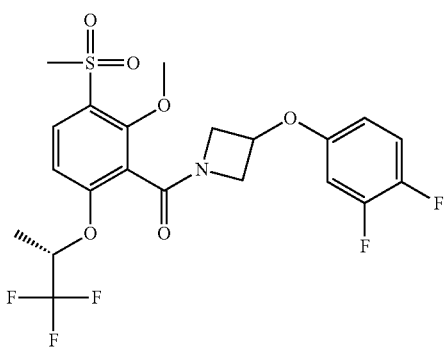 [SMILES: COc1c(S(C)(=O)=O)ccc(O[C@@H](C)C(F)(F)F)c1C(=O)N1CC(Oc2ccc(F)c(F)c2)C1]

¹H NMR (400 MHz, CDCl₃) δ=7.92-8.03 (m, 1H) 7.26 (s, 2H) 6.94-7.06 (m, 1H) 6.77-6.84 (m, 1H) 6.70-6.77 (m, 2H) 4.95-5.06 (m, 1H) 4.72-4.90 (m, 1H) 4.51-4.66 (m, 1H) 4.19-4.34 (m, 2H) 4.07 (s, 4H) 3.18 (s, 3H) 1.55 (d, J=6.65 Hz, 3H); [M+H]=510.25.

Example 196. 3-(3,5-Difluorophenyl)-1-(3-methanesulfonyl-2-methoxy-6-{[(2S)-1,1,1-trifluoropropan-2-yl]oxy}benzoyl)azetidine

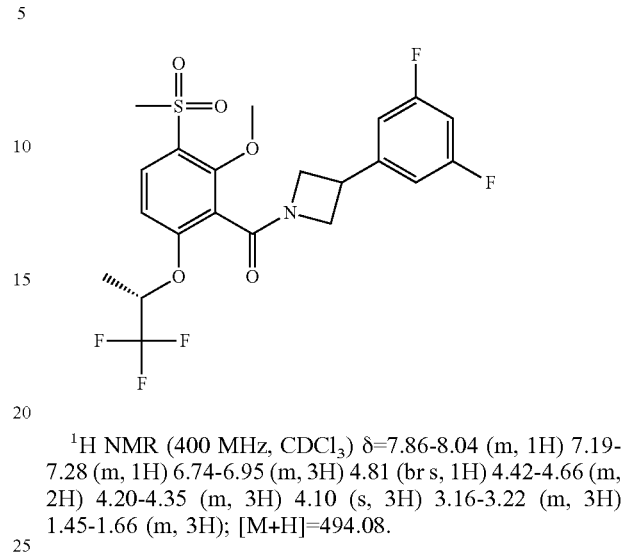

¹H NMR (400 MHz, CDCl₃) δ=7.86-8.04 (m, 1H) 7.19-7.28 (m, 1H) 6.74-6.95 (m, 3H) 4.81 (br s, 1H) 4.42-4.66 (m, 2H) 4.20-4.35 (m, 3H) 4.10 (s, 3H) 3.16-3.22 (m, 3H) 1.45-1.66 (m, 3H); [M+H]=494.08.

Example 197. 4-(1-Fluorocyclopentyl)-2-methoxy-3-{3-[4-(trifluoromethyl)phenyl]azetidine-1-carbonyl}benzonitrile

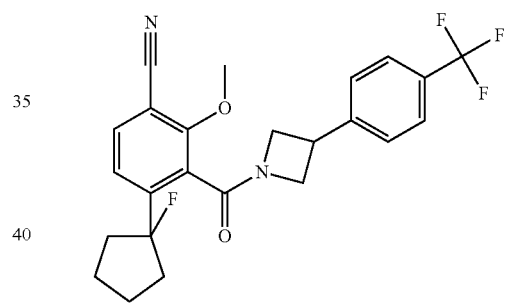

¹H NMR (400 MHz, CDCl₃) δ=7.86-8.04 (m, 1H) 7.19-7.28 (m, 1H) 6.74-6.95 (m, 3H) 4.81 (br s, 1H) 4.42-4.66 (m, 2H) 4.20-4.35 (m, 3H) 4.10 (s, 3H) 3.16-3.22 (m, 3H) 1.45-1.66 (m, 3H); [M+H]=446.99.

Example 198. 3-(3,4-Difluorophenyl)-1-(3-methanesulfonyl-2-methoxy-6-{[(2S)-1,1,1-trifluoropropan-2-yl]oxy}benzoyl)azetidine

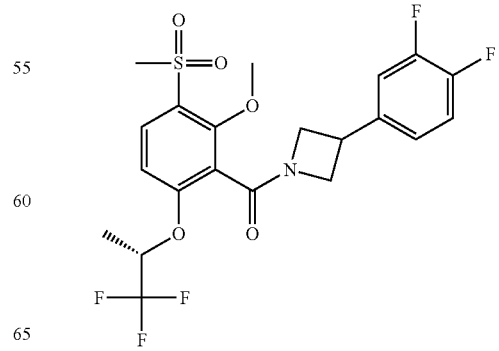

¹H NMR (400 MHz, CDCl₃) δ=7.88-8.07 (m, 1H) 7.00-7.20 (m, 3H) 6.71-6.91 (m, 1H) 4.75-4.91 (m, 1H) 4.54-4.70 (m, 1H) 4.09 (d, J=10.56 Hz, 7H) 3.19 (d, J=7.83 Hz, 3H) 1.45-1.64 (m, 3H); [M+H]=494.13.

Example 199. 1-(3-Methanesulfonyl-2-methoxy-6-{[(2S)-1,1,1-trifluoropropan-2-yl]oxy}benzoyl)-3-[2-(trifluoromethyl)phenyl]azetidine

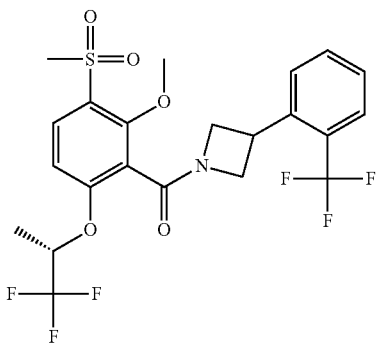 [SMILES: COc1c(S(C)(=O)=O)ccc(O[C@@H](C)C(F)(F)F)c1C(=O)N1CC(c2ccccc2C(F)(F)F)C1]

¹H NMR (400 MHz, CDCl₃) δ=7.96-8.02 (m, 1H) 7.59-7.78 (m, 3H) 7.36-7.46 (m, 1H) 6.75-6.89 (m, 1H) 4.74-4.90 (m, 1H) 4.54-4.68 (m, 1H) 4.26-4.46 (m, 3H) 4.03-4.14 (m, 3H) 3.84-4.01 (m, 1H) 3.14-3.25 (m, 3H) 1.55 (s, 3H); [M+H]=525.99.

Example 200. 3-(3-Chlorophenoxy)-1-(3-methanesulfonyl-2-methoxy-6-{[(2S)-1,1,1-trifluoropropan-2-yl]oxy}benzoyl)azetidine

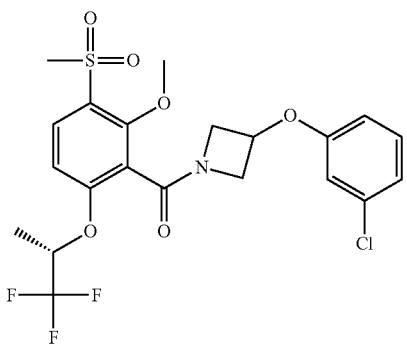 [SMILES: COc1c(S(C)(=O)=O)ccc(O[C@@H](C)C(F)(F)F)c1C(=O)N1CC(Oc2cccc(Cl)c2)C1]

¹H NMR (400 MHz, CDCl₃) δ=7.89-7.99 (m, 1H) 7.15-7.23 (m, 1H) 6.90-7.01 (m, 1H) 6.77-6.86 (m, 1H) 6.68-6.74 (m, 1H) 6.56-6.67 (m, 1H) 4.74-5.02 (m, 2H) 4.48-4.66 (m, 1H) 4.15-4.33 (m, 2H) 4.02-4.07 (m, 3H) 3.91-4.01 (m, 1H) 3.14-3.21 (m, 3H) 1.47-1.59 (m, 3H); [M+H]=508.08.

Example 201. 3-(4-Chlorophenoxy)-1-(3-methanesulfonyl-2-methoxy-6-{[(2S)-1,1,1-trifluoropropan-2-yl]oxy}benzoyl)azetidine

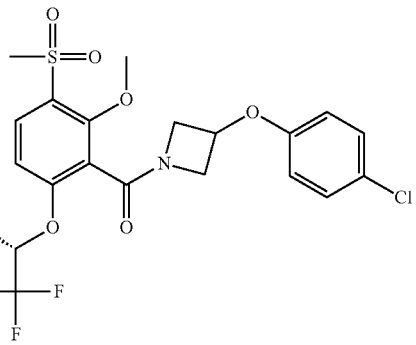

¹H NMR (400 MHz, CDCl₃) δ=7.93-8.04 (m, 1H) 7.22-7.26 (m, 2H) 6.76-6.87 (m, 1H) 6.61-6.72 (m, 2H) 4.92-5.03 (m, 1H) 4.72-4.88 (m, 1H) 4.50-4.65 (m, 1H) 4.18-4.32 (m, 2H) 4.07 (s, 3H) 3.93-4.03 (m, 1H) 3.20 (d, J=4.70 Hz, 3H) 1.45-1.64 (m, 3H); [M+H]=508.28.

Example 202. 1-(3-Methanesulfonyl-2-methoxy-6-{[(2S)-1,1,1-trifluoropropan-2-yl]oxy}benzoyl)-3-[4-(trifluoromethyl)phenoxy]azetidine

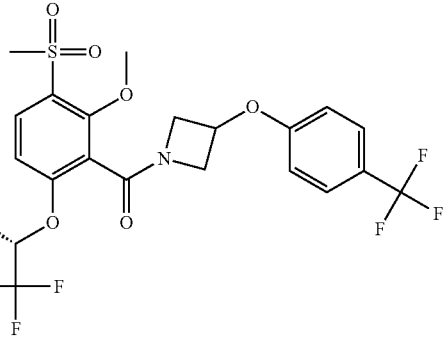

¹H NMR (400 MHz, CDCl₃) δ=7.95-8.05 (m, 1H) 7.51-7.62 (m, 2H) 6.76-6.88 (m, 3H) 4.98-5.12 (m, 1H) 4.72-4.90 (m, 1H) 4.54-4.70 (m, 1H) 4.21-4.37 (m, 2H) 4.07 (s, 3H) 3.97-4.05 (m, 1H) 3.14-3.28 (m, 3H) 1.48-1.68 (m, 3H); [M+H]=542.29.

Example 203. 3-(2,6-Difluorophenoxy)-1-(3-methanesulfonyl-2-methoxy-6-{[(2S)-1,1,1-trifluoropropan-2-yl]oxy}benzoyl)azetidine

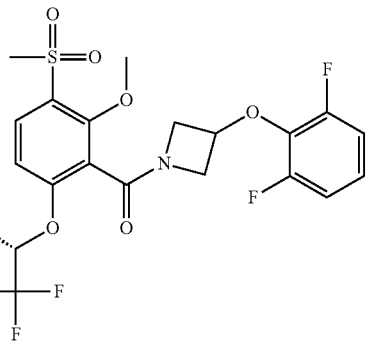

¹H NMR (400 MHz, CDCl₃) δ=7.91-8.02 (m, 1H) 6.73-7.06 (m, 4H) 4.96-5.08 (m, 1H) 4.74-4.87 (m, 1H) 4.44-4.57 (m, 1H) 4.30-4.42 (m, 1H) 4.10 (s, 5H) 3.20 (s, 3H) 1.48-1.64 (m, 3H); [M+H]=509.91.

Example 204. 3-(2,4-Difluorophenoxy)-1-(3-methanesulfonyl-2-methoxy-6-{[(2S)-1,1,1-trifluoropropan-2-yl]oxy}benzoyl)azetidine

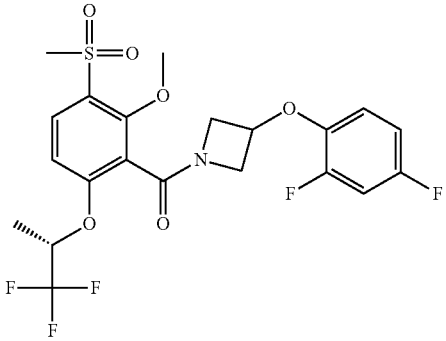 [SMILES: COc1c(S(C)(=O)=O)ccc(O[C@@H](C)C(F)(F)F)c1C(=O)N1CC(Oc2ccc(F)cc2F)C1]

¹H NMR (400 MHz, CDCl₃) δ=7.93-8.03 (m, 1H) 6.64-6.93 (m, 4H) 4.92-5.04 (m, 1H) 4.74-4.89 (m, 1H) 4.48-4.63 (m, 1H) 4.16-4.37 (m, 2H) 4.08 (s, 4H) 3.19 (s, 3H) 1.50-1.61 (m, 3H); [M+H]=510.21.

Example 205. 3-(2,5-Difluorophenoxy)-1-(3-methanesulfonyl-2-methoxy-6-{[(2S)-1,1,1-trifluoropropan-2-yl]oxy}benzoyl)azetidine

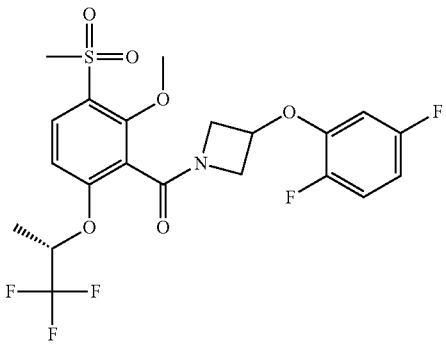 [SMILES: COc1c(S(C)(=O)=O)ccc(O[C@@H](C)C(F)(F)F)c1C(=O)N1CC(Oc2cc(F)ccc2F)C1]

¹H NMR (400 MHz, CDCl₃) δ=7.93-8.03 (m, 1H) 6.98-7.12 (m, 1H) 6.76-6.87 (m, 1H) 6.60-6.72 (m, 1H) 6.36-6.50 (m, 1H) 4.94-5.08 (m, 1H) 4.74-4.91 (m, 1H) 4.52-4.68 (m, 1H) 4.20-4.39 (m, 2H) 4.07 (d, J=3.13 Hz, 4H) 3.19 (d, J=2.35 Hz, 3H) 1.50-1.62 (m, 3H); [M+H]=509.90.

Example 206. 3-(2,3-Difluorophenoxy)-1-(3-methanesulfonyl-2-methoxy-6-{[(2S)-1,1,1-trifluoropropan-2-yl]oxy}benzoyl)azetidine

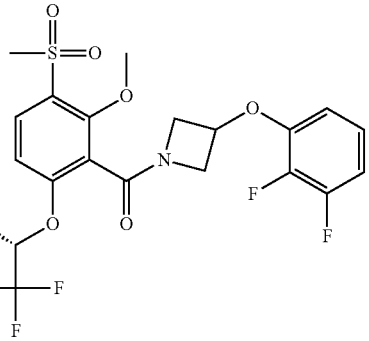

¹H NMR (400 MHz, CDCl₃) δ=7.93-8.03 (m, 1H) 6.92-7.03 (m, 1H) 6.77-6.90 (m, 2H) 6.42-6.52 (m, 1H) 4.98-5.10 (m, 1H) 4.73-4.89 (m, 1H) 4.51-4.66 (m, 1H) 4.19-4.37 (m, 2H) 4.08 (d, J=4.30 Hz, 4H) 3.20 (d, J=1.57 Hz, 3H) 1.48-1.66 (m, 3H); [M+H]=510.20.

Example 207. 3-(3-Fluorophenoxy)-1-(3-methanesulfonyl-2-methoxy-6-{[(2S)-1,1,1-trifluoropropan-2-yl]oxy}benzoyl)azetidine

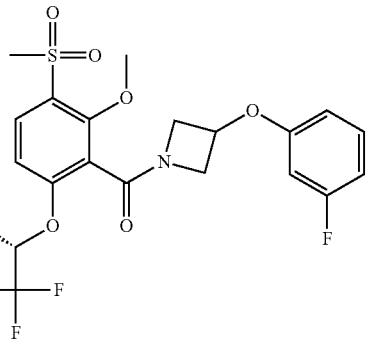

¹H NMR (400 MHz, CDCl₃) δ=7.93-8.02 (m, 1H) 7.18-7.26 (m, 1H) 6.78-6.85 (m, 1H) 6.67-6.76 (m, 1H) 6.42-6.54 (m, 2H) 4.93-5.03 (m, 1H) 4.74-4.90 (m, 1H) 4.52-4.66 (m, 1H) 4.19-4.34 (m, 2H) 4.06 (s, 4H) 3.15-3.24 (m, 3H) 1.48-1.62 (m, 3H); [M+H]=492.10.

Example 208-Example 255 were prepared in a manner analogous to Example 12, with the appropriate starting material substitutions.

Example 208. 4-(4-Fluorooxan-4-yl)-2-methoxy-3-({3-[4-(trifluoromethyl)phenyl]azetidin-1-yl}carbonyl)benzonitrile

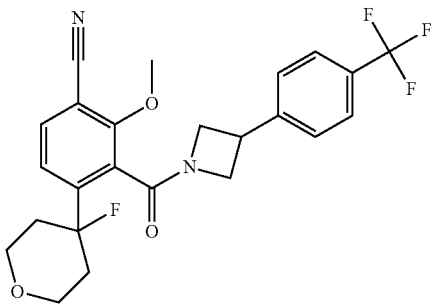 [SMILES: COc1c(C#N)ccc(C2(F)CCOCC2)c1C(=O)N1CC(c2ccc(C(F)(F)F)cc2)C1]

¹H NMR (400 MHz, CDCl₃) δ=7.72-7.57 (m, 3H), 7.47 (dd, J=8.2, 11.3 Hz, 2H), 7.18-7.03 (m, 1H), 4.70-4.54 (m, 1H), 4.37-4.16 (m, 2H), 4.13 (d, J=9.4 Hz, 3H), 4.06-3.69 (m, 6H), 2.64-2.27 (m, 2H), 2.10-1.75 (m, 2H); [M+H]=463.3.

Example 209. 3-{3-[3-Chloro-5-(trifluoromethyl)pyridin-2-yl]azetidine-1-carbonyl}-4-cyclopentyl-2-methoxybenzonitrile

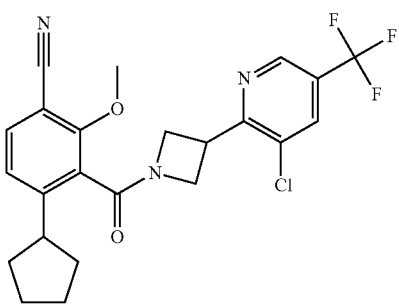 [SMILES: COc1c(C#N)ccc(C2CCCC2)c1C(=O)N1CC(c2ncc(C(F)(F)F)cc2Cl)C1]

¹H NMR (400 MHz, DMSO-d₆) δ=9.06-8.90 (m, 1H), 8.47 (dd, J=1.6, 5.9 Hz, 1H), 7.76 (dd, J=1.2, 8.2 Hz, 1H), 7.29 (t, J=8.2 Hz, 1H), 4.52-4.32 (m, 3H), 4.28-4.13 (m, 1H), 4.10-4.01 (m, 0.5H), 3.95-3.84 (m, 2H), 3.08-2.83 (m, 1H), 2.13-1.85 (m, 2H), 1.84-1.71 (m, 2H), 1.70-1.39 (m, 4H); [M+H]=464.20.

Example 210. 4-Cyclopentyl-3-{3-[3-fluoro-5-(trifluoromethyl)pyridin-2-yl]azetidine-1-carbonyl}-2-methoxybenzonitrile

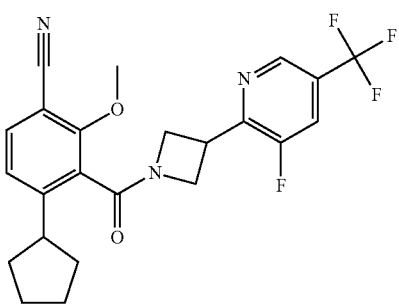 [SMILES: COc1c(C#N)ccc(C2CCCC2)c1C(=O)N1CC(c2ncc(C(F)(F)F)cc2F)C1]

¹H NMR (400 MHz, DMSO-d₆) δ=8.97-8.79 (m, 1H), 8.32-8.24 (m, 1H), 7.76 (dd, J=2.3, 8.2 Hz, 1H), 7.29 (dd, J=2.3, 8.2 Hz, 1H), 4.50-4.41 (m, 1H), 4.40-4.26 (m, 2H), 4.25-4.10 (m, 1H), 4.05 (t, J=8.2 Hz, 0.5H), 3.95-3.87 (m, 2H), 3.07-2.92 (m, 1H), 2.12-1.89 (m, 2H), 1.88-1.72 (m, 2H), 1.71-1.43 (m, 4H); [M+H]=448.09.

Example 211. 4-Cyclopentyl-2-methoxy-3-{3-[4-(trifluoromethyl)phenoxy]azetidine-1-carbonyl}benzonitrile

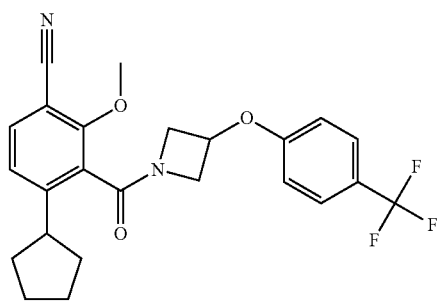 [SMILES: COc1c(C#N)ccc(C2CCCC2)c1C(=O)N1CC(Oc2ccc(C(F)(F)F)cc2)C1]

¹H NMR (400 MHz, DMSO-d₆)=7.77 (dd, J=1.6, 8.2 Hz, 1H), 7.63 (dd, J=2.7, 8.6 Hz, 2H), 7.30 (t, J=8.2 Hz, 1H), 7.03 (dd, J=3.3, 8.8 Hz, 2H), 5.19 (dd, J=3.5, 6.3 Hz, 1H), 4.62-4.52 (m, 1H), 4.35-4.13 (m, 1H), 4.04 (d, J=11.0 Hz, 1H), 3.94 (d, J=16.8 Hz, 3H), 3.79 (dd, J=3.1, 9.8 Hz, 1H), 3.64 (dd, J=3.1, 9.8 Hz, 1H), 2.94 (td, J=8.5, 12.7 Hz, 1H), 2.10-1.89 (m, 2H), 1.85-1.71 (m, 2H), 1.70-1.45 (m, 4H); [M+H]=445.16.

Example 212. 4-Cyclopentyl-2-methoxy-3-[3-(2,4,6-trifluorophenoxy)azetidine-1-carbonyl]benzonitrile

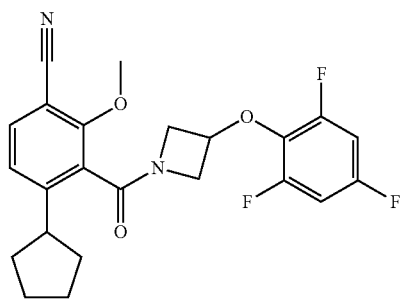 [SMILES: COc1c(C#N)ccc(C2CCCC2)c1C(=O)N1CC(Oc2c(F)cc(F)cc2F)C1]

¹H NMR (400 MHz, CDCl₃) δ=7.54 (d, J=8.2 Hz, 1H), 7.20-7.10 (m, 1H), 6.75-6.66 (m, 2H), 4.95 (d, J=3.5 Hz, 1H), 4.54 (dd, J=5.9, 11.0 Hz, 1H), 4.49-4.36 (m, 1H), 4.31 (dd, J=2.9, 11.5 Hz, 1H), 4.23-4.15 (m, 1H), 4.13-4.03 (m, 3H), 4.00-3.84 (m, 1H), 3.19-3.01 (m, 1H), 2.19-1.93 (m, 2H), 1.90-1.77 (m, 2H), 1.74-1.47 (m, 4H); [M+H]=431.06.

Example 213. 2-{1-[3-Methanesulfonyl-2-methoxy-6-(propan-2-yloxy)benzoyl]azetidin-3-yl}-5-(trifluoromethyl)pyridine

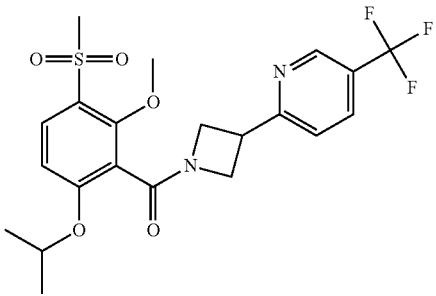 [SMILES: COc1c(S(C)(=O)=O)ccc(OC(C)C)c1C(=O)N1CC(c2ccc(C(F)(F)F)cn2)C1]

¹H NMR (400 MHz, DMSO-d₆) δ=8.96 (br s, 1H), 8.24-8.13 (m, 1H), 7.77 (d, J=9.0 Hz, 1H), 7.59 (d, J=8.2 Hz, 1H), 7.09-6.97 (m, 1H), 4.83-4.66 (m, 1H), 4.48-4.35 (m, 1H), 4.33-4.14 (m, 3H), 4.06 (dd, J=4.9, 7.6 Hz, 1H), 3.93 (s, 3H), 3.25-3.15 (m, 3H), 1.42-1.11 (m, 6H); [M+H]=473.17.

Example 214. 3-Chloro-2-{1-[3-methanesulfonyl-2-methoxy-6-(propan-2-yloxy)benzoyl]azetidin-3-yl}-5-(trifluoromethyl)pyridine

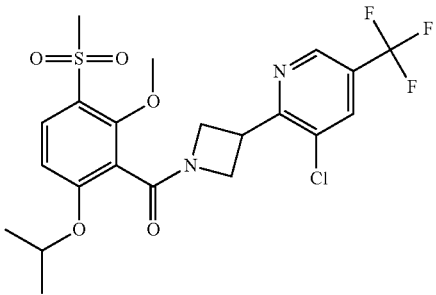 [SMILES: COc1c(S(C)(=O)=O)ccc(OC(C)C)c1C(=O)N1CC(c2ncc(C(F)(F)F)cc2Cl)C1]

¹H NMR (400 MHz, DMSO-d₆) δ=8.97 (s, 1H), 8.55-8.42 (m, 1H), 7.77 (d, J=8.6 Hz, 1H), 7.10-6.96 (m, 1H), 4.84-4.65 (m, 1H), 4.50-4.35 (m, 3H), 4.34-4.05 (m, 3H), 3.97-3.82 (m, 3H), 3.23-3.13 (m, 3H), 1.43-1.00 (m, 6H); [M+H]=506.99.

Example 215. 3-Fluoro-2-{1-[3-methanesulfonyl-2-methoxy-6-(propan-2-yloxy)benzoyl]azetidin-3-yl}-5-(trifluoromethyl)pyridine

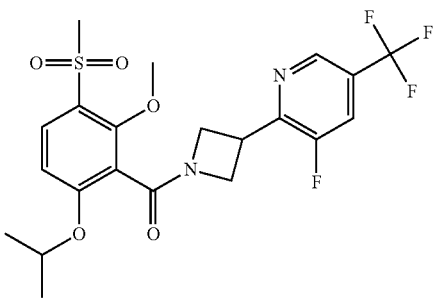 [SMILES: COc1c(S(C)(=O)=O)ccc(OC(C)C)c1C(=O)N1CC(c2ncc(C(F)(F)F)cc2F)C1]

¹H NMR (400 MHz, DMSO-d₆) δ=8.86 (s, 1H), 8.33-8.25 (m, 1H), 7.77 (d, J=9.0 Hz, 1H), 7.01 (d, J=9.0 Hz, 1H), 4.84-4.67 (m, 1H), 4.49-4.20 (m, 4H), 4.17-4.09 (m, 1H), 3.96-3.87 (m, 3H), 3.23-3.14 (m, 3H), 1.43-1.09 (m, 6H); [M+H]=491.98.

Example 216. 3-(3,4-Difluorophenyl)-1-[3-methanesulfonyl-2-methoxy-6-(propan-2-yloxy)benzoyl]azetidine

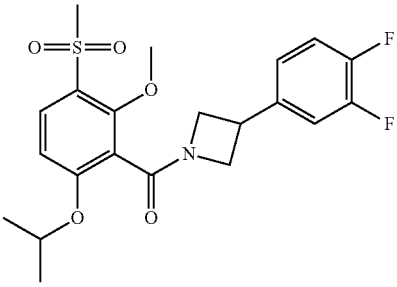 [SMILES: COc1c(S(C)(=O)=O)ccc(OC(C)C)c1C(=O)N1CC(c2ccc(F)c(F)c2)C1]

¹H NMR (400 MHz, DMSO-d₆) δ=7.77 (d, J=9.0 Hz, 1H), 7.40-7.19 (m, 3H), 7.10-7.00 (m, 1H), 4.75 (td, J=6.1, 12.1 Hz, 1H), 4.44 (t, J=9.6 Hz, 1H), 4.34-3.98 (m, 4H), 3.94-3.81 (m, 4H), 3.20 (s, 3H), 1.41-1.13 (m, 6H); [M+H]=440.21.

Example 217. 1-[3-Methanesulfonyl-2-methoxy-6-(propan-2-yloxy)benzoyl]-3-[4-(trifluoromethyl)phenyl]azetidine

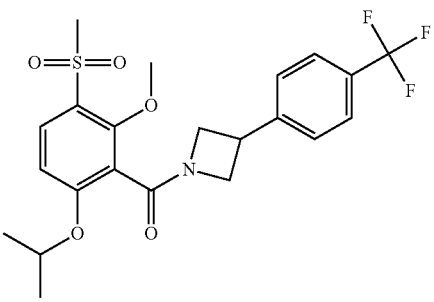 [SMILES: COc1c(S(C)(=O)=O)ccc(OC(C)C)c1C(=O)N1CC(c2ccc(C(F)(F)F)cc2)C1]

¹H NMR (400 MHz, DMSO-d₆) δ=7.75 (dd, J=8.4, 18.2 Hz, 3H), 7.58 (d, J=8.2 Hz, 2H), 7.11-7.00 (m, 1H), 4.83-4.70 (m, 1H), 4.53-4.42 (m, 1H), 4.36-4.21 (m, 1H), 4.17-3.97 (m, 2H), 3.86-3.71 (m, 1H), 3.24-3.14 (m, 3H), 1.40-1.14 (m, 6H); [M+H]=471.88.

Example 218. 1-[3-Methanesulfonyl-2-methoxy-6-(propan-2-yloxy)benzoyl]-3-[4-(trifluoromethyl)phenoxy]azetidine

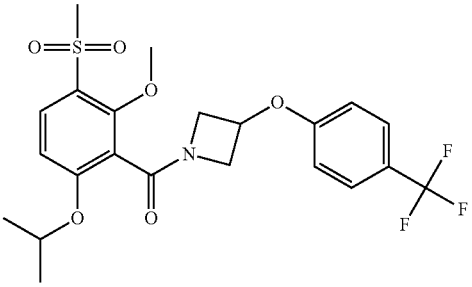 [SMILES: COc1c(S(C)(=O)=O)ccc(OC(C)C)c1C(=O)N1CC(Oc2ccc(C(F)(F)F)cc2)C1]

¹H NMR (400 MHz, DMSO-d₆) δ=7.77 (d, J=8.6 Hz, 1H), 7.65 (d, J=8.2 Hz, 2H), 7.09-6.99 (m, 3H), 5.18 (br s,

1H), 4.82-4.71 (m, 1H), 4.52 (d, J=6.3 Hz, 1H), 4.39-4.26 (m, 1H), 4.00 (dd, J=2.7, 11.0 Hz, 1H), 3.92-3.75 (m, 4H), 3.23-3.15 (m, 3H), 1.40-1.17 (m, 6H); [M+H]=488.29.

Example 219. 3-(4-Chlorophenoxy)-1-[3-methanesulfonyl-2-methoxy-6-(propan-2-yloxy)benzoyl]azetidine

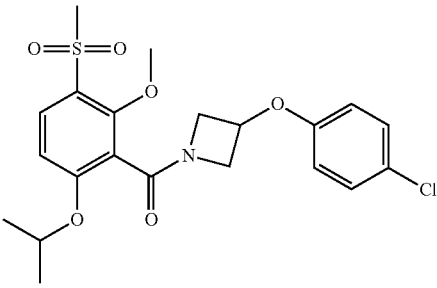 [SMILES: COc1c(S(C)(=O)=O)ccc(OC(C)C)c1C(=O)N1CC(Oc2ccc(Cl)cc2)C1]

$^1$H NMR (400 MHz, DMSO-d$_6$) δ=7.77 (d, J=9.0 Hz, 1H), 7.32 (d, J=9.0 Hz, 2H), 7.01 (d, J=9.0 Hz, 1H), 6.92-6.82 (m, 2H), 5.07 (br s, 1H), 4.74 (d, J=5.5 Hz, 1H), 4.48 (d, J=6.3 Hz, 1H), 4.30 (d, J=7.4 Hz, 1H), 3.96 (dd, J=3.5, 11.0 Hz, 1H), 3.89 (br s, 4H), 3.20 (br s, 3H), 1.38-1.17 (m, 6H); [M+H]=454.00.

Example 220. 3-(2,4-Difluorophenoxy)-1-[3-methanesulfonyl-2-methoxy-6-(propan-2-yloxy)benzoyl]azetidine

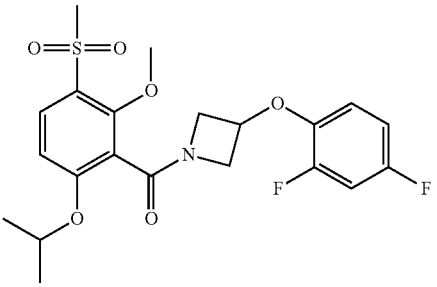 [SMILES: COc1c(S(C)(=O)=O)ccc(OC(C)C)c1C(=O)N1CC(Oc2ccc(F)cc2F)C1]

$^1$H NMR (400 MHz, DMSO-d$_6$) δ=7.77 (d, J=9.0 Hz, 1H), 7.39-7.29 (m, 1H), 7.09-6.94 (m, 3H), 5.11 (br s, 1H), 4.74 (br s, 1H), 4.47 (br s, 1H), 4.30 (br s, 1H), 3.99 (dd, J=3.1, 11.0 Hz, 1H), 3.88 (s, 3H), 3.80 (d, J=9.8 Hz, 1H), 3.19 (s, 3H), 1.38-1.19 (m, 6H); [M+H]=456.49.

Example 221. 1-[3-Methanesulfonyl-2-methoxy-6-(propan-2-yloxy)benzoyl]-3-(2,4,6-trifluorophenoxy)azetidine

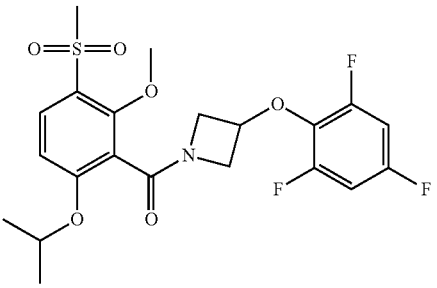 [SMILES: COc1c(S(C)(=O)=O)ccc(OC(C)C)c1C(=O)N1CC(Oc2c(F)cc(F)cc2F)C1]

$^1$H NMR (400 MHz, DMSO-d$_6$) δ=7.78 (d, J=9.0 Hz, 1H), 7.29 (t, J=9.0 Hz, 2H), 7.04 (d, J=9.0 Hz, 1H), 5.04 (br s, 1H), 4.76 (br s, 1H), 4.35 (br s, 1H), 4.15 (br s, 1H), 4.05 (d, J=11.3 Hz, 1H), 3.96-3.82 (m, 4H), 3.19 (s, 3H), 1.34-1.20 (m, 6H); [M+H]=473.66.

Example 222. 3-(4-Chlorophenoxy)-1-[3-methanesulfonyl-2-methoxy-6-(2,2,2-trifluoroethoxy)benzoyl]azetidine

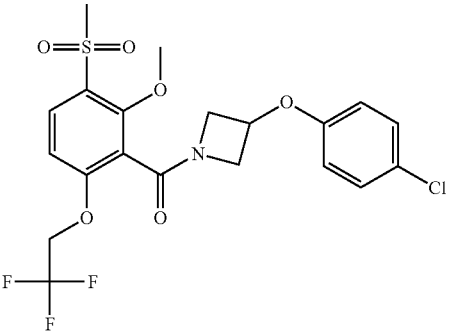

$^1$H NMR (400 MHz, DMSO-d$_6$) δ=7.85 (d, J=9.0 Hz, 1H), 7.36-7.28 (m, 2H), 7.21-7.09 (m, 1H), 6.91-6.81 (m, 2H), 5.13-4.88 (m, 3H), 4.53-4.45 (m, 1H), 4.37-4.23 (m, 1H), 3.92 (br s, 4H), 3.79 (br s, 1H), 3.23 (br s, 3H); [M+H]=493.82.

Example 223. 1-[3-Methanesulfonyl-2-methoxy-6-(2,2,2-trifluoroethoxy)benzoyl]-3-[4-(trifluoromethyl)phenoxy]azetidine

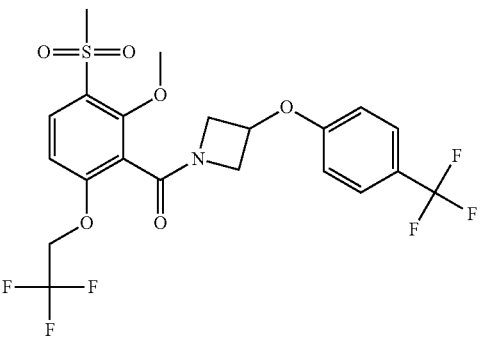 [SMILES: COc1c(S(C)(=O)=O)ccc(OCC(F)(F)F)c1C(=O)N1CC(Oc2ccc(C(F)(F)F)cc2)C1]

$^1$H NMR (400 MHz, DMSO-d$_6$) δ=7.85 (d, J=9.0 Hz, 1H), 7.64 (d, J=8.6 Hz, 2H), 7.12 (d, J=9.0 Hz, 1H), 7.01 (d, J=8.2 Hz, 2H), 5.24-5.09 (m, 1H), 5.03-4.86 (m, 2H), 4.53 (dd, J=6.7, 11.3 Hz, 1H), 4.43-4.25 (m, 1H), 4.08-3.89 (m, 4H), 3.82 (d, J=6.3 Hz, 1H), 3.26-3.16 (m, 3H); [M+H]=527.93.

Example 224. 3-(4-Fluoro-2-methylphenoxy)-1-[3-methanesulfonyl-2-methoxy-6-(2,2,2-trifluoroethoxy)benzoyl]azetidine

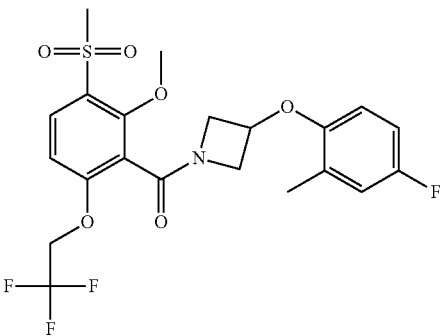 [SMILES: COc1c(S(C)(=O)=O)ccc(OCC(F)(F)F)c1C(=O)N1CC(Oc2ccc(F)cc2C)C1]

$^1$H NMR (400 MHz, DMSO-d$_6$) δ=7.85 (d, J=9.0 Hz, 1H), 7.20-7.10 (m, 1H), 7.07-6.99 (m, 1H), 6.90 (dt, J=2.9, 8.7 Hz, 1H), 6.70-6.60 (m, 1H), 5.12-4.86 (m, 3H), 4.49 (dd, J=6.7, 10.6 Hz, 1H), 4.36-4.23 (m, 1H), 4.05-3.75 (m, 5H), 3.28-3.16 (m, 3H), 2.15 (s, 3H); [M+H]=492.07.

Example 225. 1-[3-Methanesulfonyl-2-methoxy-6-(2,2,2-trifluoroethoxy)benzoyl]-3-(2,4,6-trifluorophenoxy)azetidine

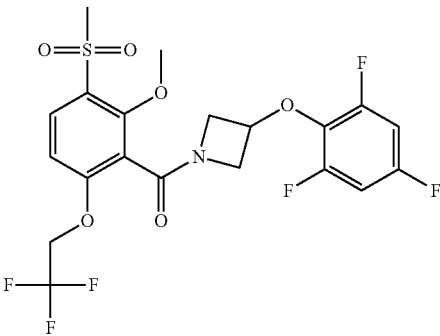 [SMILES: COc1c(S(C)(=O)=O)ccc(OCC(F)(F)F)c1C(=O)N1CC(Oc2c(F)cc(F)cc2F)C1]

$^1$H NMR (400 MHz, DMSO-d$_6$) δ=7.86 (d, J=9.0 Hz, 1H), 7.28 (t, J=8.8 Hz, 2H), 7.16 (d, J=9.0 Hz, 1H), 5.09-4.90 (m, 3H), 4.38 (dd, J=6.8, 10.4 Hz, 1H), 4.24-3.86 (m, 6H), 3.22 (s, 3H); [M+H]=513.85.

Example 226. 1-[3-Methanesulfonyl-2-methoxy-6-(2,2,2-trifluoroethoxy)benzoyl]-3-(2,4,5-trifluorophenoxy)azetidine

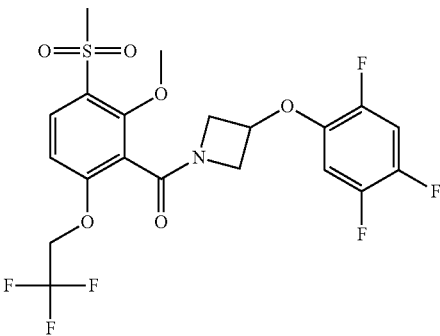 [SMILES: COc1c(S(C)(=O)=O)ccc(OCC(F)(F)F)c1C(=O)N1CC(Oc2cc(F)c(F)cc2F)C1]

$^1$H NMR (400 MHz, DMSO-d$_6$) δ=7.86 (d, J=9.0 Hz, 1H), 7.64 (dt, J=7.8, 11.0 Hz, 1H), 7.29-7.10 (m, 2H), 5.11 (d, J=18.4 Hz, 1H), 4.95 (d, J=6.7 Hz, 2H), 4.56-4.47 (m, 1H), 4.38-4.25 (m, 1H), 4.00 (d, J=11.0 Hz, 1H), 3.92 (s, 3H), 3.84 (br s, 1H), 3.23 (br s, 3H); [M+H]=514.05.

Example 227. 3-(2,4-Difluorophenoxy)-1-[3-methanesulfonyl-2-methoxy-6-(2,2,2-trifluoroethoxy)benzoyl]azetidine

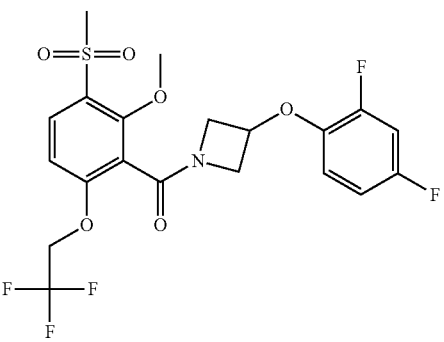 [SMILES: COc1c(S(C)(=O)=O)ccc(OCC(F)(F)F)c1C(=O)N1CC(Oc2ccc(F)cc2F)C1]

$^1$H NMR (400 MHz, DMSO-d$_6$) δ=7.85 (d, J=9.0 Hz, 1H), 7.37-7.28 (m, 1H), 7.20-7.10 (m, 1H), 7.03-6.92 (m, 2H), 5.17-5.03 (m, 1H), 5.01-4.87 (m, 2H), 4.49 (dd, J=6.5, 10.8 Hz, 1H), 4.36-4.21 (m, 1H), 4.11-3.97 (m, 1H), 3.92 (s, 3H), 3.84 (d, J=7.8 Hz, 1H), 3.23 (br s, 3H); [M+H]=496.17.

Example 228. 3-(3,4-Difluorophenyl)-1-[3-methanesulfonyl-2-methoxy-6-(2,2,2-trifluoroethoxy)benzoyl]azetidine

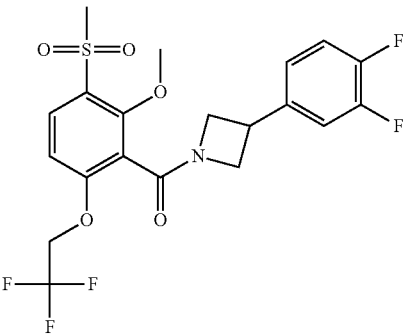 [SMILES: COc1c(S(C)(=O)=O)ccc(OCC(F)(F)F)c1C(=O)N1CC(c2ccc(F)c(F)c2)C1]

$^1$H NMR (400 MHz, DMSO-d$_6$) δ=7.85 (d, J=9.0 Hz, 1H), 7.39-7.12 (m, 4H), 5.08-4.87 (m, 2H), 4.51-4.42 (m, 1H), 4.33-3.99 (m, 4H), 3.94 (d, J=16.4 Hz, 3H), 3.26-3.18 (m, 3H); [M+H]=479.49

Example 229. 2-{1-[3-Methanesulfonyl-2-methoxy-6-(2,2,2-trifluoroethoxy)benzoyl]azetidin-3-yl}-5-(trifluoromethyl)pyridine

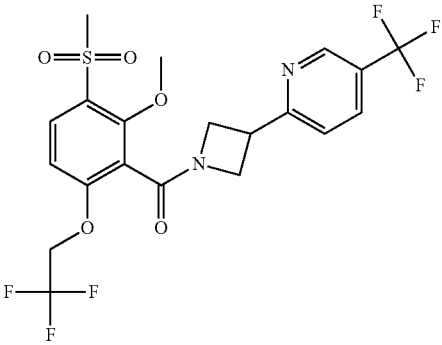 [SMILES: COc1c(S(C)(=O)=O)ccc(OCC(F)(F)F)c1C(=O)N1CC(c2ccc(C(F)(F)F)cn2)C1]

¹H NMR (400 MHz, DMSO-d₆) δ=9.01-8.90 (m, 1H), 8.22-8.13 (m, 1H), 7.85 (d, J=9.0 Hz, 1H), 7.58 (t, J=9.2 Hz, 1H), 7.15 (d, J=9.0 Hz, 1H), 5.06-4.84 (m, 2H), 4.41 (d, J=5.9 Hz, 1H), 4.35-4.05 (m, 4H), 4.03-3.92 (m, 3H), 3.23 (d, J=7.4 Hz, 3H); [M+H]=512.49.

Example 230. 3-Chloro-2-{1-[3-methanesulfonyl-2-methoxy-6-(2,2,2-trifluoroethoxy)benzoyl]azetidin-3-yl}-5-(trifluoromethyl)pyridine

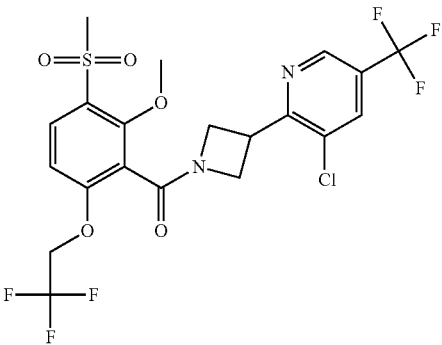 [SMILES: COc1c(S(C)(=O)=O)ccc(OCC(F)(F)F)c1C(=O)N1CC(c2ncc(C(F)(F)F)cc2Cl)C1]

¹H NMR (400 MHz, DMSO-d₆) δ=8.96 (d, J=11.3 Hz, 1H), 8.47 (s, 1H), 7.84 (d, J=9.0 Hz, 1H), 7.20-7.06 (m, 1H), 5.00 (d, J=5.5 Hz, 1H), 4.92-4.77 (m, 1H), 4.58-4.13 (m, 5H), 4.05-3.85 (m, 3H), 3.22 (d, J=13.3 Hz, 3H); [M+H]= 546.89.

Example 231. 3-Fluoro-2-{1-[3-methanesulfonyl-2-methoxy-6-(2,2,2-trifluoroethoxy)benzoyl]azetidin-3-yl}-5-(trifluoromethyl)pyridine

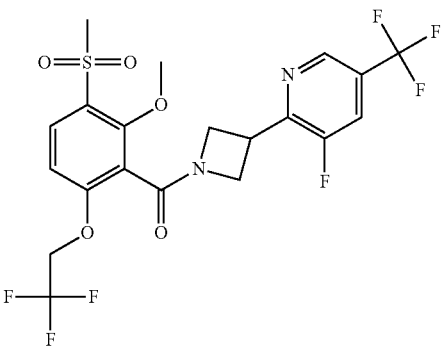 [SMILES: COc1c(S(C)(=O)=O)ccc(OCC(F)(F)F)c1C(=O)N1CC(c2ncc(C(F)(F)F)cc2F)C1]

¹H NMR (400 MHz, DMSO-d₆) δ=8.86 (d, J=17.6 Hz, 1H), 8.33-8.25 (m, 1H), 7.85 (d, J=9.0 Hz, 1H), 7.14 (t, J=10.2 Hz, 1H), 5.00 (d, J=9.0 Hz, 1H), 4.87 (d, J=8.6 Hz, 1H), 4.48-4.20 (m, 4H), 4.18-3.99 (m, 1H), 3.95 (d, J=8.2 Hz, 3H), 3.22 (d, J=9.4 Hz, 3H); [M+H]=530.87.

Example 232. 5-Chloro-2-({1-[3-methanesulfonyl-2-methoxy-6-(2,2,2-trifluoroethoxy)benzoyl]azetidin-3-yl}oxy)pyridine

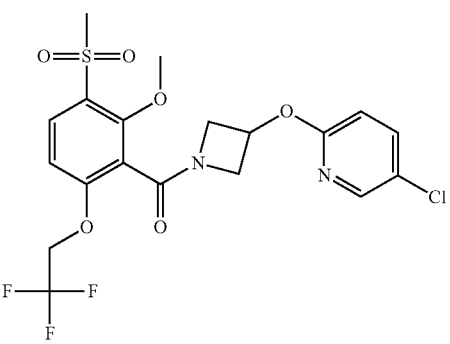 [SMILES: COc1c(S(C)(=O)=O)ccc(OCC(F)(F)F)c1C(=O)N1CC(Oc2ccc(Cl)cn2)C1]

¹H NMR (400 MHz, DMSO-d₆) δ=8.15 (br s, 1H), 7.86-7.83 (m, 2H), 7.19-7.09 (m, 1H), 6.94 (dd, J=7.8, 18.4 Hz, 1H), 5.34 (br s, 1H), 4.96 (br s, 2H), 4.44 (br s, 1H), 4.27 (br s, 1H), 4.09-3.97 (m, 1H), 3.92 (br s, 3H), 3.83 (br s, 1H), 3.22 (d, J=9.4 Hz, 3H); [M+H]=495.01.

Example 233. 5-Chloro-2-{[1-(3-methanesulfonyl-2-methoxy-6-{[(2S)-1,1,1-trifluoropropan-2-yl]oxy}benzoyl)azetidin-3-yl]oxy}pyridine

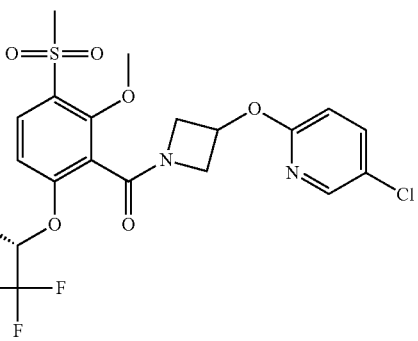

¹H NMR (400 MHz, DMSO-d₆) δ=8.19-8.12 (m, 1H), 7.88-7.80 (m, 2H), 7.30-7.19 (m, 1H), 6.94 (dd, J=9.0, 20.0 Hz, 1H), 5.52-5.42 (m, 1H), 5.34 (br s, 1H), 4.49-4.39 (m, 1H), 4.32-4.23 (m, 1H), 3.91 (d, J=8.6 Hz, 3H), 3.25-3.17 (m, 3H), 3.09-2.90 (m, 1H), 1.53-1.34 (m, 3H); [M+H]=508.94.

Example 234. 3-Chloro-2-[1-(3-methanesulfonyl-2-methoxy-6-{[(2S)-1,1,1-trifluoropropan-2-yl]oxy}benzoyl)azetidin-3-yl]pyridine

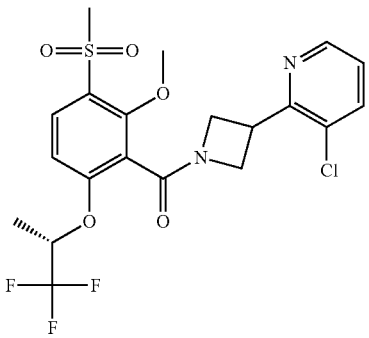 [SMILES: COc1c(S(C)(=O)=O)ccc(O[C@@H](C)C(F)(F)F)c1C(=O)N1CC(c2ncccc2Cl)C1]

$^1$H NMR (400 MHz, DMSO-d$_6$) δ=8.58-8.50 (m, 1H), 7.97-7.89 (m, 1H), 7.86-7.78 (m, 1H), 7.37 (td, J=4.1, 8.2 Hz, 1H), 7.29-7.17 (m, 1H), 5.57-5.34 (m, 1H), 4.58-4.40 (m, 1H), 4.39-4.11 (m, 4H), 4.00-3.86 (m, 3H), 3.26-3.17 (m, 3H), 1.56-1.27 (m, 3H); [M+H]=493.08.

Example 235. 1-[3-Methanesulfonyl-2-methoxy-6-(2,2,2-trifluoroethoxy)benzoyl]-3-[4-(trifluoromethyl)phenyl]azetidine

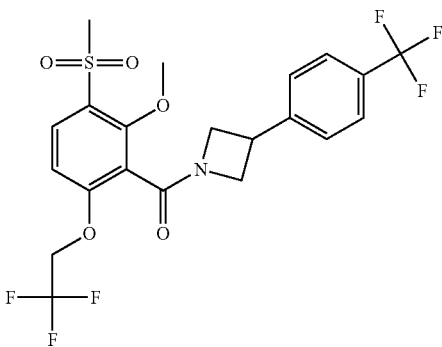 [SMILES: COc1c(S(C)(=O)=O)ccc(OCC(F)(F)F)c1C(=O)N1CC(c2ccc(C(F)(F)F)cc2)C1]

$^1$H NMR (400 MHz, DMSO-d$_6$) δ=7.85 (d, J=9.0 Hz, 1H), 7.70 (d, J=7.4 Hz, 2H), 7.61-7.50 (m, 2H), 7.16 (d, J=8.6 Hz, 1H), 5.04-4.91 (m, 2H), 4.52-4.45 (m, 1H), 4.34-4.23 (m, 1H), 4.12-3.81 (m, 6H), 3.26-3.20 (m, 3H); [M+H]=512.2.

Example 236. 3-Chloro-4-[1-(3-methanesulfonyl-2-methoxy-6-{[(2S)-1,1,1-trifluoropropan-2-yl]oxy}benzoyl)azetidin-3-yl]benzonitrile

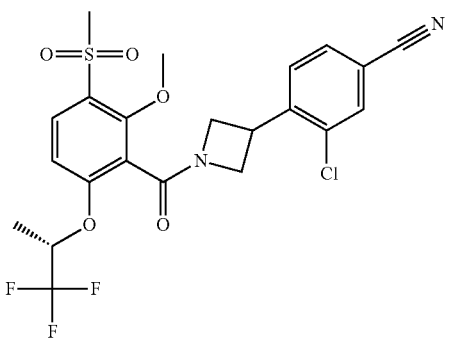 [SMILES: COc1c(S(C)(=O)=O)ccc(O[C@@H](C)C(F)(F)F)c1C(=O)N1CC(c2ccc(C#N)cc2Cl)C1]

$^1$H NMR (400 MHz, DMSO-d$_6$) δ=8.09-8.04 (m, 1H), 7.91-7.80 (m, 2H), 7.79-7.63 (m, 1H), 7.30-7.18 (m, 1H), 5.58-5.37 (m, 1H), 4.52-4.42 (m, 1H), 4.39-4.21 (m, 3H), 4.20-4.01 (m, 1H), 3.96 (d, J=2.3 Hz, 2H), 3.90-3.75 (m, 2H), 3.26-3.19 (m, 3H), 1.57-1.22 (m, 3H); [M+H]=517.1.

Example 237. 3-Chloro-4-{1-[3-methanesulfonyl-2-methoxy-6-(2,2,2-trifluoroethoxy)benzoyl]azetidin-3-yl}benzonitrile

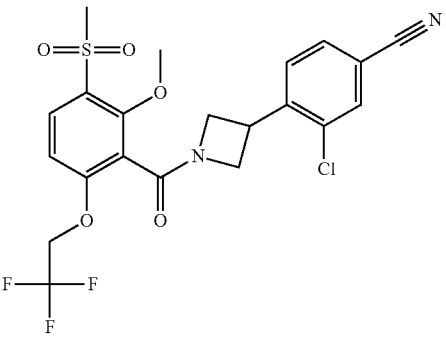 [SMILES: COc1c(S(C)(=O)=O)ccc(OCC(F)(F)F)c1C(=O)N1CC(c2ccc(C#N)cc2Cl)C1]

$^1$H NMR (400 MHz, DMSO-d$_6$) δ=8.09-7.82 (m, 3H), 7.79-7.65 (m, 1H), 7.19-7.08 (m, 1H), 5.06-4.84 (m, 2H), 4.47 (t, J=8.2 Hz, 1H), 4.37-4.14 (m, 3H), 4.11-3.93 (m, 2H), 3.93-3.81 (m, 2H), 3.27-3.18 (m, 3H); [M+H]=503.03.

Example 238. 1-[6-(2,2-Dimethylpropoxy)-3-methanesulfonyl-2-methoxybenzoyl]-3-[4-(trifluoromethyl)phenyl]azetidine

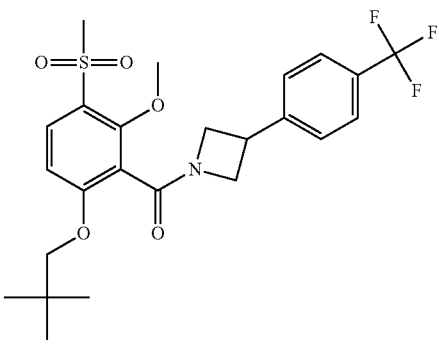 [SMILES: COc1c(S(C)(=O)=O)ccc(OCC(C)(C)C)c1C(=O)N1CC(c2ccc(C(F)(F)F)cc2)C1]

$^1$H NMR (400 MHz, DMSO-d$_6$) δ=7.79 (dd, J=3.7, 8.8 Hz, 1H), 7.70 (dd, J=8.2, 14.9 Hz, 2H), 7.57 (d, J=8.2 Hz, 1H), 7.48 (d, J=8.2 Hz, 1H), 7.01 (dd, J=9.0, 10.2 Hz, 1H), 4.53-4.45 (m, 1H), 4.33-4.22 (m, 1H), 4.18-4.04 (m, 2H), 4.00-3.90 (m, 4H), 3.87-3.65 (m, 3H), 3.20 (d, J=9.8 Hz, 3H), 1.05-0.79 (m, 9H); [M+H]=500.07.

Example 239. 3-Chloro-2-{1-[6-(2,2-dimethyl-propoxy)-3-methanesulfonyl-2-methoxybenzoyl]azetidin-3-yl}-5-(trifluoromethyl)pyridine

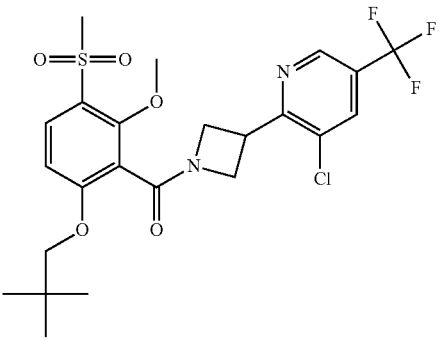 [SMILES: COc1c(S(C)(=O)=O)ccc(OCC(C)(C)C)c1C(=O)N1CC(c2ncc(C(F)(F)F)cc2Cl)C1]

$^1$H NMR (400 MHz, DMSO-$d_6$) δ=9.00-8.90 (m, 1H), 8.51-8.44 (m, 1H), 7.83-7.74 (m, 1H), 7.05-6.94 (m, 1H), 4.55-4.46 (m, 1H), 4.45-4.28 (m, 3H), 4.25-4.14 (m, 1H), 4.02 (dd, J=5.5, 8.6 Hz, 1H), 3.98-3.85 (m, 3H), 3.85-3.73 (m, 1H), 3.72-3.56 (m, 1H), 3.23-3.14 (m, 3H), 1.08-0.69 (m, 9H); [M+H]=535.19.

Example 240. 1-[6-(2,2-Dimethylpropoxy)-3-methanesulfonyl-2-methoxybenzoyl]-3-(2,4,6-trifluorophenoxy)azetidine

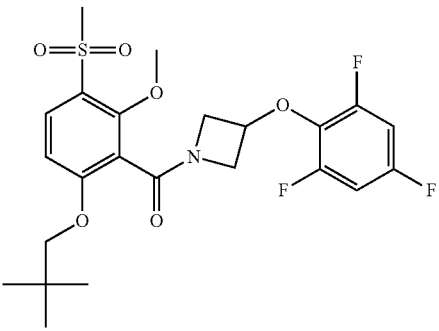 [SMILES: COc1c(S(C)(=O)=O)ccc(OCC(C)(C)C)c1C(=O)N1CC(Oc2c(F)cc(F)cc2F)C1]

$^1$H NMR (400 MHz, DMSO-$d_6$) δ=7.79 (d, J=9.0 Hz, 1H), 7.27 (t, J=9.0 Hz, 2H), 7.05-6.98 (m, 1H), 5.08-4.95 (m, 1H), 4.37 (dd, J=7.2, 10.4 Hz, 1H), 4.22-4.02 (m, 2H), 3.99-3.86 (m, 4H), 3.87-3.69 (m, 3H), 3.22-3.16 (m, 3H), 1.01-0.93 (m, 9H); [M+H]=502.24.

Example 241. 1-[6-(2,2-Dimethylpropoxy)-3-methanesulfonyl-2-methoxybenzoyl]-3-(2,4,5-trifluorophenoxy)azetidine

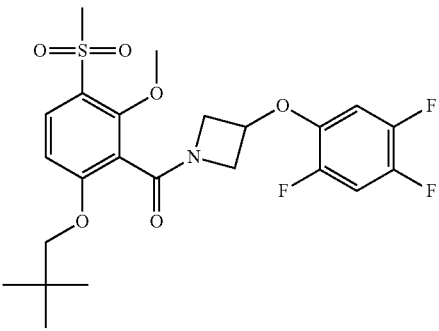 [SMILES: COc1c(S(C)(=O)=O)ccc(OCC(C)(C)C)c1C(=O)N1CC(Oc2cc(F)c(F)cc2F)C1]

$^1$H NMR (400 MHz, DMSO-$d_6$) δ=7.79 (d, J=9.0 Hz, 1H), 7.63 (dt, J=7.6, 10.9 Hz, 1H), 7.33-7.12 (m, 1H), 7.06-6.97 (m, 1H), 5.18-5.02 (m, 1H), 4.56-4.48 (m, 1H), 4.35 (dd, J=6.7, 8.6 Hz, 1H), 4.25 (dd, J=5.9, 10.2 Hz, 1H), 4.00 (dd, J=3.3, 10.8 Hz, 1H), 3.93-3.89 (m, 3H), 3.88-3.66 (m, 3H), 3.22-3.17 (m, 3H), 1.01-0.92 (m, 9H); [M+H]=502.2.

Example 242. 1-[3-(Ethanesulfonyl)-2-methoxy-6-(propan-2-yloxy)benzoyl]-3-[4-(trifluoromethyl)phenyl]azetidine

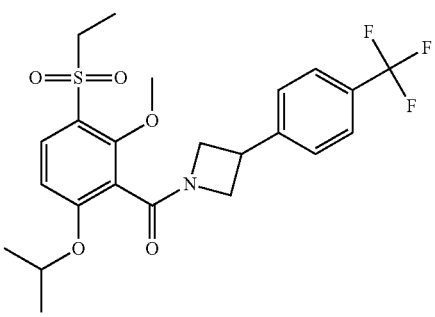 [SMILES: CCS(=O)(=O)c1ccc(OC(C)C)c(C(=O)N2CC(c3ccc(C(F)(F)F)cc3)C2)c1OC]

$^1$H NMR (400 MHz, DMSO-$d_6$) δ=7.78-7.70 (m, 3H), 7.57 (d, J=7.8 Hz, 2H), 7.06 (d, J=9.0 Hz, 1H), 4.82-4.72 (m, 1H), 4.51-4.42 (m, 1H), 4.31-4.22 (m, 1H), 4.14-3.97 (m, 2H), 3.90 (s, 3H), 3.85-3.73 (m, 1H), 3.34 (br s, 2H), 1.39-1.16 (m, 6H), 1.05 (t, J=7.0 Hz, 3H); [M+H]=485.67.

Example 243. 3-Chloro-2-{1-[3-(ethanesulfonyl)-2-methoxy-6-(propan-2-yloxy)benzoyl]azetidin-3-yl}-5-(trifluoromethyl)pyridine

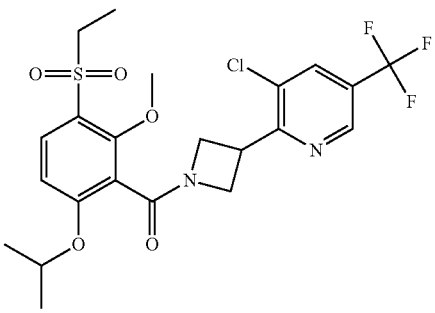 [SMILES: CCS(=O)(=O)c1ccc(OC(C)C)c(C(=O)N2CC(c3ncc(C(F)(F)F)cc3Cl)C2)c1OC]

$^1$H NMR (400 MHz, DMSO-$d_6$) δ=8.97 (d, J=0.8 Hz, 1H), 8.54-8.43 (m, 1H), 7.74 (d, J=9.0 Hz, 1H), 7.12-6.96 (m, 1H), 4.85-4.64 (m, 1H), 4.50-4.04 (m, 6H), 3.96-3.77 (m, 3H), 3.42-3.32 (m, 2H), 1.42-1.06 (m, 6H), 1.04 (d, J=7.0 Hz, 3H); [M+H]=521.05.

Example 244. 1-[3-(Ethanesulfonyl)-2-methoxy-6-(propan-2-yloxy)benzoyl]-3-(2,4,6-trifluorophenoxy)azetidine

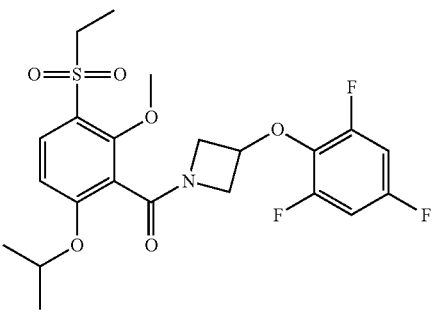 [SMILES: CCS(=O)(=O)c1ccc(OC(C)C)c(C(=O)N2CC(Oc3c(F)cc(F)cc3F)C2)c1OC]

¹H NMR (400 MHz, DMSO-d₆) δ=7.76 (d, J=9.0 Hz, 1H), 7.35-7.23 (m, 2H), 7.06 (d, J=9.4 Hz, 1H), 5.07-4.99 (m, 1H), 4.77 (d, J=5.1 Hz, 1H), 4.35 (br s, 1H), 4.14 (br s, 1H), 4.05 (d, J=11.0 Hz, 1H), 3.94-3.82 (m, 4H), 3.29-3.23 (m, 2H), 1.36-1.21 (m, 6H), 1.04 (t, J=7.4 Hz, 3H); [M+H]=488.22.

Example 245. 1-[3-(Ethanesulfonyl)-2-methoxy-6-(propan-2-yloxy)benzoyl]-3-(2,4,5-trifluorophenoxy)azetidine

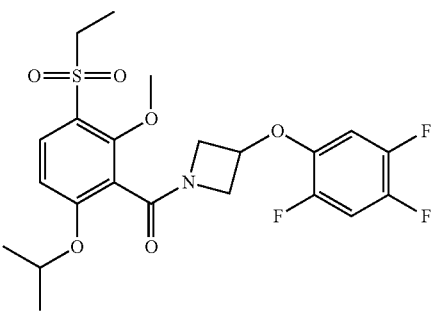 [SMILES: CCS(=O)(=O)c1ccc(OC(C)C)c(C(=O)N2CC(Oc3cc(F)c(F)cc3F)C2)c1OC]

¹H NMR (400 MHz, DMSO-d₆) δ=7.75 (d, J=9.0 Hz, 1H), 7.70-7.59 (m, 1H), 7.23 (br s, 1H), 7.04 (d, J=9.0 Hz, 1H), 5.12 (br s, 1H), 4.75 (br. s., 1H), 4.49 (br s, 1H), 4.29 (d, J=6.3 Hz, 1H), 4.02-3.97 (m, 1H), 3.87 (s, 3H), 3.81 (br s, 1H), 3.25 (br s, 2H), 1.39-1.17 (m, 6H), 1.05 (br s, 3H); [M+H]=488.07.

Example 246. 6-[1-(3-Methanesulfonyl-2-methoxy-6-{[(2S)-1,1,1-trifluoropropan-2-yl]oxy}benzoyl)azetidin-3-yl]-1,3-benzoxazole

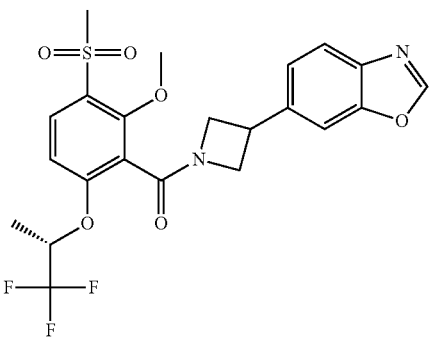 [SMILES: COc1c(S(C)(=O)=O)ccc(O[C@@H](C)C(F)(F)F)c1C(=O)N1CC(c2ccc3ncoc3c2)C1]

¹H NMR (400 MHz, CDCl₃) δ=8.11 (s, 1H), 7.99 (d, J=9.0 Hz, 1H), 7.78 (dd, J=3.9, 8.2 Hz, 1H), 7.55 (d, J=7.4 Hz, 1H), 7.40-7.29 (m, 1H), 6.85 (dd, J=6.8, 8.8 Hz, 1H), 4.90-4.80 (m, 1H), 4.76-4.62 (m, 1H), 4.41-4.26 (m, 2H), 4.17-4.09 (m, 3H), 4.07-3.95 (m, 2H), 3.24-3.17 (m, 3H), 1.61-1.52 (m, 3H); [M+H]=499.24.

Example 247. 6-{1-[3-Methanesulfonyl-2-methoxy-6-(2,2,2-trifluoroethoxy)benzoyl]azetidin-3-yl}-1,3-benzoxazole

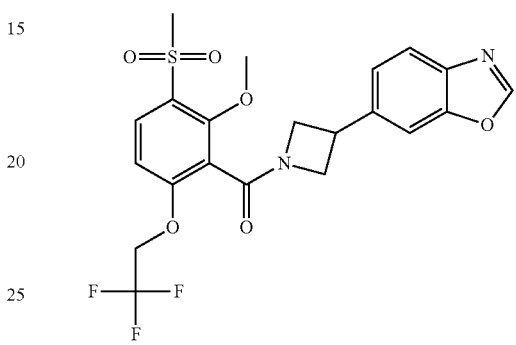

¹H NMR (400 MHz, CDCl₃) δ=3.21 (s, 3H) 3.98-4.09 (m, 2H) 4.11-4.16 (m, 3H) 4.27-4.41 (m, 2H) 4.48-4.60 (m, 2H) 4.63-4.77 (m, 1H) 6.80 (d, J=9.00 Hz, 1H) 7.29-7.38 (m, 1H) 7.55 (br s, 1H) 7.78 (d, J=8.22 Hz, 1H) 8.01 (d, J=9.00 Hz, 1H) 8.11 (s, 1H); [M+H]=485.25.

Example 248. 6-{1-[3-Methanesulfonyl-2-methoxy-6-(propan-2-yloxy)benzoyl]azetidin-3-yl}-1,3-benzoxazole

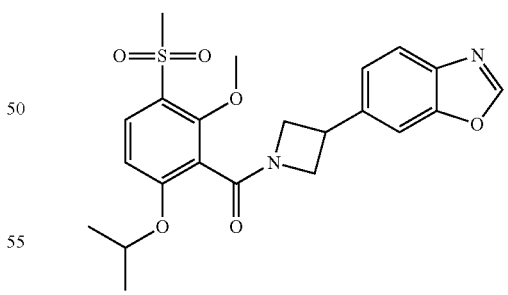

¹H NMR (400 MHz, CDCl₃) δ=8.11 (s, 1H), 7.93 (d, J=9.0 Hz, 1H), 7.78 (d, J=8.2 Hz, 1H), 7.64-7.53 (m, 1H), 7.42-7.30 (m, 1H), 6.77 (d, J=9.0 Hz, 1H), 4.76-4.61 (m, 2H), 4.42-4.26 (m, 2H), 4.14-4.08 (m, 3H), 3.98 (d, J=5.1 Hz, 2H), 3.19 (s, 3H), 1.41 (dd, J=5.5, 15.7 Hz, 6H); [M+H]=445.16.

Example 249. 6-{1-[6-(2,2-Dimethylpropoxy)-3-methanesulfonyl-2-methoxybenzoyl]azetidin-3-yl}-1,3-benzoxazole

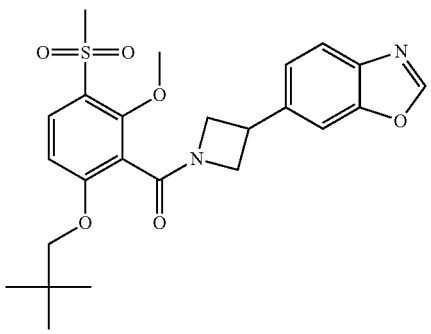 [SMILES: COc1c(S(C)(=O)=O)ccc(OCC(C)(C)C)c1C(=O)N1CC(c2ccc3ncoc3c2)C1]

$^1$H NMR (400 MHz, CDCl$_3$) δ=8.10 (d, J=2.0 Hz, 1H), 7.93 (dd, J=4.1, 8.8 Hz, 1H), 7.75 (dd, J=8.2, 16.4 Hz, 1H), 7.52 (d, J=10.6 Hz, 1H), 7.34-7.27 (m, 1H), 6.76 (dd, J=2.7, 9.0 Hz, 1H), 4.74-4.63 (m, 1H), 4.42-4.26 (m, 2H), 4.14-4.08 (m, 3H), 4.03-3.94 (m, 2H), 3.78-3.65 (m, 2H), 3.18 (d, J=7.0 Hz, 3H), 1.14-0.97 (m, 9H); [M+H]=473.25.

Example 250. 6-{1-[3-(Ethanesulfonyl)-2-methoxy-6-(propan-2-yloxy)benzoyl]azetidin-3-yl}-1,3-benzoxazole

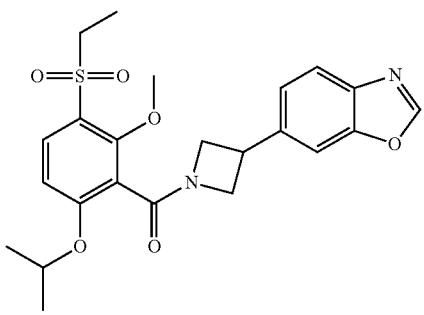 [SMILES: CCS(=O)(=O)c1ccc(OC(C)C)c(C(=O)N2CC(c3ccc4ncoc4c3)C2)c1OC]

$^1$H NMR (400 MHz, CDCl$_3$) δ=8.11 (s, 1H), 7.90 (d, J=9.0 Hz, 1H), 7.77 (d, J=8.2 Hz, 1H), 7.64-7.52 (m, 1H), 7.40-7.30 (m, 1H), 6.77 (d, J=9.0 Hz, 1H), 4.75-4.61 (m, 2H), 4.33 (br s, 2H), 4.07 (s, 3H), 3.96 (br s, 2H), 3.33 (br s, 2H), 1.41 (dd, J=5.3, 16.6 Hz, 6H), 1.21 (t, J=7.4 Hz, 3H); [M+H]=459.30.

Example 251. 3-(5-Chloro-2-fluorophenyl)-1-(3-methanesulfonyl-2-methoxy-6-{[(2S)-1,1,1-trifluoropropan-2-yl]oxy}benzoyl)azetidine

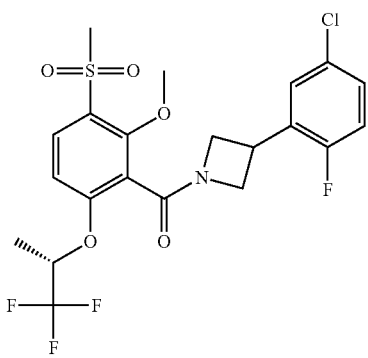 [SMILES: COc1c(S(C)(=O)=O)ccc(O[C@@H](C)C(F)(F)F)c1C(=O)N1CC(c2cc(Cl)ccc2F)C1]

$^1$H NMR (400 MHz, DMSO-d$_6$) δ=7.86-7.80 (m, 1H), 7.58-7.46 (m, 1H), 7.45-7.36 (m, 1H), 7.30-7.19 (m, 2H), 5.55-5.41 (m, 1H), 4.47-4.39 (m, 1H), 4.27 (t, J=8.2 Hz, 1H), 4.21-4.00 (m, 3H), 3.96-3.90 (m, 3H), 3.89-3.79 (m, 1H), 3.26-3.19 (m, 3H), 1.53-1.34 (m, 3H); [M+H]=509.96.

Example 252. 3-(3-Chloro-2-fluorophenyl)-1-(3-methanesulfonyl-2-methoxy-6-{[(2S)-1,1,1-trifluoropropan-2-yl]oxy}benzoyl)azetidine

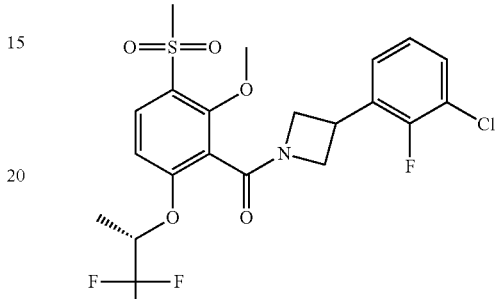

$^1$H NMR (400 MHz, DMSO-d$_6$) δ=7.83 (d, J=9.0 Hz, 1H), 7.49 (d, J=6.3 Hz, 1H), 7.41 (br s, 1H), 7.30-7.17 (m, 2H), 5.46 (s, 1H), 4.48-4.41 (m, 1H), 4.33-4.25 (m, 1H), 4.15 (d, J=6.3 Hz, 3H), 4.05 (br s, 1H), 3.97-3.87 (m, 3H), 3.27-3.19 (m, 2H), 1.54-1.32 (m, 3H); [M+H]=510.11.

Example 253. 3-(2-Chloro-3-fluorophenyl)-1-(3-methanesulfonyl-2-methoxy-6-{[(2S)-1,1,1-trifluoropropan-2-yl]oxy}benzoyl)azetidine

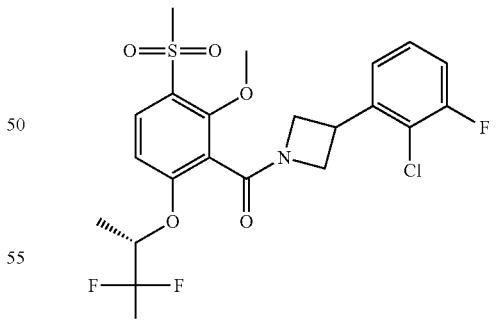

$^1$H NMR (400 MHz, DMSO-d$_6$) δ=7.86-7.79 (m, 1H), 7.46-7.20 (m, 4H), 5.58-5.39 (m, 1H), 4.52-4.43 (m, 1H), 4.38-4.28 (m, 1H), 4.27-4.18 (m, 2H), 4.17-3.99 (m, 1H), 3.98-3.85 (m, 3H), 3.85-3.75 (m, 1H), 3.25-3.18 (m, 3H), 1.56-1.23 (m, 3H); [M+H]=510.00.

Example 254. 3-(2-Chloro-4,5-difluorophenyl)-1-(3-methanesulfonyl-2-methoxy-6-{[(2S)-1,1,1-trifluoropropan-2-yl]oxy}benzoyl)azetidine

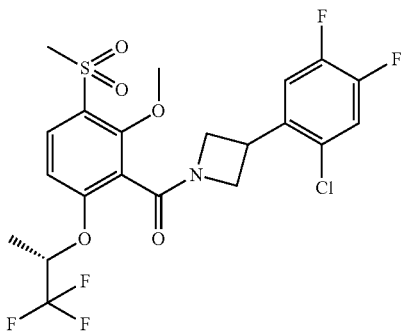 [SMILES: COc1c(S(C)(=O)=O)ccc(O[C@@H](C)C(F)(F)F)c1C(=O)N1CC(c2cc(F)c(F)cc2Cl)C1]

$^1$H NMR (400 MHz, DMSO-$d_6$) δ=7.86-7.80 (m, 1H), 7.74 (dd, J=7.4, 10.6 Hz, 1H), 7.67-7.55 (m, 1H), 7.29-7.21 (m, 1H), 5.56-5.42 (m, 1H), 4.47-4.40 (m, 1H), 4.32 (t, J=8.6 Hz, 1H), 4.26-4.03 (m, 3H), 3.95-3.86 (m, 2H), 3.82-3.71 (m, 1H), 3.27-3.20 (m, 3H), 1.53-1.27 (m, 3H); [M+H]=528.1.

Example 255. 3-Chloro-2-(1-{3-methanesulfonyl-2-methoxy-6-[(1,1,1-trifluoropropan-2-yl)oxy]benzoyl}azetidin-3-yl)-5-(trifluoromethyl)pyridine

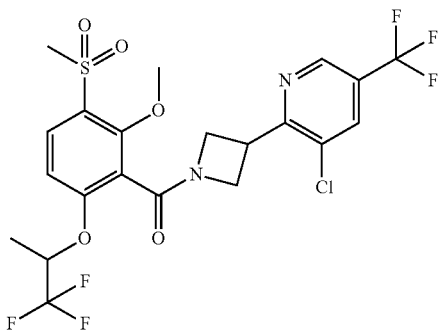 [SMILES: COc1c(S(C)(=O)=O)ccc(OC(C)C(F)(F)F)c1C(=O)N1CC(c2ncc(C(F)(F)F)cc2Cl)C1]

$^1$H NMR (400 MHz, DMSO-$d_6$) δ=8.98 (d, J=14.8 Hz, 1H), 8.49 (d, J=7.5 Hz, 1H), 7.90-7.80 (m, 1H), 7.31-7.19 (m, 1H), 5.54 (dt, J=6.4, 12.8 Hz, 1H), 5.47-5.35 (m, 1H), 4.69-4.14 (m, 5H), 4.00-3.88 (m, 3H), 3.24 (d, J=13.7 Hz, 3H), 1.59-1.28 (m, 3H); [M+H]=561.1.

Example 256. 2-Methoxy-3-({3-[4-(trifluoromethyl)phenyl]azetidin-1-yl}carbonyl)-4-{[(2R)-1,1,1-trifluoropropan-2-yl]oxy}benzonitrile

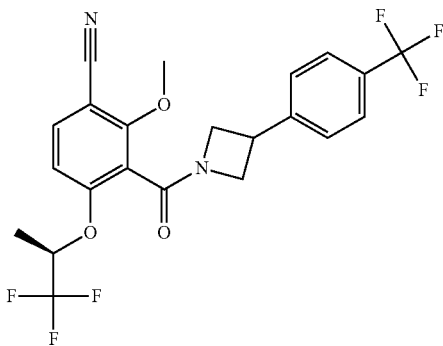 [SMILES: COc1c(C#N)ccc(O[C@H](C)C(F)(F)F)c1C(=O)N1CC(c2ccc(C(F)(F)F)cc2)C1]

$^1$H NMR (400 MHz, DMSO-$d_6$) δ=7.87 (d, J=8.6 Hz, 1H), 7.75-7.67 (m, 2H), 7.60-7.49 (m, 2H), 7.22 (d, J=9.4 Hz, 1H), 5.55-5.45 (m, 1H), 4.45 (d, J=8.2 Hz, 1H), 4.30-4.02 (m, 3H), 3.99-3.95 (m, 3H), 3.80-3.70 (m, 1H), 1.51-1.33 (m, 3H); [M+H]=473.17.

BIOLOGICAL EXAMPLES

The present disclosure will be further illustrated by the following biological examples. These examples are understood to be exemplary only and are not intended to limit the scope of the embodiments disclosed herein.

Glycine Transporter 1 (GlyT1) Uptake Assay

A scintillation proximity assay (SPA) was used to measure the uptake of [$^{14}$C]-glycine in HEK293 cells stably expressing human GlyT1c and in cultured primary rat cortical neurons (Williams et al., *Anal. Biochem.* 2003, 321, 31-37).

Human GlyT1c Assay

HEK293 cells stably expressing hGlyT1c were plated onto 96-well Cytostar plates at a density of 4.5×10$^4$ cells per well in 100 μL of growth media (DMEM containing 10% fetal bovine serum) and incubated overnight in a 37° C., 10% CO$_2$ incubator. The following day, stock compounds in 10 mM DMSO were serially diluted in DMSO, and 2× compound solutions were prepared by diluting compound again (1:100) in HBSS. Growth media was removed from the plate, and 30 μL of 2× compound solution was added Immediately after, 30 μL of 15 μM [$^{14}$C] glycine in HBSS was added, and plates were sealed and allowed to incubate at rt for 2 hours. Plates were then read on a MicroBeta plate counter (Perkin Elmer). Dose-response data for tested compounds were analyzed and curves were fit using a four parameter logistic fit to determine IC$_{50}$ values.

Rat Primary Cortical Neuron Assay

Primary rat cortical neurons were harvested from rat E18 pups and plated onto poly-D-lysine-coated 96-well Cytostar plates at a density of 3.5×10$^4$ cells per well in 100 μL of astrocyte media (MEM media with 20 mM glucose, 1× penicillin/streptomycin, and 10% fetal bovine serum) and incubated at 37° C. in a 5% CO$_2$ environment. Twenty-four hours later, media was replaced with 200 μL of neuronal media (BME media with 20 mM glucose, 1 mM sodium pyruvate, 2 mM GlutaMAX, 1× penicillin/streptomycin, 1% horse serum, and B27 supplement) and the cells were cultured for an additional 5 days in a 37° C., 5% CO$_2$ incubator. The following day, stock compounds in 10 mM DMSO were serially diluted in DMSO, and 2× compound solutions were prepared by diluting compound again (1:100) in HBSS. Neuronal media was removed from the plate, and 30 μL of 2× compound solution was added Immediately after, 30 μL of 25 μM [$^{14}$C] glycine in HBSS supplemented with 5 mM L-Alanine and 5 mM HEPES was added and plates were sealed and allowed to incubate at rt for 2 hours. Plates were then read on a MicroBeta plate counter (Perkin Elmer). Dose-response data for tested compounds were analyzed and curves were fit using a four parameter logistic fit to determine IC$_{50}$ values.

| GlyT1 (pIC$_{50}$) | Example Number |
|---|---|
| >7 | 1, 2, 3, 4, 8, 9, 10, 12, 15, 16, 19, 20, 29, 35, 38, 42, 58, 59, 65, 73, 89, 90, 91, 93, 96, 99, 101, 103, 106, 107, 112, 113, 116, 117, 118, 119, 120, 121, 122, 123, 124, 125, 126, 127, 128, 130, 131, 132, 133, 134, 137, 139, 146, 147, 148, 149, 150, 152, 153, 154, 155, 156, 157, 158, 159, 160, 161, 163, 164, 165, 167, 168, 169, 170, 171, 172, 173, 174, 175, 176, 179, 180, 183, 187, 188, 189, 190, 191, 192, 193, 194, 196, 197, 199, 200, 201, 202, 204, 205, 206, 207, 208, 210, 214, 221, 232, 234, 235, 236, 237, 238, 239, 244, 245, 246, 247, 248, 250, 251, 252, 253, 254, 255; |
| 6-7 | 5, 6, 7, 11, 13, 14, 17, 18, 23, 24, 25, 27, 28, 30, 31, 32, 34, 36, 39, 41, 43, 44, 46, 50, 52, 53, 54, 55, 56, 57, 60, 61, 62, 63, 64, 66, 68, 69, 70, 71, 72, 74, 83, 84, 85, 86, 87, 88, 92, 95, 97, 98, 100, 102, 104, 105, 109, 110, 111, 114, 115, 129, 135, 136, 138, 140, 141, 143, 145, 151, 162, 166, 177, 178, 181, 182, 184, 185, 186, 195, 198, 203, 209, 211, 212, 213, 215, 216, 217, 218, 219, 220, 222, 223, 224, 225, 226, 227, 228, 229, 230, 231, 233, 240, 241, 242, 243, 249; |
| 5-6 | 21, 26, 33, 37, 40, 45, 47, 48, 49, 51, 67, 75, 76, 77, 78, 79, 80, 81, 82, 108, 142, 144, 256; |
| <5 | 22, 94. |

Behavioral Assays

Numerous behavioral assays are available to assess the ability of a candidate compound to enhance memory formation, including contextual conditioning (e.g., fear conditioning), temporal conditioning (e.g., trace conditioning), and object recognition. Other non-limiting examples of appropriate assays to assess memory include those that incorporate or relate to multiple training sessions, spaced training sessions, contextual fear training with single or multiple trials, trace fear conditioning with single or multiple trials, contextual memory generally, temporal memory, spatial memory, episodic memory, passive avoidance memory, active avoidance memory, food preference memory, conditioned taste avoidance, and social recognition memory.

The behavioral assays can also be used in accordance with the present embodiments, as will be understood by those of ordinary skill in the art. These assays can be directed towards the evaluation of, without limitation, hippocampus-, cortex, and/or amygdala-dependent memory formation or cognitive performance.

Biological Example 1

Effect of GlyT1 Inhibitors on Contextual Memory
Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. The percent of time during the test that the animal exhibits such freezing provides a quantitative measure of the contextual associative memory (e.g., Fanselow, Behav. Neurosci. 1984, 98, 269-277; Fanselow, Behav. Neurosci. 1984, 98, 79-95; and Phillips and LeDoux, Behav. Neurosci. 1992, 106, 274-285).

Contextual conditioning has been extensively used to investigate the neural substrates mediating fear-motivated learning (e.g., Phillips and LeDoux, Behav. Neurosci. 1992, 106, 274-285; Kim et al., Behav. Neurosci. 1993, 107, 1093-1098; and Bourtchouladze et al., Learn. Mem. 1998, 5, 365-374). Studies in mice and rats have provided evidence for functional interaction between hippocampal and nonhippocampal systems during contextual conditioning training (e.g., Maren et al., Behav. Brain Res. 1997, 88, 261-274; Maren et al., Neurobiol. Learn. Mem. 1997, 67, 142-149; and Frankland et al., Behav. Neurosci. 1998, 112, 863-874). Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning, as well as strain and genetic background differences in mice (e.g., Bourtchouladze et al., Cell 1994, 79, 59-68; Bourtchouladze et al., Learn Mem. 1998, 5, 365-374; Kogan et al., Current Biology 1997, 7, 1-11; Silva et al., Current Biology 1996, 6, 1509-1518; Abel et al., Cell 1997, 88, 615-626; Giese et al., Science 1998, 279, 870-873; Logue et al., Neuroscience 1997, 80, 1075-1086; Chen et al., Behav. Neurosci. 1996, 110, 1177-1180; and Nguyen et al., Learn Mem. 2000, 7, 170-179).

Because robust learning can be triggered with a few minutes training session, contextual conditioning has been especially useful to study the biology of temporally distinct processes of short- and long-term memory (e.g., Kim et al., Behav. Neurosci. 1993, 107, 1093-1098; Bourtchouladze et al., Cell 1994, 79, 59-68; Abel et al., Cell 1997, 88, 615-626; Logue et al., Behav. Neurosci. 1997, 111, 104-113; Bourtchouladze et al., Learn. Mem. 1998, 5, 365-374; and Nguyen et al., Learn. Mem. 2000, 7, 170-179). As such, contextual conditioning provides an excellent model to evaluate the effects of novel drug compounds on hippocampal-dependent memory formation.

Procedures

Previous investigations have established that training with 1× or 2× CS-US pairings induces sub-maximal (weak) memory in wild-type mice (e.g., U.S.2009/0053140; Tully et al., Nat. Rev. Drug Discov. 2003, 2, 267-77; and Bourtchouladze et al. Learn. Mem. 1998, 5, 365-374). Such sub-maximal memory is facilitated by augmenting CREB, while inhibition of CREB impairs maximal memory induced with 5× CS-US pairings (Barad et al. Proc Natl Acad Sci. 1998, 95, 15020-15025; Peters et al. Genes Brain Behav. 2009, 8, 320-329). Accordingly, contextual conditioning in this study was performed as described by Barad et al. Proc Natl Acad Sci. 1998, 95, 15020-15025 and Peters et al. Genes Brain Behav. 2009, 8, 320-329.

Long-Evans male rats (each weighting about 330-450 grams) were used for contextual conditioning. Rats were group-housed in standard laboratory and maintained on a 12:12 light-dark cycle. The experiments were always conducted during the light phase of the cycle. Except for testing times, the animals had ad libidum access to food and water. To assess contextual memory, a modified contextual fear conditioning task originally developed for evaluation of memory in CREB knock-out mice was used (Bourtchouladze et al., 1994). Training sessions comprised a baseline period in the conditioning chamber (Med Associates, Inc.) followed by presentation of unconditioned stimuli (1-5 footshocks each at 0.2-1.0 mA for 2-sec) spaced at 60-sec intervals. Thirty seconds following the last shock, the animal was returned to its home cage. One to 7 days later, the animals were returned to the chamber and freezing behavior was scored. Freezing (complete immobility except respiration) was scored by Video Freeze software (Med Associates, Inc.) over an 8 minute test period. Treatment with cognition enhancers is expected to significantly increase freezing when compared to controls.

All experiments were designed and performed in a counterbalanced fashion. In each experiment, the experimenter was unaware (blind) to the treatment of the subjects during training and testing. Training and test sessions were recorded as digital video files. Data were analyzed by one-way ANOVA with appropriate post-hoc tests using GraphPad Prism software package.

Results

Exemplary compounds of Formula (I), are found to enhance contextual memory in the fear conditioning assay. For one or more compounds, significant enhancing effects were seen at several concentrations, including 0.01 mg/kg, 0.03 mg/kg, and 0.3 mg/kg.

Biological Example 2

Effect of GlyT1 Inhibitors on Novel Object Recognition

Rationale

Novel Object Recognition (NOR) is an assay of recognition learning and memory retrieval; it takes advantage of the spontaneous preference of rodents to investigate a novel object compared with a familiar one. It is an ethologically relevant task, which in contrast to fear conditioning, does not result from negative reinforcement (foot shock) (e.g., Ennaceur and Delacour, *Behav. Brain Res.* 1988, 31, 47-59).

The NOR test has been employed extensively to assess the potential cognitive-enhancing properties of novel compounds derived from high-throughput screening. In object recognition, the task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze et. al., *Proc. Natl. Acad. Sci. USA* 2003, 100, 10518-10522).

Neuroimaging, pharmacological, and lesion studies have demonstrated that the hippocampus and adjacent perirhinal cortex are critical for object recognition memory in rodents, monkeys, and humans (e.g., Mitchell, *Behav. Brain Res.* 1998, 97, 107-113; Teng et al., *J. Neurosci.* 2000, 20, 3853-3863; Mumby, *Brain Res.* 2001, 127, 159-181; Eichenbaum et al., *Annu. Rev. Neurosci.* 2007, 30, 127-152; Squire et al., *Nat. Rev. Neurosci.* 2007, 8, 872-883; and Vann and Alabasser, *Curr. Opin. Neurobiol.* 2011, 21, 440-445). Hence, object recognition provides an excellent behavioral model to evaluate drug-compound effects on cognitive tasks associated with function of the hippocampus and cortex.

Procedures

Object recognition was tested in Long-Evans male rats (each weighing about 330-450 grams) using the following protocol. Animals were briefly handled by the experimenter 2-5 days prior to training. Each compound was administered between 15 minutes and 24-hours prior to, or following, training. Habituation sessions (duration 1-20 min, over 1-3 days) were conducted to familiarize the animal to the arena. During training trials (duration of 1-20 min) the animals were allowed to explore two identical objects. A test trial (duration of 1-20 min) was then performed 1-96 h later.

For novel object recognition, one object was replaced with one that is novel. All combinations and locations of objects were used in a balanced manner to reduce potential biases attributable to preference for particular locations or objects. Training and test trials were recorded and scored by video-tracking software (e.g. Noldus Ethovision). An animal was scored as exploring an object when its head was oriented toward the object within a distance of 1-2 cm (rat) or when its nose was touching the object. Turning around, climbing, or sitting on an object was not considered as exploration. If the animal generates a long-term memory for the familiar object, it will spend significantly more time exploring the novel object compared to the familiar object during the retention test (Cognitive enhancers are therefore expected to facilitate this discrimination between the familiar and novel object).

A discrimination index was calculated as previously described (Bourtchouladze et al., *Proc. Natl. Acad. Sci. USA* 2003, 100, 10518-10522). In each experiment, the experimenter was unaware (blind) to the treatment of the subjects during training and testing. Data were analyzed by one-way ANOVA with appropriate post-hoc tests using GraphPad Prism or JMP software package.

Results

Exemplary compounds are tested for enhancement of memory, in the NOR assay. For one or more compounds of Formula (I), significant enhancement effects were seen at 0.03 mg/kg.

The specification, including the examples, is intended to be exemplary only, and it will be apparent to those skilled in the art that various modifications and variations can be made in the present embodiments without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A compound of Formula (I):

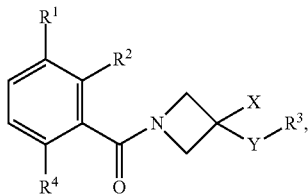

or pharmaceutically acceptable salt thereof,
wherein,
$R^1$ is —SO$_2$(C$_{1-6}$alkyl) or —CN;
$R^2$ is halo or —C$_{1-6}$alkoxy;
X is selected from the group consisting of: —H, —F, and —OH;
Y is a bond;
$R^3$ is phenyl or pyridyl, each unsubstituted or substituted with one, two or three members independently selected from the group consisting of: halo, —C$_{1-6}$alkyl, —C$_{2-6}$alkynyl, —C$_{1-6}$haloalkyl, —C$_{1-6}$alkoxy, —CN, —NO$_2$, -benzoxazolyl, -oxane optionally substituted with one or more —CH$_3$, and —C$_{3-6}$cycloalkyl optionally substituted with one or more —F; and
$R^4$ is a selected from the group consisting of: —OC$_{1-6}$alkyl, —OCH$_2$C$_{3-6}$cycloalkyl, —OC$_{1-6}$haloalkyl, —C$_{3-6}$cycloalkyl, and five or six-membered monocyclic heterocycloalkyl; wherein each said cycloalkyl or heterocycloalkyl is optionally unsubstituted or substituted with one or more —F.

2. The compound of claim 1, wherein $R^1$ is —SO$_2$(C$_{1-4}$alkyl) or —CN.

3. The compound of claim 1, wherein $R^1$ is —SO$_2$CH$_3$, —SO$_2$CH$_2$CH$_3$, or —CN.

4. The compound of claim 1, wherein $R^2$ is —Cl, or —OCH$_3$.

5. The compound of claim 1, wherein X is —H, or —F.

6. The compound of claim 1, wherein X is —H.

7. The compound of claim 1, wherein $R^3$ is phenyl or pyridyl, each unsubstituted or substituted with one, two or three members independently selected from the group consisting of: -halo, —C$_{1-6}$alkyl, —C$_{1-6}$alkynyl, —C$_{1-6}$haloalkyl, —C$_{1-6}$alkoxy, —CN, —NO$_2$, oxan-4-yl, 2,2-dimethyloxan-4-yl, and 4,4-difluorocyclohexyl.

8. The compound of claim 1, wherein each $R^3$ is phenyl or pyridyl, each unsubstituted or substituted with one, two or three members independently selected from the group consisting of: —Cl, —F, —CH$_3$, —CH$_2$CH$_3$, ethynyl, —CHF$_2$, —CF$_3$, —OCH$_3$, —OCH$_2$CH$_3$, —CN, —NO$_2$, oxan-4-yl, 2,2-dimethyloxan-4-yl, and 4,4-difluorocyclohexyl.

9. The compound of claim 1, wherein $R^3$ is 1,3-benzoxazol-6-yl, 2-(trifluoromethyl)phenyl, 2,3,4-trifluorophenyl, 2,3,5-trifluorophenyl, 2,3-difluorophenyl, 2,4,5-trifluorophenyl, 2,5-difluorophenyl, 2-chloro-3-fluorophenyl, 2-chloro-4-(difluoromethyl)phenyl, 2-chloro-4-(trifluoromethyl)phenyl, 2-chloro-4,5-difluorophenyl, 2-chloro-4-cyano-3-ethoxyphenyl, 2-chloro-4-cyano-3-fluorophenyl, 2-chloro-4-cyano-3-methoxyphenyl, 2-chloro-4-cyanophenyl, 2-chloro-4-fluorophenyl, 2-cyano-4-fluorophenyl, 2-cyanophenyl, 2-fluoro-4-(trifluoromethyl)phenyl, 2-fluoro-5-methylphenyl, 2-fluorophenyl, 2-methoxy-4-(trifluoromethyl)phenyl, 2-methyl-4-(trifluoromethyl)phenyl, 3-(trifluoromethyl)phenyl, 3-(trifluoromethyl)phenyl, 3,4,5-trifluorophenyl, 3,4-difluorophenyl, 3,5-difluorophenyl, 3-chloro-2-fluorophenyl, 3-chloro-4-cyanophenyl, 3-fluoro-4-(oxan-4-yl)phenyl, 3-fluoro-4-(trifluoromethyl)phenyl, 3-methoxy-4-(trifluoromethyl)phenyl, 4-(2,2-dimethyloxan-4-yl)phenyl, 4-(4,4-difluorocyclohexyl)phenyl, 4-(difluoromethyl)-2-fluorophenyl, 4-(difluoromethyl)-3-fluorophenyl, 4-(oxan-4-yl)phenyl, 4-(trifluoromethyl)phenyl, 4-chloro-2-cyanophenyl, 4-chlorophenyl, 4-cyano-2-methoxyphenyl, 4-cyano-3-fluorophenyl, 4-cyano-3-methoxyphenyl, 4-cyanophenyl, 4-fluorophenyl, 4-methoxyphenyl, 4-nitrophenyl, 5-chloro-2-fluorophenyl, or phenyl.

10. The compound of claim 1, wherein $R^3$ is 5-difluoropyridin-2-yl, 3-chloro-5-(trifluoromethyl)pyridin-2-yl, 3-chloro-5-cyanopyridin-2-yl, 3-chloropyridin-2-yl, 3-ethyl-5-(trifluoromethyl)pyridin-2-yl, 3-ethynyl-5-(trifluoromethyl)pyridin-2-yl, 3-fluoro-5-(trifluoromethyl)pyridin-2-yl, 3-methoxy-5-(trifluoromethyl)pyridin-2-yl, 3-methyl-5-(trifluoromethyl)pyridin-2-yl, 5-(4,4-difluorocyclohexyl)pyridin-2-yl, 5-(difluoromethyl)pyridin-2-yl, 5-(oxan-4-yl)pyridin-2-yl, 5-(trifluoromethyl)pyridin-2-yl, 5-fluoropyridin-2-yl, 5-methylpyridin-3-yl, 6-(trifluoromethyl)pyridin-3-yl, pyridin-2-yl, pyridin-3-yl, pyridin-4-yl, or 1,3-benzoxazole.

11. The compound of claim 1, wherein $R^4$ is —OC$_{1-6}$alkyl, —OC$_{1-6}$haloalkyl, —C$_{3-6}$cycloalkyl, or 4-fluorooxan-4-yl.

12. The compound of claim 1, wherein $R^4$ is —OCH$_2$CH$_3$, —OCH(CH$_3$)$_2$, —OCH$_2$C(CH$_3$)$_3$, —OCH$_2$cyclopropyl, —OCH(CH$_3$)(CF$_3$), —OCH$_2$CF$_3$, 1-fluorocyclobutyl, 3,3-difluorocyclobutyl, cyclopentyl, 1-fluorocyclopentyl, cyclohexyl, 1,4,4-trifluorocyclohexyl, or 4-fluorooxan-4-yl.

13. The compound of claim 1, wherein $R^4$ is [(2S)-1,1,1-trifluoropropan-2-yl]oxy, or [(2R)-1,1,1-trifluoropropan-2-yl]oxy.

14. The compound of claim 1, wherein $R^1$ is —SO$_2$(C$_{1-6}$alkyl), $R^2$ is —OC$_{1-6}$alkyl, and $R^4$ is —OC$_{1-6}$alkyl or —OC$_{1-6}$haloalkyl.

15. The compound of claim 1, wherein $R^1$ is —SO$_2$(C$_{1-6}$alkyl); $R^3$ is phenyl or pyridyl, each unsubstituted or substituted with one, two or three members independently selected from the group consisting of: halo, —C$_{1-6}$alkyl, —C$_{2-6}$alkynyl, —C$_{1-6}$haloalkyl, —C$_{1-6}$alkoxy, —CN, —NO$_2$, oxan-4-yl, 2,2-dimethyloxan-4-yl, and 4,4-difluorocyclohexyl; and $R^4$ is —OCH$_2$CH$_3$, —OCH(CH$_3$)$_2$, —OCH$_2$C(CH$_3$)$_3$, —OCH$_2$cyclopropyl, —OCH(CH$_3$)(CF$_3$), [(2S)-1,1,1-trifluoropropan-2-yl]oxy, [(2R)-1,1,1-trifluoropropan-2-yl]oxy, or —OCH$_2$CF$_3$.

16. The compound of claim 1, wherein $R^3$ is 2-chloro-4-(difluoromethyl)phenyl, 2-chloro-4-(trifluoromethyl)phenyl, 2-fluoro-4-(trifluoromethyl)phenyl, 4-(oxan-4-yl)phenyl, 4-cyanophenyl, 3-chloro-5-(trifluoromethyl)pyridin-2-yl, 3-fluoro-5-(trifluoromethyl)pyridin-2-yl, or 5-(trifluoromethyl)pyridin-2-yl; and X is —H.

17. A compound selected from the group consisting of:
4-(1-Fluorocyclobutyl)-2-methoxy-3-({3-[4-(trifluoromethyl)phenyl]azetidin-1-yl}carbonyl)benzonitrile;
3-[(3-{Difluoro[4-(trifluoromethyl)phenyl]methyl}azetidin-1-yl)carbonyl]-2-methoxy-4-{[(2S)-1,1,1-trifluoropropan-2-yl]oxy}benzonitrile;
3-({3-[3-Fluoro-5-(trifluoromethyl)pyridin-2-yl]azetidin-1-yl}carbonyl)-2-methoxy-4-{[(2S)-1,1,1-trifluoropropan-2-yl]oxy}benzonitrile;
2-Methoxy-3-({3-[4-(oxan-4-yl)phenyl]azetidin-1-yl}carbonyl)-4-[(1,1,1-trifluoropropan-2-yl)oxy]benzonitrile;

3-({3-[3-Ethynyl-5-(trifluoromethyl)pyridin-2-yl]azetidin-1-yl}carbonyl)-2-methoxy-4-{[(2S)-1,1,1-trifluoropropan-2-yl]oxy}benzonitrile;

3-({3-[3-Ethyl-5-(trifluoromethyl)pyridin-2-yl]azetidin-1-yl}carbonyl)-2-methoxy-4-{[(2S)-1,1,1-trifluoropropan-2-yl]oxy}benzonitrile;

2-Methoxy-3-({3-[3-methoxy-5-(trifluoromethyl)pyridin-2-yl]azetidin-1-yl}carbonyl)-4-{[(2S)-1,1,1-trifluoropropan-2-yl]oxy}benzonitrile;

1-(3-Methanesulfonyl-2-methoxy-6-{[(2S)-1,1,1-trifluoropropan-2-yl]oxy}benzoyl)-3-[3-(trifluoromethyl)phenyl]azetidine 2-Methoxy-3-({3-[3-methyl-5-(trifluoromethyl)pyridin-2-yl]azetidin-1-yl}carbonyl)-4-{[(2S)-1,1,1-trifluoropropan-2-yl]oxy}benzonitrile;

4-Cyclopentyl-2-methoxy-3-{3-[5-(trifluoromethyl)pyridin-2-yl]azetidine-1-carbonyl}benzonitrile;

5-Chloro-6-{1-[(3-cyano-2-methoxy-6-{[(2S)-1,1,1-trifluoropropan-2-yl]oxy}phenyl)carbonyl]azetidin-3-yl}pyridine-3-carbonitrile;

3-(3,4-Difluorophenyl)-1-({3-methanesulfonyl-2-methoxy-6-[(1,1,1-trifluoropropan-2-yl)oxy]phenyl}carbonyl)azetidine;

3-({3-Fluoro-3-[4-(trifluoromethyl)phenyl]azetidin-1-yl}carbonyl)-4-(4-fluorooxan-4-yl)-2-methoxybenzonitrile;

3-{[3-(3,4-Difluorophenyl)-3-fluoroazetidin-1-yl]carbonyl}-4-(4-fluorooxan-4-yl)-2-methoxybenzonitrile;

3-{[3-(3,5-Difluorophenyl)azetidin-1-yl]carbonyl}-4-(4-fluorooxan-4-yl)-2-methoxybenzonitrile;

3-{[3-(4-Chlorophenyl)azetidin-1-yl]carbonyl}-4-(4-fluorooxan-4-yl)-2-methoxybenzonitrile;

3-{[3-(3,4-Difluorophenyl)azetidin-1-yl]carbonyl}-4-(4-fluorooxan-4-yl)-2-methoxybenzonitrile;

4-(4-Fluorooxan-4-yl)-3-{[3-(4-fluorophenyl)azetidin-1-yl]carbonyl}-2-methoxybenzonitrile;

4-(4-Fluorooxan-4-yl)-2-methoxy-3-({3-[3-(trifluoromethyl)phenyl]azetidin-1-yl}carbonyl)benzonitrile;

4-(4-Fluorooxan-4-yl)-2-methoxy-3-({3-[6-(trifluoromethyl)pyridin-3-yl]azetidin-1-yl}carbonyl)benzonitrile;

2-Methoxy-3-({3-[6-(trifluoromethyl)pyridin-3-yl]azetidin-1-yl}carbonyl)-4-{[(2S)-1,1,1-trifluoropropan-2-yl]oxy}benzonitrile;

3-{[3-(4-Chlorophenyl)azetidin-1-yl]carbonyl}-2-methoxy-4-{[(2S)-1,1,1-trifluoropropan-2-yl]oxy}benzonitrile;

2-Methoxy-3-({3-[5-(trifluoromethyl)pyridin-2-yl]azetidin-1-yl}carbonyl)-4-{[(2S)-1,1,1-trifluoropropan-2-yl]oxy}benzonitrile;

2-Methoxy-3-({3-[5-(trifluoromethyl)pyridin-2-yl]azetidin-1-yl}carbonyl)-4-[(1,1,1,1-trifluoropropan-2-yl)oxy]benzonitrile;

3-{[3-(3-Chloropyridin-2-yl)azetidin-1-yl]carbonyl}-2-methoxy-4-{[(2S)-1,1,1-trifluoropropan-2-yl]oxy}benzonitrile;

1-(3-Methanesulfonyl-2-methoxy-6-{[(2S)-1,1,1-trifluoropropan-2-yl]oxy}benzoyl)-3-[2-methyl-4-(trifluoromethyl)phenyl]azetidine;

3-(2,5-Difluorophenyl)-1-(3-methanesulfonyl-2-methoxy-6-{[(2S)-1,1,1-trifluoropropan-2-yl]oxy}benzoyl)azetidine;

3-(2-Fluoro-5-methylphenyl)-1-(3-methanesulfonyl-2-methoxy-6-{[(2S)-1,1,1-trifluoropropan-2-yl]oxy}benzoyl)azetidine;

1-(3-Methanesulfonyl-2-methoxy-6-{[(2S)-1,1,1-trifluoropropan-2-yl]oxy}benzoyl)-3-phenylazetidine;

2-Methoxy-3-(3-phenylazetidine-1-carbonyl)-4-{[(2S)-1,1,1-trifluoropropan-2-yl]oxy}benzonitrile;

3-[3-(3,4-Difluorophenyl)azetidine-1-carbonyl]-2-methoxy-4-{[(2S)-1,1,1-trifluoropropan-2-yl]oxy}benzonitrile;

3-[3-(4-Fluorophenyl)azetidine-1-carbonyl]-2-methoxy-4-{[(2S)-1,1,1-trifluoropropan-2-yl]oxy}benzonitrile;

3-[3-(3,5-Difluorophenyl)azetidine-1-carbonyl]-2-methoxy-4-{[(2S)-1,1,1-trifluoropropan-2-yl]oxy}benzonitrile;

2-Chloro-3-(3-phenylazetidine-1-carbonyl)-4-{[(2S)-1,1,1-trifluoropropan-2-yl]oxy}benzonitrile;

2-Chloro-3-[3-(3,4-difluorophenyl)azetidine-1-carbonyl]-4-{[(2S)-1,1,1-trifluoropropan-2-yl]oxy}benzonitrile;

2-Chloro-3-[3-(4-fluorophenyl)azetidine-1-carbonyl]-4-{[(2S)-1,1,1-trifluoropropan-2-yl]oxy}benzonitrile;

2-Chloro-3-[3-(3,5-difluorophenyl)azetidine-1-carbonyl]-4-{[(2S)-1,1,1-trifluoropropan-2-yl]oxy}benzonitrile;

2-Chloro-3-({3-[4-(trifluoromethyl)phenyl]azetidin-1-yl}carbonyl)-4-[(1,1,1-trifluoropropan-2-yl)oxy]benzonitrile;

3-({3-Hydroxy-3-[4-(trifluoromethyl)phenyl]azetidin-1-yl}carbonyl)-2-methoxy-4-[(1,1,1-trifluoropropan-2-yl)oxy]benzonitrile;

3-{[3-(5-Fluoropyridin-2-yl)azetidin-1-yl]carbonyl}-2-methoxy-4-[(1,1,1-trifluoropropan-2-yl)oxy]benzonitrile;

2-Chloro-3-{[3-(5-fluoropyridin-2-yl)azetidin-1-yl]carbonyl}-4-[(1,1,1-trifluoropropan-2-yl)oxy]benzonitrile;

3-({3-Fluoro-3-[4-(trifluoromethyl)phenyl]azetidin-1-yl}carbonyl)-2-methoxy-4-{[(2S)-1,1,1-trifluoropropan-2-yl]oxy}benzonitrile;

3-{[3-(3,4-Difluorophenyl)-3-fluoroazetidin-1-yl]carbonyl}-2-methoxy-4-{[(2S)-1,1,1-trifluoropropan-2-yl]oxy}benzonitrile;

2-Chloro-3-{[3-(pyridin-3-yl)azetidin-1-yl]carbonyl}-4-[(1,1,1-trifluoropropan-2-yl)oxy]benzonitrile;

2-Chloro-3-{[3-(pyridin-4-yl)azetidin-1-yl]carbonyl}-4-[(1,1,1-trifluoropropan-2-yl)oxy]benzonitrile;

2-Methoxy-3-{[3-(pyridin-4-yl)azetidin-1-yl]carbonyl}-4-[(1,1,1-trifluoropropan-2-yl)oxy]benzonitrile;

2-Chloro-3-{[3-(4-cyanophenyl)azetidin-1-yl]carbonyl}-4-[(1,1,1-trifluoropropan-2-yl)oxy]benzonitrile;

2-Chloro-3-{[3-(4-methoxyphenyl)azetidin-1-yl]carbonyl}-4-[(1,1,1-trifluoropropan-2-yl)oxy]benzonitrile;

2-Chloro-3-{[3-(3,4-difluorophenyl)azetidin-1-yl]carbonyl}-4-[(1,1,1-trifluoropropan-2-yl)oxy]benzonitrile;

2-Chloro-3-{[3-(3,5-difluorophenyl)azetidin-1-yl]carbonyl}-4-[(1,1,1-trifluoropropan-2-yl)oxy]benzonitrile;

2-Chloro-3-{[3-(4-chlorophenyl)azetidin-1-yl]carbonyl}-4-[(1,1,1-trifluoropropan-2-yl)oxy]benzonitrile;

2-Chloro-3-({3-[2-(trifluoromethyl)phenyl]azetidin-1-yl}carbonyl)-4-[(1,1,1-trifluoropropan-2-yl)oxy]benzonitrile;

2-Chloro-3-({3-[3-(trifluoromethyl)phenyl]azetidin-1-yl}carbonyl)-4-[(1,1,1-trifluoropropan-2-yl)oxy]benzonitrile;

2-Chloro-3-{[3-(4-fluorophenyl)azetidin-1-yl]carbonyl}-4-[(1,1,1-trifluoropropan-2-yl)oxy]benzonitrile;

2-Chloro-3-{[3-(2-fluorophenyl)azetidin-1-yl]carbonyl}-4-[(1,1,1-trifluoropropan-2-yl)oxy]benzonitrile;

2-Chloro-3-{[3-(pyridin-2-yl)azetidin-1-yl]carbonyl}-4-[(1,1,1-trifluoropropan-2-yl)oxy]benzonitrile;

2-Methoxy-3-({3-[2-(trifluoromethyl)phenyl]azetidin-1-yl}carbonyl)-4-[(1,1,1-trifluoropropan-2-yl)oxy]benzonitrile;
3-{[3-(4-Fluorophenyl)azetidin-1-yl]carbonyl}-2-methoxy-4-[(1,1,1-trifluoropropan-2-yl)oxy]benzonitrile;
3-{[3-(2-Fluorophenyl)azetidin-1-yl]carbonyl}-2-methoxy-4-[(1,1,1-trifluoropropan-2-yl)oxy]benzonitrile;
2-Methoxy-3-{[3-(pyridin-2-yl)azetidin-1-yl]carbonyl}-4-[(1,1,1-trifluoropropan-2-yl)oxy]benzonitrile;
3-{[3-(4-Cyanophenyl)azetidin-1-yl]carbonyl}-2-methoxy-4-[(1,1,1-trifluoropropan-2-yl)oxy]benzonitrile;
2-Methoxy-3-{[3-(4-methoxyphenyl)azetidin-1-yl]carbonyl}-4-[(1,1,1-trifluoropropan-2-yl)oxy]benzonitrile;
3-{[3-(4-Chlorophenyl)azetidin-1-yl]carbonyl}-2-methoxy-4-[(1,1,1-trifluoropropan-2-yl)oxy]benzonitrile;
2-Methoxy-3-({3-[4-(trifluoromethyl)phenyl]azetidin-1-yl}carbonyl)-4-[(1,1,1-trifluoropropan-2-yl)oxy]benzonitrile;
2-Methoxy-3-({3-[3-(trifluoromethyl)phenyl]azetidin-1-yl}carbonyl)-4-[(1,1,1-trifluoropropan-2-yl)oxy]benzonitrile;
3-{[3-(3,5-Difluorophenyl)azetidin-1-yl]carbonyl}-2-methoxy-4-[(1,1,1-trifluoropropan-2-yl)oxy]benzonitrile;
3-{[3-(3,4-Difluorophenyl)azetidin-1-yl]carbonyl}-2-methoxy-4-[(1,1,1-trifluoropropan-2-yl)oxy]benzonitrile;
3-{[3-(4-Cyanophenyl)azetidin-1-yl]carbonyl}-4-(1-fluorocyclobutyl)-2-methoxybenzonitrile;
2-Chloro-4-(2,2,2-trifluoroethoxy)-3-({3-[4-(trifluoromethyl)phenyl]azetidin-1-yl}carbonyl)benzonitrile;
2-Chloro-3-{[3-(4-cyanophenyl)azetidin-1-yl]carbonyl}-4-(2,2,2-trifluoroethoxy)benzonitrile;
2-Chloro-3-({3-[4-(trifluoromethyl)phenyl]azetidin-1-yl}carbonyl)-4-{[(2S)-1,1,1-trifluoropropan-2-yl]oxy}benzonitrile;
3-{[3-(4-Cyanophenyl)azetidin-1-yl]carbonyl}-2-methoxy-4-{[(2S)-1,1,1-trifluoropropan-2-yl]oxy}benzonitrile;
2-Chloro-3-{[3-(4-cyanophenyl)azetidin-1-yl]carbonyl}-4-{[(2S)-1,1,1-trifluoropropan-2-yl]oxy}benzonitrile;
2-Chloro-3-{[3-(5-methylpyridin-3-yl)azetidin-1-yl]carbonyl}-4-[(1,1,1-trifluoropropan-2-yl)oxy]benzonitrile;
2-Methoxy-3-{[3-(5-methylpyridin-3-yl)azetidin-1-yl]carbonyl}-4-[(1,1,1-trifluoropropan-2-yl)oxy]benzonitrile;
2-Chloro-3-({3-[6-(trifluoromethyl)pyridin-3-yl]azetidin-1-yl}carbonyl)-4-[(1,1,1,1-trifluoropropan-2-yl)oxy]benzonitrile;
2-Methoxy-3-({3-[6-(trifluoromethyl)pyridin-3-yl]azetidin-1-yl}carbonyl)-4-[(1,1,1,1-trifluoropropan-2-yl)oxy]benzonitrile;
3-({3-[3-Chloro-5-(trifluoromethyl)pyridin-2-yl]azetidin-1-yl}carbonyl)-2-methoxy-4-{[(2S)-1,1,1-trifluoropropan-2-yl]oxy}benzonitrile;
3-({3-[5-(Difluoromethyl)pyridin-2-yl]azetidin-1-yl}carbonyl)-2-methoxy-4-{[(2S)-1,1,1-trifluoropropan-2-yl]oxy}benzonitrile;
3-{[3-(4-Cyano-3-fluorophenyl)azetidin-1-yl]carbonyl}-2-methoxy-4-{[(2S)-1,1,1-trifluoropropan-2-yl]oxy}benzonitrile;
3-({3-[3-Chloro-5-(trifluoromethyl)pyridin-2-yl]azetidin-1-yl}carbonyl)-4-(4-fluorooxan-4-yl)-2-methoxybenzonitrile;
3-{[3-(2-Chloro-4-cyanophenyl)azetidin-1-yl]carbonyl}-2-methoxy-4-{[(2S)-1,1,1-trifluoropropan-2-yl]oxy}benzonitrile;
3-({3-[3-Chloro-5-(trifluoromethyl)pyridin-2-yl]azetidin-1-yl}carbonyl)-2-methoxy-4-(2,2,2-trifluoroethoxy)benzonitrile;
2-Chloro-3-({3-[5-(trifluoromethyl)pyridin-2-yl]azetidin-1-yl}carbonyl)-4-{[(2S)-1,1,1-trifluoropropan-2-yl]oxy}benzonitrile;
3-{[3-(3,5-Difluoropyridin-2-yl)azetidin-1-yl]carbonyl}-2-methoxy-4-{[(2S)-1,1,1-trifluoropropan-2-yl]oxy}benzonitrile;
3-{[3-(3-Chloro-4-cyanophenyl)azetidin-1-yl]carbonyl}-2-methoxy-4-{[(2S)-1,1,1-trifluoropropan-2-yl]oxy}benzonitrile;
3-{[3-(2-Cyanophenyl)azetidin-1-yl]carbonyl}-2-methoxy-4-{[(2S)-1,1,1-trifluoropropan-2-yl]oxy}benzonitrile;
3-Chloro-4-{1-[(3-cyano-2-methoxy-6-{[(2S)-1,1,1-trifluoropropan-2-yl]oxy}phenyl)carbonyl]azetidin-3-yl}-2-fluorobenzonitrile;
2-Methoxy-4-(2,2,2-trifluoroethoxy)-3-({3-[5-(trifluoromethyl)pyridin-2-yl]azetidin-1-yl}carbonyl)benzonitrile;
3-{[3-(4-Chloro-2-cyanophenyl)azetidin-1-yl]carbonyl}-2-methoxy-4-{[(2S)-1,1,1-trifluoropropan-2-yl]oxy}benzonitrile;
3-{[3-(2-Cyano-4-fluorophenyl)azetidin-1-yl]carbonyl}-2-methoxy-4-{[(2S)-1,1,1-trifluoropropan-2-yl]oxy}benzonitrile;
3-{[3-(4-Cyano-2-methoxyphenyl)azetidin-1-yl]carbonyl}-2-methoxy-4-{[(2S)-1,1,1-trifluoropropan-2-yl]oxy}benzonitrile;
2-Methoxy-3-({3-[2-methoxy-4-(trifluoromethyl)phenyl]azetidin-1-yl}carbonyl)-4-{[(2S)-1,1,1-trifluoropropan-2-yl]oxy}benzonitrile;
3-{[3-(1,3-Benzoxazol-6-yl)azetidin-1-yl]carbonyl}-2-methoxy-4-{[(2S)-1,1,1-trifluoropropan-2-yl]oxy}benzonitrile;
2-Chloro-3-{[3-(2-chloro-4-cyanophenyl)azetidin-1-yl]carbonyl}-4-{[(2S)-1,1,1-trifluoropropan-2-yl]oxy}benzonitrile;
3-{[3-(2-Chloro-4-cyanophenyl)azetidin-1-yl]carbonyl}-4-(4-fluorooxan-4-yl)-2-methoxybenzonitrile;
3-{[3-(2-Chloro-4-cyanophenyl)azetidin-1-yl]carbonyl}-2-methoxy-4-(1,4,4-trifluorocyclohexyl)benzonitrile;
3-{[3-(2-Chloro-4-cyanophenyl)azetidin-1-yl]carbonyl}-4-(1-fluorocyclobutyl)-2-methoxybenzonitrile;
2-Methoxy-3-{3-[5-(trifluoromethyl)pyridin-2-yl]azetidine-1-carbonyl}-4-{[(2R)-1,1,1-trifluoropropan-2-yl]oxy}benzonitrile;
3-{3-[3-Chloro-5-(trifluoromethyl)pyridin-2-yl]azetidine-1-carbonyl}-2-methoxy-4-{[(2R)-1,1,1-trifluoropropan-2-yl]oxy}benzonitrile;
3-{3-[5-(Difluoromethyl)pyridin-2-yl]azetidine-1-carbonyl}-2-methoxy-4-{[(2R)-1,1,1-trifluoropropan-2-yl]oxy}benzonitrile;
3-[2-Fluoro-4-(trifluoromethyl)phenyl]-1-(3-methanesulfonyl-2-methoxy-6-{[(2R)-1,1,1-trifluoropropan-2-yl]oxy}benzoyl)azetidine;
3-[2-Fluoro-4-(trifluoromethyl)phenyl]-1-(3-methanesulfonyl-2-methoxy-6-{[(2S)-1,1,1-trifluoropropan-2-yl]oxy}benzoyl)azetidine;

3-[3-Fluoro-4-(trifluoromethyl)phenyl]-1-(3-methanesulfonyl-2-methoxy-6-{[(2R)-1,1,1-trifluoropropan-2-yl]oxy}benzoyl)azetidine;

3-[3-Fluoro-4-(trifluoromethyl)phenyl]-1-(3-methanesulfonyl-2-methoxy-6-{[(2S)-1,1,1-trifluoropropan-2-yl]oxy}benzoyl)azetidine;

3-[4-(Difluoromethyl)-3-fluorophenyl]-1-(3-methanesulfonyl-2-methoxy-6-{[(2S)-1,1,1-trifluoropropan-2-yl]oxy}benzoyl)azetidine;

3-[4-(Difluoromethyl)-2-fluorophenyl]-1-(3-methanesulfonyl-2-methoxy-6-{[(2S)-1,1,1-trifluoropropan-2-yl]oxy}benzoyl)azetidine;

1-(3-Methanesulfonyl-2-methoxy-6-{[(2S)-1,1,1-trifluoropropan-2-yl]oxy}benzoyl)-3-[3-methoxy-4-(trifluoromethyl)phenyl]azetidine;

3-(2-Chloro-4-fluorophenyl)-1-(3-methanesulfonyl-2-methoxy-6-{[(2S)-1,1,1-trifluoropropan-2-yl]oxy}benzoyl)azetidine;

3-[2-Chloro-4-(trifluoromethyl)phenyl]-1-(3-methanesulfonyl-2-methoxy-6-{[(2S)-1,1,1-trifluoropropan-2-yl]oxy}benzoyl)azetidine;

3-[2-Chloro-4-(difluoromethyl)phenyl]-1-(3-methanesulfonyl-2-methoxy-6-{[(2S)-1,1,1-trifluoropropan-2-yl]oxy}benzoyl)azetidine;

1-(3-Methanesulfonyl-2-methoxy-6-{[(2S)-1,1,1-trifluoropropan-2-yl]oxy}benzoyl)-3-(4-nitrophenyl)azetidine;

1-(3-Methanesulfonyl-2-methoxy-6-{[(2S)-1,1,1-trifluoropropan-2-yl]oxy}benzoyl)-3-(3,4,5-trifluorophenyl)azetidine;

4-(3,3-Difluorocyclobutyl)-2-methoxy-3-{3-[5-(trifluoromethyl)pyridin-2-yl]azetidine-1-carbonyl}benzonitrile;

3-{3-[3-Chloro-5-(trifluoromethyl)pyridin-2-yl]azetidine-1-carbonyl}-4-(3,3-difluorocyclobutyl)-2-methoxybenzonitrile;

4-(3,3-Difluorocyclobutyl)-3-{3-[3-fluoro-5-(trifluoromethyl)pyridin-2-yl]azetidine-1-carbonyl}-2-methoxybenzonitrile;

1-(3-Methanesulfonyl-2-methoxy-6-{[(2S)-1,1,1-trifluoropropan-2-yl]oxy}benzoyl)-3-(2,4,5-trifluorophenyl)azetidine;

1-(3-Methanesulfonyl-2-methoxy-6-{[(2S)-1,1,1-trifluoropropan-2-yl]oxy}benzoyl)-3-(2,3,4-trifluorophenyl)azetidine;

1-(3-Methanesulfonyl-2-methoxy-6-{[(2S)-1,1,1-trifluoropropan-2-yl]oxy}benzoyl)-3-(2,3,5-trifluorophenyl)azetidine;

3-(2,3-Difluorophenyl)-1-(3-methanesulfonyl-2-methoxy-6-{[(2S)-1,1,1-trifluoropropan-2-yl]oxy}benzoyl)azetidine;

2-Methoxy-3-{3-[4-(oxan-4-yl)phenyl]azetidine-1-carbonyl}-4-{[(2S)-1,1,1-trifluoropropan-2-yl]oxy}benzonitrile;

2-Methoxy-3-{3-[5-(oxan-4-yl)pyridin-2-yl]azetidine-1-carbonyl}-4-{[(2S)-1,1,1-trifluoropropan-2-yl]oxy}benzonitrile;

3-{3-[4-(2,2-Dimethyloxan-4-yl)phenyl]azetidine-1-carbonyl}-2-methoxy-4-{[(2S)-1,1,1-trifluoropropan-2-yl]oxy}benzonitrile;

2-Methoxy-3-{3-[4-(oxan-4-yl)phenyl]azetidine-1-carbonyl}-4-{[(2R)-1,1,1-trifluoropropan-2-yl]oxy}benzonitrile;

4-(1-Fluorocyclobutyl)-2-methoxy-3-{3-[5-(oxan-4-yl)pyridin-2-yl]azetidine-1-carbonyl}benzonitrile;

3-{3-[3-Fluoro-4-(oxan-4-yl)phenyl]azetidine-1-carbonyl}-2-methoxy-4-{[(2S)-1,1,1-trifluoropropan-2-yl]oxy}benzonitrile;

1-(3-Methanesulfonyl-2-methoxy-6-{[(2R)-1,1,1-trifluoropropan-2-yl]oxy}benzoyl)-3-[4-(oxan-4-yl)phenyl]azetidine;

2-Chloro-3-{3-[5-(oxan-4-yl)pyridin-2-yl]azetidine-1-carbonyl}-4-{[(2S)-1,1,1-trifluoropropan-2-yl]oxy}benzonitrile;

2-Chloro-3-{3-[5-(oxan-4-yl)pyridin-2-yl]azetidine-1-carbonyl}-4-{[(2R)-1,1,1-trifluoropropan-2-yl]oxy}benzonitrile;

4-Ethoxy-2-methoxy-3-{3-[5-(oxan-4-yl)pyridin-2-yl]azetidine-1-carbonyl}benzonitrile;

2-Methoxy-3-{3-[5-(oxan-4-yl)pyridin-2-yl]azetidine-1-carbonyl}-4-(propan-2-yloxy)benzonitrile;

3-[4-(4,4-Difluorocyclohexyl)phenyl]-1-(3-methanesulfonyl-2-methoxy-6-{[(2R)-1,1,1-trifluoropropan-2-yl]oxy}benzoyl)azetidine;

3-{3-[5-(4,4-Difluorocyclohexyl)pyridin-2-yl]azetidine-1-carbonyl}-2-methoxy-4-{[(2S)-1,1,1-trifluoropropan-2-yl]oxy}benzonitrile;

3-{3-[5-(4,4-Difluorocyclohexyl)pyridin-2-yl]azetidine-1-carbonyl}-2-methoxy-4-{[(2R)-1,1,1-trifluoropropan-2-yl]oxy}benzonitrile;

1-(3-Methanesulfonyl-2-methoxy-6-{[(2S)-1,1,1-trifluoropropan-2-yl]oxy}benzoyl)-3-[4-(oxan-4-yl)phenyl]azetidine;

3-{[3-(4-Cyanophenyl)azetidin-1-yl]carbonyl}-4-(cyclopropylmethoxy)-2-methoxybenzonitrile;

3-{[3-(4-Cyano-3-methoxyphenyl)azetidin-1-yl]carbonyl}-2-methoxy-4-{[(2S)-1,1,1-trifluoropropan-2-yl]oxy}benzonitrile;

3-Chloro-4-{1-[(3-cyano-2-methoxy-6-{[(2S)-1,1,1-trifluoropropan-2-yl]oxy}phenyl)carbonyl]azetidin-3-yl}-2-methoxybenzonitrile;

3-Chloro-4-[1-(3-cyano-2-methoxy-6-{[(2S)-1,1,1-trifluoropropan-2-yl]oxy}benzoyl)azetidin-3-yl]-2-ethoxybenzonitrile;

3-[3-(4-Cyano-3-methoxyphenyl)azetidine-1-carbonyl]-2-methoxy-4-{[(2R)-1,1,1-trifluoropropan-2-yl]oxy}benzonitrile;

2-Methoxy-3-({3-[4-(trifluoromethyl)phenyl]azetidin-1-yl}carbonyl)-4-{[(2S)-1,1,1-trifluoropropan-2-yl]oxy}benzonitrile;

1-({3-Methanesulfonyl-2-methoxy-6-[(1,1,1-trifluoropropan-2-yl)oxy]phenyl}carbonyl)-3-[4-(trifluoromethyl)phenyl]azetidine;

3-(3,5-Difluorophenyl)-1-({3-methanesulfonyl-2-methoxy-6-[(1,1,1-trifluoropropan-2-yl)oxy]phenyl}carbonyl)azetidine;

1-(3-Methanesulfonyl-2-methoxy-6-{[(2R)-1,1,1-trifluoropropan-2-yl]oxy}benzoyl)-3-[4-(trifluoromethyl)phenyl]azetidine;

2-[1-(3-Methanesulfonyl-2-methoxy-6-{[(2R)-1,1,1-trifluoropropan-2-yl]oxy}benzoyl)azetidin-3-yl]-5-(trifluoromethyl)pyridine 5-(Difluoromethyl)-2-[1-(3-methanesulfonyl-2-methoxy-6-{[(2R)-1,1,1-trifluoropropan-2-yl]oxy}benzoyl)azetidin-3-yl]pyridine;

3-Chloro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine;

1-(3-Methanesulfonyl-2-methoxy-6-{[(2S)-1,1,1-trifluoropropan-2-yl]oxy}benzoyl)-3-[4-(trifluoromethyl)phenyl]azetidine;

3-Fluoro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine;
3-Chloro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine;
3-Ethynyl-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine;
4-(1-Fluorocyclopentyl)-2-methoxy-3-{3-[5-(trifluoromethyl)pyridin-2-yl]azetidine-1-carbonyl}benzonitrile;
3-(3,5-Difluorophenyl)-1-(3-methanesulfonyl-2-methoxy-6-{[(2S)-1,1,1-trifluoropropan-2-yl]oxy}benzoyl)azetidine;
4-(1-Fluorocyclopentyl)-2-methoxy-3-{3-[4-(trifluoromethyl)phenyl]azetidine-1-carbonyl}benzonitrile;
3-(3,4-Difluorophenyl)-1-(3-methanesulfonyl-2-methoxy-6-{[(2S)-1,1,1-trifluoropropan-2-yl]oxy}benzoyl)azetidine;
1-(3-Methanesulfonyl-2-methoxy-6-{[(2S)-1,1,1-trifluoropropan-2-yl]oxy}benzoyl)-3-[2-(trifluoromethyl)phenyl]azetidine;
4-(4-Fluorooxan-4-yl)-2-methoxy-3-({3-[4-(trifluoromethyl)phenyl]azetidin-1-yl}carbonyl)benzonitrile;
3-{3-[3-Chloro-5-(trifluoromethyl)pyridin-2-yl]azetidine-1-carbonyl}-4-cyclopentyl-2-methoxybenzonitrile;
4-Cyclopentyl-3-{3-[3-fluoro-5-(trifluoromethyl)pyridin-2-yl]azetidine-1-carbonyl}-2-methoxybenzonitrile;
2-{1-[3-Methanesulfonyl-2-methoxy-6-(propan-2-yloxy)benzoyl]azetidin-3-yl}-5-(trifluoromethyl)pyridine;
3-Chloro-2-{1-[3-methanesulfonyl-2-methoxy-6-(propan-2-yloxy)benzoyl]azetidin-3-yl}-5-(trifluoromethyl)pyridine;
3-Fluoro-2-{1-[3-methanesulfonyl-2-methoxy-6-(propan-2-yloxy)benzoyl]azetidin-3-yl}-5-(trifluoromethyl)pyridine;
3-(3,4-Difluorophenyl)-1-[3-methanesulfonyl-2-methoxy-6-(propan-2-yloxy)benzoyl]azetidine
1-[3-Methanesulfonyl-2-methoxy-6-(propan-2-yloxy)benzoyl]-3-[4-(trifluoromethyl)phenyl]azetidine;
3-(3,4-Difluorophenyl)-1-[3-methanesulfonyl-2-methoxy-6-(2,2,2-trifluoroethoxy)benzoyl]azetidine;
2-{1-[3-Methanesulfonyl-2-methoxy-6-(2,2,2-trifluoroethoxy)benzoyl]azetidin-3-yl}-5-(trifluoromethyl)pyridine
3-Chloro-2-{1-[3-methanesulfonyl-2-methoxy-6-(2,2,2-trifluoroethoxy)benzoyl]azetidin-3-yl}-5-(trifluoromethyl)pyridine;
3-Fluoro-2-{1-[3-methanesulfonyl-2-methoxy-6-(2,2,2-trifluoroethoxy)benzoyl]azetidin-3-yl}-5-(trifluoromethyl)pyridine;
3-Chloro-2-[1-(3-methanesulfonyl-2-methoxy-6-{[(2S)-1,1,1-trifluoropropan-2-yl]oxy}benzoyl)azetidin-3-yl]pyridine
1-[3-Methanesulfonyl-2-methoxy-6-(2,2,2-trifluoroethoxy)benzoyl]-3-[4-(trifluoromethyl)phenyl]azetidine;
3-Chloro-4-[1-(3-methanesulfonyl-2-methoxy-6-{[(2S)-1,1,1-trifluoropropan-2-yl]oxy}benzoyl)azetidin-3-yl]benzonitrile;
3-Chloro-4-{1-[3-methanesulfonyl-2-methoxy-6-(2,2,2-trifluoroethoxy)benzoyl]azetidin-3-yl}benzonitrile;
1-[6-(2,2-Dimethylpropoxy)-3-methanesulfonyl-2-methoxybenzoyl]-3-[4-(trifluoromethyl)phenyl]azetidine;
3-Chloro-2-{1-[6-(2,2-dimethylpropoxy)-3-methanesulfonyl-2-methoxybenzoyl]azetidin-3-yl}-5-(trifluoromethyl)pyridine;
1-[3-(Ethanesulfonyl)-2-methoxy-6-(propan-2-yloxy)benzoyl]-3-[4-(trifluoromethyl)phenyl]azetidine
3-Chloro-2-{1-[3-(ethanesulfonyl)-2-methoxy-6-(propan-2-yloxy)benzoyl]azetidin-3-yl}-5-(trifluoromethyl)pyridine
6-[1-(3-Methanesulfonyl-2-methoxy-6-{[(2S)-1,1,1-trifluoropropan-2-yl]oxy}benzoyl)azetidin-3-yl]-1,3-benzoxazole;
6-{1-[3-Methanesulfonyl-2-methoxy-6-(2,2,2-trifluoroethoxy)benzoyl]azetidin-3-yl}-1,3-benzoxazole;
6-{1-[3-Methanesulfonyl-2-methoxy-6-(propan-2-yloxy)benzoyl]azetidin-3-yl}-1,3-benzoxazole;
6-{1-[6-(2,2-Dimethylpropoxy)-3-methanesulfonyl-2-methoxybenzoyl]azetidin-3-yl}-1,3-benzoxazole;
6-{1-[3-(Ethanesulfonyl)-2-methoxy-6-(propan-2-yloxy)benzoyl]azetidin-3-yl}-1,3-benzoxazole;
3-(5-Chloro-2-fluorophenyl)-1-(3-methanesulfonyl-2-methoxy-6-{[(2S)-1,1,1-trifluoropropan-2-yl]oxy}benzoyl)azetidine;
3-(3-Chloro-2-fluorophenyl)-1-(3-methanesulfonyl-2-methoxy-6-{[(2S)-1,1,1-trifluoropropan-2-yl]oxy}benzoyl)azetidine;
3-(2-Chloro-3-fluorophenyl)-1-(3-methanesulfonyl-2-methoxy-6-{[(2S)-1,1,1-trifluoropropan-2-yl]oxy}benzoyl)azetidine;
3-(2-Chloro-4,5-difluorophenyl)-1-(3-methanesulfonyl-2-methoxy-6-{[(2S)-1,1,1-trifluoropropan-2-yl]oxy}benzoyl)azetidine;
3-Chloro-2-(1-{3-methanesulfonyl-2-methoxy-6-[(1,1,1-trifluoropropan-2-yl)oxy]benzoyl}azetidin-3-yl)-5-(trifluoromethyl)pyridine;
2-Methoxy-3-({3-[4-(trifluoromethyl)phenyl]azetidin-1-yl}carbonyl)-4-{[(2R)-1,1,1-trifluoropropan-2-yl]oxy}benzonitrile;
and pharmaceutically acceptable salt thereof.
18. A compound selected from the group consisting of:
4-(4-Fluorooxan-4-yl)-2-methoxy-3-[(3-{[5-(trifluoromethyl)pyridin-2-yl]amino}azetidin-1-yl)carbonyl]benzonitrile;
2-Methoxy-3-[(3-{[5-(trifluoromethyl)pyridin-2-yl]amino}azetidin-1-yl)carbonyl]-4-{[(2S)-1,1,1-trifluoropropan-2-yl]oxy}benzonitrile;
4-(1-Fluorocyclobutyl)-2-methoxy-3-({3-[4-(trifluoromethyl)phenyl]azetidin-1-yl}carbonyl)benzonitrile;
3-[(3-{Difluoro[4-(trifluoromethyl)phenyl]methyl}azetidin-1-yl)carbonyl]-2-methoxy-4-{[(2S)-1,1,1-trifluoropropan-2-yl]oxy}benzonitrile;
3-({3-[3-Fluoro-5-(trifluoromethyl)pyridin-2-yl]azetidin-1-yl}carbonyl)-2-methoxy-4-{[(2S)-1,1,1-trifluoropropan-2-yl]oxy}benzonitrile;
2-Methoxy-3-({3-[4-(oxan-4-yl)phenyl]azetidin-1-yl}carbonyl)-4-[(1,1,1-trifluoropropan-2-yl)oxy]benzonitrile;
3-({3-[3-Ethynyl-5-(trifluoromethyl)pyridin-2-yl]azetidin--yl}carbonyl)-2-methoxy-4-{[(2S)-1,1,1-trifluoropropan-2-yl]oxy}benzonitrile;
3-({3-[3-Ethyl-5-(trifluoromethyl)pyridin-2-yl]azetidin-1-yl}carbonyl)-2-methoxy-4-{[(2S)-1,1,1-trifluoropropan-2-yl]oxy}benzonitrile;
2-Methoxy-3-({3-[3-methoxy-5-(trifluoromethyl)pyridin-2-yl]azetidin-1-yl}carbonyl)-4-{[(2S)-1,1,1-trifluoropropan-2-yl]oxy}benzonitrile;

1-(3-Methanesulfonyl-2-methoxy-6-{[(2S)-1,1,1-trifluoropropan-2-yl]oxy}benzoyl)-3-[3-(trifluoromethyl)phenyl]azetidine;
2-Methoxy-3-({3-[3-methyl-5-(trifluoromethyl)pyridin-2-yl]azetidin-1-yl}carbonyl)-4-{[(2S)-1,1,1-trifluoropropan-2-yl]oxy}benzonitrile;
4-Cyclopentyl-2-methoxy-3-{3-[5-(trifluoromethyl)pyridin-2-yl]azetidine-1-carbonyl}benzonitrile;
5-Chloro-6-{1-[(3-cyano-2-methoxy-6-{[(2S)-1,1,1-trifluoropropan-2-yl]oxy}phenyl)carbonyl]azetidin-3-yl}pyridine-3-carbonitrile;
3-[(3-{[3-Fluoro-5-(trifluoromethyl)pyridin-2-yl]amino}azetidin-1-yl)carbonyl]-2-methoxy-4-{[(2S)-1,1,1-trifluoropropan-2-yl]oxy}benzonitrile;
3-(3,4-Difluorophenyl)-1-({3-methanesulfonyl-2-methoxy-6-[(1,1,1-trifluoropropan-2-yl)oxy]phenyl}carbonyl)azetidine;
3-(4-Fluorophenoxy)-1-({3-methanesulfonyl-2-methoxy-6-[(1,1,1-trifluoropropan-2-yl)oxy]phenyl}carbonyl)azetidine;
3-({3-Fluoro-3-[4-(trifluoromethyl)phenyl]azetidin-1-yl}carbonyl)-4-(4-fluorooxan-4-yl)-2-methoxybenzonitrile;
3-{[3-(3,4-Difluorophenyl)-3-fluoroazetidin-1-yl]carbonyl}-4-(4-fluorooxan-4-yl)-2-methoxybenzonitrile;
3-{[3-(3,5-Difluorophenyl)azetidin-1-yl]carbonyl}-4-(4-fluorooxan-4-yl)-2-methoxybenzonitrile;
3-{[3-(4-Chlorophenyl)azetidin-1-yl]carbonyl}-4-(4-fluorooxan-4-yl)-2-methoxybenzonitrile;
3-{[3-(3,4-Difluorophenyl)azetidin-1-yl]carbonyl}-4-(4-fluorooxan-4-yl)-2-methoxybenzonitrile;
4-(4-Fluorooxan-4-yl)-3-{[3-(4-fluorophenyl)azetidin-1-yl]carbonyl}-2-methoxybenzonitrile;
4-(4-Fluorooxan-4-yl)-2-methoxy-3-({3-[3-(trifluoromethyl)phenyl]azetidin-1-yl}carbonyl)benzonitrile;
4-(4-Fluorooxan-4-yl)-2-methoxy-3-({3-[4-(trifluoromethyl)phenoxy]azetidin-1-yl}carbonyl)benzonitrile;
3-{[3-(3,4-Difluorophenoxy)azetidin-1-yl]carbonyl}-4-(4-fluorooxan-4-yl)-2-methoxybenzonitrile;
4-(4-Fluorooxan-4-yl)-3-{[3-(4-fluorophenoxy)azetidin-1-yl]carbonyl}-2-methoxybenzonitrile;
4-(4-Fluorooxan-4-yl)-2-methoxy-3-({3-[6-(trifluoromethyl)pyridin-3-yl]azetidin-1-yl}carbonyl)benzonitrile;
3-{[3-(4-Chlorophenoxy)azetidin-1-yl]carbonyl}-4-(4-fluorooxan-4-yl)-2-methoxybenzonitrile;
3-{[3-(4-Chlorophenoxy)azetidin-1-yl]carbonyl}-2-methoxy-4-{[(2S)-1,1,1-trifluoropropan-2-yl]oxy}benzonitrile;
2-Methoxy-3-({3-[4-(trifluoromethyl)phenoxy]azetidin-1-yl}carbonyl)-4-{[(2S)-1,1,1-trifluoropropan-2-yl]oxy}benzonitrile;
2-Methoxy-3-({3-[6-(trifluoromethyl)pyridin-3-yl]azetidin-1-yl}carbonyl)-4-{[(2S)-1,1,1-trifluoropropan-2-yl]oxy}benzonitrile;
3-{[3-(4-Chlorophenyl)azetidin-1-yl]carbonyl}-2-methoxy-4-{[(2S)-1,1,1-trifluoropropan-2-yl]oxy}benzonitrile;
3-{[3-(4-Fluorophenoxy)azetidin-1-yl]carbonyl}-2-methoxy-4-{[(2S)-1,1,1-trifluoropropan-2-yl]oxy}benzonitrile;
2-Methoxy-3-({3-[5-(trifluoromethyl)pyridin-2-yl]azetidin-1-yl}carbonyl)-4-{[(2S)-1,1,1-trifluoropropan-2-yl]oxy}benzonitrile;
2-Methoxy-3-{[3-(pyridin-4-yloxy)azetidin-1-yl]carbonyl}-4-{[(2S)-1,1,1-trifluoropropan-2-yl]oxy}benzonitrile;
2-Methoxy-3-({3-[5-(trifluoromethyl)pyridin-2-yl]azetidin-1-yl}carbonyl)-4-[(1,1,1-trifluoropropan-2-yl)oxy]benzonitrile;
3-({3-[(4-Fluorophenyl)methyl]azetidin-1-yl}carbonyl)-2-methoxy-4-{[(2S)-1,1,1-trifluoropropan-2-yl]oxy}benzonitrile;
3-{[3-(3-Chloropyridin-2-yl)azetidin-1-yl]carbonyl}-2-methoxy-4-{[(2S)-1,1,1-trifluoropropan-2-yl]oxy}benzonitrile;
3-[(4-Fluorophenyl)methyl]-1-(3-methanesulfonyl-2-methoxy-6-{[(2R)-1,1,1-trifluoropropan-2-yl]oxy}benzoyl)azetidine;
1-(3-Methanesulfonyl-2-methoxy-6-{[(2S)-1,1,1-trifluoropropan-2-yl]oxy}benzoyl)-3-[2-methyl-4-(trifluoromethyl)phenyl]azetidine;
3-(2,5-Difluorophenyl)-1-(3-methanesulfonyl-2-methoxy-6-{[(2S)-1,1,1-trifluoropropan-2-yl]oxy}benzoyl)azetidine;
3-(2-Fluoro-5-methylphenyl)-1-(3-methanesulfonyl-2-methoxy-6-{[(2S)-1,1,1-trifluoropropan-2-yl]oxy}benzoyl)azetidine;
3-(4-Fluoro-3-methylphenoxy)-1-(3-methanesulfonyl-2-methoxy-6-{[(2S)-1,1,1-trifluoropropan-2-yl]oxy}benzoyl)azetidine;
1-(3-Methanesulfonyl-2-methoxy-6-{[(2S)-1,1,1-trifluoropropan-2-yl]oxy}benzoyl)-3-[3-(trifluoromethyl)phenoxy]azetidine;
3-(2,6-Dimethylphenoxy)-1-(3-methanesulfonyl-2-methoxy-6-{[(2S)-1,1,1-trifluoropropan-2-yl]oxy}benzoyl)azetidine;
3-(2-Chlorophenoxy)-1-(3-methanesulfonyl-2-methoxy-6-{[(2S)-1,1,1-trifluoropropan-2-yl]oxy}benzoyl)azetidine;
1-(3-Methanesulfonyl-2-methoxy-6-{[(2S)-1,1,1-trifluoropropan-2-yl]oxy}benzoyl)-3-(3-methylphenoxy)azetidine;
1-(3-Methanesulfonyl-2-methoxy-6-{[(2S)-1,1,1-trifluoropropan-2-yl]oxy}benzoyl)-3-(2-methylphenoxy)azetidine;
1-(3-Methanesulfonyl-2-methoxy-6-{[(2S)-1,1,1-trifluoropropan-2-yl]oxy}benzoyl)-3-phenylazetidine;
2-Methoxy-3-(3-phenylazetidine-1-carbonyl)-4-{[(2S)-1,1,1-trifluoropropan-2-yl]oxy}benzonitrile;
3-[3-(3,4-Difluorophenyl)azetidine-1-carbonyl]-2-methoxy-4-{[(2S)-1,1,1-trifluoropropan-2-yl]oxy}benzonitrile;
3-[3-(4-Fluorophenyl)azetidine-1-carbonyl]-2-methoxy-4-{[(2S)-1,1,1-trifluoropropan-2-yl]oxy}benzonitrile;
3-[3-(3,5-Difluorophenyl)azetidine-1-carbonyl]-2-methoxy-4-{[(2S)-1,1,1-trifluoropropan-2-yl]oxy}benzonitrile;
2-Chloro-3-(3-phenylazetidine-1-carbonyl)-4-{[(2S)-1,1,1-trifluoropropan-2-yl]oxy}benzonitrile;
2-Chloro-3-[3-(3,4-difluorophenyl)azetidine-1-carbonyl]-4-{[(2S)-1,1,1-trifluoropropan-2-yl]oxy}benzonitrile;
2-Chloro-3-[3-(4-fluorophenyl)azetidine-1-carbonyl]-4-{[(2S)-1,1,1-trifluoropropan-2-yl]oxy}benzonitrile;
2-Chloro-3-[3-(3,5-difluorophenyl)azetidine-1-carbonyl]-4-{[(2S)-1,1,1-trifluoropropan-2-yl]oxy}benzonitrile;
3-(4-Fluoro-2-methylphenoxy)-1-(3-methanesulfonyl-2-methoxy-6-{[(2S)-1,1,1-trifluoropropan-2-yl]oxy}benzoyl)azetidine;
1-(3-Methanesulfonyl-2-methoxy-6-{[(2S)-1,1,1-trifluoropropan-2-yl]oxy}benzoyl)-3-(2,4,6-trifluorophenoxy)azetidine;

1-(3-Methanesulfonyl-2-methoxy-6-{[(2S)-1,1,1-trifluoropropan-2-yl]oxy}benzoyl)-3-(2,4,5-trifluorophenoxy)azetidine;
2-{[1-(3-Methanesulfonyl-2-methoxy-6-{[(2S)-1,1,1-trifluoropropan-2-yl]oxy}benzoyl)azetidin-3-yl]oxy}-5-(trifluoromethyl)pyridine;
4-{[1-(3-Methanesulfonyl-2-methoxy-6-{[(2S)-1,1,1-trifluoropropan-2-yl]oxy}benzoyl)azetidin-3-yl]oxy}pyridine;
2-Chloro-3-({3-[4-(trifluoromethyl)phenyl]azetidin-1-yl}carbonyl)-4-[(1,1,1-trifluoropropan-2-yl)oxy]benzonitrile;
3-({3-Hydroxy-3-[4-(trifluoromethyl)phenyl]azetidin-1-yl}carbonyl)-2-methoxy-4-[(1,1,1-trifluoropropan-2-yl)oxy]benzonitrile;
3-{[3-(5-Fluoropyridin-2-yl)azetidin-1-yl]carbonyl}-2-methoxy-4-[(1,1,1-trifluoropropan-2-yl)oxy]benzonitrile;
2-Chloro-3-{[3-(5-fluoropyridin-2-yl)azetidin-1-yl]carbonyl}-4-[(1,1,1-trifluoropropan-2-yl)oxy]benzonitrile;
3-{[3-(3,4-Difluorophenoxy)azetidin-1-yl]carbonyl}-2-methoxy-4-[(1,1,1-trifluoropropan-2-yl)oxy]benzonitrile;
2-Chloro-3-{[3-(3,4-difluorophenoxy)azetidin-1-yl]carbonyl}-4-[(1,1,1-trifluoropropan-2-yl)oxy]benzonitrile;
3-({3-Fluoro-3-[4-(trifluoromethyl)phenyl]azetidin-1-yl}carbonyl)-2-methoxy-4-{[(2S)-1,1,1-trifluoropropan-2-yl]oxy}benzonitrile;
3-{[3-(3,4-Difluorophenyl)-3-fluoroazetidin-1l-yl]carbonyl}-2-methoxy-4-{[(2S)-1,1,1-trifluoropropan-2-yl]oxy}benzonitrile;
2-Chloro-3-{[3-(pyridin-3-yl)azetidin-1-yl]carbonyl}-4-[(1,1,1-trifluoropropan-2-yl)oxy]benzonitrile;
2-Chloro-3-{[3-(pyridin-4-yl)azetidin-1-yl]carbonyl}-4-[(1,1,1-trifluoropropan-2-yl)oxy]benzonitrile;
2-Chloro-3-{[3-(4-fluorophenoxy)azetidin-1-yl]carbonyl}-4-[(1,1,1-trifluoropropan-2-yl)oxy]benzonitrile;
3-{[3-(4-Fluorophenoxy)azetidin-1-yl]carbonyl}-2-methoxy-4-[(1,1,1-trifluoropropan-2-yl)oxy]benzonitrile;
2-Methoxy-3-{[3-(pyridin-4-yl)azetidin-1l-yl]carbonyl}-4-[(1,1,1-trifluoropropan-2-yl)oxy]benzonitrile;
2-Chloro-3-[(3-phenoxyazetidin-1l-yl)carbonyl]-4-[(1,1,1-trifluoropropan-2-yl)oxy]benzonitrile;
2-Chloro-3-{[3-(4-methylphenoxy)azetidin-1-yl]carbonyl}-4-[(1,1,1-trifluoropropan-2-yl)oxy]benzonitrile;
2-Methoxy-3-{[3-(4-methylphenoxy)azetidin-1-yl]carbonyl}-4-[(1,1,1-trifluoropropan-2-yl)oxy]benzonitrile;
2-Chloro-3-{[3-(4-cyanophenyl)azetidin-1-yl]carbonyl}-4-[(1,1,1-trifluoropropan-2-yl)oxy]benzonitrile;
2-Chloro-3-{[3-(4-methoxyphenyl)azetidin-1-yl]carbonyl}-4-[(1,1,1-trifluoropropan-2-yl)oxy]benzonitrile;
2-Chloro-3-{[3-(3,4-difluorophenyl)azetidin-1-yl]carbonyl}-4-[(1,1,1-trifluoropropan-2-yl)oxy]benzonitrile;
2-Chloro-3-{[3-(3,5-difluorophenyl)azetidin-1-yl]carbonyl}-4-[(1,1,1-trifluoropropan-2-yl)oxy]benzonitrile;
2-Chloro-3-{[3-(4-chlorophenyl)azetidin-1-yl]carbonyl}-4-[(1,1,1-trifluoropropan-2-yl)oxy]benzonitrile;
2-Chloro-3-({3-[2-(trifluoromethyl)phenyl]azetidin-1-yl}carbonyl)-4-[(1,1,1-trifluoropropan-2-yl)oxy]benzonitrile;
2-Chloro-3-({3-[3-(trifluoromethyl)phenyl]azetidin-1-yl}carbonyl)-4-[(1,1,1-trifluoropropan-2-yl)oxy]benzonitrile;
2-Chloro-3-{[3-(4-fluorophenyl)azetidin-1-yl]carbonyl}-4-[(1,1,1-trifluoropropan-2-yl)oxy]benzonitrile;
2-Chloro-3-{[3-(2-fluorophenyl)azetidin-1-yl]carbonyl}-4-[(1,1,1-trifluoropropan-2-yl)oxy]benzonitrile;
2-Chloro-3-{[3-(pyridin-2-yl)azetidin-1-yl]carbonyl}-4-[(1,1,1-trifluoropropan-2-yl)oxy]benzonitrile;
2-Chloro-3-{[3-(4-methoxyphenoxy)azetidin-1-yl]carbonyl}-4-[(1,1,1-trifluoropropan-2-yl)oxy]benzonitrile;
2-Methoxy-3-({3-[2-(trifluoromethyl)phenyl]azetidin-1-yl}carbonyl)-4-[(1,1,1-trifluoropropan-2-yl)oxy]benzonitrile;
3-{[3-(4-Fluorophenyl)azetidin-1-yl]carbonyl}-2-methoxy-4-[(1,1,1-trifluoropropan-2-yl)oxy]benzonitrile;
3-{[3-(2-Fluorophenyl)azetidin-1-yl]carbonyl}-2-methoxy-4-[(1,1,1-trifluoropropan-2-yl)oxy]benzonitrile;
2-Methoxy-3-{[3-(pyridin-2-yl)azetidin-1-yl]carbonyl}-4-[(1,1,1-trifluoropropan-2-yl)oxy]benzonitrile;
2-Methoxy-3-{[3-(4-methoxyphenoxy)azetidin-1-yl]carbonyl}-4-[(1,1,1-trifluoropropan-2-yl)oxy]benzonitrile;
3-{[3-(4-Cyanophenyl)azetidin-1-yl]carbonyl}-2-methoxy-4-[(1,1,1-trifluoropropan-2-yl)oxy]benzonitrile;
2-Methoxy-3-{[3-(4-methoxyphenyl)azetidin-1-yl]carbonyl}-4-[(1,1,1-trifluoropropan-2-yl)oxy]benzonitrile;
3-{[3-(4-Chlorophenyl)azetidin-1-yl]carbonyl}-2-methoxy-4-[(1,1,1-trifluoropropan-2-yl)oxy]benzonitrile;
2-Methoxy-3-({3-[4-(trifluoromethyl)phenyl]azetidin-1-yl}carbonyl)-4-[(1,1,1-trifluoropropan-2-yl)oxy]benzonitrile;
2-Methoxy-3-({3-[3-(trifluoromethyl)phenyl]azetidin-1-yl}carbonyl)-4-[(1,1,1-trifluoropropan-2-yl)oxy]benzonitrile;
3-{[3-(3,5-Difluorophenyl)azetidin-1-yl]carbonyl}-2-methoxy-4-[(1,1,1-trifluoropropan-2-yl)oxy]benzonitrile;
3-{[3-(3,4-Difluorophenyl)azetidin-1-yl]carbonyl}-2-methoxy-4-[(1,1,1-trifluoropropan-2-yl)oxy]benzonitrile;
2-Methoxy-3-{[3-(pyridin-3-yloxy)azetidin-1-yl]carbonyl}-4-[(1,1,1-trifluoropropan-2-yl)oxy]benzonitrile;
2-Chloro-3-{[3-(pyridin-3-yloxy)azetidin-1-yl]carbonyl}-4-[(1,1,1-trifluoropropan-2-yl)oxy]benzonitrile;
3-{[3-(4-Cyanophenyl)azetidin-1-yl]carbonyl}-4-(1-fluorocyclobutyl)-2-methoxybenzonitrile;
2-Chloro-4-(2,2,2-trifluoroethoxy)-3-({3-[4-(trifluoromethyl)phenyl]azetidin-1-yl}carbonyl)benzonitrile;
2-Chloro-3-{[3-(4-cyanophenyl)azetidin-1-yl]carbonyl}-4-(2,2,2-trifluoroethoxy)benzonitrile;
2-Chloro-3-({3-[4-(trifluoromethyl)phenyl]azetidin-1-yl}carbonyl)-4-{[(2S)-1,1,1-trifluoropropan-2-yl]oxy}benzonitrile;
3-{[3-(4-Cyanophenyl)azetidin-1-yl]carbonyl}-2-methoxy-4-{[(2S)-1,1,1-trifluoropropan-2-yl]oxy}benzonitrile;
2-Chloro-3-{[3-(4-cyanophenyl)azetidin-1-yl]carbonyl}-4-{[(2S)-1,1,1-trifluoropropan-2-yl]oxy}benzonitrile;
2-Chloro-3-{[3-(5-methylpyridin-3-yl)azetidin-1-yl]carbonyl}-4-[(1,1,1-trifluoropropan-2-yl)oxy]benzonitrile;
2-Methoxy-3-{[3-(5-methylpyridin-3-yl)azetidin-1-yl]carbonyl}-4-[(1,1,1-trifluoropropan-2-yl)oxy]benzonitrile;

2-Chloro-3-({3-[6-(trifluoromethyl)pyridin-3-yl]azetidin-1-yl}carbonyl)-4-[(1,1,1-trifluoropropan-2-yl)oxy]benzonitrile;
2-Methoxy-3-({3-[6-(trifluoromethyl)pyridin-3-yl]azetidin-1-yl}carbonyl)-4-[(1,1,1-trifluoropropan-2-yl)oxy]benzonitrile;
3-({3-[3-Chloro-5-(trifluoromethyl)pyridin-2-yl]azetidin-1-yl}carbonyl)-2-methoxy-4-{[(2S)-1,1,1-trifluoropropan-2-yl]oxy}benzonitrile;
3-({3-[5-(Difluoromethyl)pyridin-2-yl]azetidin-1-yl}carbonyl)-2-methoxy-4-{[(2S)-1,1,1-trifluoropropan-2-yl]oxy}benzonitrile;
3-{[3-(4-Cyano-3-fluorophenyl)azetidin-1-yl]carbonyl}-2-methoxy-4-{[(2S)-1,1,1-trifluoropropan-2-yl]oxy}benzonitrile;
3-({3-[3-Chloro-5-(trifluoromethyl)pyridin-2-yl]azetidin-1-yl}carbonyl)-4-(4-fluorooxan-4-yl)-2-methoxybenzonitrile;
3-{[3-(2-Chloro-4-cyanophenyl)azetidin-1-yl]carbonyl}-2-methoxy-4-{[(2S)-1,1,1-trifluoropropan-2-yl]oxy}benzonitrile;
3-({3-[3-Chloro-5-(trifluoromethyl)pyridin-2-yl]azetidin-1-yl}carbonyl)-2-methoxy-4-(2,2,2-trifluoroethoxy)benzonitrile;
2-Chloro-3-({3-[5-(trifluoromethyl)pyridin-2-yl]azetidin-1-yl}carbonyl)-4-{[(2S)-1,1,1-trifluoropropan-2-yl]oxy}benzonitrile;
3-{[3-(3,5-Difluoropyridin-2-yl)azetidin-1-yl]carbonyl}-2-methoxy-4-{[(2S)-1,1,1-trifluoropropan-2-yl]oxy}benzonitrile;
3-{[3-(3-Chloro-4-cyanophenyl)azetidin-1-yl]carbonyl}-2-methoxy-4-{[(2S)-1,1,1-trifluoropropan-2-yl]oxy}benzonitrile;
3-{[3-(2-Cyanophenyl)azetidin-1-yl]carbonyl}-2-methoxy-4-{[(2S)-1,1,1-trifluoropropan-2-yl]oxy}benzonitrile;
3-Chloro-4-{1-[(3-cyano-2-methoxy-6-{[(2S)-1,1,1-trifluoropropan-2-yl]oxy}phenyl)carbonyl]azetidin-3-yl}-2-fluorobenzonitrile;
2-Methoxy-4-(2,2,2-trifluoroethoxy)-3-({3-[5-(trifluoromethyl)pyridin-2-yl]azetidin-1-yl}carbonyl)benzonitrile;
3-{[3-(4-Chloro-2-cyanophenyl)azetidin-1-yl]carbonyl}-2-methoxy-4-{[(2S)-1,1,1-trifluoropropan-2-yl]oxy}benzonitrile;
3-{[3-(2-Cyano-4-fluorophenyl)azetidin-1-yl]carbonyl}-2-methoxy-4-{[(2S)-1,1,1-trifluoropropan-2-yl]oxy}benzonitrile;
3-{[3-(4-Cyano-2-methoxyphenyl)azetidin-1-yl]carbonyl}-2-methoxy-4-{[(2S)-1,1,1-trifluoropropan-2-yl]oxy}benzonitrile;
2-Methoxy-3-({3-[2-methoxy-4-(trifluoromethyl)phenyl]azetidin-1-yl}carbonyl)-4-{[(2S)-1,1,1-trifluoropropan-2-yl]oxy}benzonitrile;
3-{[3-(1,3-Benzoxazol-6-yl)azetidin-1-yl]carbonyl}-2-methoxy-4-{[(2S)-1,1,1-trifluoropropan-2-yl]oxy}benzonitrile;
2-Chloro-3-{[3-(2-chloro-4-cyanophenyl)azetidin-1-yl]carbonyl}-4-{[(2S)-1,1,1-trifluoropropan-2-yl]oxy}benzonitrile;
3-{[3-(2-Chloro-4-cyanophenyl)azetidin-1-yl]carbonyl}-4-(4-fluorooxan-4-yl)-2-methoxybenzonitrile;
3-{[3-(2-Chloro-4-cyanophenyl)azetidin-1-yl]carbonyl}-2-methoxy-4-(1,4,4-trifluorocyclohexyl)benzonitrile;
3-{[3-(2-Chloro-4-cyanophenyl)azetidin-1-yl]carbonyl}-4-(1-fluorocyclobutyl)-2-methoxybenzonitrile;
2-Methoxy-3-{3-[5-(trifluoromethyl)pyridin-2-yl]azetidine-1-carbonyl}-4-{[(2R)-1,1,1-trifluoropropan-2-yl]oxy}benzonitrile;
3-{3-[3-Chloro-5-(trifluoromethyl)pyridin-2-yl]azetidine-1-carbonyl}-2-methoxy-4-{[(2R)-1,1,1-trifluoropropan-2-yl]oxy}benzonitrile;
3-{3-[5-(Difluoromethyl)pyridin-2-yl]azetidine-1-carbonyl}-2-methoxy-4-{[(2R)-1,1,1-trifluoropropan-2-yl]oxy}benzonitrile;
3-[2-Fluoro-4-(trifluoromethyl)phenyl]-1-(3-methanesulfonyl-2-methoxy-6-{[(2R)-1,1,1-trifluoropropan-2-yl]oxy}benzoyl)azetidine;
3-[2-Fluoro-4-(trifluoromethyl)phenyl]-1-(3-methanesulfonyl-2-methoxy-6-{[(2S)-1,1,1-trifluoropropan-2-yl]oxy}benzoyl)azetidine;
3-[3-Fluoro-4-(trifluoromethyl)phenyl]-1-(3-methanesulfonyl-2-methoxy-6-{[(2R)-1,1,1-trifluoropropan-2-yl]oxy}benzoyl)azetidine;
3-[3-Fluoro-4-(trifluoromethyl)phenyl]-1-(3-methanesulfonyl-2-methoxy-6-{[(2S)-1,1,1-trifluoropropan-2-yl]oxy}benzoyl)azetidine;
3-[4-(Difluoromethyl)-3-fluorophenyl]-1-(3-methanesulfonyl-2-methoxy-6-{[(2S)-1,1,1-trifluoropropan-2-yl]oxy}benzoyl)azetidine;
3-[4-(Difluoromethyl)-2-fluorophenyl]-1-(3-methanesulfonyl-2-methoxy-6-{[(2S)-1,1,1-trifluoropropan-2-yl]oxy}benzoyl)azetidine;
1-(3-Methanesulfonyl-2-methoxy-6-{[(2S)-1,1,1-trifluoropropan-2-yl]oxy}benzoyl)-3-[3-methoxy-4-(trifluoromethyl)phenyl]azetidine;
3-(2-Chloro-4-fluorophenyl)-1-(3-methanesulfonyl-2-methoxy-6-{[(2S)-1,1,1-trifluoropropan-2-yl]oxy}benzoyl)azetidine;
3-[2-Chloro-4-(trifluoromethyl)phenyl]-1-(3-methanesulfonyl-2-methoxy-6-{[(2S)-1,1,1-trifluoropropan-2-yl]oxy}benzoyl)azetidine;
3-[2-Chloro-4-(difluoromethyl)phenyl]-1-(3-methanesulfonyl-2-methoxy-6-{[(2S)-1,1,1-trifluoropropan-2-yl]oxy}benzoyl)azetidine;
1-(3-Methanesulfonyl-2-methoxy-6-{[(2S)-1,1,1-trifluoropropan-2-yl]oxy}benzoyl)-3-(4-nitrophenyl)azetidine;
1-(3-Methanesulfonyl-2-methoxy-6-{[(2R)-1,1,1-trifluoropropan-2-yl]oxy}benzoyl)-3-{[4-(trifluoromethyl)phenyl]methyl}azetidine;
1-(3-Methanesulfonyl-2-methoxy-6-{[(2S)-1,1,1-trifluoropropan-2-yl]oxy}benzoyl)-3-(3,4,5-trifluorophenyl)azetidine;
4-(3,3-Difluorocyclobutyl)-2-methoxy-3-{3-[5-(trifluoromethyl)pyridin-2-yl]azetidine-1-carbonyl}benzonitrile;
3-{3-[3-Chloro-5-(trifluoromethyl)pyridin-2-yl]azetidine-1-carbonyl}-4-(3,3-difluorocyclobutyl)-2-methoxybenzonitrile;
4-(3,3-Difluorocyclobutyl)-3-{3-[3-fluoro-5-(trifluoromethyl)pyridin-2-yl]azetidine-1-carbonyl}-2-methoxybenzonitrile;
1-(3-Methanesulfonyl-2-methoxy-6-{[(2S)-1,1,1-trifluoropropan-2-yl]oxy}benzoyl)-3-(2,4,5-trifluorophenyl)azetidine;
1-(3-Methanesulfonyl-2-methoxy-6-{[(2S)-1,1,1-trifluoropropan-2-yl]oxy}benzoyl)-3-(2,3,4-trifluorophenyl)azetidine;
1-(3-Methanesulfonyl-2-methoxy-6-{[(2S)-1,1,1-trifluoropropan-2-yl]oxy}benzoyl)-3-(2,3,5-trifluorophenyl)azetidine;

3-(2,3-Difluorophenyl)-1-(3-methanesulfonyl-2-methoxy-6-{[(2S)-1,1,1-trifluoropropan-2-yl]oxy}benzoyl)azetidine;

2-Methoxy-3-{3-[4-(oxan-4-yl)phenyl]azetidine-1-carbonyl}-4-{[(2S)-1,1,1-trifluoropropan-2-yl]oxy}benzonitrile;

2-Methoxy-3-{3-[5-(oxan-4-yl)pyridin-2-yl]azetidine-1-carbonyl}-4-{[(2S)-1,1,1-trifluoropropan-2-yl]oxy}benzonitrile;

3-{3-[4-(2,2-Dimethyloxan-4-yl)phenyl]azetidine-1-carbonyl}-2-methoxy-4-{[(2S)-1,1,1-trifluoropropan-2-yl]oxy}benzonitrile;

2-Methoxy-3-{3-[4-(oxan-4-yl)phenyl]azetidine-1-carbonyl}-4-{[(2R)-1,1,1-trifluoropropan-2-yl]oxy}benzonitrile;

4-(1-Fluorocyclobutyl)-2-methoxy-3-{3-[5-(oxan-4-yl)pyridin-2-yl]azetidine-1-carbonyl}benzonitrile;

3-{3-[3-Fluoro-4-(oxan-4-yl)phenyl]azetidine-1-carbonyl}-2-methoxy-4-{[(2S)-1,1,1-trifluoropropan-2-yl]oxy}benzonitrile;

1-(3-Methanesulfonyl-2-methoxy-6-{[(2R)-1,1,1-trifluoropropan-2-yl]oxy}benzoyl)-3-[4-(oxan-4-yl)phenyl]azetidine;

4-Ethoxy-2-methoxy-3-{3-[5-(oxan-4-yl)pyridin-2-yl]azetidine-1-carbonyl}benzonitrile;

2-Methoxy-3-{3-[5-(oxan-4-yl)pyridin-2-yl]azetidine-1-carbonyl}-4-(propan-2-yloxy)benzonitrile;

3-[4-(4,4-Difluorocyclohexyl)phenyl]-1-(3-methanesulfonyl-2-methoxy-6-{[(2R)-1,1,1-trifluoropropan-2-yl]oxy}benzoyl)azetidine;

1-(3-Methanesulfonyl-2-methoxy-6-{[(2S)-1,1,1-trifluoropropan-2-yl]oxy}benzoyl)-3-[4-(oxan-4-yl)phenyl]azetidine;

2-Chloro-3-{3-[5-(oxan-4-yl)pyridin-2-yl]azetidine-1-carbonyl}-4-{[(2S)-1,1,1-trifluoropropan-2-yl]oxy}benzonitrile;

2-Chloro-3-{3-[5-(oxan-4-yl)pyridin-2-yl]azetidine-1-carbonyl}-4-{[(2R)-1,1,1-trifluoropropan-2-yl]oxy}benzonitrile;

3-{3-[5-(4,4-Difluorocyclohexyl)pyridin-2-yl]azetidine-1-carbonyl}-2-methoxy-4-{[(2S)-1,1,1-trifluoropropan-2-yl]oxy}benzonitrile;

3-{3-[5-(4,4-Difluorocyclohexyl)pyridin-2-yl]azetidine-1-carbonyl}-2-methoxy-4-{[(2R)-1,1,1-trifluoropropan-2-yl]oxy}benzonitrile;

3-{[3-(4-Cyanophenyl)azetidin-1-yl]carbonyl}-4-(cyclopropylmethoxy)-2-methoxybenzonitrile;

3-{[3-(4-Cyano-3-methoxyphenyl)azetidin-1-yl]carbonyl}-2-methoxy-4-{[(2S)-1,1,1-trifluoropropan-2-yl]oxy}benzonitrile;

3-Chloro-4-{1-[(3-cyano-2-methoxy-6-{[(2S)-1,1,1-trifluoropropan-2-yl]oxy}phenyl)carbonyl]azetidin-3-yl}-2-methoxybenzonitrile;

3-Chloro-4-[1-(3-cyano-2-methoxy-6-{[(2S)-1,1,1-trifluoropropan-2-yl]oxy}benzoyl)azetidin-3-yl]-2-ethoxybenzonitrile;

3-[3-(4-Cyano-3-methoxyphenyl)azetidine-1-carbonyl]-2-methoxy-4-{[(2R)-1,1,1-trifluoropropan-2-yl]oxy}benzonitrile;

2-Methoxy-3-({3-[4-(trifluoromethyl)phenyl]azetidin-1-yl}carbonyl)-4-{[(2S)-1,1,1-trifluoropropan-2-yl]oxy}benzonitrile;

1-({3-Methanesulfonyl-2-methoxy-6-[(1,1,1-trifluoropropan-2-yl)oxy]phenyl}carbonyl)-3-[4-(trifluoromethyl)phenyl]azetidine;

3-(3,4-Difluorophenoxy)-1-({3-methanesulfonyl-2-methoxy-6-[(1,1,1-trifluoropropan-2-yl)oxy]phenyl})carbonyl)azetidine;

2-Methoxy-3-[(3-{[4-(trifluoromethyl)phenyl]methyl}azetidin-1-yl)carbonyl]-4-{[(2S)-1,1,1-trifluoropropan-2-yl]oxy}benzonitrile;

3-(3,5-Difluorophenyl)-1-({3-methanesulfonyl-2-methoxy-6-[(1,1,1-trifluoropropan-2-yl)oxy]phenyl}carbonyl)azetidine;

1-(3-Methanesulfonyl-2-methoxy-6-{[(2R)-1,1,1-trifluoropropan-2-yl]oxy}benzoyl)-3-[4-(trifluoromethyl)phenyl]azetidine;

2-[1-(3-Methanesulfonyl-2-methoxy-6-{[(2R)-1,1,1-trifluoropropan-2-yl]oxy}benzoyl)azetidin-3-yl]-5-(trifluoromethyl)pyridine;

5-(Difluoromethyl)-2-[1-(3-methanesulfonyl-2-methoxy-6-{[(2R)-1,1,1-trifluoropropan-2-yl]oxy}benzoyl)azetidin-3-yl]pyridine;

3-Chloro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine;

1-(3-Methanesulfonyl-2-methoxy-6-{[(2S)-1,1,1-trifluoropropan-2-yl]oxy}benzoyl)-3-[4-(trifluoromethyl)phenyl]azetidine;

3-(4-Fluorophenoxy)-1-(3-methanesulfonyl-2-methoxy-6-{[(2R)-1,1,1-trifluoropropan-2-yl]oxy}benzoyl)azetidine;

3-Fluoro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine;

3-Chloro-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine;

3-Ethynyl-2-[1-(3-methanesulfonyl-2-methoxy-6-{[(2S)-1,1,1-trifluoropropan-2-yl]oxy}benzoyl)azetidin-3-yl]-5-(trifluoromethyl)pyridine;

3-(4-Fluorophenoxy)-1-(3-methanesulfonyl-2-methoxy-6-{[(2S)-1,1,1-trifluoropropan-2-yl]oxy}benzoyl)azetidine;

4-(1-Fluorocyclopentyl)-2-methoxy-3-{3-[5-(trifluoromethyl)pyridin-2-yl]azetidine-1-carbonyl}benzonitrile;

1-(3-Methanesulfonyl-2-methoxy-6-{[(2S)-1,1,1-trifluoropropan-2-yl]oxy}benzoyl)-3-phenoxyazetidine;

3-(3,4-Difluorophenoxy)-1-(3-methanesulfonyl-2-methoxy-6-{[(2S)-1,1,1-trifluoropropan-2-yl]oxy}benzoyl)azetidine;

3-(3,5-Difluorophenyl)-1-(3-methanesulfonyl-2-methoxy-6-{[(2S)-1,1,1-trifluoropropan-2-yl]oxy}benzoyl)azetidine;

4-(1-Fluorocyclopentyl)-2-methoxy-3-{3-[4-(trifluoromethyl)phenyl]azetidine-1-carbonyl}benzonitrile;

3-(3,4-Difluorophenyl)-1-(3-methanesulfonyl-2-methoxy-6-{[(2S)-1,1,1-trifluoropropan-2-yl]oxy}benzoyl)azetidine;

1-(3-Methanesulfonyl-2-methoxy-6-{[(2S)-1,1,1-trifluoropropan-2-yl]oxy}benzoyl)-3-[2-(trifluoromethyl)phenyl]azetidine;

3-(3-Chlorophenoxy)-1-(3-methanesulfonyl-2-methoxy-6-{[(2S)-1,1,1-trifluoropropan-2-yl]oxy}benzoyl)azetidine;

3-(4-Chlorophenoxy)-1-(3-methanesulfonyl-2-methoxy-6-{[(2S)-1,1,1-trifluoropropan-2-yl]oxy}benzoyl)azetidine;

1-(3-Methanesulfonyl-2-methoxy-6-{[(2S)-1,1,1-trifluoropropan-2-yl]oxy}benzoyl)-3-[4-(trifluoromethyl)phenoxy]azetidine;

3-(2,6-Difluorophenoxy)-1-(3-methanesulfonyl-2-methoxy-6-{[(2S)-1,1,1-trifluoropropan-2-yl]oxy}benzoyl)azetidine;

3-(2,4-Difluorophenoxy)-1-(3-methanesulfonyl-2-methoxy-6-{[(2S)-1,1,1-trifluoropropan-2-yl]oxy}benzoyl)azetidine;

3-(2,5-Difluorophenoxy)-1-(3-methanesulfonyl-2-methoxy-6-{[(2S)-1,1,1-trifluoropropan-2-yl]oxy}benzoyl)azetidine;

3-(2,3-Difluorophenoxy)-1-(3-methanesulfonyl-2-methoxy-6-{[(2S)-1,1,1-trifluoropropan-2-yl]oxy}benzoyl)azetidine;

3-(3-Fluorophenoxy)-1-(3-methanesulfonyl-2-methoxy-6-{[(2S)-1,1,1-trifluoropropan-2-yl]oxy}benzoyl)azetidine;

4-(4-Fluorooxan-4-yl)-2-methoxy-3-({3-[4-(trifluoromethyl)phenyl]azetidin-1-yl}) carbonyl)benzonitrile;

3-{3-[3-Chloro-5-(trifluoromethyl)pyridin-2-yl]azetidine-1-carbonyl}-4-cyclopentyl-2-methoxybenzonitrile;

4-Cyclopentyl-3-{3-[3-fluoro-5-(trifluoromethyl)pyridin-2-yl]azetidine-1-carbonyl}-2-methoxybenzonitrile;

4-Cyclopentyl-2-methoxy-3-{3-[4-(trifluoromethyl)phenoxy]azetidine-1-carbonyl}benzonitrile;

4-Cyclopentyl-2-methoxy-3-[3-(2,4,6-trifluorophenoxy)azetidine-1-carbonyl]benzonitrile;

2-{1-[3-Methanesulfonyl-2-methoxy-6-(propan-2-yloxy)benzoyl]azetidin-3-yl}-5-(trifluoromethyl)pyridine;

3-Chloro-2-{1-[3-methanesulfonyl-2-methoxy-6-(propan-2-yloxy)benzoyl]azetidin-3-yl}-5-(trifluoromethyl)pyridine;

3-Fluoro-2-{1-[3-methanesulfonyl-2-methoxy-6-(propan-2-yloxy)benzoyl]azetidin-3-yl}-5-(trifluoromethyl)pyridine;

3-(3,4-Difluorophenyl)-1-[3-methanesulfonyl-2-methoxy-6-(propan-2-yloxy)benzoyl]azetidine;

1-[3-Methanesulfonyl-2-methoxy-6-(propan-2-yloxy)benzoyl]-3-[4-(trifluoromethyl)phenyl]azetidine;

1-[3-Methanesulfonyl-2-methoxy-6-(propan-2-yloxy)benzoyl]-3-[4-(trifluoromethyl)phenoxy]azetidine;

3-(4-Chlorophenoxy)-1-[3-methanesulfonyl-2-methoxy-6-(propan-2-yloxy)benzoyl]azetidine;

3-(2,4-Difluorophenoxy)-1-[3-methanesulfonyl-2-methoxy-6-(propan-2-yloxy)benzoyl]azetidine;

1-[3-Methanesulfonyl-2-methoxy-6-(propan-2-yloxy)benzoyl]-3-(2,4,6-trifluorophenoxy)azetidine;

3-(4-Chlorophenoxy)-1-[3-methanesulfonyl-2-methoxy-6-(2,2,2-trifluoroethoxy)benzoyl]azetidine;

1-[3-Methanesulfonyl-2-methoxy-6-(2,2,2-trifluoroethoxy)benzoyl]-3-[4-(trifluoromethyl)phenoxy]azetidine;

3-(4-Fluoro-2-methylphenoxy)-1-[3-methanesulfonyl-2-methoxy-6-(2,2,2-trifluoroethoxy)benzoyl]azetidine;

1-[3-Methanesulfonyl-2-methoxy-6-(2,2,2-trifluoroethoxy)benzoyl]-3-(2,4,6-trifluorophenoxy)azetidine;

1-[3-Methanesulfonyl-2-methoxy-6-(2,2,2-trifluoroethoxy)benzoyl]-3-(2,4,5-trifluorophenoxy)azetidine;

3-(2,4-Difluorophenoxy)-1-[3-methanesulfonyl-2-methoxy-6-(2,2,2-trifluoroethoxy)benzoyl]azetidine;

3-(3,4-Difluorophenyl)-1-[3-methanesulfonyl-2-methoxy-6-(2,2,2-trifluoroethoxy)benzoyl]azetidine;

2-{1-[3-Methanesulfonyl-2-methoxy-6-(2,2,2-trifluoroethoxy)benzoyl]azetidin-3-yl}-5-(trifluoromethyl)pyridine;

3-Chloro-2-{1-[3-methanesulfonyl-2-methoxy-6-(2,2,2-trifluoroethoxy)benzoyl]azetidin-3-yl}-5-(trifluoromethyl)pyridine;

3-Fluoro-2-{1-[3-methanesulfonyl-2-methoxy-6-(2,2,2-trifluoroethoxy)benzoyl]azetidin-3-yl}-5-(trifluoromethyl)pyridine;

5-Chloro-2-({1-[3-methanesulfonyl-2-methoxy-6-(2,2,2-trifluoroethoxy)benzoyl]azetidin-3-yl}oxy)pyridine;

5-Chloro-2-{[1-(3-methanesulfonyl-2-methoxy-6-{[(2S)-1,1,1-trifluoropropan-2-yl]oxy}benzoyl)azetidin-3-yl]oxy}pyridine;

3-Chloro-2-[1-(3-methanesulfonyl-2-methoxy-6-{[(2S)-1,1,1-trifluoropropan-2-yl]oxy}benzoyl)azetidin-3-yl]pyridine;

1-[3-Methanesulfonyl-2-methoxy-6-(2,2,2-trifluoroethoxy)benzoyl]-3-[4-(trifluoromethyl)phenyl]azetidine;

3-Chloro-4-[1-(3-methanesulfonyl-2-methoxy-6-{[(2S)-1,1,1-trifluoropropan-2-yl]oxy}benzoyl)azetidin-3-yl]benzonitrile;

3-Chloro-4-{1-[3-methanesulfonyl-2-methoxy-6-(2,2,2-trifluoroethoxy)benzoyl]azetidin-3-yl}benzonitrile;

1-[6-(2,2-Dimethylpropoxy)-3-methanesulfonyl-2-methoxybenzoyl]-3-[4-(trifluoromethyl)phenyl]azetidine;

3-Chloro-2-{1-[6-(2,2-dimethylpropoxy)-3-methanesulfonyl-2-methoxybenzoyl]azetidin-3-yl}-5-(trifluoromethyl)pyridine;

1-[6-(2,2-Dimethylpropoxy)-3-methanesulfonyl-2-methoxybenzoyl]-3-(2,4,6-trifluorophenoxy)azetidine;

1-[6-(2,2-Dimethylpropoxy)-3-methanesulfonyl-2-methoxybenzoyl]-3-(2,4,5-trifluorophenoxy)azetidine;

1-[3-(Ethanesulfonyl)-2-methoxy-6-(propan-2-yloxy)benzoyl]-3-[4-(trifluoromethyl)phenyl]azetidine;

3-Chloro-2-{1-[3-(ethanesulfonyl)-2-methoxy-6-(propan-2-yloxy)benzoyl]azetidin-3-yl}-5-(trifluoromethyl)pyridine;

1-[3-(Ethanesulfonyl)-2-methoxy-6-(propan-2-yloxy)benzoyl]-3-(2,4,6-trifluorophenoxy)azetidine;

1-[3-(Ethanesulfonyl)-2-methoxy-6-(propan-2-yloxy)benzoyl]-3-(2,4,5-trifluorophenoxy)azetidine;

6-[1-(3-Methanesulfonyl-2-methoxy-6-{[(2S)-1,1,1-trifluoropropan-2-yl]oxy}benzoyl)azetidin-3-yl]-1,3-benzoxazole;

6-{1-[3-Methanesulfonyl-2-methoxy-6-(2,2,2-trifluoroethoxy)benzoyl]azetidin-3-yl}-1,3-benzoxazole;

6-{1-[3-Methanesulfonyl-2-methoxy-6-(propan-2-yloxy)benzoyl]azetidin-3-yl}-1,3-benzoxazole;

6-{1-[6-(2,2-Dimethylpropoxy)-3-methanesulfonyl-2-methoxybenzoyl]azetidin-3-yl}-1,3-benzoxazole;

6-{1-[3-(Ethanesulfonyl)-2-methoxy-6-(propan-2-yloxy)benzoyl]azetidin-3-yl}-1,3-benzoxazole;

3-(5-Chloro-2-fluorophenyl)-1-(3-methanesulfonyl-2-methoxy-6-{[(2S)-1,1,1-trifluoropropan-2-yl]oxy}benzoyl)azetidine;

3-(3-Chloro-2-fluorophenyl)-1-(3-methanesulfonyl-2-methoxy-6-{[(2S)-1,1,1-trifluoropropan-2-yl]oxy}benzoyl)azetidine;

3-(2-Chloro-3-fluorophenyl)-1-(3-methanesulfonyl-2-methoxy-6-{[(2S)-1,1,1-trifluoropropan-2-yl]oxy}benzoyl)azetidine;

3-(2-Chloro-4,5-difluorophenyl)-1-(3-methanesulfonyl-2-methoxy-6-{[(2S)-1,1,1-trifluoropropan-2-yl]oxy}benzoyl)azetidine;

3-Chloro-2-(1-{3-methanesulfonyl-2-methoxy-6-[(1,1,1-trifluoropropan-2-yl)oxy]benzoyl}azetidin-3-yl)-5-(trifluoromethyl)pyridine;

2-Methoxy-3-({3-[4-(trifluoromethyl)phenyl]azetidin-1-yl}carbonyl)-4-{[(2R)-1,1,1-trifluoropropan-2-yl]oxy}benzonitrile; and pharmaceutically acceptable salt thereof.

19. A pharmaceutical composition comprising: a pharmaceutically acceptable excipient; and an effective amount of one or more compounds of claim 1.

20. A pharmaceutical composition comprising: a pharmaceutically acceptable excipient; and an effective amount of one or more compounds of claim 18.

* * * * *